US012473262B2

(12) United States Patent
Kolluri et al.

(10) Patent No.: US 12,473,262 B2
(45) Date of Patent: Nov. 18, 2025

(54) ARYL HYDROCARBON RECEPTOR ACTIVATORS

(71) Applicant: Oregon State University, Corvallis, OR (US)

(72) Inventors: Siva Kumar Kolluri, Corvallis, OR (US); Nancy I. Kerkvliet, Corvallis, OR (US); Sebastian Bernales, San Francisco, CA (US); Jit Chakravarty, Edmond, OK (US); Brahmam Pujala, Greater Noida (IN); Pasha Khan, New Delhi (IN); Varun Kumar, New Delhi (IN); Abhinandan Danodia, Greater Noida (IN); Gonzalo Ureta, Santiago (CL)

(73) Assignee: Oregon State University, Corvallis, OR (US)

( * ) Notice: Subject to any disclaimer, the term of this patent is extended or adjusted under 35 U.S.C. 154(b) by 754 days.

(21) Appl. No.: 17/630,763

(22) PCT Filed: Jul. 30, 2020

(86) PCT No.: PCT/US2020/044294

§ 371 (c)(1),
(2) Date: Jan. 27, 2022

(87) PCT Pub. No.: WO2021/022061

PCT Pub. Date: Feb. 4, 2021

(65) Prior Publication Data

US 2022/0281824 A1 Sep. 8, 2022

Related U.S. Application Data

(60) Provisional application No. 62/880,478, filed on Jul. 30, 2019.

(51) Int. Cl.

| | |
|---|---|
| ***C07D 235/06*** | (2006.01) |
| ***C07D 209/12*** | (2006.01) |
| ***C07D 307/80*** | (2006.01) |
| ***C07D 401/04*** | (2006.01) |
| ***C07D 401/06*** | (2006.01) |
| ***C07D 403/04*** | (2006.01) |
| ***C07D 405/04*** | (2006.01) |
| ***C07D 405/06*** | (2006.01) |
| ***C07D 409/04*** | (2006.01) |
| ***C07D 471/06*** | (2006.01) |
| ***C07D 471/16*** | (2006.01) |
| ***C07D 487/04*** | (2006.01) |

(52) U.S. Cl.

CPC ......... *C07D 235/06* (2013.01); *C07D 209/12* (2013.01); *C07D 307/80* (2013.01); *C07D 401/04* (2013.01); *C07D 401/06* (2013.01); *C07D 403/04* (2013.01); *C07D 405/04* (2013.01); *C07D 405/06* (2013.01); *C07D 409/04* (2013.01); *C07D 471/06* (2013.01); *C07D 471/16* (2013.01); *C07D 487/04* (2013.01)

(58) Field of Classification Search

CPC .................................................... C07D 235/06

See application file for complete search history.

(56) References Cited

U.S. PATENT DOCUMENTS

| | | | |
|---|---|---|---|
| 7,592,363 | B2 | 9/2009 | Steffan et al. |
| 9,371,319 | B2 | 6/2016 | Bavetsias et al. |
| 2011/0104110 | A1 | 5/2011 | Anikumar et al. |

FOREIGN PATENT DOCUMENTS

| | | |
|---|---|---|
| WO | 2018/141855 A1 | 8/2018 |

OTHER PUBLICATIONS

Database Registry Chemical Abstracts Service, Columbus, Ohio, Accession No. RN 1026752-03-3, Entered STN: Jun. 9, 2008.*

International Search Report and Written Opinion mailed Dec. 7, 2020, issued in corresponding International Application No. PCT/US2020/044294, filed Jul. 30, 2020, 11 pages.

"1-Benzyl-2-phenyl-1H-benzimidazole," C20H16N2-PubChem, CID 1221687, Jul. 10, 2005, <https://pubchem.ncbi.nlm.nih.gov/compound/1221687> [retrieved Nov. 7, 2020], 18 pages.

"3-Benzyl-1H-indazole," C14H12N2-PubChem, CID 3139604, Aug. 9, 2005, <https://pubchem.ncbi.nlm.nih.gov/compound/3139604> [retrieved Nov. 7, 2020], 15 pages.

* cited by examiner

*Primary Examiner* — Yong S. Chong

(74) *Attorney, Agent, or Firm* — Christensen O'Connor Johnson Kindness PLLC

(57) ABSTRACT

Small molecule AhR ligands are disclosed. The ligands can induce the differentiation of Tr1 cells to suppress pathogenic immune responses without inducing nonspecific immune suppression. Methods of treatment of autoimmune diseases using the AhR ligands are also disclosed.

10 Claims, No Drawings

ARYL HYDROCARBON RECEPTOR ACTIVATORS

CROSS-REFERENCE TO RELATED APPLICATION

This application is the US national phase of PCT/US2020/044294, filed on Jul. 30, 2020, which claims the benefit of U.S. Application No. 62/880,478, filed Jul. 30, 2019, each application expressly incorporated herein by reference in its entirety.

STATEMENT OF GOVERNMENT LICENSE RIGHTS

This invention was made with Government support under R01ES016651 awarded by National Institutes of Health. The Government has certain rights in the invention.

BACKGROUND OF THE INVENTION

Autoimmune disease is caused by a failure of the immune system to recognize the difference between healthy cells and cells that have been altered as a result of infectious disease or mutations leading to cancer. When the immune system attacks healthy cells, the resulting damage may affect one or several tissue types or organs. For example, type 1 diabetes (T1D), also known as diabetes mellitus type 1, is an autoimmune disease in which cytotoxic T-lymphocytes (CTL) attack and destroy the insulin-producing beta cells (β-cells) in the pancreas. Current management of T1D involves administration of insulin and various formulations of insulin. Currently, an estimated 80,000 children develop TIDM each year and approximately 3 million people have TID in the United States. Complications from TID include heart disease, stroke, kidney failure, foot ulcers, and diabetic retinopathy. In addition, insulin treatment can lead to low blood sugar, or hypoglycemia, which can result in coma and death. Another immune-mediated disease, graft versus host disease (GVHD), can occur after a tissue transplant or blood transfusion. GVHD develops when grafted donor T cells recognize the recipient's cells as foreign and differentiate into CTL that attack a recipient's healthy cells. GVHD can cause a range of symptoms from mild to severe, including death.

Current immune-suppressing drug therapies for GVHD, TID, and other autoimmune disorders act by nonspecifically inhibiting cellular proliferation or by suppressing inflammatory responses; the intended target cells (e.g. CTL) that are responsible for the autoimmune disease are suppressed as well. However, such nonspecific immune suppression results in undesirable side effects including an increased risk of infection and certain cancers. Thus, conventional immunosuppressive treatments of autoimmune diseases fail to provide long-term remission without severe side effects.

Targeting T cells is a promising therapeutic strategy for the prevention or treatment of autoimmune diseases. The aryl hydrocarbon receptor (AhR) represents a potential drug target as a ligand-activated transcription factor that specifically targets T cell differentiation rather than inhibiting cellular proliferation. Activation of the AhR has been shown to prevent the development of T1D in the NOD mouse model, and to suppress the development of murine GVHD, implicating the AhR as a novel therapeutic target.

Two potent AhR ligands, 10- and 11-chloro-7H-benzimidazo[2,1-a]benzo[de]-Iso-quinolin-7-one (11-Cl-BBQ) have been identified that suppress the development of T1D and GVHD in murine models. Acute or chronic treatment of mice with these compounds produced no overt toxicity at the therapeutic dose. Furthermore, extensive studies have shown that activation of the AhR by these compounds in T cells drives their differentiation into type 1 regulatory T cells (Tr1 cells) that suppress pathogenic T cell responses.

A need exists for non-toxic, small molecule AhR ligands with favorable pharmacokinetic properties that can induce the differentiation of Tr1 cells to suppress pathogenic immune responses without inducing nonspecific immune suppression.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, provided herein is a compound of the formula:

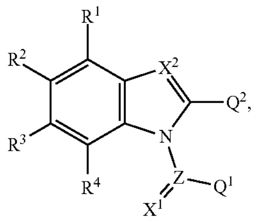

a tautomer thereof, a stereoisomer thereof, a hydrate thereof, or a pharmaceutically acceptable salt thereof, wherein:

$Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl;

$Q^2$ is an optionally substituted C6-C14 aryl; optionally substituted C5-C10 heteroaryl; optionally substituted C5-C10 heterocyclyl; optionally substituted C1-C10 alkyl, or optionally substituted C3-C10 cycloalkyl;

Z is C, S(O),

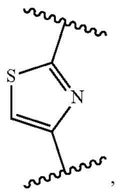, 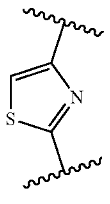, 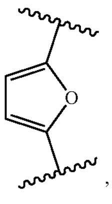, 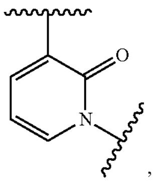, or Z is CH when X1 is absent;

$X^1$ is absent, O, NH, S, or X1 is

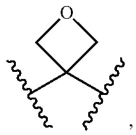 [SMILES: *C1(*)COC1], wherein the wavy lines denote points of attachment to Z;

$X^2$ is N, CCl, CF, CBr, CI, CCN, CCONH2, CCOOH, or CH;

$R^1$, $R^2$, $R^3$, and $R^4$ are independently H, halogen, CN, optionally substituted C1-C10 alkyl, optionally substituted C3-C10 cycloalkyl, optionally substituted C1-C6 alkoxy, $SO_2R^5$, CO2$R^5$, or CONR$^5$R$^6$, or any one of $R^1$ and $R^2$, $R^2$ and $R^3$, and $R^3$ and $R^4$ pairs, together with the carbon atoms to which they are attached, forms an optionally substituted a five- or six-membered cycloalkenyl, heterocyclenyl, aryl or heteroaryl; and $R^5$ and $R^6$ are independently H, optionally substituted C1-C10 alkyl, or optionally substituted C3-C10 cycloalkyl, or $R^5$ and $R^6$, together with the nitrogen atom to which they are attached, form an optionally substituted 5-membered ring or an optionally substituted 6-membered ring.

In another aspect, provided herein is a compound of the formula:

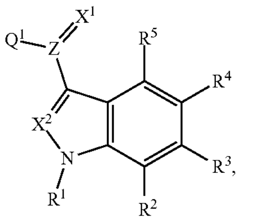

a tautomer thereof, a stereoisomer thereof, a hydrate thereof, or a pharmaceutically acceptable salt thereof, wherein:

$Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl;

Z is C, S(O),

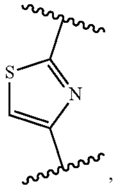 , 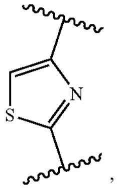 , 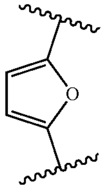 , 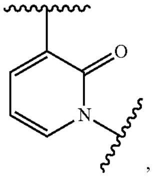 , or Z is CH when $X^1$ is absent, or —Z($X^1$)$Q^1$ is absent;

$X^1$ is absent, O, NH, S, or X1 is

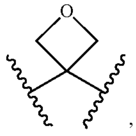 [SMILES: *C1(*)COC1] , wherein the wavy lines denote points of attachment to Z;

$X^2$ is N or $CQ^2$;

$Q^2$ is H, halogen, CN, $CONH_2$, COOH, optionally substituted C1-C10 alkyl, optionally substituted C3-C10 cycloalkyl, optionally substituted C3-C10 heteroalkyl, optionally substituted C3-C10 heterocyclyl, optionally substituted C6-C14 aryl, or optionally substituted C5-C14 heteroaryl;

$R^1$ is H, optionally substituted C1-C10 alkyl, optionally substituted C3-C10 cycloalkyl, optionally substituted C3-C10 heteroalkyl, optionally substituted C3-C10 heterocyclyl, optionally substituted C6-C10 aryl, optionally substituted C5-C10 heteroaryl, or C1-C12 acyl;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^7$, CO2$R^7$, or CONR$^7$R$^6$, or any one of $R^2$ and $R^3$, $R^3$ and $R^4$, and $R^4$ and $R^5$ pairs, together with the carbon atoms to which they are attached, forms an optionally substituted a five- or six-membered cycloalkenyl, heterocyclenyl, aryl or heteroaryl; and $R^6$ and $R^7$ are independently H, optionally substituted C1-C10 alkyl, or optionally substituted C3-C10 cycloalkyl, or $R^6$ and $R^7$, together with the nitrogen atom to which they are attached, form an optionally substituted 5-membered ring or an optionally substituted 6-membered ring.

In another aspect, provided herein is a compound of the formula:

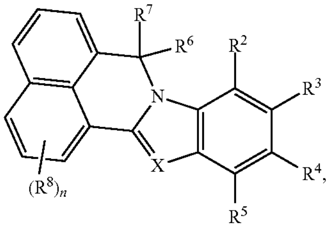

a tautomer thereof, a stereoisomer thereof, a hydrate thereof, or a pharmaceutically acceptable salt thereof, wherein:

$R^6$ and $R^7$ are independently H, halogen, OH, or optionally substituted C1-C6 alkyl, or $R^6$ and $R^7$ taken together are =O or =S;

X is N or $CR^1$;

$R^1$ is H, optionally substituted C6-C10 aryl; optionally substituted C5-C10 heteroaryl, or optionally substituted C1-C6 alkyl;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^9$, $CO_2R^9$, or CONR$^9$R$^{10}$, or any one of $R^2$ and $R^3$, $R^3$ and $R^4$, and $R^4$ and $R^5$ pairs, together with the carbon atoms to which they are attached, forms an optionally substituted a five- or six-membered cycloalkenyl, heterocyclenyl, aryl or heteroaryl; and;

$R^8$, at each occurrence, is independently CN, optionally substituted C1-C6 alkyl, or halogen;

$R^9$ and $R^{10}$ are independently H, optionally substituted C1-C10 alkyl, or optionally substituted C3-C10 cycloalkyl, or $R^9$ and $R^{10}$, together with the nitrogen atom to which they are attached, form an optionally substituted 5-membered ring or an optionally substituted 6-membered ring; and m is 0, 1, 2, 3, 4, 5, or 6.

In another aspect, provided herein is a compound of the formula:

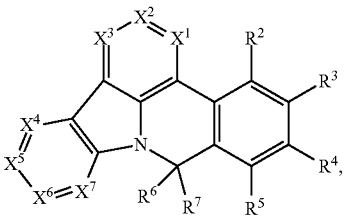

a tautomer thereof, a stereoisomer thereof, a hydrate thereof, or a pharmaceutically acceptable salt thereof, wherein:

$R^6$ and $R^7$ are independently H, halogen, OH, or optionally substituted C1-C6 alkyl, or $R^6$ and $R^7$ taken together are =O or =S;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^9$, $CO_2R^9$, or $CONR^9R^{10}$, or any one of $R^2$ and $R^3$, $R^3$ and $R^4$, and $R^4$ and $R^5$ pairs, together with the carbon atoms to which they are attached, forms an optionally substituted a five- or six-membered cycloalkenyl, heterocyclenyl, aryl or heteroaryl; and;

each of $X^1$, $X^2$, $X^3$, $X^4$, $X^5$, $X^6$, and $X^7$ is, independently N or $CR^8$, provided that no more than two of $X^1$, $X^2$, $X^3$, $X^4$, $X^5$, $X^6$, and $X^7$ are N;

each of $R^8$ is, independently, H, CN, halogen, optionally substituted C1-C10 alkyl, optionally substituted C3-C10 cycloalkyl, optionally substituted C1-C6 alkoxy, $SO_2R^9$, $CO_2R^9$, or $CONR^9R^{10}$; and $R^9$ and $R^{10}$ are independently H, optionally substituted C1-C10 alkyl, or optionally substituted C3-C10 cycloalkyl, or $R^9$ and $R^{19}$, together with the nitrogen atom to which they are attached, form an optionally substituted 5-membered ring or an optionally substituted 6-membered ring.

In another aspect, provided herein is a method of treating an autoimmune disease treatable through induction of regulatory T-cells comprising administering a therapeutically effective amount of an aryl hydrocarbon receptor (AhR) ligand to a subject in need thereof, wherein the aryl hydrocarbon receptor (AhR) ligand is a compound disclosed herein.

In some embodiments, the autoimmune disease is diabetes mellitus type 1.

In some embodiments, the autoimmune disease is graft versus host disease, Celiac disease, autoimmune hepatitis, autoimmune pancreatitis, Crohn's disease, interstitial cystitis, microscopic colitis, or ulcerative colitis.

In some embodiments, the autoimmune disease is alopecia areata, atopic dermatitis, cicatricial pemphigoid, dermatomyositis, dermatitis herpetiformis, lichen planus, pemphigus vulgaris, or psoriasis.

In some embodiments, the aryl hydrocarbon receptor (AhR) ligand is administered topically. In other embodiments, the aryl hydrocarbon receptor (AhR) ligand is administered orally, transdermally, intravenously, subcutaneously, or with a nanoparticle.

In some embodiments, the method further includes administering the AhR ligand with a pharmaceutically acceptable carrier.

In another aspect, provided herein is a pharmaceutical composition comprising an AhR ligand of the disclosure.

DETAILED DESCRIPTION

A need exists for a non-toxic therapy to suppress an autoimmune response without inducing general immune suppression. Accordingly, in one aspect, provided herein is an AhR ligand compound of the Formula I:

(I)

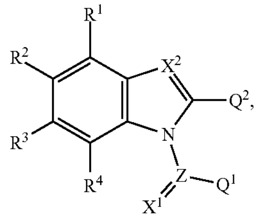

a tautomer thereof, a stereoisomer thereof, a hydrate thereof, or a pharmaceutically acceptable salt thereof, wherein:

$Q^1$ is an optionally substituted C6-C14 aryl; optionally substituted C5-C14 heteroaryl; optionally substituted C5-C14 heterocyclyl; optionally substituted C1-C10 alkyl, or optionally substituted C3-C10 cycloalkyl; optionally substituted C2-C10 alkenyl, or optionally substituted C2-C10 alkynyl;

$Q^2$ is an optionally substituted C6-C14 aryl; optionally substituted C5-C14 heteroaryl; optionally substituted C5-C10 heterocyclyl; optionally substituted C1-C10 alkyl, or optionally substituted C3-C10 cycloalkyl;

Z is C, S(O),

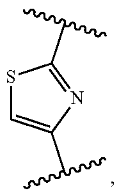, 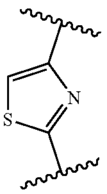, 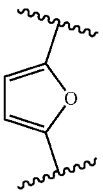, 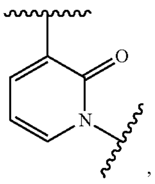, or Z is

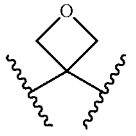 [SMILES: *C1(*)COC1]

when $X^1$ is absent;

$X^1$ is absent, O, NH, or S;

$X^2$ is N, CCl, CF, CBr, CI, CCN, $CCONH_2$, CCOOH, or CH;

$R^1$, $R^2$, $R^3$, and $R^4$ are independently H, halogen, CN, $OCF_3$, optionally substituted C1-C10 alkyl, optionally substituted C3-C8 cycloalkyl, optionally substituted C3-C8 heterocycloalkyl, optionally substituted C1-C6 alkoxy, $SO_2R^5$, $CO_2R^5$, or $CONR^5R^6$, or any one of $R^1$ and $R^2$, $R^2$ and $R^3$, and $R^3$ and $R^4$ pairs, together with the carbon atoms to which they are attached, forms an optionally substituted five- or six-membered cycloalkenyl, heterocyclenyl, aryl or heteroaryl; and $R^5$ and $R^6$ are independently H, optionally substituted C1-C10 alkyl, or optionally substituted C3-C10 cycloalkyl, or $R^5$ and $R^6$, together with the nitrogen atom to which they are attached, form an optionally substituted 5-membered ring or an optionally substituted 6-membered ring.

In some embodiments of Formula I, $X^2$ is N. In certain embodiments of Formula I, Z is C.

In some embodiments, the compound is represented by the Formula IA:

(IA)

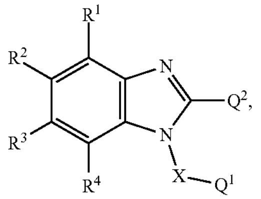

a tautomer thereof, a stereoisomer thereof, a hydrate thereof, or a pharmaceutically acceptable salt thereof, wherein:

$Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl;

$Q^2$ is an optionally substituted C6-C14 aryl; optionally substituted C5-C10 heteroaryl; optionally substituted C5-C10 heterocyclyl; optionally substituted C1-C10 alkyl, or optionally substituted C3-C10 cycloalkyl;

X is CO or $S(O)_2$;

$R^1$, $R^2$, $R^3$, and $R^4$ are independently H, halogen, CN, optionally substituted C1-C10 alkyl, optionally substituted C3-C10 cycloalkyl, optionally substituted C1-C6 alkoxy, $SO_2R^5$, $CO_2R^5$, or $CONR^5R^6$, or any one of $R^1$ and $R^2$, $R^2$ and $R^3$, and $R^3$ and $R^4$ pairs, together with the carbon atoms to which they are attached, forms an optionally substituted a five- or six-membered cycloalkenyl, heterocyclenyl, aryl or heteroaryl; and $R^5$ and $R^6$ are independently H, optionally substituted C1-C10 alkyl, or optionally substituted C3-C10 cycloalkyl, or $R^5$ and $R^6$, together with the nitrogen atom to which they are attached, form an optionally substituted 5-membered ring or an optionally substituted 6-membered ring.

In some embodiments of Formula IA, X is CO. In some embodiments of Formula IA, X is $SO_2$.

In some embodiments of Formula IA, the compound is a compound of the formula IB or IC:

(IB)

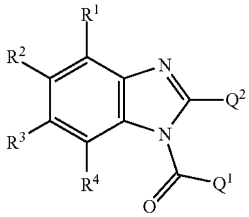

or

-continued (IC)

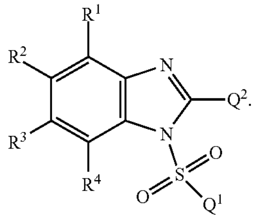

In some embodiments of Formula IA, IB, or IC, $Q^2$ is a 1-naphthyl.

In some embodiments of Formulae I, IA, IB, or IC, the compound is a compound of the formula ID:

(ID)

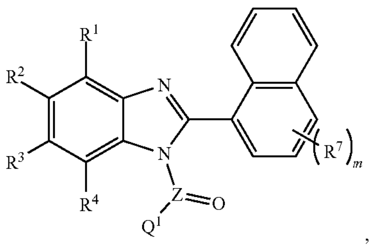

, a tautomer thereof, a stereoisomer thereof, a hydrate thereof, or a pharmaceutically acceptable salt thereof, wherein:

$Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl;

Z is C or SO;

$R^1$, $R^2$, $R^3$, and $R^4$ are independently H, halogen, CN, optionally substituted C1-C10 alkyl, optionally substituted C3-C10 cycloalkyl, optionally substituted C1-C6 alkoxy, $SO_2R^5$, $CO_2R^5$, or $CONR^5R^6$, or any one of $R^1$ and $R^2$, $R^2$ and $R^3$, and $R^3$ and $R^4$ pairs, together with the carbon atoms to which they are attached, forms an optionally substituted a five- or six-membered cycloalkenyl, heterocyclenyl, aryl or heteroaryl;

$R^5$ and $R^6$ are independently H, optionally substituted C1-C10 alkyl, or optionally substituted C3-C10 cycloalkyl, or $R^5$ and $R^6$, together with the nitrogen atom to which they are attached, form an optionally substituted 5-membered ring or an optionally substituted 6-membered ring;

$R^7$, at each occurrence, is independently H, halogen, CN, optionally substituted C1-C10 alkyl, optionally substituted C2-C6 alkenyl, optionally substituted C1-C10 heteroalkyl, optionally substituted C1-C10 heterocyclyl, optionally substituted C6-C10 aryl, optionally substituted C5-C10 heteroaryl, optionally substituted C1-C6 alkoxy, optionally substituted C1-C6 cycloalkyloxy, $OCF_3$, $NR^5R^6$, $SCF_3$, or $C(O)NR^5R^6$; and m is an integer ranging from 1 to 7.

In some embodiments of Formulae I, IA, IB, IC, or ID, $Q^1$ is an optionally substituted phenyl, an optionally substituted naphthyl, an optionally substituted optionally substituted C3-C6 cycloalkyl or an optionally substituted quinolinyl. In some embodiments, $Q^1$ is a phenyl optionally substituted with one, two, or three substituents independently selected from F, Cl, Br, $OCH_3$, CN, $OCF_3$, $SCF_3$, t-Bu, $NMe_2$, $CONH_2$, piperazyl, piperidyl, $OCH_2CH_2OH$, $OCH_2CH_2NMe_2$, and 1-naphthyl.

In some embodiments of Formulae I, IA, IB, IC, or ID, $R^1$ is H or halogen, such as F, Cl, or Br. In some embodiments of Formulae I, IA, IB, IC, or ID, $R^4$ is H or halogen, such as F, Cl, or Br. In some embodiments of Formulae I, IA, IB, IC, or ID, all $R^7$ are H.

In some embodiments of Formulae I, IA, IB, IC, or ID, the compound is a compound of formula IE:

(IE)

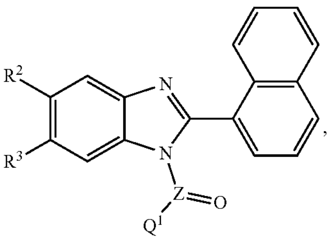

a tautomer thereof, a stereoisomer thereof, a hydrate thereof, or a pharmaceutically acceptable salt thereof, wherein $R^2$ and $R^3$, independently, F, Cl, Br, O(C1-C5 alkyl), $SCF_3$, $OCF_3$, $CO_2H$, $CO_2$(C1-C5 alkyl), or $CONR^5R^6$, wherein $R^5$ and $R^6$ are independently H, optionally substituted C1-C10 alkyl, optionally substituted C3-C10 cycloalkyl, or $R^5$ and $R^6$, together with the nitrogen atom to which they are attached, form an optionally substituted morpholinyl; and $Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl.

In some embodiments of Formula IE, $Q^1$ is a phenyl, cyclopropyl, naphthyl, benzodioxanyl, or quinolinyl, each of which is optionally substituted with one, two, or three substituents independently selected from the group consisting of F, Cl, Br, $CF_3$, $SCF_3$, CN, and $OCH_3$.

In some embodiments of Formulae I, IA, IB, IC, ID, or IE, the compound is a compound of Table 1.

In a second aspect, provided herein is an AhR ligand compound represented by Formula II:

(II)

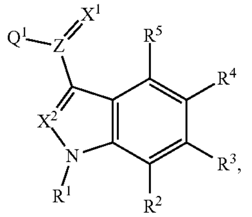

a tautomer thereof, a stereoisomer thereof, a hydrate thereof, or a pharmaceutically acceptable salt thereof, wherein:

$Q^1$ is an optionally substituted C6-C14 aryl; optionally substituted C5-C14 heteroaryl; optionally substituted C5-C14 heterocyclyl; optionally substituted C1-C10 alkyl, or optionally substituted C3-C10 cycloalkyl; optionally substituted C2-C10 alkenyl, or optionally substituted C2-C10 alkynyl;

Z is C, S(O),

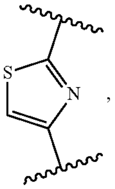 , 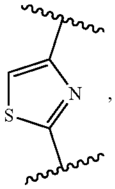 , 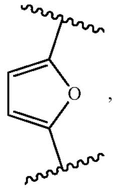 , 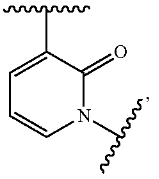

or Z is

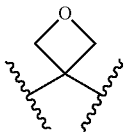

when $X^1$ is absent, or —$Z(X^1)Q^1$ is H;

$X^1$ is absent, O, NH, S, $X^2$ is N, CCl, CF, CBr, CI, CCN, $CCONH_2$, CCOOH, CH, or $CQ^2$, wherein $Q^2$ is optionally substituted C6-C10 aryl, optionally substituted C5-C10 heteroaryl, optionally substituted C6-C10 aryl, optionally substituted C3-C10 cycloalkyl, or optionally substituted C3-C10 heterocyclyl;

$R^1$ is H, optionally substituted C1-C10 alkyl, optionally substituted C3-C10 cycloalkyl, optionally substituted C3-C10 heteroalkyl, optionally substituted C3-C10 hetercyclyl, optionally substituted C6-C10 aryl, optionally substituted C5-C10 heteroaryl, or C1-C12 acyl;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^7$, $CO_2R^7$, or $CONR^7R^6$, or any one of $R^2$ and $R^3$, $R^3$ and $R^4$, and $R^4$ and $R^5$ pairs, together with the carbon atoms to which they are attached, form an optionally substituted five-membered or six-membered cycloalkenyl, heterocyclenyl, aryl, or heteroaryl; and $R^6$ and $R^7$ are independently H, optionally substituted C1-C10 alkyl, or optionally substituted C3-C10 cycloalkyl, or $R^6$ and $R^7$, together with the nitrogen atom to which they are attached, form an optionally substituted 5-membered ring or an optionally substituted 6-membered ring.

In some embodiments of Formula II, $X^2$ is CH, CF, CBr, or CCl. In some embodiments of Formula II, Z is CH.

In some embodiments of Formula II, the compound is represented by Formula IIA:

(IIA)

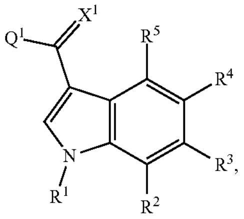

wherein $Q^1$, $X^1$, $R^1$, $R^2$, $R^3$, $R^4$, and $R^5$ are as defined above for Formula II.

In some embodiments of Formulae II or HA, $X^1$ is O.

In some embodiments of Formulae II or HA, the compound is represented by the Formula IIC:

(IIC)

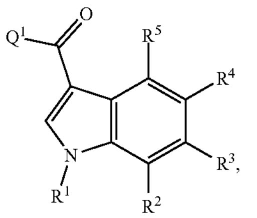

wherein all substituents are as defined for Formula II.

In some embodiments of Formulae II, IIA, IIB, or IIC, $Q^1$ is selected from optionally substituted pyridyl, optionally substituted naphthyl, optionally substituted benzodioxanyl, optionally substituted cyclopropyl, optionally substituted benzyl, optionally substituted phenyl, optionally substituted cyclohexyl, optionally substituted piperidinyl, optionally substituted quinolinyl, optionally substituted benzofuryl, optionally substituted benzomorpholinyl, and optionally substituted benzimidazolyl.

In some embodiments of Formulae II or IIA, $Q^1$ is a C5 heterocyclyl. In certain embodiments, $Q^1$ is thiazolyl, imidazolyl, pyrrolyl, pyrazolyl, thiophenyl, triazolyl, or furyl, each of which can be optionally substituted. In some embodiments of Formulae II or IIA, $Q^1$ is a C6 heterocyclyl. In some embodiments of Formulae II or IIA, $Q^1$ is pyridyl, pyrimidinyl, phenyl optionally substituted with alkyl or halogen, or pyridonyl, each of which can be optionally substituted. In other embodiments, $Q^1$ is indolyl, indazolyl, benzimidazolyl, or benzthiazolyl, each of which can be optionally substituted.

In some embodiments of Formulae II, IIA, IIB, or IIC, $Q^1$ is:

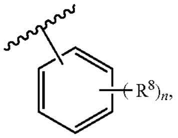

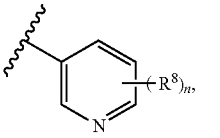

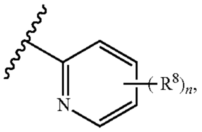

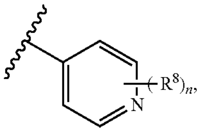

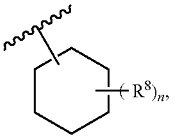

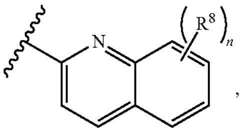

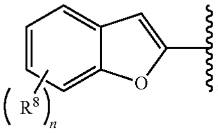

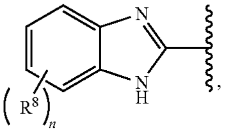

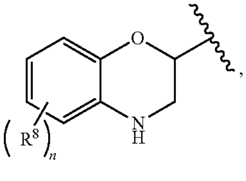

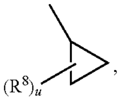

-continued

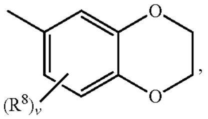

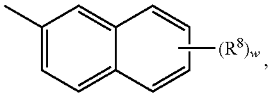

or

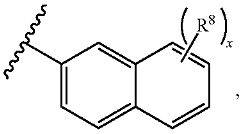

wherein $R^8$, at each occurrence, is independently H, F, Cl, Br, I, CN, optionally substituted C1-C10 alkyl, optionally substituted C3-C8 cycloalkyl, optionally substituted C2-C6 alkenyl, optionally substituted C2-C6 alkynyl, optionally substituted C3-C10 heteroalkyl, optionally substituted C3-C10 heterocyclyl, optionally substituted C6-C10 aryl, optionally substituted C5-C10 heteroaryl, optionally substituted C1-C6 alkoxy, optionally substituted C3-C8 cycloalkyloxy, $OCF_3$, $CF_3$, NR'R", $SCF_3$, or C(O)NR'R";

R' and R" are H, optionally substituted C1-C10 alkyl, optionally substituted C3-C8 cycloalkyl, optionally substituted C2-C6 alkenyl, optionally substituted C2-C6 alkynyl, or optionally substituted C3-C10 heteroalkyl; or R' and R", together with the nitrogen atom to which they are attached, form an optionally substituted 5-membered ring or an optionally substituted 6-membered ring; and n is an integer ranging from 1 to 5; m is an integer ranging from 1 to 4; p is an integer ranging from 1 to 11; q is an integer ranging from 1 to 6; r is an integer ranging from 1 to 5; s is an integer ranging from 1 to 4; t is an integer ranging from 1 to 8; u is an integer ranging from 1 to 5; v is an integer ranging from 1 to 7; w is an integer ranging from 1 to 7; and x is an integer ranging from 1 to 11.

In some embodiments of Formulae II, IIA, IIB, or IIC, $Q^1$ is morpholinyl, piperazinyl, pyrrolidinyl, piperidinyl, or alkylamino.

In certain embodiments of Formulae II, IIA, IIB, or IIC, $Q^1$ is a phenyl optionally substituted with one or two substituents independently selected from F, Cl, Br, I, $OCH_3$, CN, $OCF_3$, $SCF_3$, t-Bu, $NMe_2$, $CO_2H$, $CO_2$(C1-C10 alkyl), $CONH_2$, piperazyl, piperidyl, $OCH_2CH_2OH$, $OCH_2CH_2NMe_2$, and 1-naphthoyl.

In certain embodiments of Formulae II, IIA, IIB, or IIC, $Q^1$ is:

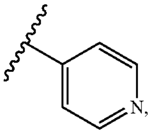

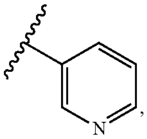

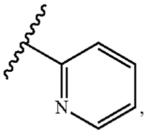

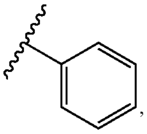

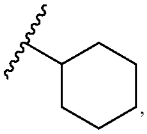

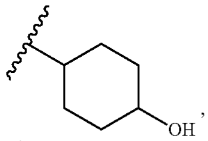

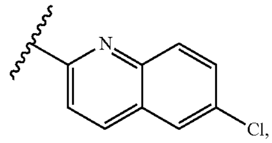

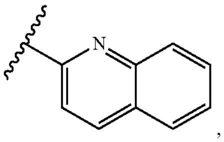

-continued

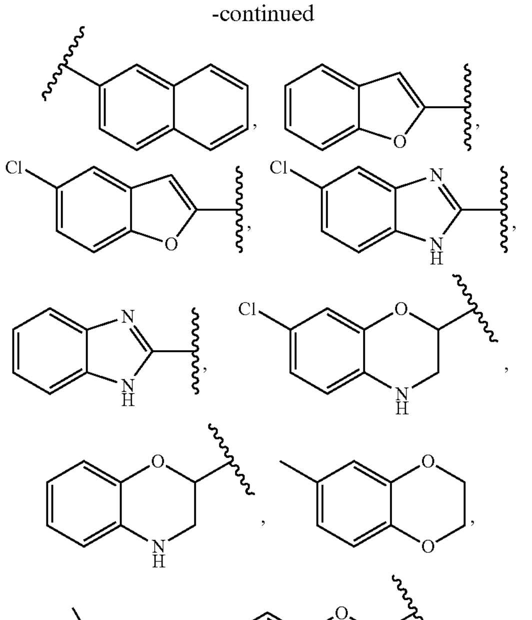

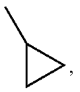

or

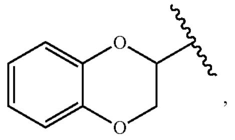

each of which can be further optionally substituted with one to four substituents independently selected from F, Br, Cl, I, $OCH_3$, CN, $OCF_3$, $CF_3$, $SCF_3$, Me, Et, i-Pr, t-Bu, $NMe_2$, $CONH_2$, $OCH_2CH_2OH$, $OCH_2CH_2NMe_2$, $CHCH_2$, OMe, OEt, O(iPr), O(tBu), and $OC_5H_{11}$.

In some embodiments of Formula II, $Z(X^1)Q^1$ is H.

In some embodiments of Formula II, the compound represented by Formula IID:

(IID)

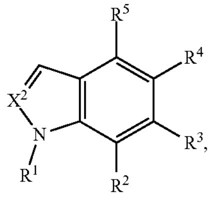

a tautomer thereof, a stereoisomer thereof, a hydrate thereof, or a pharmaceutically acceptable salt thereof, wherein:

$X^2$ is N, CCl, CF, CBr, CI, CCN, $CCONH_2$, CCOOH, CH, or $CQ^2$, wherein $Q^2$ is optionally substituted C6-C10 aryl, optionally substituted C5-C10 heteroaryl, optionally substituted C6-C10 aryl, optionally substituted C3-C10 cycloalkyl, or optionally substituted C3-C10 hetercyclyl; and $R^1$, $R^2$, $R^3$, $R^4$, and $R^5$ are independently as defined for Formula II.

In some embodiments of Formula IID, $X^2$ is $CQ^2$, wherein $Q^2$ is optionally substituted C6-C10 aryl, optionally substituted C5-C10 heteroaryl, optionally substituted C6-C10 aryl, optionally substituted C3-C10 cycloalkyl, or optionally substituted C3-C10 hetercyclyl.

In some embodiments of Formula IID, $X^2$ is $CQ^2$, wherein $Q^2$ is optionally substituted phenyl, optionally substituted naphthyl, optionally substituted quinolinyl, optionally substituted cyclopropyl, or optionally substituted cyclohexyl.

In some embodiments, the compound represented by Formula IIE:

(IIE)

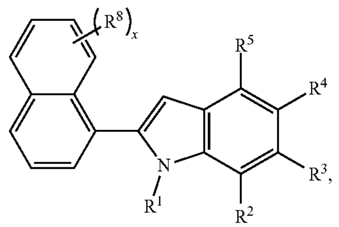

a tautomer thereof, a stereoisomer thereof, a hydrate thereof, or a pharmaceutically acceptable salt thereof, wherein $R^1$, $R^2$, $R^3$, $R^4$, and $R^5$ are independently as defined for Formula II; $R^8$, at each occurrence, is independently H, halogen, CN, optionally substituted C1-C10 alkyl, optionally substituted C3-C8 cycloalkyl, optionally substituted C2-C6 alkenyl, optionally substituted C2-C6 alkynyl, optionally substituted C3-C10 heteroalkyl, optionally substituted C3-C10 heterocyclyl, optionally substituted C6-C10 aryl, optionally substituted C5-C10 heteroaryl, optionally substituted C1-C6 alkoxy, optionally substituted C3-C8 cycloalkyloxy, $OCF_3$, $CF_3$, NR'R", $SCF_3$, or C(O)NR'R"; x is an integer ranging from 1 to 7; and R' and R" are H, optionally substituted C1-C10 alkyl, optionally substituted C3-C8 cycloalkyl, optionally substituted C2-C6 alkenyl, optionally substituted C2-C6 alkynyl, or optionally substituted C3-C10 heteroalkyl; or R' and R', together with the nitrogen atom to which they are attached, form an optionally substituted 5-membered ring or an optionally substituted 6-membered ring.

In some embodiments of Formula IIE, $R^1$ is H or an optionally substituted C1-C10 alkyl. In some embodiments of Formula IIE, $R^1$ is H. In some embodiments of Formula IIE, all $R^8$ are H.

In some embodiments of Formulae II, IIA, IIB, IIC, or IID, $R^1$ is H, $CH_3$, or $C(O)R^9$, wherein $R^9$ is H, an optionally substituted C1-C10 alkyl, optionally substituted C3-C10 cycloalkyl, optionally substituted C3-C10 heteroalkyl, optionally substituted C3-C10 hetercyclyl, optionally substituted C6-C10 aryl, or optionally substituted C5-C10 heteroaryl.

In some embodiments of Formulae II, IIA, IIB, or IIC, $Q^1$ is a phenyl optionally substituted with one or two substituents independently selected from F, Cl, $OCH_3$, $CH_3$, CN, $CF_3$, $OCF_3$, $SCF_3$, t-Bu, $NMe_2$, $CONH_2$, 1-piperazyl, $OCH_2CH_2OH$, $OCH_2CH_2NMe_2$, and 1-naphthoyl.

In some embodiments of Formulae II, IIA, IIB, IIC, IID, or IIE, $R^2$ is H, F, Cl, Br, or I. In some embodiments of Formulae II, IIA, IIB, IIC, IID, or IIE, $R^3$ is H, F, Cl, Br, or I. In some embodiments of Formulae II, IIA, IIB, IIC, IID, or IIE, $R^4$ is H, F, Cl, Br, or I. In some embodiments of Formulae II, IIA, IIB, IIC, IID, or IIE, $R^5$ is H, F, Cl, Br, or I.

In some embodiments of Formulae II, IIA, IIB, IIC, IID, or IIE, the compound is a compound of Table 2.

In a third aspect, provided herein is an AhR ligand compound represented by Formula III:

(III)

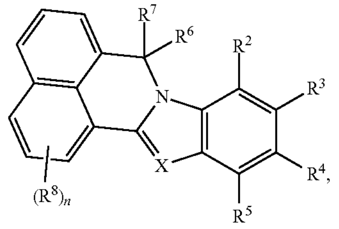

a tautomer thereof, a stereoisomer thereof, a hydrate thereof, or a pharmaceutically acceptable salt thereof, wherein:

$R^6$ and $R^7$ are independently H, halogen, OH, or optionally substituted C1-C6 alkyl, or $R^6$ and $R^7$ taken together are =O or =S;

X is N or $CR^1$;

$R^1$ is H, halogen, optionally substituted C6-C10 aryl; optionally substituted C5-C10 heteroaryl, or optionally substituted C1-C6 alkyl;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^9$, $CO_2R^9$, or $CONR^9R^{10}$, or any one of $R^2$ and $R^3$, $R^3$ and $R^4$, and $R^4$ and $R^5$ pairs, together with the carbon atoms to which they are attached, forms an optionally substituted a five- or six-membered cycloalkenyl, heterocyclenyl, aryl or heteroaryl; and;

$R^8$, at each occurrence, is independently CN, optionally substituted C1-C6 alkyl, or halogen;

$R^9$ and $R^{10}$ are independently H, optionally substituted C1-C10 alkyl, or optionally substituted C3-C10 cycloalkyl, or $R^9$ and $R^{10}$, together with the nitrogen atom to which they are attached, form an optionally substituted 5-membered ring or an optionally substituted 6-membered ring; and n is 0, 1, 2, 3, 4, 5, or 6.

In some embodiments of Formula III, $R^6$ and $R^7$ taken together are =O. In other embodiments, $R^6$ is H or C1-C10 alkyl and $R^7$ is OH. In some embodiments of Formula III, X is CH.

In some embodiments of Formula III, the compound is represented by Formula IIIA:

(IIIA)

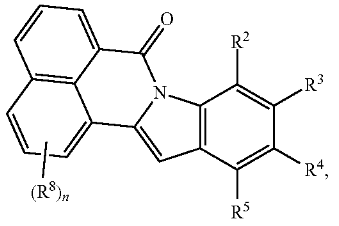

wherein all substituents are as defined for Formula III above.

In some embodiments of Formulae III or IIIA, $R^6$ and $R^7$ are H. In certain embodiments of Formulae III or IIIA, X is N.

In some embodiments of Formulae III or IIIA, the compound is represented by Formula IIIB:

(IIIB)

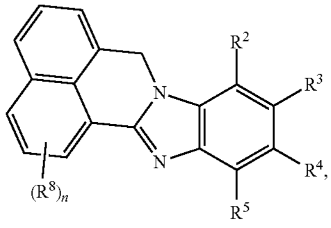

wherein all substituents are as defined for Formula III above. In some embodiments of Formulae III, IIIA, or IIIB, $R^2$ is H or halogen. In some embodiments of Formulae III, IIIA, or IIIB, $R^3$ is H or halogen. In certain embodiments of Formulae III, IIIA, or IIIB, $R^4$ is H or halogen. In particular embodiments of Formulae III, IIIA, or IIIB, $R^5$ is H or halogen.

In some embodiments of Formulae III, IIIA, or IIIB, n is 0.

In a fourth aspect, provided herein is an AhR ligand compound represented by Formula IV:

(IV)

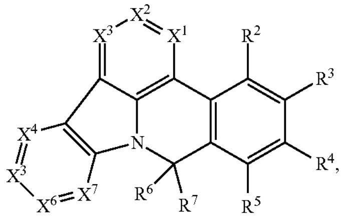

a tautomer thereof, a stereoisomer thereof, a hydrate thereof, or a pharmaceutically acceptable salt thereof, wherein:

$R^6$ and $R^7$ are independently H, halogen, OH, or optionally substituted C1-C6 alkyl, or $R^6$ and $R^7$ taken together are =O or =S;

$R^2$, $R^3$, $R^4$, and $R^5$ are independently H, halogen, CN, optionally substituted C1-C10 alkyl, optionally substituted C3-C10 cycloalkyl, optionally substituted C1-C6 alkoxy, $SO_2R^9$, $CO_2R^9$, or $CONR^9R^{10}$, or any one of $R^2$ and $R^3$, $R^3$ and $R^4$, and $R^4$ and $R^5$ pairs, together with the carbon atoms to which they are attached, forms an optionally substituted a five- or six-membered cycloalkenyl, heterocyclenyl, aryl, or heteroaryl; and $X^1$, $X^2$, $X^3$, $X^4$, $X^5$, $X^6$, and $X^7$ are independently N or $CR^8$, provided that no more than two of $X^1$, $X^2$, $X^3$, $X^4$, $X^5$, $X^6$, and $X^7$ are N;

each of $R^8$ is independently H, CN, halogen, optionally substituted C1-C10 alkyl, optionally substituted C3-C10 cycloalkyl, optionally substituted C1-C6 alkoxy, $SO_2R^9$, $CO_2R^9$, or $CONR^9R^{10}$; and $R^9$ and $R^{10}$ are independently H, optionally substituted C1-C10 alkyl, or optionally substituted C3-C10 cycloalkyl, or $R^9$ and $R^{19}$, together with the nitrogen atom to which they are attached, form an optionally substituted 5-membered ring or an optionally substituted 6-membered ring.

In some embodiments of Formula IV, $R^6$ is H and $R^7$ is H. In particular embodiments of Formula IV, $X^1$ is N. In other embodiments of Formula IV, $R^6$ and $R^7$ together are =O.

In some embodiments of Formula IV, the compound is represented by Formula IVA or (IVB):

(IVA)

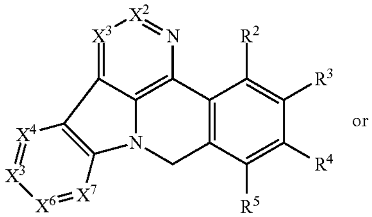

or (IVB)

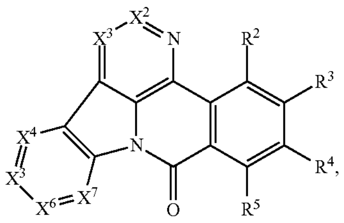

wherein all substituents are as defined above for Formula IV.

In some embodiments of Formulae IV, IVA, or IVB, $R^2$ is H or halogen. In some embodiments of Formulae IV, IVA, or IVB, $R^3$ is H or halogen. In particular embodiments of Formulae IV, IVA, or IVB, $R^4$ is H or halogen. In some embodiments of Formulae IV, IVA, or IVB, $R^5$ is H or halogen.

In certain embodiments of Formulae IV, IVA, or IVB, each of $X^1$, $X^2$, $X^3$, $X^4$, $X^5$, $X^6$, and $X^7$ is $CR^8$, wherein $R^8$ is H, optionally substituted C1-C10 alkyl, or halogen.

In some embodiments of the Formulae above, the AhR ligand is one or more compounds of Tables 1-5.

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C, as $C_1$-$C_{10}$, C—C10, or C1-10.

The terms "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain and the number of such heteroatoms that are included as replacements for carbon atoms in the cycle or chain being described.

Typically, the alkyl, alkenyl, and alkynyl substituents contain 1-10 carbon atoms (alkyl) or 2-10 carbon atoms (alkenyl or alkynyl). Preferably, they contain 1-8 carbon atoms (alkyl) or 2-8 carbon atoms (alkenyl or alkynyl). Sometimes they refer to as "lower alkyl," meaning that they contain 1-6 carbon atoms (alkyl) or 2-6 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

As used herein, the terms "alkylene," "alkenylene," and "alkynylene" include straight-chain, branched-chain, and cyclic divalent hydrocarbyl radicals, and combinations thereof.

Alkyl, alkenyl, and alkynyl groups can be optionally substituted to the extent that such substitution makes sense chemically. Typical substituents include, but are not limited to, halogens (F, Cl, Br, I), =O, =N—CN, =N—OR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halogens (F, Cl, Br, I), =O, =N—CN, =N—OR', =NR, OR', $NR'_2$, SR', $SO_2R'$, $SO_2NR'_2$, $NR'SO_2R'$, $NR'CONR'_2$, NR'C(O)OR', NR'C(O)R', CN, C(O)OR', C(O)$NR'_2$, OC(O)R', C(O)R', and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl, or $C_5$-$C_{10}$ heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples include phenyl and naphthyl. Similarly, the terms "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably, the monocyclic heteroaryls contain 5-6 ring members, and the bicyclic heteroaryls contain 8-10 ring members.

Aryl and heteroaryl moieties can be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent, e.g., $C_1$-$C_6$ alkyl, $C_2$-$C_6$ heteroalkyl, alkynyl, halogens (F, Cl, Br, $N_3$, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, oxo, and $NO_2$, wherein each R is independently H, $C_1$-$C_6$ alkyl, or $C_2$-$C_6$ heteroalkyl. Where an optional substituent is attached via a double bond, such as a carbonyl oxygen or oxo (=O), the group takes up two available valences, so the total number of substituents that may be included is reduced according to the number of available valences.

Salts, stereoisomers, and tautomers of the compounds disclosed herein, such as compounds disclosed herein, are also within the scope of this disclosure. As used herein, "stereoisomer" or "stereoisomers" refer to compounds that differ in the chirality of one or more stereocenters. Stereoisomers include enantiomers and diastereomers. As used herein, "tautomer" refers to alternate forms of a compound that differ in the position of a proton, such as enol-keto and imine-enamine tautomers. As used herein, "salt" of a compound refers to an ion of the compound ionically association with a counterion. A salt of a compound can be formed by the neutralization reaction of an acid and a base. Salts can be derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. Although structures of the compounds disclosed herein can be shown in only one resonance form, it is understood that all resonance forms are included.

Synthesis of the compounds disclosed herein, e.g., compounds of Formulae I, IA, IB, IC, ID, IE, II, IIA, IIB, IIC, IID, IIE, III, IIA, IIB, IV, IVA, and IVB can be achieved in any suitable manner using techniques and methods known in the art.

In certain embodiments, the compounds of Formulae I, IA, IB, IC, ID, IE, II, IIA, IIB, IIC, IID, IIE, III, IIA, IIB, IV, IVA, and IVB disclosed herein are AhR activators. In some embodiments, the compounds activate AhR about 5, about 10, about 20, about 30, or about 35-fold in in vitro screening assays at about 10 nM, about 100 nM, about 1 uM, about 10 uM, or about 100 uM. In some embodiments, the compounds of the disclosure adhere to one or more of the Lipinski rules.

In a fifth aspect, the disclosure provides a method of treating an autoimmune disease treatable through induction of regulatory T-cells comprising administering a therapeutically effective amount of an aryl hydrocarbon receptor (AhR) ligand to a subject in need thereof, wherein the aryl hydrocarbon receptor (AhR) ligand is a compound of any one of compounds of Formulae I, IA, IB, IC, ID, IE, II, IIA, IIB, IIC, IID, IIE, III, IIA, IIB, IV, IVA, and IVB disclosed herein. Autoimmune diseases suitable for treatment by the methods disclosed herein include diabetes mellitus type 1, graft versus host disease, Celiac disease, autoimmune hepatitis, autoimmune pancreatitis, Crohn's disease, interstitial cystitis, microscopic colitis, ulcerative colitis, alopecia areata, atopic dermatitis, cicatricial pemphigoid, dermatomyositis, dermatitis herpetiformis, lichen planus, pemphigus vulgaris, or psoriasis.

As used herein, the term "treat" refers to medical management of a disease, disorder, or condition (e.g., diabetes) of a subject (e.g., a human or non-human mammal, such as another primate, horse, dog, mouse, rat, guinea pig, rabbit, and the like). Treatment can encompass any indicia of success in the treatment or amelioration of a disease or condition (e.g., diabetes), including any parameter such as abatement, remission, diminishing of symptoms or making the disease or condition more tolerable to the subject, slowing in the rate of degeneration or decline, and/or making the degeneration less debilitating. The treatment or amelioration of symptoms can be based on objective or subjective parameters, including the results of an examination by a physician. Accordingly, the term "treating" includes the administration of the compounds and/or compositions of the present disclosure to alleviate, or to arrest or inhibit development of the symptoms or conditions associated with disease or condition (e.g., diabetes). The term "therapeutically effective" refers to an amount of the compound or composition that results in a therapeutic effect and can be readily determined.

The compounds of the disclosure can be administered in any suitable manner. In some embodiments, the compounds can be delivered locally (e.g., topically) or systemically. In some embodiments, the aryl hydrocarbon receptor (AhR) ligands of the disclosure are administered orally. In some embodiments, the compounds are administered topically, intravenously, or subcutaneously. A physiologically or pharmaceutically acceptable carrier or vehicle can be used to formulate the compound for administration and can be selected according to the mode of administration. In some embodiments, the compounds are delivered orally together with a suitable pharmaceutically acceptable carrier, e.g., at a predetermined dose.

Typically, the AhR ligands disclosed herein can be administered with one or more pharmaceutically acceptable carriers. Any suitable pharmaceutically acceptable carriers can be used with the compounds of the disclosure. Non-limiting examples of pharmaceutically acceptable carriers include saline, phosphate buffered saline (PBS), water, aqueous ethanol, emulsions such as oil/water emulsions, triglyceride emulsions, wetting agents, tablets, and capsules. In some embodiments, the compounds are formulated with a nanoparticle, e.g., a micelle or a liposome. Nanoparticles can include lipids, polymers, dendrimers, silicon materials, carbon materials, cyclodextrins, or other suitable components.

Thus, in another aspect provided herein is a pharmaceutical composition comprising a compound of the disclosure, e.g., an aryl hydrocarbon receptor (AhR) ligand of Formulae I, IA, IB, IC, ID, IE, II, IIA, IIB, IIC, IID, IIE, III, IIA, IIB, IV, IVA, and IVB described above.

Publications cited herein and the subject matter for which they are cited are hereby specifically incorporated by reference in their entireties.

While illustrative embodiments have been described, it will be appreciated that various changes can be made therein without departing from the spirit and scope of the invention.

The following examples are provided for the purpose of illustrating, not limiting, the invention.

EXAMPLES

Synthesis of Exemplary Compounds

Compound 359

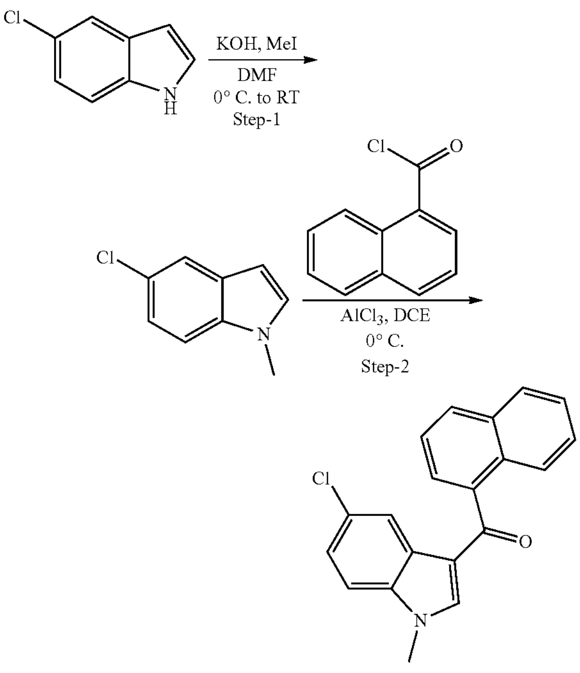

Compound-359

Step 1: 5-chloro-1H-indole (1.0 g, 6.59 mmol) was dissolved in DMF (8.0 ml) and potassium hydroxide (0.56 g, 7.9 mmol) was added to it. The reaction mixture was stirred at room temperature for one hour followed by cooling the reaction mixture to 0° C. and addition of iodomethane (0.05 ml, 7.9 mmol). Reaction mixture was then stirred at room temperature for three hours followed by extraction with ethyl acetate and washing with brine solution. The organic layer was dried to get crude which was purified by column chromatography to afford 5-chloro-1-methyl-1H-indole (0.8 g) as a brown solid.

Step 2: 5-chloro-1-methyl-1H-indole (0.2 g, 1.2 mmol) was dissolved in dichloroethane (4.0 ml) and cooled to 0° C. Aluminum trichloride (0.19 g, 1.45 mmol) was added to it. After few minutes of stirring, 1-naphthoyl chloride (0.218 ml, 1.44 mmol) was added dropwise. The resulting mixture was stirred at same temperature for one hour. After this, the reaction mixture was quenched with water and extracted with ethyl acetate. The organic layer was dried over anhydrous sodium sulphate and concentrated under vacuum to provide crude. The crude was purified by column chromatography to afford (5-chloro-1-methyl-1H-indol-3-yl)(naphthalen-1-yl)methanone (62 mg) as an off white solid.

Compound 359: LCMS—UPLC 320.2 $(M)^+$; @ 254 nm=99.89%, @ 220 nm=99.83%. $^1H$ NMR (400 MHz, $CDCl_3$) δ 8.55 (d, J=1.75 Hz, 1H), 8.15 (d, J=8.33 Hz, 1H), 7.98 (d, J=8.33 Hz, 1H), 7.91 (d, J=7.89 Hz, 1H), 7.64 (d, J=5.70 Hz, 1H), 7.46-7.56 (m, 3H), 7.27-7.35 (m, 3H), 3.76 (s, 3H).

Compound 360 and Compound 361

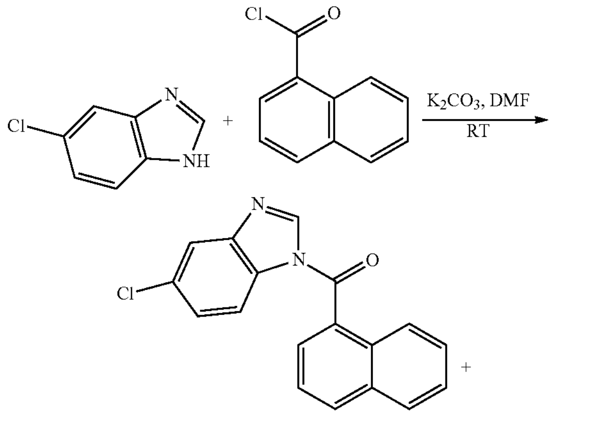

Isomer 1, Peak-1
Compound-360

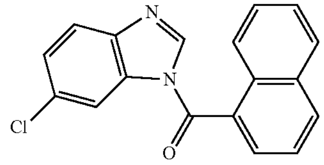

Isomer 2, Peak-2
Compound-361

Step 1: To a solution of 5-chloro-1H-benzo[d]imidazole (0.46 g, 3.0 mmol) in DMF was added K2CO3 (0.83 g, 6.0 mmol) followed by addition of 1-naphthoyl chloride (0.5 mL, 1.1 mmol) and the reaction mixture was stirred at rt for overnight. After completion of reaction, the reaction mixture was diluted with sodium bicarbonate (20 mL) and extracted with DCM (50 mL×2). The combined organic layer was washed with water (50 mL), brine solution (50 mL), dried over anhydrous sodium sulfate and concentrated under reduced pressure to afford crude product, which was purified by flash chromatography to afford the first isomer (Peak 1), (5-chloro-1H-benzo[d]imidazol-1-yl) (naphthalen-1-yl) methanone (0.12 g) as an off white solid.

Compound 360: LCMS—UPLC 307.1 $(M)^+$, Purity @ 254 nm=99.18% and @ 220 nm=97.92%. $^1H$ NMR (400 MHz, DMSO-$d_6$): 8.40 (s, 1H), 8.28 (d, J=8.33 Hz, 1H), 8.09-8.17 (m, 2H), 7.96-8.03 (m, 2H), 7.88-7.94 (m, 1H), 7.63-7.74 (m, 3H), 7.54 (d, J=1.32 Hz, 1H).

Flash chromatography also afforded the second isomer (Peak 2), (6-chloro-1H-benzo[d]imidazol-1-yl)(naphthalen-1-yl)methanone (0.2 g) as an off white solid.

Compound 361: LCMS—UPLC 307.1 $(M)^+$ Purity @ 254 nm=99.62% and @ 220 nm=98.22%. $^1H$ NMR (400 MHz, DMSO-$d_6$): 8.34 (s, 1H), 8.28 (d, J=8.33 Hz, 1H), 8.07-8.21 (m, 2H), 7.92-8.03 (m, 2H), 7.85 (s, J=8.33 Hz, 1H), 7.58-7.73 (m, 3H), 7.53 (m, J=8.33 Hz, 1H).

Compound 362 and Compound 363

Procedure 1

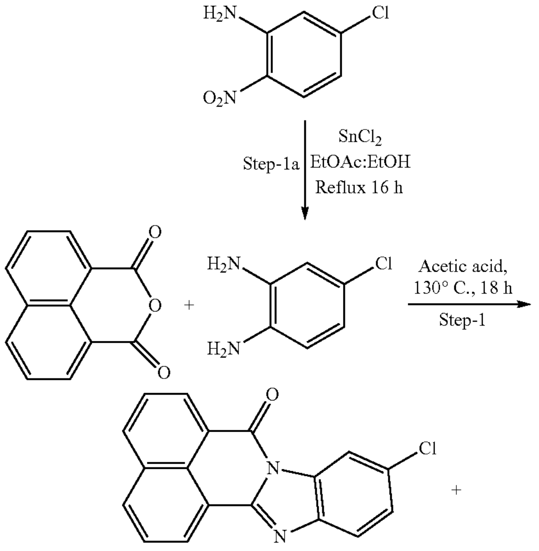

Compound-363

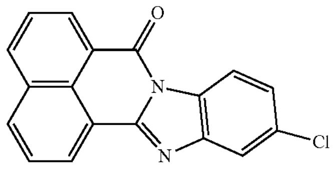

Compound-362

Step 1a: To a solution of 5-chloro-2-nitroaniline (10 g, 0.058 mol) in ethyl acetate (30 ml) and ethanol (15 mL) was added tin chloride (54.6 g. 29 mol). The reaction mixture was then refluxed at 80° C. for 16 h. TLC (30% ethyl acetate in hexane) and NMR showed the formation of desired product. Reaction mixture was concentrated under reduced pressure to remove excess solvent and then neutralized with saturated solution of sodium bicarbonate (1000 mL). The reaction mixture was extracted using ethyl acetate (2000 mL). Organic layer was dried over sodium sulphate and concentrated under reduced pressure to afford crude product which was purified by column chromatography (eluent was 0-30% ethyl acetate in hexane) to obtain 7.0 g of 4-chlorobenzene-1,2-diamine as an off-white solid.

Step 1: To a solution of benzo[d]isochromene-1,3-dione (4.10 g, 0.020 mmol) in acetic acid (20 ml) was added 4-chlorobenzene-1,2-diamine (4.01 g. 0.028 mol). The reaction mixture was then heated to 130° C. for 18 h. LCMS showed the formation of desired product. The reaction mixture was diluted with diethyl ether (50 mL). The precipitate thus obtained was filtered to get crude solid. This solid mass was further triturated in diethyl ether (100 mL) and filtered to get mixture of two regioisomers.

Step 2: Purification of Compound 362 and Compound 363

The crude (mixture of isomers, 1.0 g, 3.27 mmol) was purified by column chromatography to yield 50 mg of Compound 362: -6-chloro-3,10-diazapentacyclo[10.7.1.$0^{2,10}.0^{4,9},0^{16,20}$]icosa-1(19),2,4(9),5,7,12,14,16(20),17-nonaen-11-on (yellow solid) and 20 mg of Compound 363: -7-chloro-3,10-diazapentacyclo[10.7.1.$0^{2,10}.0^{4,9},0^{16,20}$]icosa-1(19),2,4(9),5,7,12,14,16(20),17-nonaen-11-on (yellow solid) along with mixture of isomers.

Compound 362: LCMS: 305.2 (M)+, HPLC 220 nm=99.88%, UPLCMS @ 220 nm=99.20%, @ 220 nm=99.03%. $^1H$ NMR (400 MHz, DMSO-$d^6$) δ 8.73 (dd, J=16.0, 7.3 Hz, 2H), 8.56 (d, J=8.1 Hz, 1H), 8.41 (dd, J=8.4, 3.5 Hz, 2H), 8.01-7.88 (m, 3H), 7.52 (dd, J=8.6, 2.1 Hz, 1H). $^1H$ NMR (400 MHz, Chloroform-d) δ 8.83 (dd, J=16.1, 7.3 Hz, 2H), 8.49 (d, J=8.5 Hz, 1H), 8.32 (d, J=8.2 Hz, 1H), 8.19 (d, J=8.2 Hz, 1H), 7.90-7.79 (m, 3H), 7.44 (dd, J=8.5, 2.0 Hz, 1H).

Compound 363: LCMS: 305.2 (M)+; HPLC @ 220 nm=99.12%, UPLCMS @ 220 nm=98.74%, 254 nm=97.84%. $^1H$ NMR (400 MHz, Chloroform-d) δ 8.89-8.79 (m, 2H), 8.61 (s, 1H), 8.32 (d, J=8.2 Hz, 1H), 8.19 (d, J=8.2 Hz, 1H), 7.88-7.81 (m, 3H), 7.46 (dd, J=8.4, 2.2 Hz, 1H). $^1H$ NMR (400 MHz, DMSO-$d_6$) δ 8.78 (d, J=7.3 Hz, 1H), 8.74 (d, J=7.3 Hz, 1H), 8.58 (d, J=8.2 Hz, 1H), 8.47-8.40 (m, 2H), 8.03-7.88 (m, 3H), 7.56 (dd, J=8.5, 2.2 Hz, 1H).

Procedure 2

11-substituted chloro-7H-Benzimidazo[P,I-a]benz [de]-isoquinolin-7-ones (Compound 362)

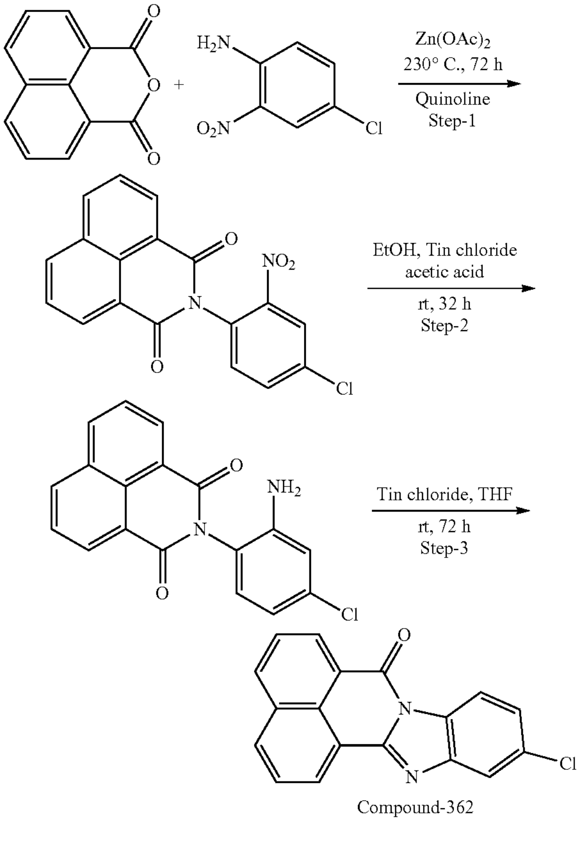

Compound-362

Step 1: The mixture of benzo[d]isochromene-1,3-dione (15 g, 0.075 mol), 4-chloro-2-nitroaniline (15.67 g, 0.090 mole), zinc acetate (13.76 g, 0.075 mol) and quinoline (80.0 ml) was heated at 230° C. using sealed tube for 72 h. The reaction mixture was then allowed to cool resulting in precipitation of solid which was filtered. The filtered solid was then further washed using MTBE (50 ml×3). The isolated product was subjected to slurry wash using DM water (350 ml) at reflux and filtered to get 19.0 g of pure 2-(4-chloro-2-nitrophenyl)-1H-benzo[de]isoquinoline-1,3(2H)-dione.

Step 2: To the suspension of 2-(4-chloro-2-nitrophenyl)-1H-benzo[d]isoquinoline-1,3(2H)-dione (10.0 g, 0.0283 mole) in ethanol (300 ml), was added acetic acid (10.0 ml) and tin chloride (51.17 g, 0.226 mole). The reaction mixture was then stirred for 72 h. The reaction mixture was then concentrated to get crude product. The crude product was subjected to slurry wash using DM water (150 ml) and filtered to get 10.0 g 2-(2-amino-4-chlorophenyl)-1H-benzo[de]isoquinoline-1,3(2H)-dione.

Step 3: To the suspension of 2-(2-amino-4-chlorophenyl)-1H-benzo[de]isoquinoline-1,3(2H)-dione (10.0 g, 0.031 mol) in THF (600 ml) was added acetic acid (20.0 ml) followed by tin chloride (69.7 g, 0.309 mol) in 5 portion (2.0 equiv. in each portion) over a period of 40 h. The TLC showed the formation of desired product along with starting material. The reaction mixture was then concentrated and partitioned between DM water (600 ml) and ethyl acetate (600 ml). The aqueous layer was extracted using ethyl acetate (400 ml). The organic layer was then dried over sodium sulfate and concentrated to get crude product. The crude product was purified by flash chromatography (eluent: 0-30% ethyl acetate in hexane) to get 1.21 g of 6-chloro-3,10-diazapentacyclo[10.7.1.$0^{2,10}$.$0^{4,9}$.$0^{16,20}$]icosa-1(19),2,4(9),5,7,12,14,16(20),17-nonaen-11-one as a yellow solid.

Compound 362: LCMS—305.1 (M)+HPLC @ 220 nm=97.56%, UPLCMS @ 220 nm=98.75%, 254 nm=98.56%. $^1$H NMR (400 MHz, DMSO-d6) δ 8.73 (dd, J=16.0, 7.3 Hz, 2H), 8.56 (d, J=8.1 Hz, 1H), 8.41 (dd, J=8.4, 3.5 Hz, 2H), 8.01-7.88 (m, 3H), 7.52 (dd, J=8.6, 2.1 Hz, 1H). $^1$H NMR (400 MHz, Chloroform-d) δ 8.83 (dd, J=16.1, 7.3 Hz, 2H), 8.49 (d, J=8.5 Hz, 1H), 8.32 (d, J=8.2 Hz, 1H), 8.19 (d, J=8.2 Hz, 1H), 7.90-7.79 (m, 3H), 7.44 (dd, J=8.5, 2.0 Hz, 1H).

Compound 363

7-chloro-3,10-diazapentacyclo[10.7.1.$0^{2,10}$.$0^{4,9}$.$0^{16,20}$]icosa-1(19),2,4(9),5,7,12,14,16(20),17-nonaen-11-one (Compound 363)

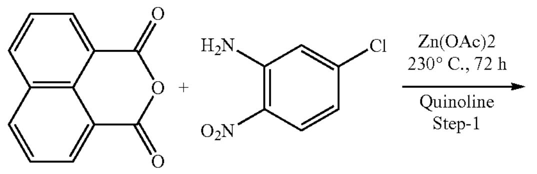

-continued

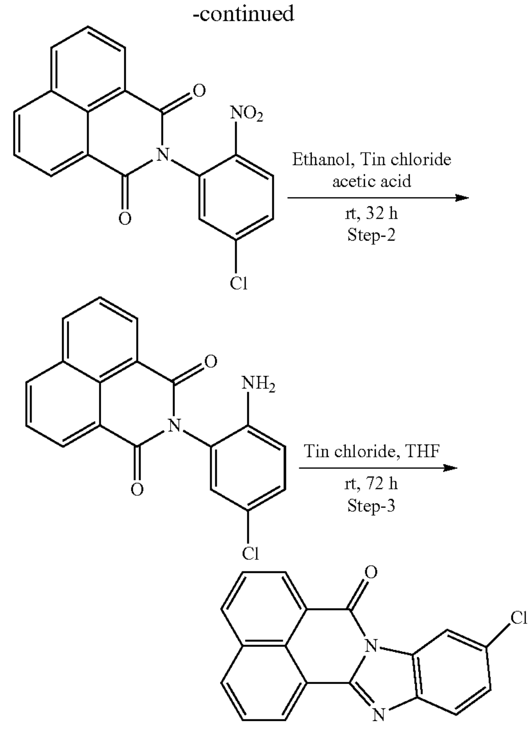

Compound-363

Steps 1-3: were performed as described above for synthesis of Compound 362 (procedure 2)

Compound 363: LCMS—305.2 $(M)^+$: HPLC @ 220 nm=99.58%, UPLCMS @ 220 nm=99.68%, @ 220 nm=99.16%. $^1$H NMR (400 MHz, DMSO-$d_6$) δ 8.78 (d, J=7.3 Hz, 1H), 8.74 (d, J=7.3 Hz, 1H), 8.58 (d, J=8.2 Hz, 1H), 8.47-8.40 (m, 2H), 8.03-7.88 (m, 3H), 7.56 (dd, J=8.5, 2.2 Hz, 1H). $^1$H NMR (400 MHz, Chloroform-d) δ 8.89-8.79 (m, 2H), 8.61 (s, 1H), 8.32 (d, J=8.2 Hz, 1H), 8.19 (d, J=8.2 Hz, 1H), 7.88-7.81 (m, 3H), 7.46 (dd, J=8.4, 2.2 Hz, 1H).

Compound 364

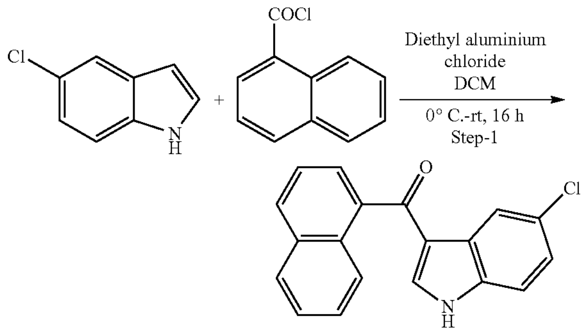

Compound-364

Step 1: To a solution of 5-chloro-1H-indole (2.0 g, 0.013 mol) in DCM (40 ml) was added diethylaluminium chloride (21 mL, 0.019 mol) drop wise at 0° C. The reaction mixture was stirred at 0° C. for 15 min. To this reaction mixture was added naphthalene-1-carbonyl chloride (3.03 g, 0.015 mol)

and the reaction mixture was allowed to stir for 16 h at room temperature. LCMS and HNMR showed the formation of desired product. The reaction mixture was quenched by DM water (100 ml) and extracted using dichloromethane (500 ml×2). The organic layer was then dried over sodium sulfate and concentrated to get the crude product. The crude product was purified by column chromatography (eluent: 0-5% ethyl acetate in hexane) which yielded 3.0 g of (5-chloro-1H-indol-3-yl)(naphthalen-1-yl)methanone as an off white solid.

Compound 364: LCMS—306.1$(M)^+$: HPLC @ 220 nm=99.53%, UPLCMS @ 220 nm=99.78%, @ 220 nm=99.80%. $^1$H NMR (400 MHz, DMSO-d6) δ 12.23 (s, 1H), 8.28 (s, 1H), 8.10 (d, J=8.2 Hz, 1H), 8.02 (dd, J=12.6, 8.1 Hz, 2H), 7.77 (d, J=3.1 Hz, 1H), 7.71 (d, J=6.9 Hz, 1H), 7.63-7.48 (m, 4H), 7.32 (dd, J=8.7, 2.2 Hz, 1H).

Compound 365

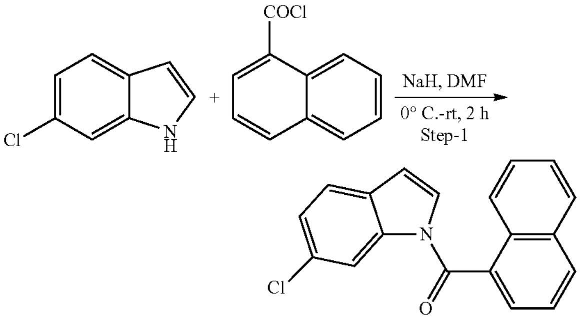

Compound-365

Step 1: To a solution of 6-chloro-1H-indole (0.5 g, 3.31 mmol) in DMF (50 ml) was added sodium hydride (198 mg. 4.96 mmol) portion-wise at 0° C. To this reaction mixture was added naphthalene-1-carbonyl chloride (754 mg, 3.97 mmol) at 0° C. and was allowed to stir for 2 h at room temperature. LCMS showed the formation of desired product. The reaction mixture was then quenched by DM water (100 ml) and extracted using ethyl acetate (200 ml×2). The organic layer was dried over sodium sulfate and concentrated to obtain crude product. The crude product was purified by column chromatography (eluent: 0-10% ethyl acetate in hexane) which yielded 0.861 g of (6-chloro-1H-indol-1-yl)(naphthalen-2-yl)methanone as off white solid.

Compound 365: LCMS—306.1(M)+: HPLC @ 220 nm=99.65%, UPLCMS @ 220 nm=99.80%, @ 254 nm=99.69%. $^1$H NMR (400 MHz, Chloroform-d) δ $^1$H NMR (400 MHz, DMSO-d6) d 8.40 (s, 1H), 8.23 (d, J=8.3 Hz, 1H), 8.11 (d, J=8.1 Hz, 1H), 7.85 (d, J=7.0 Hz, 1H), 7.79 (d, J=8.3 Hz, 1H), 7.72-7.71 (m, 1H), 7.69-7.54 (m, 3H), 7.42 (dd, J=8.3, 2.1 Hz, 1H), 7.12 (d, J=3.8 Hz, 1H), 6.72 (d, J=3.8 Hz, 1H).

Compound 366

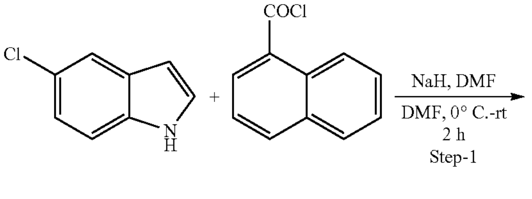

-continued

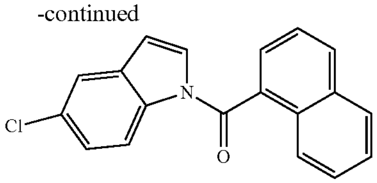

Compound-366

Step 1: was performed as described above for synthesis of Compound 365

Compound 366: LCMS: 306.1 (M)+; HPLC @ 220 nm=99.81%, @ 254 nm=99.81%. $^1$H NMR (400 MHz, Chloroform-d) δ 8.45 (d, J=8.8 Hz, 1H), 8.06 (d, J=8.2 Hz, 1H), 7.99-7.92 (m, 1H), 7.87 (d, J=8.2 Hz, 1H), 7.68-7.66 (m, 1H), 7.65-7.48 (m, 4H), 7.38 (dd, J=8.8, 2.2 Hz, 1H), 7.02 (d, J=3.8 Hz, 1H), 6.48 (d, J=3.8 Hz, 1H).

Compound 405

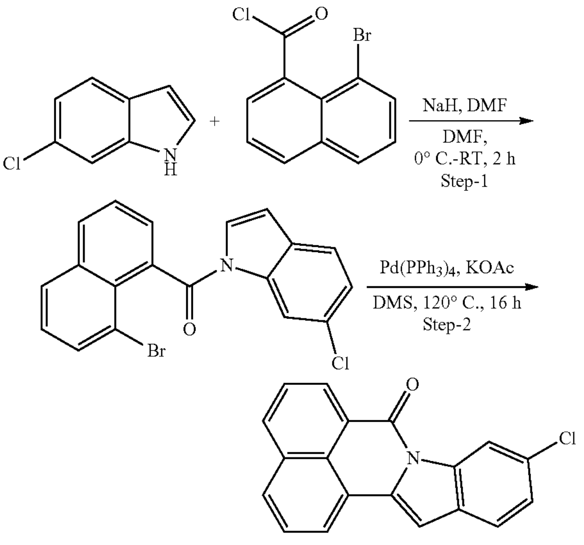

Compound-405

Step 1 was performed as described above for synthesis of Compound 365

Step 2: The mixture of (8-bromonaphthalen-1-yl)(6-chloro-1H-indol-1-yl)methanone (0.5 g, 1.3 mmol), potassium acetate (0.255 g, 2.6 mmol), tetrakistriphenylphosphine (0.150 g, 0.130 mmol) and DMS (8.0 ml) was purged for 10 min using nitrogen. The resultant reaction mixture was then stirred for 16 h at 120° C. The TLC (10% ethyl acetate in hexane) showed complete consumption of starting material. The reaction mixture was then quenched by DM water (20.0 ml) and extracted by ethyl acetate (25 ml×2). The ethyl acetate layer was then concentrated to get crude product. The crude product was then purified by flash chromatography (eluent: 0-5% ethyl acetate in hexane) to get 4.0 mg of (7-chloro-10-azapentacyclo[10.7.1.0$^{2,10}$.0$^{4,9}$.0$^{16,20}$]icosa 1(19),2,4(9),5,7,12,14,16(20),17-nonaen-11-one) as a white solid.

LCMS: 304.0 (M)+, HPLC @ 220 nm=92.30%, @ 254 nm=91.48%. $^1$H NMR (400 MHz, Chloroform-d) δ 8.85 (s, 1H), 8.73 (d, J=7.1 Hz, 1H), 8.20-8.17 (m, 2H), 7.95 (d, J=8.1 Hz, 1H), 7.77 (t, J=7.7 Hz, 1H), 7.68 (t, J=7.8 Hz, 1H), 7.58 (d, J=8.3 Hz, 1H), 7.38-7.30 (m, 2H).

Compound 406

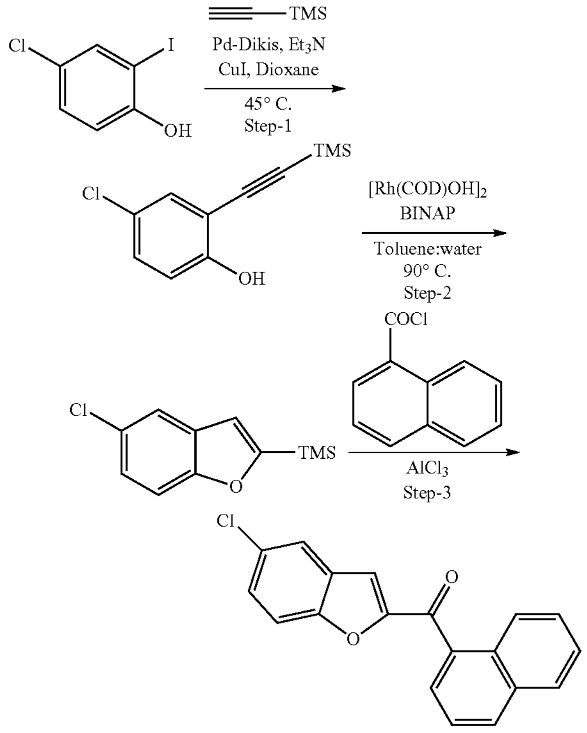

Compound-406

Step 1: To a solution of 4-chloro-2-iodophenol (4.0 g, 15.72 mmol) in dioxane (40.0 ml) under nitrogen, was added ethynyltrimethylsilane (1.852 g, 18.86 mmol), triethylamine (5.46 ml, 39.3 mmol) followed by addition of bis(triphenylphosphine)palladium(II) dichloride (1.10 g, 1.572 mmol) and copper iodide (0.598 g, 3.144 mmol). The reaction mixture was then allowed to stir at 45° C. for 1 h. The TLC (10% ethyl acetate in hexane) showed the formation of desired product. The reaction mixture was quenched by DM water (50.0 ml) and was extracted using ethyl acetate (50.0 ml×3). The organic layer was then dried over sodium sulfate and concentrated to get 4.8 g of crude product which was then purified by column chromatography (eluent: 0-10% ethyl acetate in hexane) to yield 3.2 g of 4-chloro-2-((trimethylsilyl)ethynyl)phenol as colorless oil.

$^1$H NMR (400 MHz, Chloroform-d) δ 7.31 (d, J=2.63 Hz, 1H) 7.20-7.18 (m, 1H) 6.88 (d, J=8.77 Hz, 1H) 0.28 (s, 9H).

Step 2: The mixture of $[Rh(COD)OH]_2$ (0.324 g, 0.71 mmol) and BINAP (0.707 g, 1.13 mmol) in toluene:water (48 ml, 40:8) was stirred at room temperature. To this reaction mixture, was added solution of 4-chloro-2-((trimethylsilyl)ethynyl)phenol (3.2 g, 14.23 mmol) in toluene (20.0 ml). The resultant reaction mixture was stirred at 90° C. for 2 h. The TLC (pentane) showed the formation of desired product. The reaction mixture was then filtered through a celite bed and concentrated. The obtained solid was subjected to slurry wash using pentane (150 ml). The resultant suspension was then filtered and concentrated to get 2.0 g of (5-chlorobenzofuran-2-yl)trimethylsilane as colorless oil.

$^1$H NMR (400 MHz, Chloroform-d) δ 7.89 (s, 1H) 7.78 (d, J=8.33 Hz, 1H) 7.57-7.64 (m, 2H) 0.71-0.74 (m, 9H).

Step 3: To a solution of 1-naphthoyl chloride (0.190 g, 1.0 mmol) in dichloroethane (10.0 ml) at 0° C. was added $AlCl_3$ (0.133 g, 1.0 mmol) portion-wise. The reaction mixture was allowed to stir for 30 min. To this reaction mixture was added (5-chlorobenzofuran-2-yl)(naphthalen-1-yl)methanone (0.224 g, 1.0 mmol) and it was allowed to stir for 2 h at room temperature. TLC (10% ethyl acetate in hexane) showed the formation of desired product. The reaction mixture was quenched by DM water (15.0 ml). The reaction mixture was extracted using ethyl acetate (20.0 ml×2). The organic layer was then concentrated to get crude product which was then purified by column chromatography (eluent: 0-10% ethyl acetate in hexane) to yield 0.110 g of (5-chlorobenzofuran-2-yl)(naphthalen-1-yl)methanone as an off-white solid.

LC-MS: 307.1 (M)+, HPLC@ 220 nm=99.51%, UPLCMS @ 220 nm=99.55%, @ 254 nm=99.92%. $^1$H NMR (400 MHz, Chloroform-d) δ 8.30-8.23 (m, 1H), 8.08 (d, J=8.3 Hz, 1H), 7.97-7.93 (m, 1H), 7.87 (d, J=7.1 Hz, 1H), 7.66-7.56 m, 5H), 7.47 (dd, J=8.9, 2.2 Hz, 1H), 7.29 (s, 1H).

Compound 429 and Compound 430

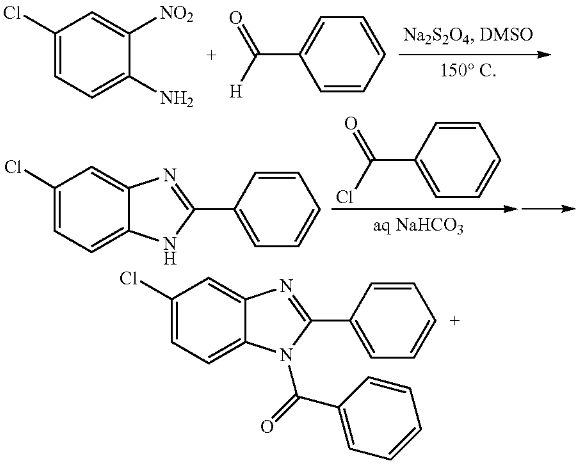

Isomer 1, Peakl
Compound-429

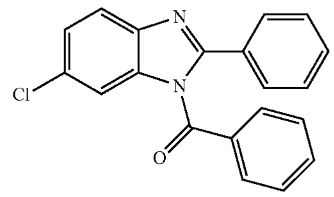

Isomer 2, Peak2
Compound-430

Step 1: To a solution of 4-chloro-2-nitroaniline (0.34 g, 2.0 mmol, 1.0 eq) and benzaldehyde (0.21 g, 2.0 mmol, 1.0 eq) in (5.0 mL) in DMSO was added $Na_2S_2O_4$ (0.61 g, 1.0 mmol, 2.0 eq) and the reaction mixture was heated at 150° C. for 3 h. After completion of reaction, solution was diluted with water and the precipitate thus obtained was filtered, washed with ether and dried to give the desired product as 5-chloro-2-phenyl-1H-benzo[d]imidazole (0.35 g) as an off-white solid.

LCMS: 229.1 (M)+

Step 2: To a solution of 5-chloro-2-phenyl-1H-benzo[d]imidazole (0.23 g, 1.0 mmol) in (30 mL) saturated aq $NaHCO_3$ was added benzoyl chloride (0.13 mL, 1.1 mmol) and the reaction mixture was stirred at room temperature for overnight. After completion of reaction, the reaction mixture was diluted with water and extracted with DCM (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-10% EtOAc in hexane] to afford the first isomer (Peak 1)(5-chloro-2-phenyl-1H-benzo[d]imidazol-1-yl)(phenyl)methanone (45 mg) as white solid.

Compound 429: LCMS—332.2 $(M)^+$ UPLC @ 254 nm=99.04% and @ 220 nm=99.39%. $^1$H NMR (400 MHz, DMSO-$d_6$): δ 7.95 (s, 1H), 7.74 (d, J=7.89 Hz, 2H), 7.51-7.65 (m, 3H), 7.29-7.45 (m, 7H).

Flash chromatography also afforded the second isomer (Peak 2), (6-chloro-2-phenyl-1H-benzo[d]imidazol-1-yl)(phenyl)methanone (25 mg) as white solid.

Compound 430: LCMS—332.2 $(M)^+$; UPLC @ 254 nm=97.48% and @ 220 nm=98.98%. $^1$H NMR (400 MHz, DMSO-$d_6$): δ 7.87 (d, J=8.77 Hz, 1H), 7.73 (d, J=7.45 Hz, 2H), 7.54-7.61 (m, 3H), 7.37-7.50 (m, 4H), 7.28-7.34 (m, 3H).

Compound 431 and Compound 432

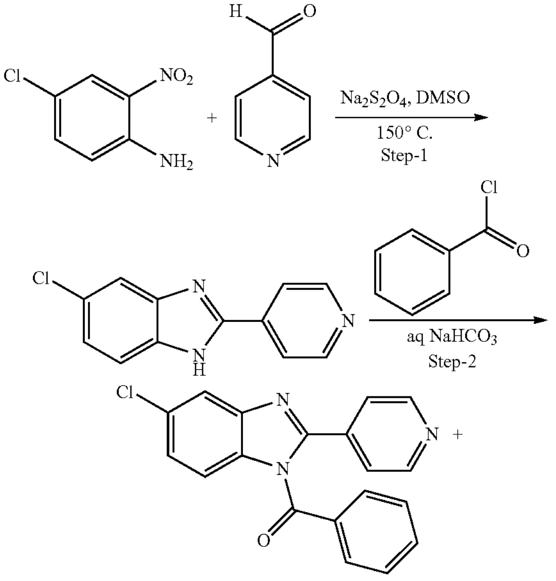

Isomer 1, Peak-1
Compound-431

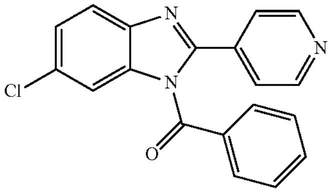

Isomer 2, Peak-2
Compound-432

Steps 1 and 2: were performed as described above for synthesis of Compound 429 LCMS: 230.1 (M)+

Compound 431: LCMS—334.2 (M)+; UPLC @ 254 nm=99.41% and @ 220 nm=96.62%. $^1$H NMR (400 MHz, DMSO-$d_6$): δ 8.54 (d, J=6.14 Hz, 1H), 8.01 (d, J=2.19 Hz, 1H), 7.79 (d, J=7.89 Hz, 2H), 7.61-7.68 (m, 2H), 7.57 (d, J=6.14 Hz, 2H), 7.39-7.46 (m, 3H), 7.30-7.36 (m, 1H).

Compound 432: LCMS—334.2 (M)+; UPLC @ 254 nm=99.64% and @ 220 nm=98.98%. $^1$H NMR (400 MHz, DMSO-$d_6$): δ 8.53 (d, J=4.82 Hz, 1H), 7.93 (d, J=8.77 Hz, 1H), 7.78 (d, J=7.02 Hz, 2H), 7.59-7.66 (m, 1H), 7.51-7.58 (m, 2H), 7.40-7.51 (m, 2H), 7.30-7.40 (m, 3H).

Compound 433

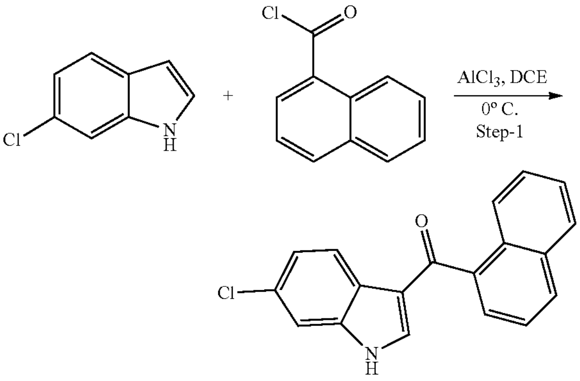

Compound-433

Step 1 and 2: were performed as described above for synthesis of Compound 359

Compound 433: LCMS—306.1 (M)+;

UPLC @ 254 nm=95.87%, @ 220 nm=99.10%. $^1$H NMR (400 MHz, DMSO-$d_6$): δ 12.14 (br. s., 1H), 8.28 (d, J=8.33 Hz, 1H), 8.10 (d, J=8.33 Hz, 1H), 8.00 (d, J=8.33 Hz, 1H), 8.04 (d, J=7.45 Hz, 1H), 7.69-7.75 (m, 2H), 7.46-7.66 (m, 4H), 7.31 (d, J=8.33 Hz, 1H).

Compound 434

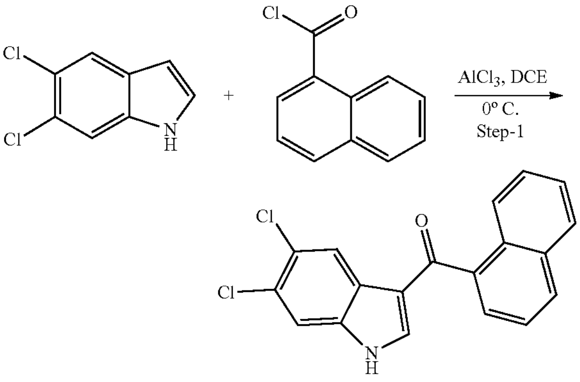

Compound-434

Step 1 was performed as described above for synthesis of Compound 359

LCMS: 340.2. (M)+; UPLC @ 254 nm=98.33% and @220 nm=98.36%. $^1$H NMR (400 MHz, DMSO-$d_6$): δ

12.30 (br. s., 1H), 8.46 (s, 1H), 8.12 (d, J=8.33 Hz, 1H), 7.99-8.07 (m, 2H), 7.83 (s, 1H), 7.79 (s, 1H), 7.73 (d, J=6.58 Hz, 1H), 7.49-7.65 (m, 3H).

Compound 435

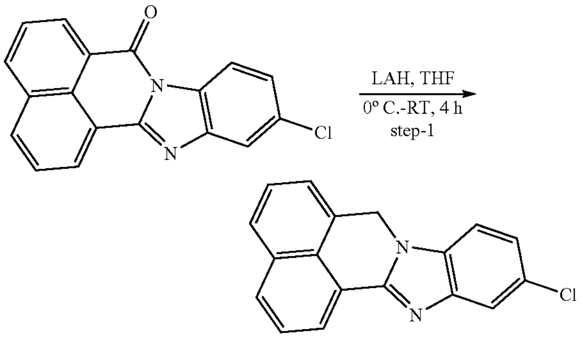

Compound 435

Step-1: To a suspension of 6-chloro-3,10-diazapentacyclo-[10.7.1.$0^{2,10}$.$0^{4,9}$.$0^{16,20}$]icosa-1(19),2,4(9),5,7,12,14,16(20),17-nonaen-11-one (0.140 g, 0.459 mmol) in THF (5.0 ml) at 0° C. was added lithium aluminium hydride (0.104 g, 2.754 mmol) portion-wise. The reaction mixture was then stirred for 4 h. The reaction mixture was quenched using ice-cold water, NaOH solution and stirred for 10.0 min. The reaction mixture was then extracted using ethyl acetate and concentrated to get 150 mg of crude product. The crude product was purified using prep chromatography and resulted in 12 mg of Compound 435 (6-chloro-3,10-diazapentacyclo[10.7.1.$0^{2,10}$.$0^{4,9}$.$0^{16,20}$]icosa-1(19),2,4(9),5,7,12,14,16(20),17-nonaene) as a white solid.

Compound 435: LCMS—291.1 $(M)^+$; HPLC @ 220 nm=98.09%, UPLCMS @ 220 nm=97.92%, @ 220 nm=97.92=97.68%. $^1$H NMR (400 MHz, Chloroform-d) δ 8.40 (d, J=7.2 Hz, 1H), 8.10 (d, J=8.3 Hz, 1H), 8.02-7.94 (m, 1H), 7.81 (s, 1H), 7.72-7.67 (m, 4H), 7.37 (dd, J=8.5, 2.0 Hz, 1H), 5.92 (s, 2H).

Compound 464

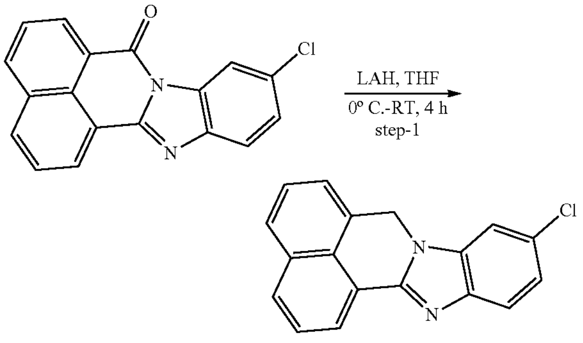

Compound 435

Step 1 was performed as described above for synthesis of Compound 435

Compound 464: LCMS—290.9 (M)+, HPLC @ 220 nm=99.29%, UPLCMS @ 220 nm=98.90%, @ 254 nm=99.44%. $^1$H NMR (400 MHz, DMSO-$d_6$) δ 8.39 (d, J=7.1 Hz, 1H), 8.09 (d, J=8.3 Hz, 1H), 7.98 (d, J=7.6 Hz, 1H), 7.81-7.63 (m, 5H), 7.31 (dd, J=8.5, 2.1 Hz, 1H), 5.90 (s, 2H).

Compound 488 and Compound 489

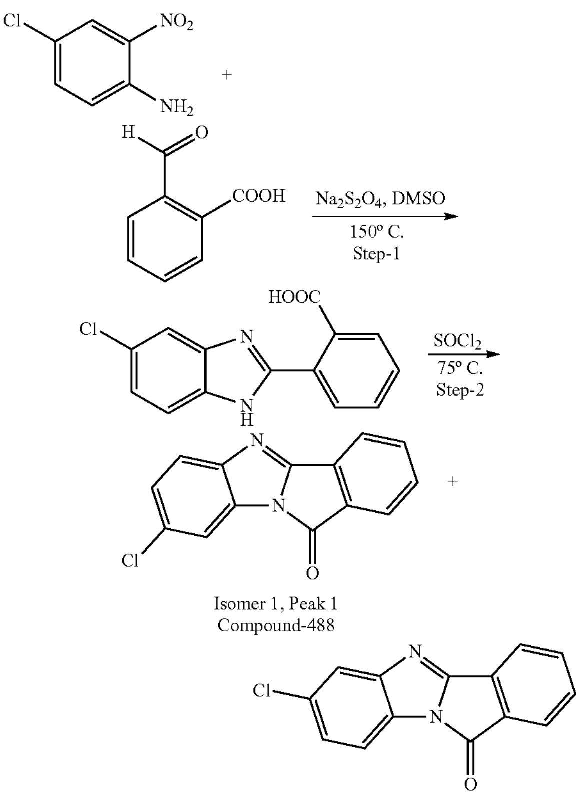

Isomer 1, Peak 1
Compound-488

Isomer 2, Peak 2
Compound-489

Step 1 was performed as described above for synthesis of Compound 429

Step 2: A solution of -(5-chloro-1H-benzo[d]imidazol-2-yl)benzoic acid (0.27 g, 1.0 mmol) in $SOCl_2$ (2 mL) was heated at 70° C. for 2 h and the progress of the reaction was monitored by TLC. After completion of reaction, solvent was evaporated, neutralized with sodium bicarbonate and extracted with DCM (50 mL×2). The combined organic layer was washed with water (50 mL), brine solution (50 mL), dried over anhydrous sodium sulfate and concentrated under reduced pressure to afford crude product, which was purified by flash chromatography (elution" 0-10% EtOAc in hexane) to afford isomer 1 (peak 1), 4-chloro-1,8-diazatetracyclo[7.7.0.$0^{2,7}$.$0^{10,15}$]hexadeca-2,4,6,8,10,12,14-heptaen-16-one (15 mg) as a light yellow solid.

Compound 488: LCMS—254.9 (M)+UPLC @ 254 nm=98.78% and @ 220 nm=98.87%. $^1$H NMR (400 MHz, DMSO-$d_6$): δ 7.90 (t, J=6.80 Hz, 2H), 7.75-7.83 (m, 2H), 7.62-7.75 (m, 2H), 7.42 (dd, J=1.75, 8.33 Hz, 1H).

Flash chromatography [silica gel 100-200 mesh; elution 0-10% EtOAc in hexane] also afforded the second isomer (Peak 2), 5-chloro-1,8-diazatetracyclo-[7.7.0.$0^{2,7}$0.$^{10,15}$]hexadeca-2,4,6,8,10,12,14-heptaen-16-one (105 mg) as a light yellow solid Compound 489: LCMS—254.9 (M)+; UPLC @ 254 nm=93.74% and @ 220 nm=92.17%. $^1$H NMR (400 MHz, DMSO-$d_6$): δ 7.91 (dd, J=3.29, 7.24 Hz, 2H), 7.73-7.83 (m, 2H), 7.61-7.73 (m, 2H), 7.37 (dd, J=1.97, 8.55 Hz, 1H).

Compound 490 and Compound 491

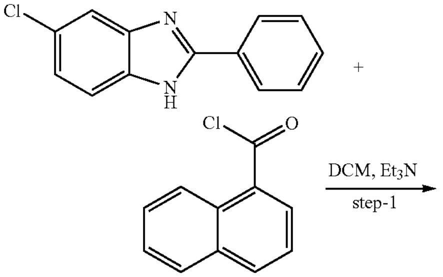

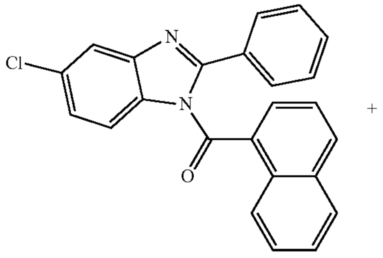

Isomer 1, Peak 1
Compound-490

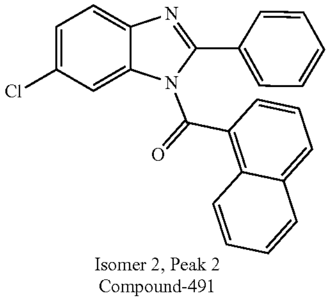

Isomer 2, Peak 2
Compound-491

Step 1: To a solution of 5-chloro-2-phenyl-1H-benzo[d]imidazole (0.23 g, 1.0 mmol) in (10 mL) DCM was added $Et_3N$ (0.57 ml, 4.0 mmol) followed by 1-naphthoyl chloride (0.2 mL, 1.1 mmol) and the reaction mixture was stirred at rt for overnight. After completion of reaction, the reaction mixture was diluted with water and extracted with DCM (50 mL×2). The combined organic layer was washed with water (50 mL), brine solution (50 mL), dried over anhydrous sodium sulfate and concentrated under reduced pressure to afford crude product, which was purified by flash chromatography (elution: 0-10% EtOAc in hexane) to afford the isomer 1 (peak 1) (5-chloro-2-phenyl-1H-benzo[d]imidazol-1-yl)(naphthalen-1-yl)methanone (25 mg) as an off white solid.

Compound 490: LCMS—383.0 (M)+UPLC @ 254 nm=99.78% and @ 220 nm=99.05%. $^1$H NMR (400 MHz, DMSO-$d_6$): δ 8.15 (d, J=8.33 Hz, 1H), 8.02 (d, J=8.33 Hz, 1H), 7.89-7.99 (m, 2H), 7.57-7.71 (m, 4H), 7.44 (d, J=7.89 Hz, 3H), 7.34 (t, J=7.67 Hz, 1H), 7.12 (d, J=7.45 Hz, 1H), 6.97-7.04 (m, 2H).

Flash chromatography also afforded the second isomer (Peak 2), 6-chloro-2-phenyl-1H-benzo[d]imidazol-1-yl)(naphthalen-1-yl)methanone (15 mg, 3.9%) as a light brown solid.

Compound 491: LCMS—383.2 (M)+UPLC @ 254 nm=97.61% and @ 220 nm=98.38%. $^1$H NMR (400 MHz, DMSO-$d_6$): δ 8.15 (d, J=8.33 Hz, 1H), 7.86-8.03 (m, 3H), 7.58-7.71 (m, 4H), 7.49-7.53 (m, 1H), 7.41 (d, J=7.45 Hz, 2H), 7.33 (t, J=7.67 Hz, 1H), 7.10 (t, J=7.02 Hz, 1H), 6.98 (t, J=7.67 Hz, 2H).

Compound 492 and Compound 493

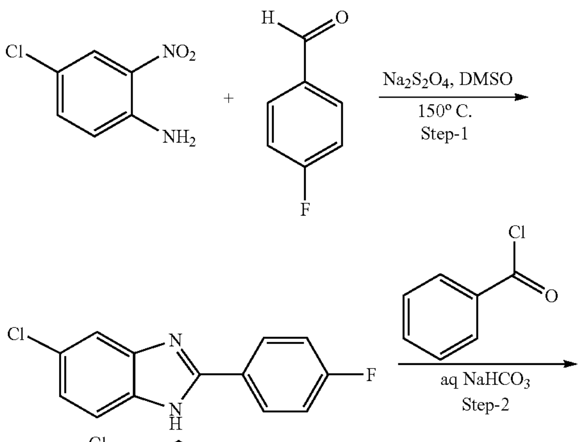

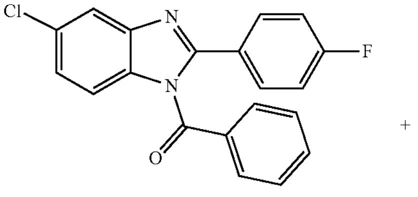

Peak 1, Isomer 1
Compound-492

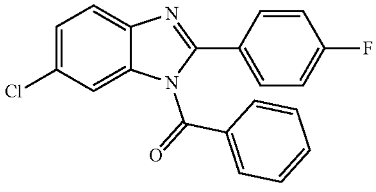

Peak 2, Isomer 2
Compound-493

Steps 1 and 2 were performed as described above for synthesis of Compound 429

Compound 492: LCMS—351.2 (M)$^+$; UPLC @ 254 nm=98.96% and @ 220 nm=97.44%. $^1$H NMR (400 MHz, DMSO-$d_6$): δ 7.94 (s, 1H), 7.73 (d, J=7.45 Hz, 2H), 7.57-7.67 (m, 3H), 7.34-7.51 (m, 4H), 7.17 (t, J=8.77 Hz, 2H).

Compound 493: LCMS—351.2 (M)$^+$; UPLC @ 254 nm=99.58% and @ 220 nm=99.31%. $^1$H NMR (400 MHz, DMSO-$d_6$): δ 7.87 (d, J=8.33 Hz, 1H), 7.72 (d, J=7.45 Hz, 2H), 7.58-7.67 (m, 3H), 7.35-7.49 (m, 4H), 7.15 (t, J=8.77 Hz, 2H).

Compound 494 and Compound 495

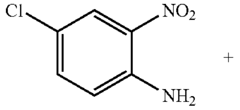

-continued

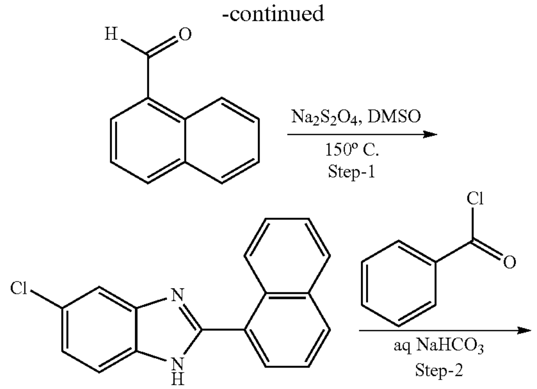

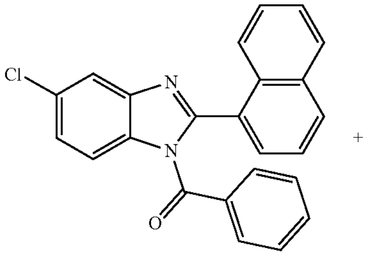

Peak 1, Isomer 1
Compound-494

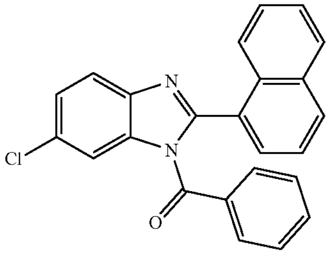

Peak 2, Isomer 2
Compound-495

Steps 1 and 2 were performed as described above for synthesis of Compound 429

Compound 494: LCMS—383.2 $(M)^+$; UPLC @ 254 nm=98.60% and @ 220 nm=97.83%. $^1H$ NMR (400 MHz, DMSO-$d_6$): δ 7.99-8.07 (m, 2H), 7.82-7.91 (m, 2H), 7.43-7.63 (m, 7H), 7.33-7.43 (m, 2H), 7.10 (t, J=7.89 Hz, 2H)

Compound 495: LCMS—383.2 (M)+; UPLC @ 254 nm=96.78% and @ 220 nm=94.04%. $^1H$ NMR (400 MHz, DMSO-$d_6$): δ 8.03 (d, J=8.77 Hz, 1H), 7.94 (d, J=8.33 Hz, 1H), 7.88 (t, J=8.77 Hz, 2H), 7.43-7.65 (m, 7H), 7.32-7.43 (m, 2H), 7.08 (t, J=7.45 Hz, 2H).

Compound 496 and Compound 497

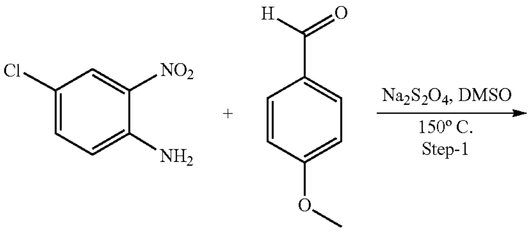

-continued

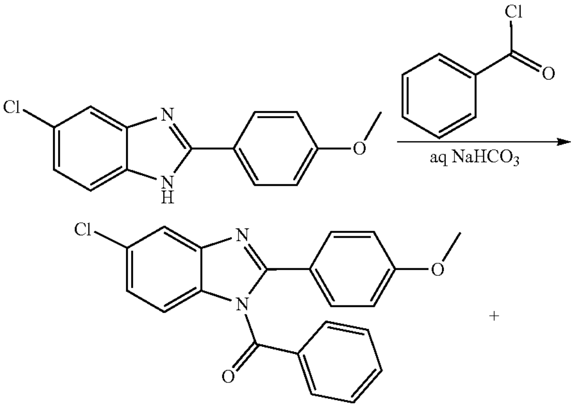

Peak 1, Isomer 1
Compound-496

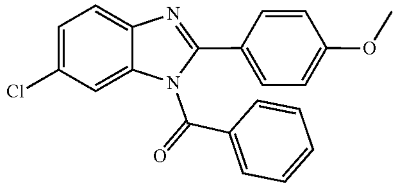

Peak 2, Isomer 2
Compound-497

Steps 1 and 2 were performed as described above for synthesis of Compound 429.

Compound 496: LCMS—363.3 $(M)^+$; UPLC @ 254 nm=99.58% and @ 220 nm=99.30%. $^1H$ NMR (400 MHz, DMSO-$d_6$): δ 7.87 (d, J=1.75 Hz, 1H), 7.70 (d, J=7.45 Hz, 2H), 7.59-7.63 (m, 1H), 7.50 (m, J=8.77 Hz, 2H), 7.41 (t, J=7.67 Hz, 2H), 7.27-7.34 (m, 2H), 3.70 (s, 3H) 6.85 (m, J=8.77 Hz, 2H).

Compound 497: LCMS—363.3 $(M)^+$; UPLC @ 254 nm=97.14% and @ 220 nm=95.46%. $^1H$ NMR (400 MHz, DMSO-$d_6$): δ 7.80 (d, J=8.33 Hz, 1H), 7.65-7.72 (m, 2H), 7.57-7.63 (m, 1H), 7.49 (m, J=8.77 Hz, 2H), 7.41 (t, J=7.67 Hz, 3H), 7.32 (d, J=1.75 Hz, 1H), 6.84 (m, J=8.77 Hz, 2H), 3.69 (s, 3H).

Compound 521

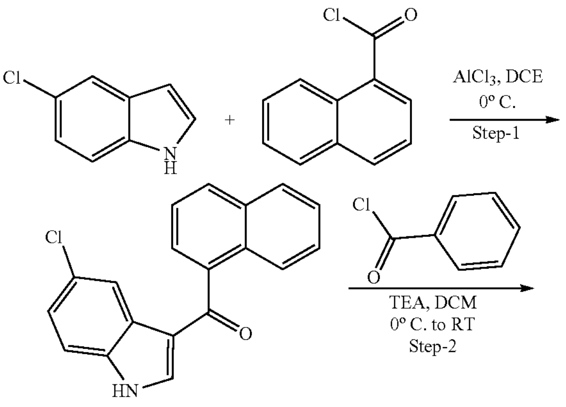

-continued

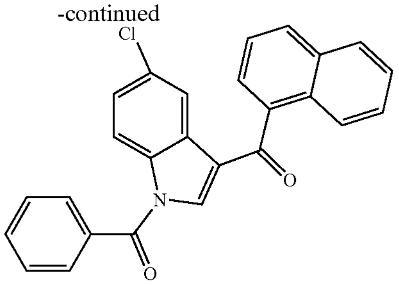

Compound-521

Step 1 was performed as described above for synthesis of Compound 359

Step 2 was performed as described above for synthesis of Compound 490

Compound 521: LCMS—410.3(M)$^+$; UPLC @ 254 nm=99.67%, % and @ 220 nm=99.58%. $^1$H NMR (400 MHz, DMSO-$d_6$): δ 8.40 (d, J=1.96 Hz, 1H), 8.29 (s, 1H), 8.11-8.19 (m, 2H), 7.98-8.04 (m, 1H), 7.90 (d, J=6.36 Hz, 1H), 7.80 (d, J=7.34 Hz, 2H), 7.59-7.66 (m, 6H), 7.47-7.52 (m, 2H).

Compound 522

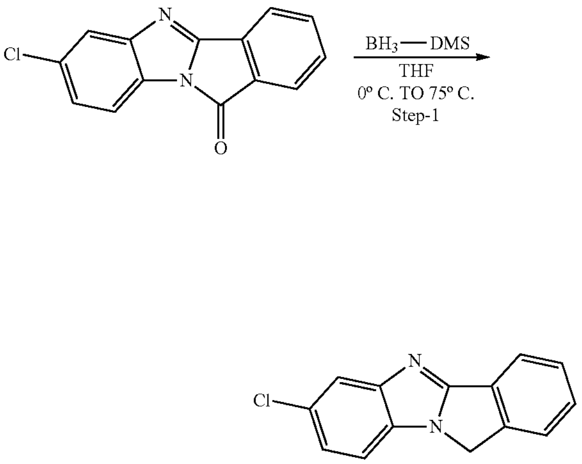

Compound-522

Step 1: 7-chloro-11H-benzo[4,5]imidazo[2,1-a]isoindol-11-one (0.500 g, 1.96 mmol, 1.0 eq) was dissolved in THF (10.0 ml) and cooled to 0° C. $BH_3$-DMS (0.3 ml, 2.95 mmol, 1.5 eq) was slowly added to it. After few minutes of stirring the reaction mixture was refluxed at 75° C. for 16 hours. After completion, the reaction mixture was cooled to 0° C. and was slowly quenched with methanol (100.0 ml). The reaction mixture was dried under vacuum to give a crude Compound. The crude was purified by prep chromatography to afford 7-chloro-11H-benzo[4,5]imidazo[2,1-a]isoindole (40 mg) as an off white solid.

Compound 522: LCMS—241.2 (M)$^+$ UPLC @ 254 nm=98.69% and @ 220 nm: 98.10%. $^1$H NMR (400 MHz, DMSO-$d_6$): δ 7.97 (d, J=4.89 Hz, 1H), 7.79 (br. s., 2H), 7.69 (d, J=8.31 Hz, 1H), 7.50-7.64 (m, 2H), 7.24 (d, J=9.29 Hz, 1H), 5.27 (s, 2H).

Compound 523

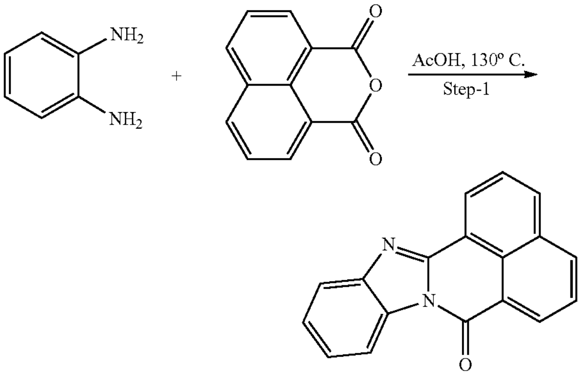

Compound-523

Step 1 was performed as described above for synthesis of Compound 362 (procedure 1)

Compound 523: LCMS—271.2 (M+H)$^+$ UPLC@ 254 nm=97.46% and @ 220 nm=99.46%. $^1$H NMR (400 MHz, DMSO-$d_6$): δ 8.78 (d, J=7.34 Hz, 1H), 8.74 (dd, J=0.98, 7.34 Hz, 1H), 8.56 (d, J=7.83 Hz, 1H), 8.47 (dd, J=2.93, 5.87 Hz, 1H), 8.41 (d, J=7.83 Hz, 1H), 7.91-7.99 (m, 2H), 7.89 (br. s., 1H), 7.44-7.54 (m, 2H).

Compound 524

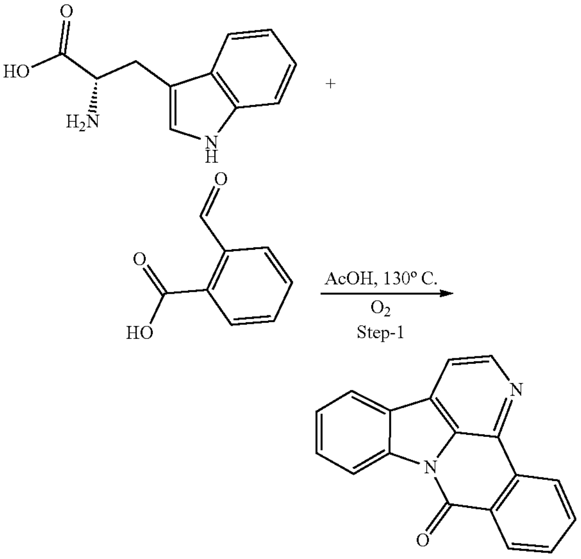

Compound-254

Step 1: L-tryptophan (1.0 g, 73.45 mmol) was dissolved in acetic acid (10.0 ml). This was followed by addition of 2-formylbenzoic acid (0.800 g, 80.80 mmol, 1.1 eq) to it. The resulting mixture was stirred at 130° C. for 16 hours. After this, the reaction mixture was stirred under oxygen at same temperature for another 16 hours. The progress of reaction was monitored by LCMS. After completion, the reaction mixture was poured in ice cold water (500.0 mL) which resulted in precipitation of a solid that was filtered, washed with water (500.0 mL) and dried under vacuum to afford 7H-benzo[de]benzo[4,5]imidazo[2,1-a]isoquinolin-7-one (1.1 g) as a yellow solid.

Compound 524: LCMS—271.2 $(M+H)^+$ UPLC@ 254 nm=98.70% and @ 220 nm=99.09%. $^1H$ NMR (400 MHz, DMSO-$d_6$): δ 8.89 (d, J=4.89 Hz, 1H), 8.78 (d, J=7.83 Hz, 1H), 8.68 (d, J=7.83 Hz, 1H), 8.55 (d, J=8.31 Hz, 1H), 8.44 (d, J=8.31 Hz, 1H), 8.33 (d, J=4.89 Hz, 1H), 8.04 (t, J=7.09 Hz, 1H), 7.79-7.89 (m, 2H), 7.64 (t, J=7.58 Hz, 1H).

Compound 525

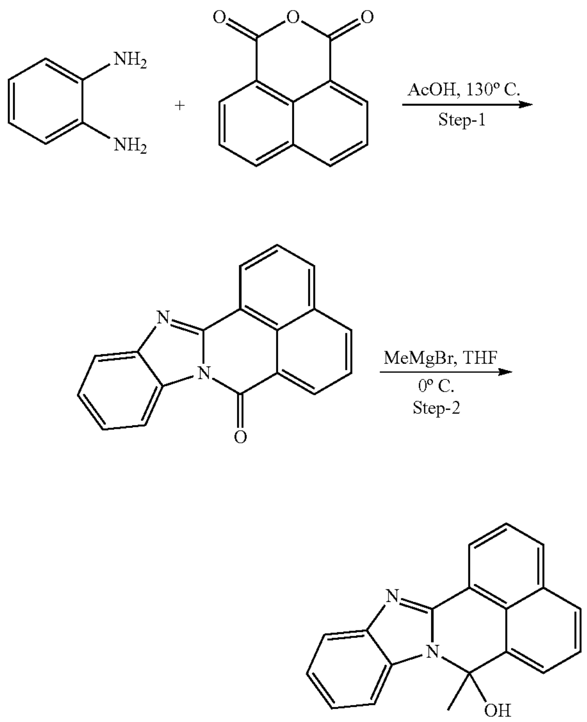

Compound-525

Step 1 was performed as described above for synthesis of Compound 362 (procedure 1).

Step 2: 7H-benzo[de]benzo[4,5]imidazo[2,1-a]isoquinolin-7-one (0.150 g, 0.55 mmol, 1.0 eq) was dissolved in THF (2.0 ml) and cooled to 0° C. This was followed by addition of methyl magnesium bromide (2M in THF, 1.4 ml, 2.78 mmol, 5.0 eq) to it. The resulting mixture was stirred at same temperature for one hour. The progress of reaction was monitored by LCMS. After completion, the reaction mixture was quenched with saturated solution of ammonium chloride and extracted with ethyl acetate. The organic layer was concentrated under vacuum to give crude product which was purified by column chromatography (0-60% EtOAc:Hexane as effluent), to afford 7-methyl-7H-benzo[de]benzo[4,5]imidazo[2,1-a]isoquinolin-7-ol (120 mg) as an off yellow solid.

Compound 525: LCMS—287.2 $(M+H)^+$ UPLC@ 254 nm=94.48% and @ 220 nm=95.05%. $^1H$ NMR (400 MHz, DMSO-$d_6$): δ 8.50 (d, J=6.85 Hz, 1H), 8.06-8.16 (m, 2H), 8.01 (s, 2H), 7.71-7.81 (m, 4H), 7.22-7.32 (m, 2H), 1.98 (s, 3H).

Compound 526

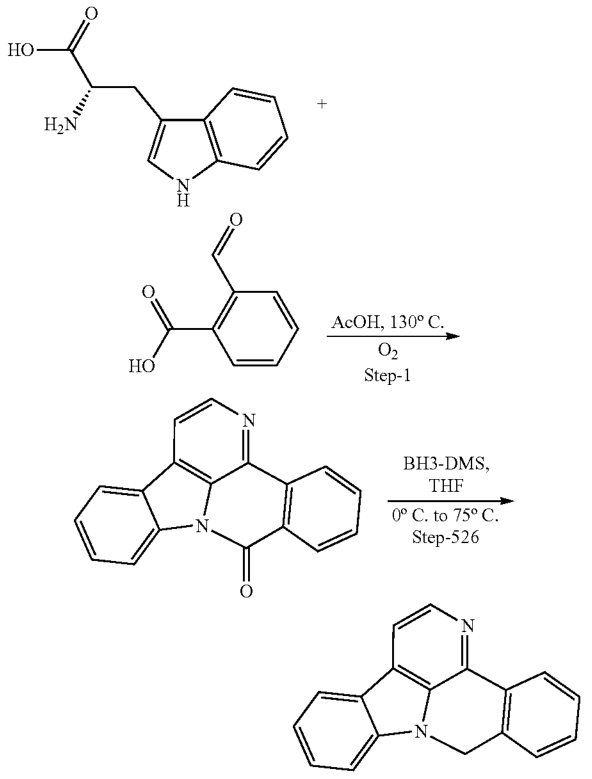

Compound-526

Step 1 was performed as described above for synthesis of Compound 524

Step 2 was performed as described above for synthesis of Compound 522

Compound 526: LCMS—257.2 $(M+H)^+$ UPLC:@ 254 nm=97.35% and @ 220 nm=98.52%.

$^1H$ NMR (400 MHz, DMSO-$d_6$): δ 8.38 (d, J=4.89 Hz, 1H), 8.23-8.34 (m, 2H), 7.96 (d, J=4.89 Hz, 1H), 7.61-7.72 (m, 2H), 7.49 (d, J=3.91 Hz, 3H), 7.35 (t, J=7.34 Hz, 1H), 5.77 (s, 2H).

Compound 527 and Compound 528

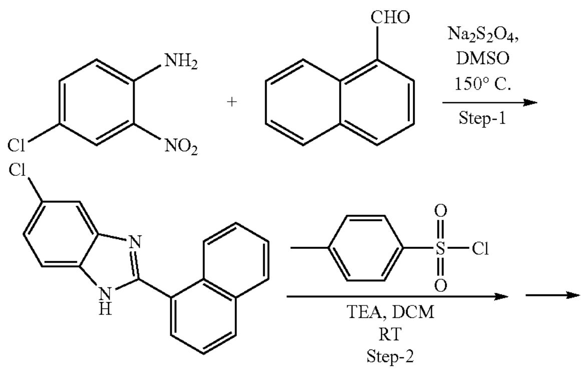

-continued

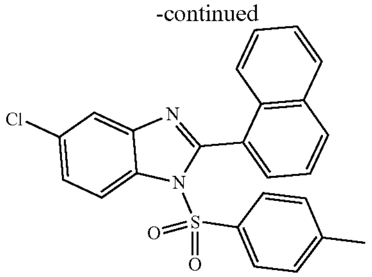

+

Isomer 1, Peak 1
Compound-527

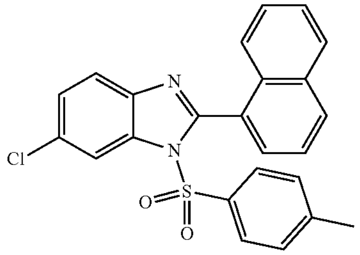

Isomer 2, Peak2
Compound-528

Step 1 was performed as described above for synthesis of Compound 429

Step 2: To a solution of 5-chloro-2-(naphthalen-1-yl)-1H-benzo[d]imidazole (100 mg, 0.3597 mmol) in DCM (7 mL) was added TEA (0.15 mL, 1.0791 mmol) and the resultant reaction mixture was stirred for 15 minutes followed by addition of 4-methylbenzenesulfonyl chloride (68 mg, 0.3597 mmol). The reaction was stirred overnight at room temperature. Reaction was monitored by TLC and LCMS. After completion of reaction mixture was diluted with DCM (100 mL) and washed with sodium bicarbonate solution (2×100 mL). The organic layer was separated and dried over sodium sulphate, concentrated under reduced pressure to yield crude product which was purified by flash chromatography (elution: 0-10% EtOAc in hexane) to afford first isomer (peak 1) 5-chloro-2-(naphthalen-1-yl)-1-tosyl-1H-benzo[d]imidazole (11.48 mg) as a yellow solid.

Compound 527: LCMS—433.1 $(M)^+$ UPLC @ 254 nm=96.11%, @ 220 nm=97.33%. $^1H$ NMR (Peak 1)-(400 MHz, DMSO-$d_6$) δ ppm 8.18 (d, J=8.80 Hz, 2H) 8.04 (d, J=8.31 Hz, 1H), 7.96 (d, J=1.96 Hz, 1H) 7.52-7.67 (m, 4H) 7.36 (br. s., 1H) 7.30 (m, J=8.31 Hz, 2H) 7.20 (d, J=8.31 Hz, 1H) 7.15 (m, J=8.31 Hz, 2H) 2.25 (s, 3H).

Flash chromatography also afforded the second isomer (Peak 2), 6-chloro-2-(naphthalen-1-yl)-1-tosyl-1H-benzo[d]imidazole (8.16 mg, 5.26%) as a yellow solid.

Compound 528: LCMS—433.2$(M)^+$ UPLC @ 254 nm=96.94%, @ 220 nm=96.27%. $^1H$ NMR (Peak 2) (400 MHz, DMSO-$d_6$) δ ppm 8.15-8.21 (m, 2H) 8.02 (d, J=8.31 Hz, 1H) 7.87 (d, J=8.31 Hz, 1H) 7.61-7.68 (m, 2H) 7.51-7.59 (m, 2H) 7.26-7.37 (m, 3H) 7.08-7.18 (m, 3H) 2.24 (s, 3H).

Compound 529 and Compound 530

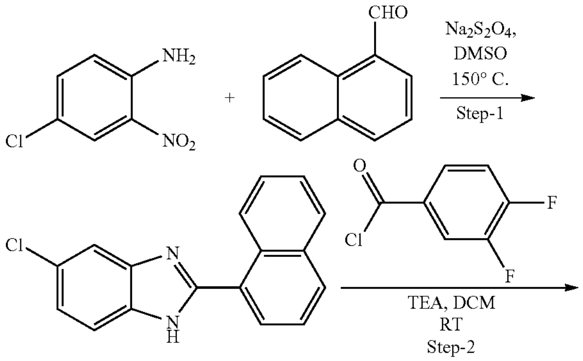

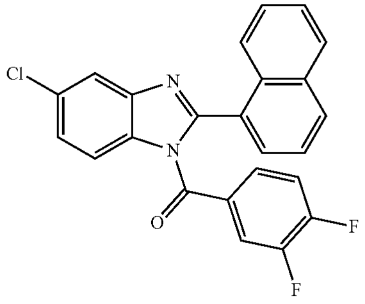

+

Isomer 1, Peak 1
Compound-529

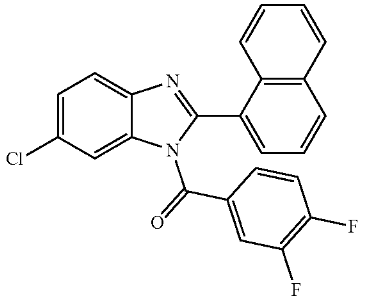

Isomer 2, Peak2
Compound-530

Steps 1 and 2 were performed as described above for synthesis of Compounds 429 and 490

Compound 529: LCMS—419.2 $(M)^+$ UPLC @ 254 nm=99.35%, @ 220 nm=99.03%. $^1H$ NMR (Peak 1) (400 MHz, DMSO-$d_6$) δ ppm 8.03 (d, J=1.96 Hz, 1H) 7.92 (d, J=7.34 Hz, 4H) 7.81 (d, J=8.80 Hz, 1H) 7.64 (s, 1H) 7.50-7.60 (m, 5H) 7.42 (s, 1H).

Compound 530: LCMS—419.1$(M)^+$ UPLC @ 254 nm=98.81%, @ 220 nm=97.93%. $^1H$ NMR (DMSO-$d_6$) δ ppm 1.23 (br. s., 3H), 7.40 (br. s., 2H), 7.56 (d, 3H), 7.63 (d, 2H), 7.85-7.98 (m, 3H).

Compound 533 and Compound 534

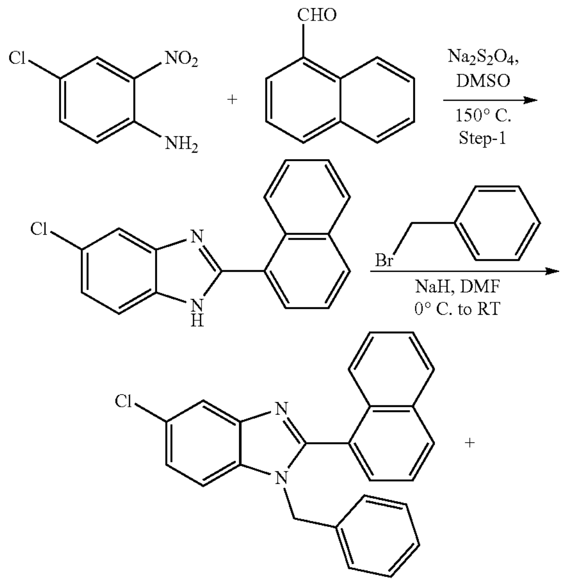

Isomer 1, Peak 1
Compound-533

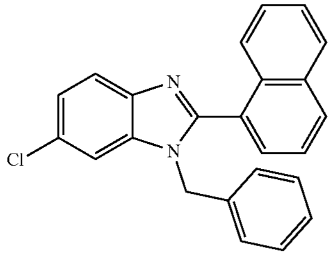

Isomer 2, Peak2
Compound-534

Step 1 was performed as described above for synthesis of Compound 429

Step 2: To an ice-cold solution of 5-chloro-2-(naphthalen-1-yl)-1H-benzimidazole (0.300 g, 1.07 mmol) in DMF (5 mL), sodium hydride (0.065 g, 1.61 mmol) was added. After five minutes of stirring, (bromomethyl)benzene (0.15 mL, 1.18 mmol) was added and the reaction mixture was stirred at room temperature for two hours. After completion of reaction, the reaction mixture was quenched with ice, extracted with ethyl acetate (50 mL×2). The combined organic layer was washed with water (50 mL), brine solution (50 mL), dried over anhydrous sodium sulfate and concentrated under reduced pressure to afford crude product, which was purified by flash chromatography (elution: 0-10% EtOAc in hexane) to afford the (Peak 1), 1-benzyl-5-chloro-2-(naphthalen-1-yl)-1H-benzimidazole (10 mg) as a white solid.

Compound 533: LCMS—369.3 $(M)^+$ UPLC @ 254 nm=95.31% and @ 220 nm=97.23%. Peak 1: $^1$H NMR (400 MHz, DMSO-$d_6$) δ ppm 8.05 (s, 1H) 7.86 (d, J=1.96 Hz, 1H) 7.67-7.74 (m, 3H) 7.64 (s, 1H) 7.58 (d, J=8.80 Hz, 3H) 7.10-7.20 (m, 4H) 6.80-6.88 (m, 2H) 5.34 (s, 2H).

Flash chromatography also afforded the second isomer (Peak 2) 1-benzyl-5-chloro-2-(naphthalen-1-yl)-1H-benzimidazole (15 mg, 3.7%) as a white solid.

Compound 534: LCMS—369.3 $(M)^+$ UPLC @ 254 nm=97.12% and @ 220 nm=96.80%. Peak 2: $^1$H NMR (400 MHz, DMSO-$d_6$) δ ppm 8.15 (d, J=8.31 Hz, 1H) 8.06 (d, J=7.83 Hz, 1H) 7.80 (d, J=8.31 Hz, 1H) 7.64-7.74 (m, 3H) 7.59 (d, J=6.85 Hz, 1H) 7.63 (d, J=7.34 Hz, 1H) 7.53 (d, J=8.31 Hz, 1H) 7.33 (dd, J=8.80, 1.96 Hz, 1H) 7.11-7.20 (m, 3H) 6.81-6.88 (m, 2H) 5.34 (s, 2H).

Compound 535 and Compound 536

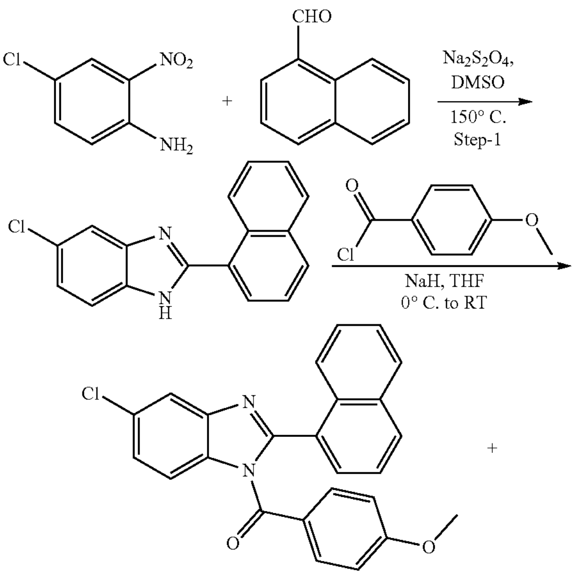

Isomer 1, Peak 1
Compound-535

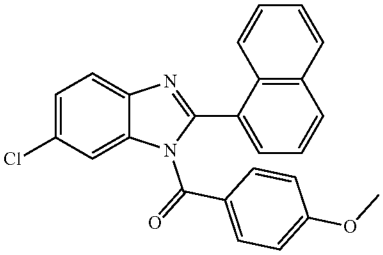

Isomer 2, Peak2
Compound-536

Step 1 was performed as described above for synthesis of Compound 429

Step 2: To an ice-cold solution of 5-chloro-2-(naphthalen-1-yl)-1H-benzimidazole (0.100 g, 0.35 mmol, 1.0 eq) in THF (5 mL), sodium hydride (0.021 g, 0.53 mmol, 1.5 eq) was added. After five minutes of stirring, 4-methoxybenzoyl chloride (0.05 mL, 0.39 mmol, 1.1 eq) was added and the reaction mixture was stirred at room temperature for two hours. After completion of reaction, the reaction mixture was quenched with ice, diluted with water and extracted with ethyl acetate (50 mL×2). The combined organic layer was washed with water (50 mL), brine solution (50 mL), dried over anhydrous sodium sulfate and concentrated under reduced pressure to afford crude product, which was purified by flash chromatography (elution: 0-10% EtOAc in hexane) to afford the desired isomer 1 (Peak 1), (5-chloro-2-(naphthalen-1-yl)-1H-benzo[d]imidazol-1-yl)(4-methoxyphenyl) methanone (10 mg) as a white solid.

Compound 535: LCMS—413.2 $(M)^+$ UPLC @ 254 nm=93.31% and @ 220 nm 98.38%. Peak 1: $^1H$ NMR (400 MHz, DMSO-$d_6$) d δ ppm 8.01 (s, 1H), 7.95 (d, J=7.34 Hz, 2H), 7.61 (d, J=8.80 Hz, 2H), 7.53-7.59 (m, 3H), 7.43 (s, 4H), 6.75 (d, J=8.31 Hz, 2H), 3.72 (s, 3H).

Flash chromatography also afforded the second isomer (Peak 2) (6-chloro-2-(naphthalen-1-yl)-1H-benzo[d]imidazol-1-yl)(4-methoxyphenyl)methanone (10 mg) as a white solid.

Compound 536: LCMS—413.2 $(M)^+$ UPLC @ 254 nm=98.48% and @ 220 nm=97.90%. Peak 2: $^1H$ NMR (400 MHz, DMSO-$d_6$) δ ppm 7.93 (d, J=8.80 Hz, 3H), 7.51-7.64 (m, 6H), 7.49 (br.s., 3H), 6.71 (d, J=8.80 Hz, 2H), 3.71 (s, 3H).

Compound 579

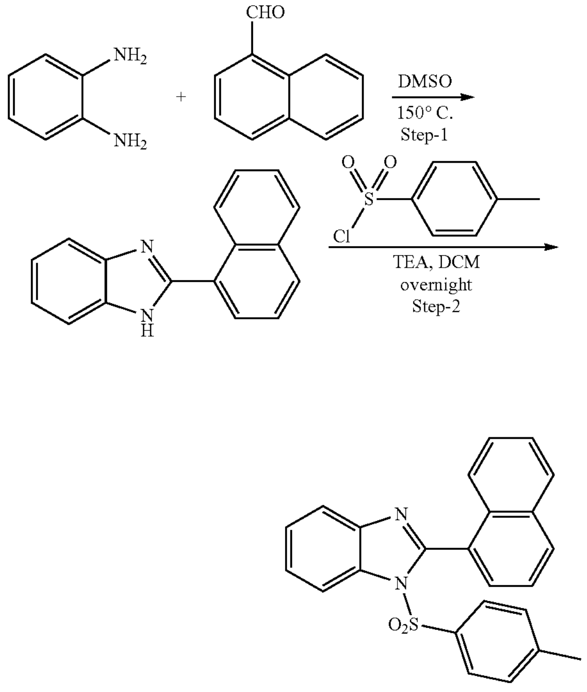

Compound-579

Step 1: To a solution of benzene-1,2-diamine (5 g, 46.236 mmol) in DMSO (20 mL), benzaldehyde (7.94 g, 50.859 mmol) was added and the reaction mixture was heated at 150° C. for 3 h. After completion of reaction, solution was diluted with water which resulted in precipitation of a solid which was filtered washed with ether and dried to give the desired product as 2-(naphthalen-1-yl)-1H-benzo[d]imidazole (6 g) as a yellow solid. LCMS: 245.2 $(M+H)^+$ Step 2: was performed as described above for synthesis of Compound 527

Compound 579: LCMS—399.1 $(M+H)^+$ UPLC @ 254 nm=99.43%, @ 220 nm=99.07%. $^1H$ NMR (400 MHz, DMSO-d6) δ 8.17 (t, J=8.1 Hz, 2H), 8.04 (d, J=8.2 Hz, 1H), 7.83 (d, J=7.8 Hz, 1H), 7.71-7.60 (m, 2H), 7.52 (dt, J=24.9, 7.3 Hz, 3H), 7.43-7.31 (m, 3H), 7.24 (d, J=8.5 Hz, 1H), 7.17 (d, J=8.1 Hz, 2H), 2.25 (s, 3H).

Compound 580 and Compound 581

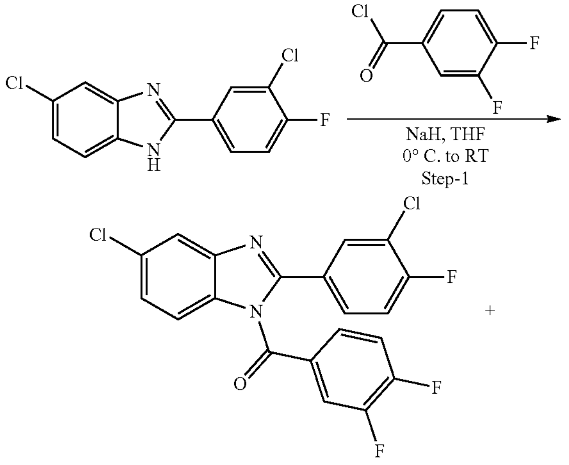

Isomer 1, Peak1
Compound 580

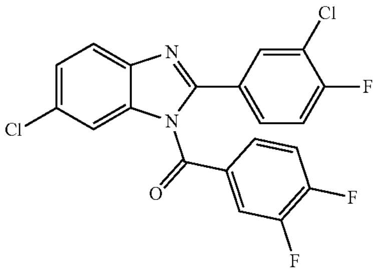

Isomer 2, Peak2
Compound 581

Step 1 was performed as described above for step 2 of synthesis of Compound 535

Compound 580: LCMS—421.2 $(M)^+$ UPLC @ 254 nm=98.71%, @ 220 nm=96.63%. $^1H$ NMR—(400 MHz, DMSO-$d_6$) δ ppm 7.42 (s, 1H) 7.44-7.48 (m, 2H) 7.52 (br. s., 1H) 7.61 (d, J=8.77 Hz, 2H) 7.83 (d, J=6.58 Hz, 1H) 7.91 (br. s., 1H) 7.96 (d, J=2.19 Hz, 1H).

Compound 581: LCMS—421.2 $(M)^+$ UPLC @ 254 nm=97.97%, @ 220 nm=95.09%. Peak 2: $^1H$ NMR (400 MHz, DMSO-$d_6$) δ ppm 7.47 (s, 1H) 7.50 (d, J=2.19 Hz, 1H) 7.52 (d, J=2.19 Hz, 1H) 7.57-7.62 (m, 2H) 7.72 (d, J=2.19 Hz, 1H) 7.80 (dd, J=7.45, 2.19 Hz, 1H) 7.88 (s, 1H) 7.89-7.91 (m, 1H).

Compound 582

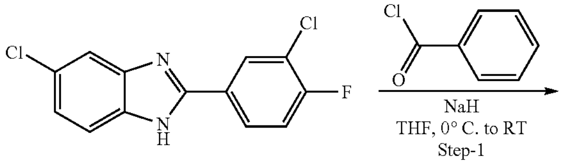

-continued

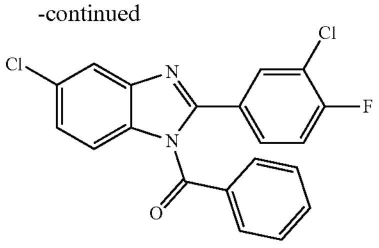

Isomer1, Peak 1
Compound 582

Step 1 was performed as described above for step 2 of synthesis of Compound 535

Compound 582: LCMS—385.1 $(M)^+$ UPLC @ 254 nm=97.91%, @ 220 nm=96.50% $^1H$ NMR (400 MHz, DMSO-$d_6$) δ ppm 7.41-7.46 (m, 4H) 7.49-7.53 (m, 2H) 7.60 (d, J=7.45 Hz, 2H) 7.72 (d, J=7.02 Hz, 2H) 7.96 (d, J=1.75 Hz, 1H).

Compound 583

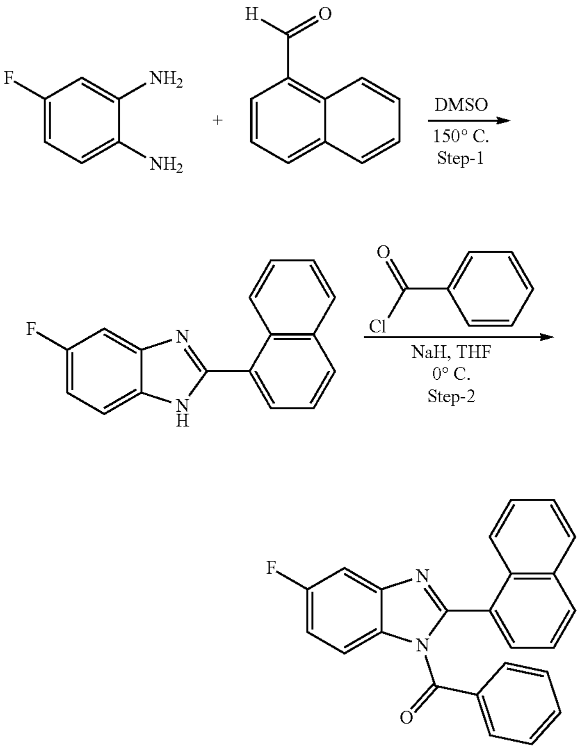

Isomer1, peak 1
Compound 583

Step 1 was performed as described above for step 1 of synthesis of Compound 579

Step 2 was performed as described above for step 2 of synthesis of Compound 535 Compound 583: LCMS—367.2 $(M+H)^+$ UPLC @ 254 nm=98.18%, @ 220 nm=96.19%. $^1H$ NMR (DMSO-$d_6$) δ ppm 7.09 (t, 2H) 7.31-7.38 (m, 2H) 7.40 (d, 1H) 7.48-7.52 (m, 2H) 7.53-7.58 (m, 2H) 7.59-7.64 (m, 2H) 7.78 (dd, 1H) 7.85-7.91 (m, 2H) 8.03 (d, 1H).

Compound 584 and Compound 585

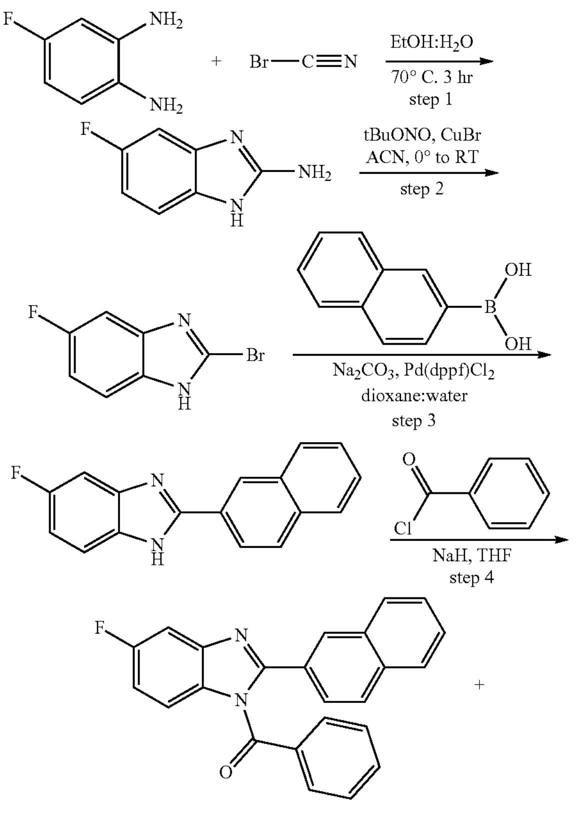

Isomer 1, Peak 1
Compound 584

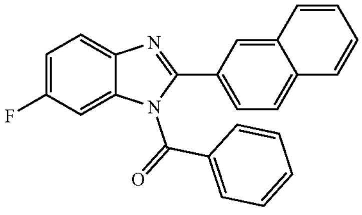

Isomer 2, Peak2
Compound 585

Step 1: A solution 4-fluorobenzene-1,2-diamine (3 g, 23.8 mmol) and cyanogen bromide (3.74 g, 35.7 mmol) in EtOH: $H_2O$ (10:10 mL) was heated at 70° C. for 3 h. After completion of reaction, the reaction mixture was concentrated under reduced pressure to remove ethanol and water and after lypholisation it afforded 5-fluoro-1H-benzo[d]imidazol-2-amine (3.25 g) as a brown solid. LCMS: 152.1 $(M+H)^+$ Step 2: To a solution 5-fluoro-1H-benzo[d]imidazol-2-amine (2 g, 13.2 mmol) in ACN (20 mL) was added $CuBr_2$(4.43 g, 19.8 mmol) at 0° C. portionwise and the reaction mixture was stirred for 15 minutes followed by addition of tertiarybutyl nitrite (2.37 mL 19.8 mmol) dropwise at 0° C. The reaction mixture was allowed to stir at room temperature for 2 hours. After completion of reaction, the reaction mixture was diluted with water and extracted with ethyl acetate (250 mL×2). The combined organic layer was washed with water (100 mL), brine solution (100 mL), dried over anhydrous sodium sulfate and concentrated under vacuum to afford the crude product, which was purified by flash chromatography (elution 0-30% EtOAc in hexane) to afford the 2-bromo-5-fluoro-1H-benzo[d]imidazole (0.6 g) as a yellow solid. LCMS—215.2 $(M+H)^+$ Step 3: To a solution of 2-bromo-5-fluoro-1H-benzo[d]imidazole (0.2 g, 0.9 mmol) and naphthalen-2-ylboronic acid (0.241 g, 1.4 mmol) in dioxane (5 mL) was added $Na_2CO_3$ (0.297 g, 2.8 mmol) which was dissolved in water (1 mL). Then the reaction mixture was purged using nitrogen for 20 minutes followed by addition of $Pd(dppf)Cl_2$ (0.034 g, 0.0467 mmol). The resulting reaction mixture was heated for 120° C. for overnight. Progress of the reaction was monitored by TLC and LCMS. After completion of reaction the reaction mixture was diluted with water and extracted with ethyl acetate (150 mL×2). The combined organic layer was washed with water (70 mL), brine solution (70 mL), dried over anhydrous sodium sulfate and concentrated under vacuum to afford the crude product, which was purified by flash chromatography (elution: 0-30% EtOAc in hexane) to afford the 5-fluoro-2-(naphthalen-2-yl)-1H-benzo[d]imidazole (0.150 g) as a white solid. LCMS—263.2 $(M+H)^+$ Step 4 was performed as described above for step 2 of synthesis of Compound Compound 535.

Compound 584: LCMS—367.3 $(M+H)^+$ UPLC @ 254 nm=93.73%, @ 220 nm=97.13%. $^1H$ NMR (400 MHz, DMSO-$d_6$) δ ppm 7.23-7.30 (m, 1H), 7.33 (t, J=7.67 Hz, 2H), 7.47 (dd, J=8.77, 4.82 Hz, 2H), 7.51-7.58 (m, 2H), 7.67-7.77 (m, 4H), 7.83-7.90 (m, 2H), 7.94 (d, J=7.89 Hz, 1H), 8.18 (s, 1H).

Compound 585: LCMS—367.1 $(M+H)^+$ UPLC @ 254 nm=98.78%, @ 220 nm=98.36%. $^1H$ NMR (400 MHz, DMSO-$d_6$) δ ppm 7.32 (t, J=7.89 Hz, 3H) 7.53 (s, 2H) 7.66-7.76 (m, 3H) 7.83 (s, 2H) 7.92 (s, 4H) 8.16 (s, 1H).

Compound 586 and Compound 587

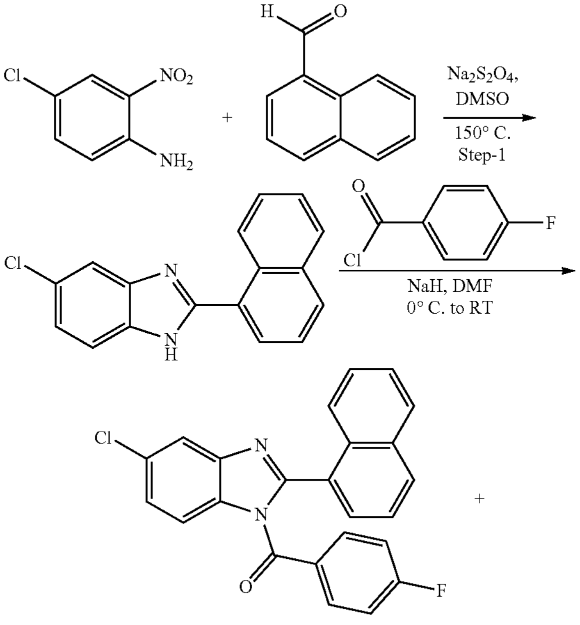

Peak1, Isomer 1
Compound-586

-continued

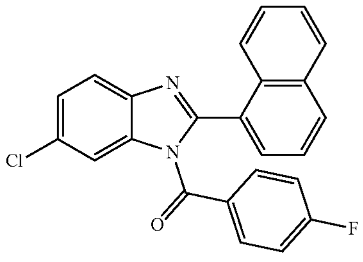

Peak 2, Isomer 2
Compound-587

Step 1 was performed as described above for step 1 of synthesis of Compound 429

Compound 586: LCMS—401.2 $(M)^+$ UPLC @ 254 nm=99.12% and @ 220 nm 97.31%. $^1H$ NMR (400 MHz, DMSO-$d_6$) δ ppm 8.02 (d, J=2.19 Hz, 1H) 7.89-7.99 (m, 3H) 7.62-7.68 (m, 2H) 7.50-7.62 (m, 4H) 7.49 (d, J=1.75 Hz, 1H) 7.43 (d, J=7.89 Hz, 1H) 6.90 (t, J=8.99 Hz, 2H)

Compound 587: LCMS—401.2 $(M)^+$ UPLC @ 254 nm=98.21% and @ 220 nm=97.84%. $^1H$ NMR (400 MHz, DMSO-$d_6$) δ ppm 7.86-7.98 (m, 4H) 7.72 (d, J=1.75 Hz, 1 H) 7.63 (d, J=6.58 Hz, 1H) 7.51-7.59 (m, 5H) 7.41 (t, J=7.67 Hz, 1H) 6.86 (t, J=8.77 Hz, 2H).

Compound 588

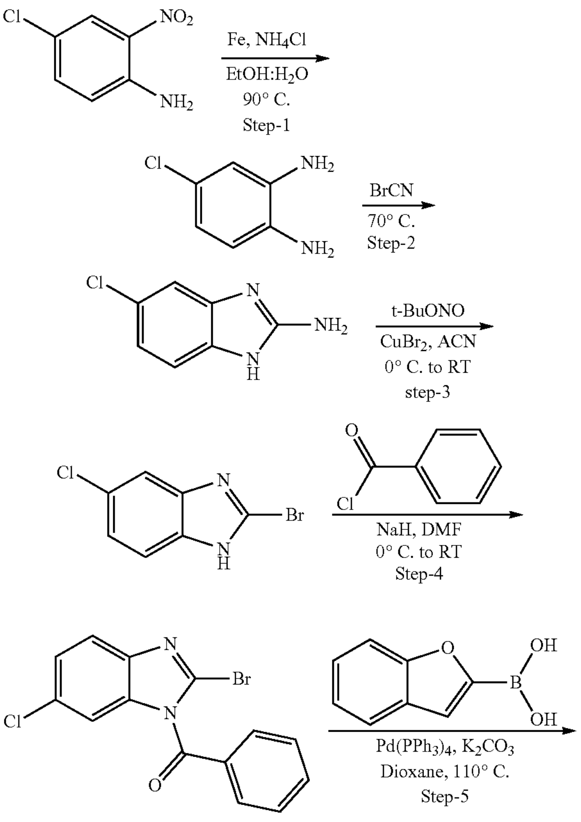

Peak 2, Isomer 2

-continued

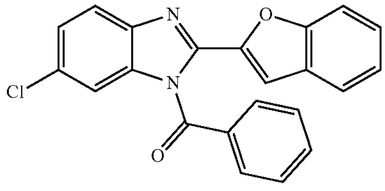

Compound-588

Step 1: To a solution of 4-chloro-2-nitro aniline (5.0 g, 28.9 mmol) and ammonium chloride (15.4 g, 289.9 mmol) in ethanol (50.0 mL) and water (50.0 mL) iron powder (12.9 g, 231.8 mmol) was added and reaction mixture was stirred at 90° C. for one hour. After completion of reaction, the reaction mixture was dried under vacuum to get crude product. The crude Compound was washed with ether and organic layer was concentrated to yield 4-chlorobenzene-1, 2-diamine (4.0 g) as a brown solid. LCMS: 143.0 $(M)^+$ Steps 2-5 were performed as described for steps 1-4 of synthesis of Compound 584

Compound 588: LCMS—373.1 $(M)^+$ UPLC @ 254 nm=97.27% and @ 220 nm 94.14%. $^1$H NMR (400 MHz, DMSO-d6) δ 7.92 (d, J=8.4 Hz, 1H), 7.82 (d, J=7.5 Hz, 2H), 7.67 (d, J=7.7 Hz, 1H), 7.60 (s, 1H), 7.56 (t, J=7.5 Hz, 1H), 7.53-7.47 (m, 2H), 7.43 (t, J=7.6 Hz, 2H), 7.38 (d, J=8.2 Hz, 1H), 7.33 (t, J=7.6 Hz, 1H), 7.26 (t, J=7.4 Hz, 1H).

Compound 590 and Compound 591

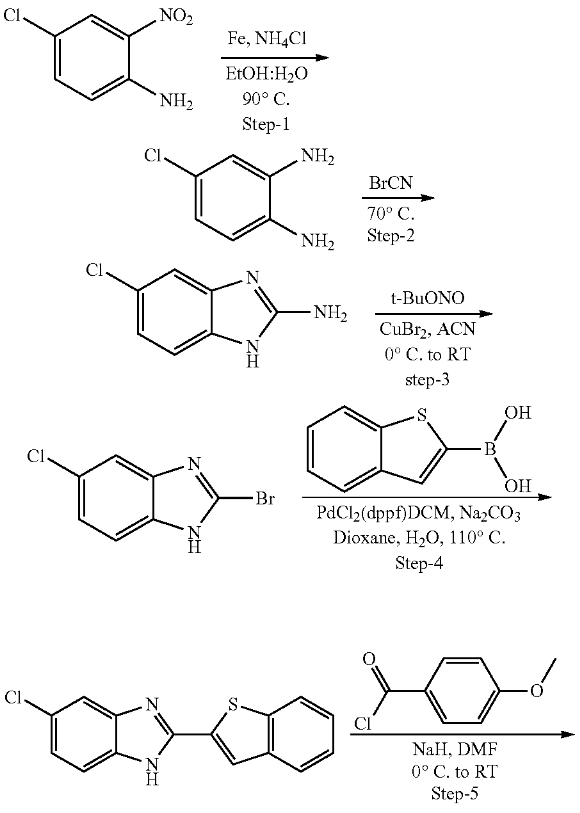

-continued

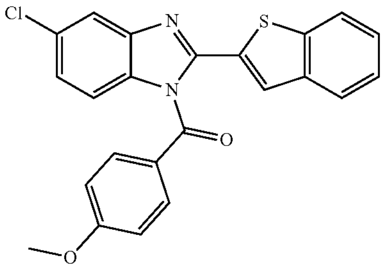

+

Isomer 1, Peak 1
Compound-590

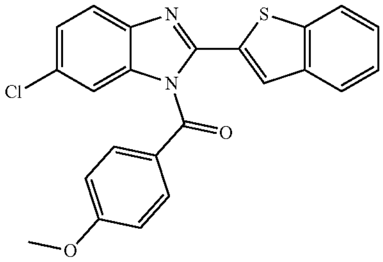

Isomer 2, Peak2
Compound-591

Steps 1-4 were performed as described for steps 1-4 of synthesis of Compound 588

Compound 590: LCMS—419.2 $(M)^+$ UPLC @ 254 nm=99.01% and @ 220 nm 99.96%. $^1$H NMR (400 MHz, DMSO-$d_6$) δ ppm 8.03 (d, J=8.33 Hz, 2H) 7.96 (d, J=1.75 Hz, 1H) 7.85-7.91 (m, 2H) 7.69 (s, 1H) 7.34 (s, 3H) 7.15 (s, 1H) 7.09 (s, 2H) 3.84 (s, 3H)

Compound 591: LCMS—419.3 $(M)^+$ UPLC @ 254 nm=96.73% and @ 220 nm=96.26%. $^1$H NMR (400 MHz, DMSO-d6) δ 8.02 (d, J=7.9 Hz, 1H), 7.87 (td, J=9.0, 5.5 Hz, 4H), 7.65 (s, 1H), 7.52-7.34 (m, 3H), 7.19 (d, J=2.0 Hz, 1H), 7.16-7.03 (m, 2H), 3.84 (s, 3H).

Compound 630

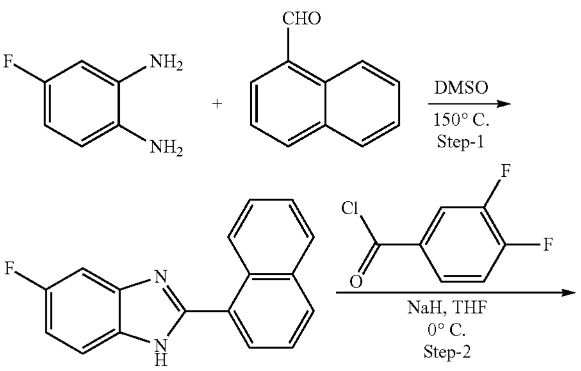

-continued

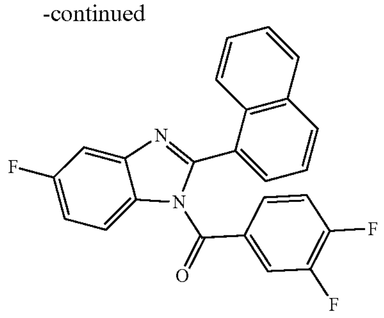

Isomerl, peak 1
Compound-630

Step 1 was performed as described for synthesis of Compound 535

Compound 630: LCMS 403.2 $(M+H)^+$ UPLC @ 254 nm=98.30%, @ 220 nm=96.71%. $^1H$ NMR (400 MHz, DMSO-$d_6$) δ ppm 7.02-7.11 (m, 1H) 7.29-7.39 (m, 2H) 7.39-7.45 (m, 1H) 7.53-7.61 (m, 3H) 7.64 (d, 1H) 7.79 (dd, 1H) 7.84 (dd, 1H) 7.88-7.95 (m, 3H).

Compound 631

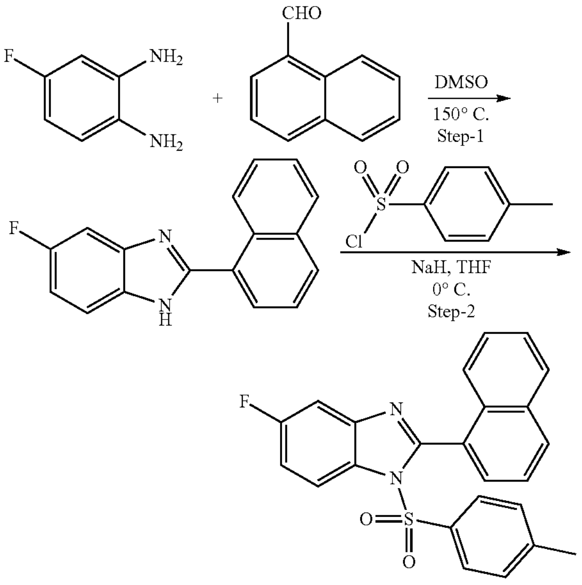

Isomerl, peak 1
Compound-631

Step 1 was performed as described for synthesis of Compound 579

Step 2: To a solution of 5-fluoro-2-(naphthalen-1-yl)-1H-benzo[d]imidazole (0.2 g, 0.7633 mmol) in THF (5 mL) was added NaH (0.045 g, 1.1449 mmol) at 0° C. and the reaction mixture was stirred for 15 minute followed by addition of 4-methylbenzenesulfonyl chloride (0.145 g, 0.7633 mmol). The reaction mixture was stirred for 3 hours at room temperature. After completion of reaction, the reaction mixture was diluted with water and extracted with ethyl acetate (50 mL×2). The combined organic layer was washed with water (50 mL), brine solution (50 mL), dried over anhydrous sodium sulfate and concentrated under vacuum to afford the crude product, which was purified by flash chromatography (elution 0-10% EtOAc in hexane) to afford the peak 1 as isomer 5-fluoro-2-(naphthalen-1-yl)-1-tosyl-1H-benzo[d]imidazole (0.016 g) as a brown solid.

Compound 631: LCMS—417.1 $(M+H)^+$ UPLC @ 254 nm=94.24%, @ 220 nm=90.24%. $^1H$ NMR (400 MHz, DMSO-$d_6$) δ 8.18 (dd, J=8.8, 5.0 Hz, 2H), 8.04 (d, J=8.3 Hz, 1H), 7.75-7.61 (m, 3H), 7.55 (t, J=7.6 Hz, 1H), 7.43 (td, J=9.3, 2.6 Hz, 1H), 7.37 (t, J=7.6 Hz, 1H), 7.31 (d, J=8.0 Hz, 2H), 7.22 (d, J=8.5 Hz, 1H), 7.15 (d, J=8.1 Hz, 2H), 2.25 (s, 3H).

Compound 632 and Compound 633

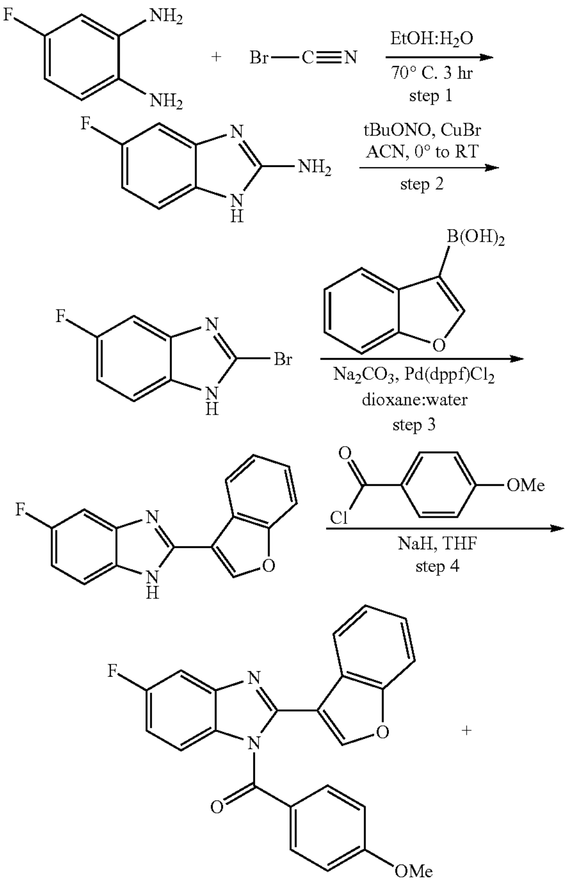

Isomer 1, Peak 1
Compound 632

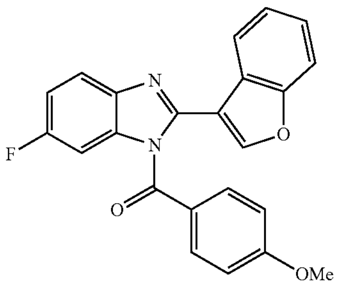

Isomer 2, Peak 2
Compound 633

Steps 1-4 were performed as described for steps 1-4 of synthesis of Compound 584

Compound 632: LCMS—387.3$(M+H)^+$ UPLC @ 254 nm=90.07%, @ 220 nm=94.62%.'H NMR (DMSO-$d_6$) δ ppm 3.79 (s, 3H) 7.03 (m, 2H) 7.29-7.32 (m, 2H) 7.33-7.39 (m, 2H) 7.45 (d, 1H) 7.61 (s, 1H) 7.70-7.75 (m, 2H) 7.84 (m, 2H)

Compound 633: LCMS—387.3 $(M+H)^+$ UPLC @ 254 nm=88.75%, @ 220 nm=96.99%.'H NMR (DMSO-$d_6$) δ ppm 3.78 (s, 3H) 7.02 (d, 2H) 7.13 (s, 1H) 7.24-7.40 (m, 3H) 7.56 (s, 2H) 7.71 (d, 2H) 7.82 (d, 2H).

Compound 634 and Compound 635

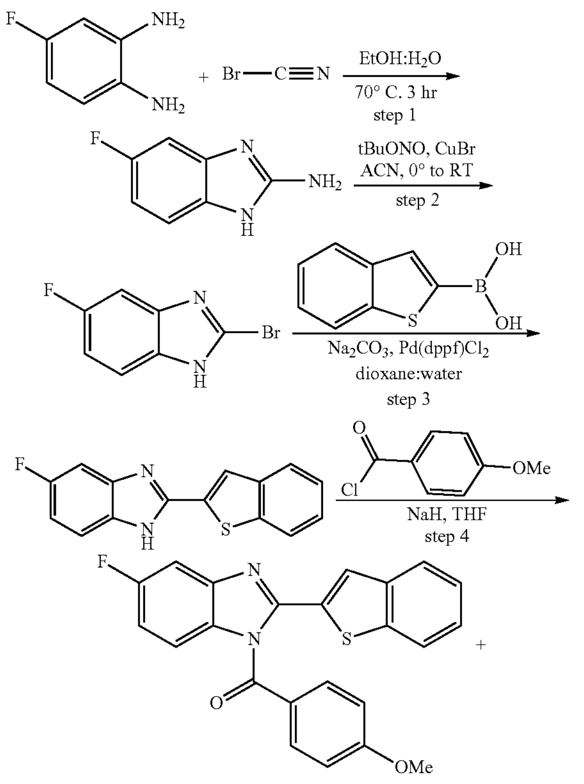

Isomer 1, Peak 1
Compound 634

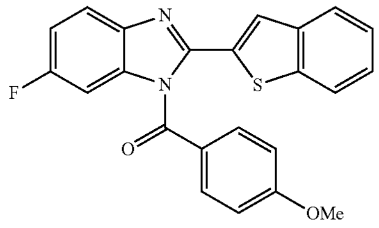

Isomer 2, Peak 2
Compound 635

Steps 1-4 were performed as described for steps 1-4 of synthesis of Compound 584

Compound 634: LCMS—403.2 $(M+H)^+$ UPLC @ 254 nm=98.36%, @ 220 nm=99.04%. $^1$H NMR (400 MHz, DMSO-$d_6$) δ ppm 8.02 (d, J=7.89 Hz, 1H) 7.84-7.91 (m, 3H) 7.66-7.74 (m, 2H) 7.36-7.47 (m, 2H) 7.07-7.21 (m, 4H) 3.84 (s, 3H)

Compound 635: LCMS—403.2 $(M+H)^+$ UPLC @ 254 nm=98.65%, @ 220 nm=98.48%. $^1$H NMR (400 MHz, DMSO-$d_6$) δ ppm 8.01 (d, J=7.89 Hz, 1H) 7.81-7.93 (m, 4H) 7.63 (s, 1H) 7.34-7.49 (m, 2H) 7.27 (td, J=9.32, 2.41 Hz, 1H) 7.09 (d, J=8.77 Hz, 2H) 6.96 (dd, J=9.21, 2.63 Hz, 1H) 3.84 (s, 3H).

Compound 636 and Compound 637

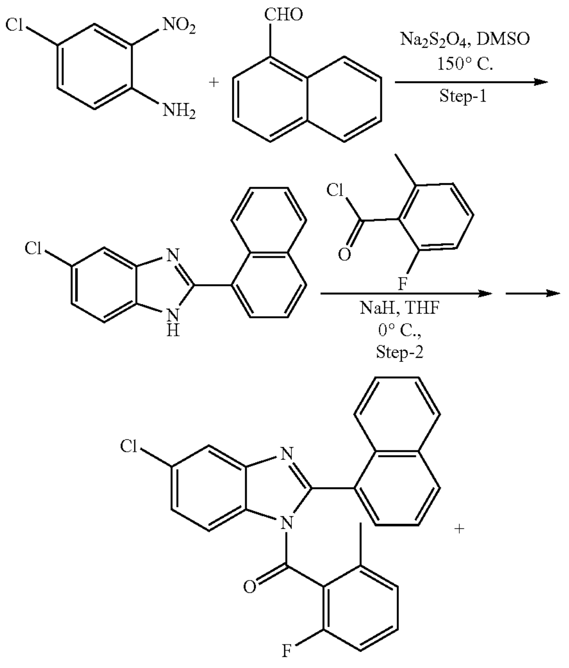

Isomer 1, Peak1
Compound 636

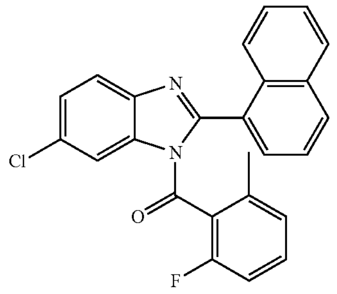

Isomer 2, Peak 2
Compound 637

Steps 1 and 2 were performed as described for synthesis of Compound 429

Compound 636: LCMS—415.2$(M)^+$ UPLC @ 254 nm=99.88%, @ 220 nm=99.93%. $^1$H NMR (400 MHz, DMSO-$d_6$) δ ppm 8.11 (d, J=8.77 Hz, 1H) 8.03 (d, J=1.75 Hz, 1H) 7.81-7.89 (m, 2H) 7.73 (br. s., 1H) 7.65 (d, J=7.02 Hz, 1H) 7.61 (dd, J=8.77, 2.19 Hz, 1H) 7.50-7.56 (m, 2H) 7.34-7.40 (m, 1H) 6.90 (br. s., 1H) 6.61 (br. s., 1H), 6.39 (s, 1H), 2.04 (br. s., 3H)

Compound 637: LCMS—415.2$(M)^+$ UPLC @ 254 nm=99.87%, @ 220 nm=99.93%. $^1$H NMR (400 MHz, DMSO-d6) δ 8.12 (d, J=2.1 Hz, 1H), 7.95 (d, J=8.5 Hz, 1H), 7.90-7.80 (m, 2H), 7.74 (s, 1H), 7.68-7.56 (m, 2H), 7.56-7.47 (m, 2H), 7.36 (t, J=7.7 Hz, 1H), 6.91 (q, J=7.5 Hz, 1H), 6.61 (s, 1H), 6.40 (s, 1H), 2.14-1.91 (m, 3H).

Compound 638

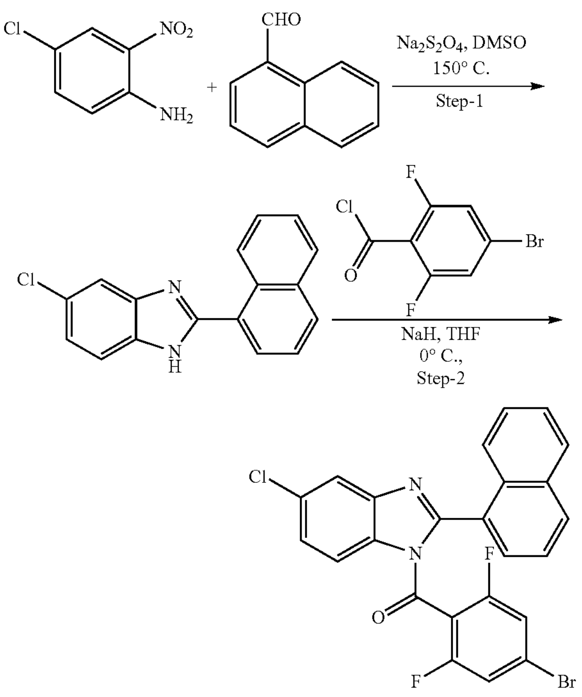

Isomer1, peak 1
Compound-638

Steps 1 and 2 were performed as described for synthesis of Compound 535

LCMS—497.2 $(M)^+$ UPLC @ 254 nm=98.37%, @ 220 nm=98.25%. $^1H$ NMR (400 MHz, DMSO-d6) δ 8.16 (d, J=8.7 Hz, 1H), 8.04 (d, J=2.1 Hz, 1H), 7.90 (dd, J=12.1, 7.2 Hz, 2H), 7.72 (q, J=4.8, 3.9 Hz, 1H), 7.67 (d, J=7.1 Hz, 1H), 7.61 (dd, J=8.7, 2.1 Hz, 1H), 7.56(dt, J=6.3, 3.8 Hz, 2H), 7.44 (t, J=7.7 Hz, 1H), 7.37 (t, J=7.1 Hz, 1H), 7.16 (dd, J=8.8, 5.3 Hz, 1H).

Compound 639

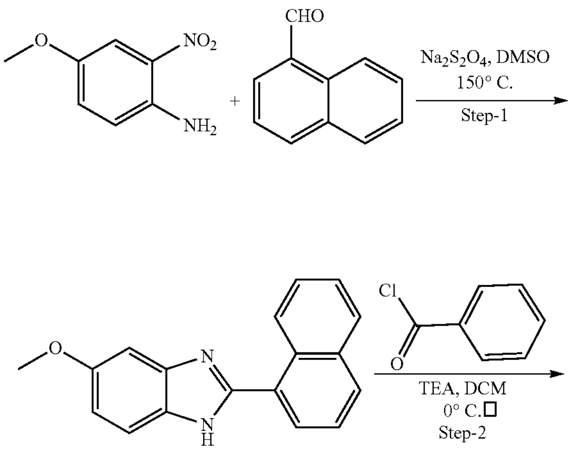

-continued

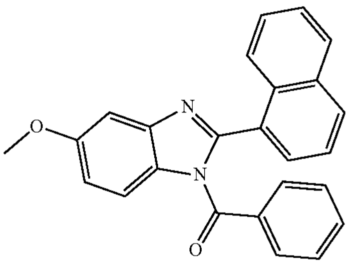

Isomer1, peak 1
Compound-639

Steps 1 and 2 were performed as described for synthesis of Compound 535

Compound 639: LCMS—379.3 $(M+H)^+$ UPLC @ 254 nm=97.63%, @ 220 nm=94.51% $^1H$ NMR (400 MHz, DMSO-d6) δ 8.08-8.00 (m, 1H), 7.91-7.77 (m, 3H), 7.60-7.49 (m, 3H), 7.47 (d, J=7.5 Hz, 2H), 7.38 (t, J=7.7 Hz, 1H), 7.32 (t, J=7.5 Hz, 1H), 7.15-7.04 (m, 4H), 3.78 (s, 3H).

Compound 640

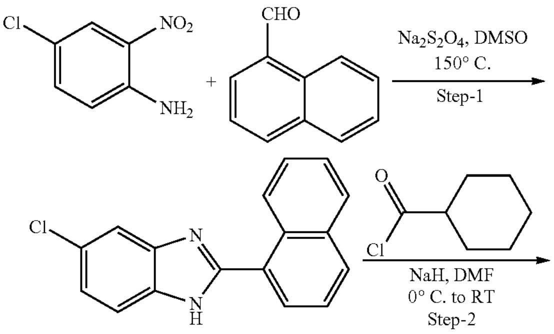

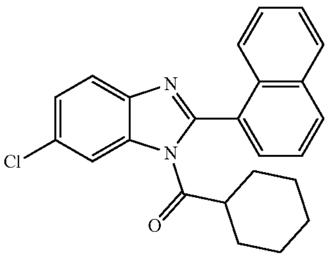

Isomer 2, Peak 2
Compound-640

Steps 1 and 2 were performed as described for synthesis of Compound 535

Compound 640: LCMS—389.3 $((M)^+$ UPLC @ 254 nm=98.16% and @ 220 nm 97.23%. $^1H$ NMR (400 MHz, DMSO-$d_6$) δ ppm 8.24 (d, J=8.33 Hz, 1H) 8.10-8.18 (m, 2H) 7.85-7.92 (m, 2H) 7.72 (t, J=7.67 Hz, 1H) 7.61-7.68 (m, 2H) 7.51-7.60 (m, 2H) 1.95 (br. s., 1H) 1.28-1.39 (m, 5H) 1.21-1.28 (m, 3H) 1.09-1.19 (m, 2H).

Compound 641 and Compound 642

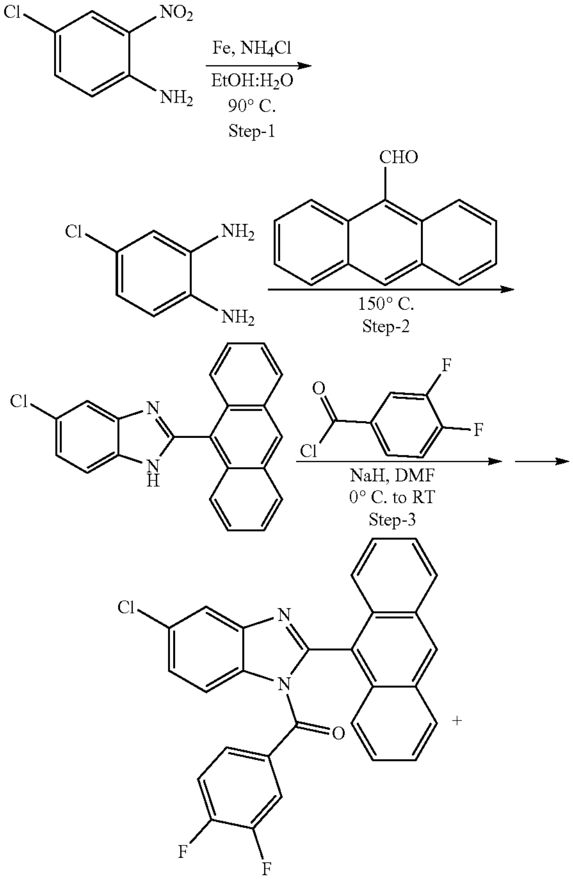

Isomer 1, Peak 1
Compound-641

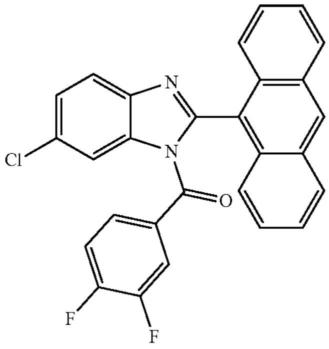

Isomer 2, Peak2
Compound-642

Step 1 was performed as described for step 1 of synthesis of Compound 588

Step 2 was performed as described for step 1 of synthesis of Compound 429

Step 3 was performed as described for step 2 of synthesis of Compound 535

Compound 641: LCMS—469.2 $(M)^+$ UPLC @ 254 nm=98.90% and @ 220 nm 99.87% $^1H$ NMR (400 MHz, DMSO-$d_6$) δ ppm 8.63 (s, 1H) 8.06-8.12 (m, 3H) 7.91 (d, J=8.77 Hz, 1H) 7.70 (d, J=7.89 Hz, 2H) 7.61 (d, J=2.19 Hz, 1H) 7.52-7.60 (m, 4H) 7.19-7.25 (m, 1H) 6.87 (br. s., 1H) 6.74 (dd, J=10.30, 8.11 Hz, 1H Compound 642: LCMS—469.2 $(M)^+$ UPLC @ 254 nm=93.75% and @ 220 nm=93.35%. $^1H$ NMR (400 MHz, DMSO-$d_6$) δ ppm 8.62 (s, 1H) 8.08 (d, J=7.02 Hz, 2H) 7.97-8.05 (m, 2H) 7.69 (d, J=8.77 Hz, 2H) 7.62 (d, J=8.33 Hz, 1H) 7.52-7.60 (m, 3H) 7.14 (br. s., 1H) 6.79 (br. s., 1H) 6.65 (s, 1H) 6.68 (s, 1H).

Compound 643 and Compound 644

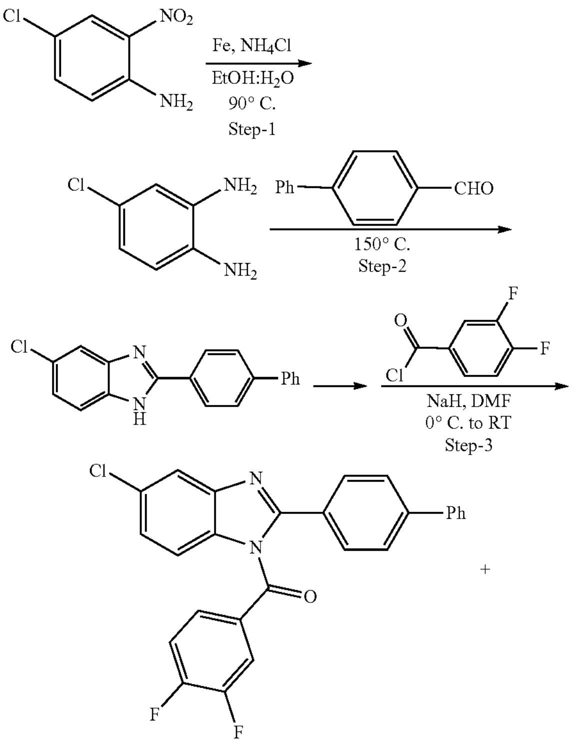

Isomer 1, Peak 1
Compound-643

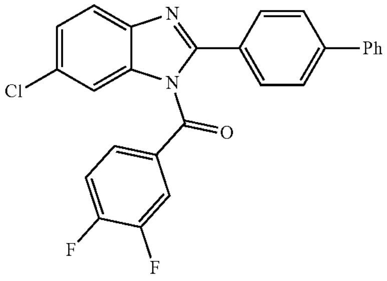

Isomer 2, Peak2
Compound-644

Step 1 was performed as described for step 1 of synthesis of Compound 588;

Step 2 was performed as described for step 1 of synthesis of Compound 429

Step 3 was performed as described for step 2 of synthesis of Compound 535

Compound 643: LCMS—445.2 $(M)^+$ UPLC @ 254 nm=97.02% and @ 220 nm 97.20% $^1H$ NMR (400 MHz, DMSO-$d_6$) δ ppm 7.97 (d, J=2.19 Hz, 1H) 7.70 (br. s., 2H) 7.68 (br. s., 1H) 7.61-7.67 (m, 4H) 7.53 (s, 1H) 7.50 (d, J=8.33 Hz, 3H) 7.47 (s, 1H) 7.40-7.45 (m, 2H)

Compound 644: LCMS:—445.2 $(M)^+$ UPLC @ 254 nm=96.82% and @ 220 nm=93.46%. $^1$H NMR (400 MHz, DMSO-$d_6$) δ 7.90 (t, J=8.9 Hz, 2H), 7.70-7.58 (m, 7H), 7.54-7.44 (m, 4H), 7.40 (t, J=7.4 Hz, 2H).

Compound 645

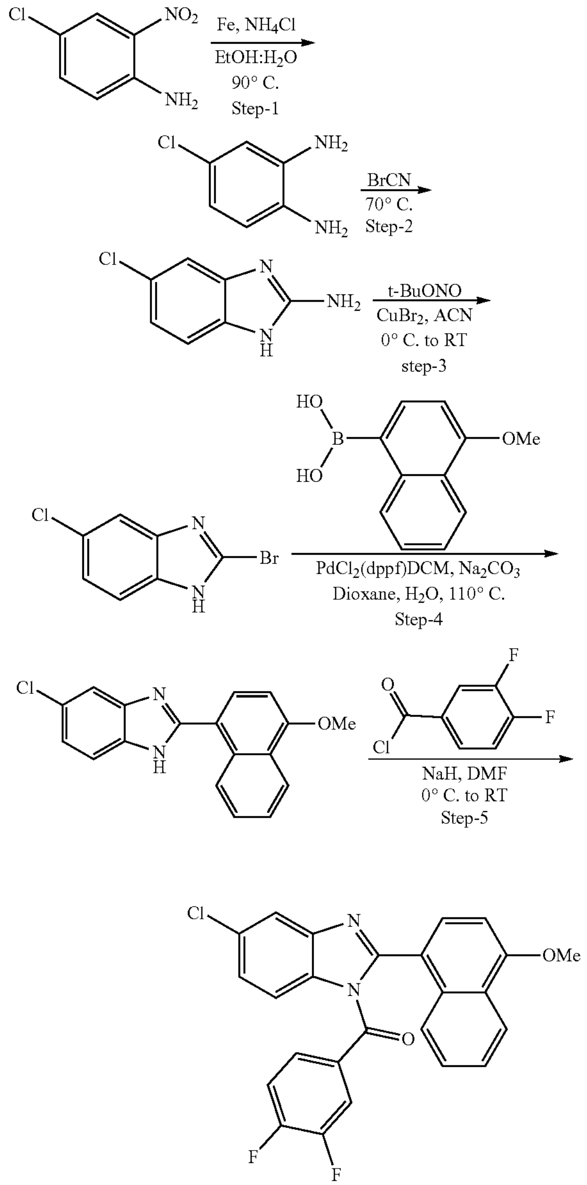

Compound-645
Isomer-1, Peak 1

Steps 1-5 were performed as described for synthesis of Compound 588

Compound 645: LCMS—449.3 $(M)^+$ UPLC @ 254 nm=98.85% and @ 220 nm 97.92%. $^1$H NMR (400 MHz, DMSO-$d_6$) δ ppm 8.11 (d, J=8.33 Hz, 1H), 8.00 (d, J=1.75 Hz, 1H), 7.91 (d, J=7.89 Hz, 1H), 7.79 (d, J=8.77 Hz, 1H), 7.47-7.61 (m, 5H), 7.28 (br. s., 1H), 7.09 (d, J=10.09 Hz, 1H), 6.89 (d, J=8.33 Hz, 1H), 3.95 (s, 3H).

Compound 681

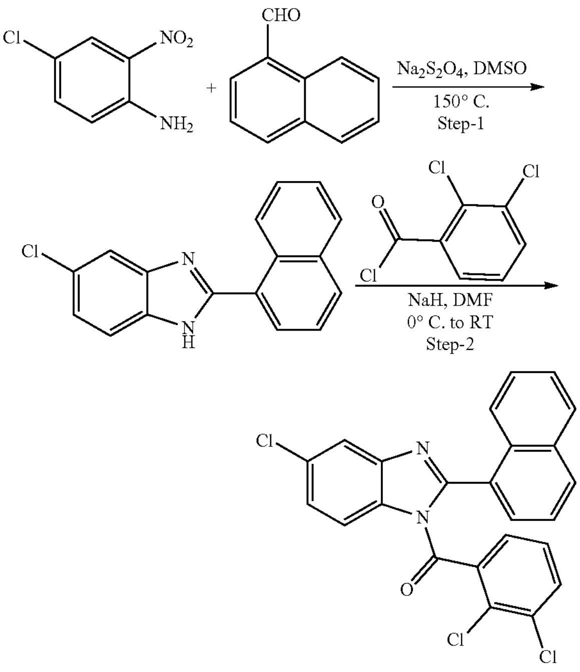

Isomer 1, Peak 1
Compound-681

Steps 1 and 2 were performed as described for synthesis of Compound 535

Compound 681: LCMS—450.1 $(M)^+$ UPLC @ 254 nm=95.09% and @ 220 nm 95.92%. $^1$H NMR (400 MHz, DMSO-$d_6$) δ ppm 8.18 (d, J=8.33 Hz, 1H) 8.04 (d, J=1.75 Hz, 1H) 7.82-7.88 (m, 2H) 7.73 (br. s., 1H) 7.61-7.67 (m, 2H) 7.50-7.56 (m, 2H) 7.34-7.40 (m, 2H) 7.19 (d, J=7.89 Hz, 2H).

Compound 682 and Compound 683

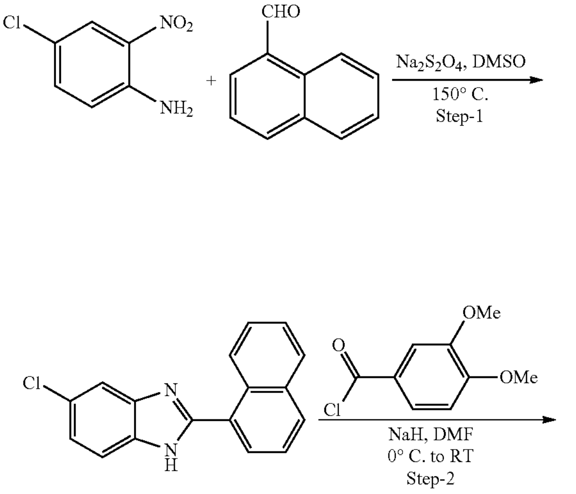

-continued

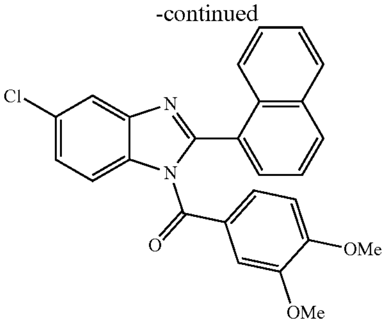

+

Peakl, Isomer 1
Compound-682

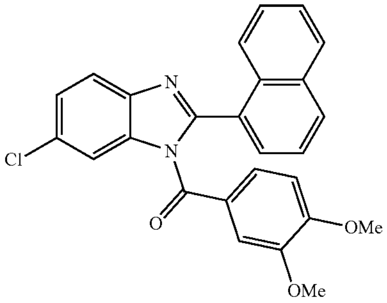

Peak 2, Isomer 2
Compound-683

Steps 1 and 2 were performed as described for synthesis of Compound 535

Compound 682: LCMS—443.2 $(M)^+$ UPLC @ 254 nm=97.75% and @ 220 nm 98.77% $^1$H NMR (400 MHz, DMSO-$d_6$) δ ppm 8.15 (d, J=3.07 Hz, 1H) 8.01 (d, J=1.75 Hz, 1H) 7.92-7.97 (m, 2H) 7.61 (d, J=6.14 Hz, 1H) 7.54-7.59 (m, 2H) 7.50-7.54 (m, 1H) 7.41-7.47 (m, 2H) 7.31 (dd, J=8.33, 1.75 Hz, 1H) 7.06 (d, J=2.19 Hz, 1H) 6.77 (d, J=8.33 Hz, 1H) 3.7 (s, 3H) 3.5 (s, 3H)

Compound 683: LCMS—443.2 $(M)^+$ UPLC @ 254 nm=99.14% and @ 220 nm=99.91%. $^1$H NMR (400 MHz, DMSO-$d_6$) δ ppm 8.16 (d, J=9.65 Hz, 1H) 7.88-7.96 (m, 3H) 7.54-7.61 (m, 3H) 7.50 (dd, J=8.77, 2.19 Hz, 1H) 7.39-7.45 (m, 2H) 7.28 (dd, J=8.55, 1.97 Hz, 1H) 7.02 (d, J=1.75 Hz, 1H) 6.74 (d, J=8.33 Hz, 1H) 3.7 (s, 3H) 3.45 (s, 3H).

Compound 684

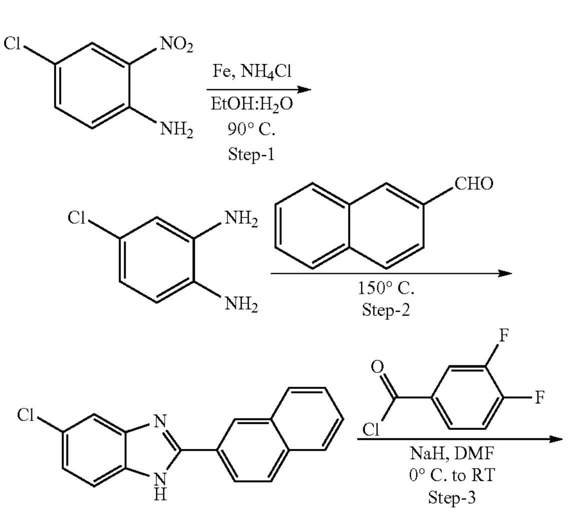

-continued

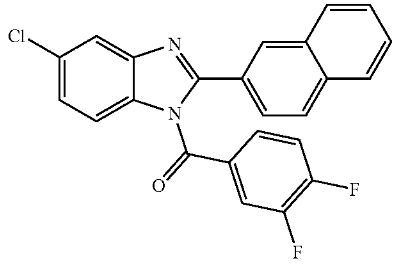

Isomer 1, Peak 1
Compound-684

Step 1 was performed as described for synthesis of Compound 588

Step 2 was performed as described for synthesis of Compound 579

Compound 684: LCMS—419.2 $(M)^+$ UPLC @ 254 nm=98.39% and @ 220 nm 97.40%. $^1$H NMR (400 MHz, DMSO-$d_6$) δ ppm 8.17 (s, 1H) 7.85-8.01 (m, 4H) 7.68 (dd, J=8.55, 1.53 Hz, 2H) 7.51-7.62 (m, 3H) 7.46 (dd, J=8.77, 2.19 Hz, 1H) 7.35 (s, 1H) 7.37 (s, 1H).

Compound 685

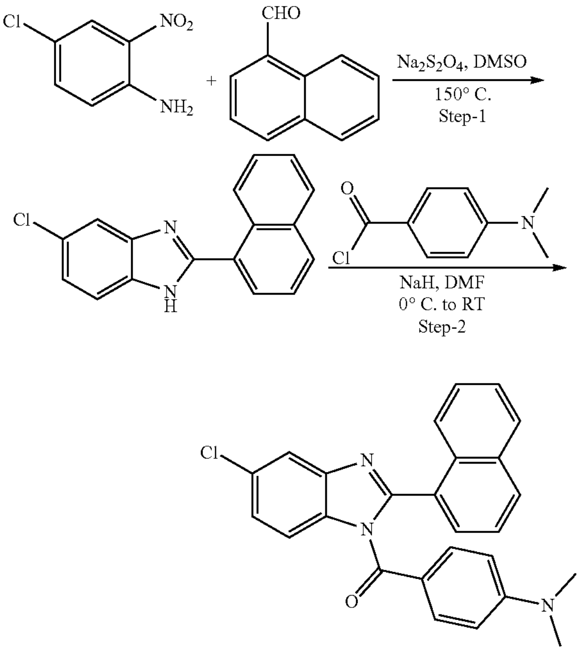

Isomer 1, Peak 1
Compound-685

Steps 1 and 2 were performed as described for synthesis of Compound 535

Compound 685: LCMS—426.2 $(M)^+$ UPLC @ 254 nm=94.85% and @ 220 nm 91.06%. $^1$H NMR (400 MHz, DMSO-$d_6$) δ ppm 8.19 (d, J=7.02 Hz, 1H) 7.94-8.02 (m, 2H) 7.92 (d, J=8.77 Hz, 1H) 7.42-7.68 (m, 7H) 7.29 (d, J=1.75 Hz, 1H) 6.57 (d, J=9.21 Hz, 2H) 2.98 (s, 6H).

Compound 686 and Compound 687

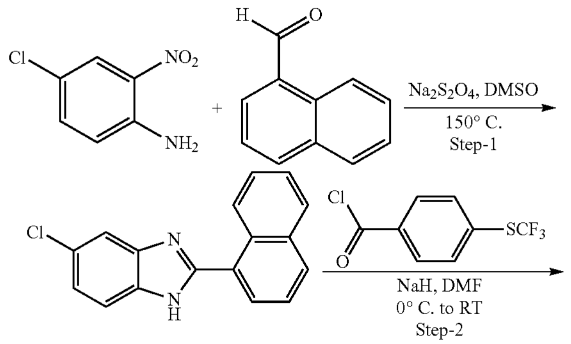

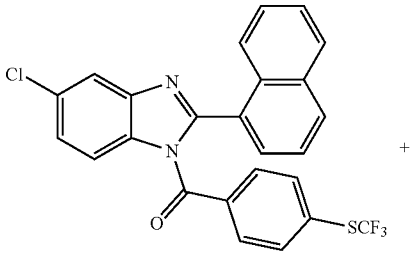

Peak1, Isomer 1
Compound-686

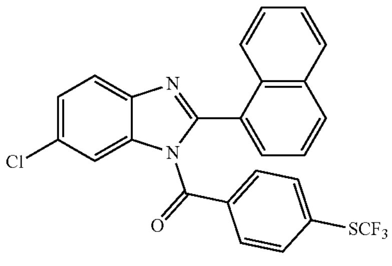

Peak 2, Isomer 2
Compound-687

Steps 1 and 2 were performed as described for synthesis of Compound 535

Compound 686: LCMS—483.2 $(M)^+$ UPLC @ 254 nm=99.24% and @ 220 nm 99.0%. $^1H$ NMR (400 MHz, DMSO-$d_6$) δ ppm 8.02-8.05 (m, 1H) 7.90 (d, J=8.77 Hz, 2H) 7.77-7.84 (m, 2H) 7.63 (d, J=6.58 Hz, 1H) 7.50-7.59 (m, 3H) 7.48 (m, J=7.89 Hz, 2H) 7.34 (t, J=7.67 Hz, 1H) 7.21 (m, J=7.89 Hz, 2H).

Compound 687: LCMS—483.2 $(M)^+$ UPLC @ 254 nm=98.55% and @ 220 nm=97.73%. $^1H$ NMR (400 MHz, DMSO-$d_6$) δ ppm 7.95 (d, J=8.33 Hz, 1H) 7.87-7.93 (m, 2H) 7.79 (d, J=8.33 Hz, 1H) 7.82 (d, J=7.89 Hz, 1H) 7.62 (d, J=7.02 Hz, 1H) 7.50-7.60 (m, 3H) 7.47 (m, J=7.45 Hz, 2H) 7.33 (t, J=7.67 Hz, 1H) 7.20 (m, J=7.45 Hz, 2H).

Compound 688 and Compound 689

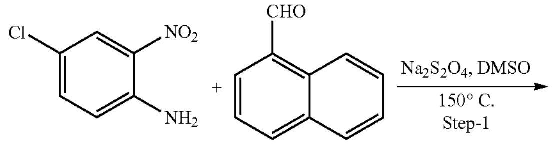

-continued

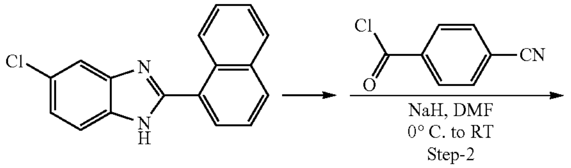

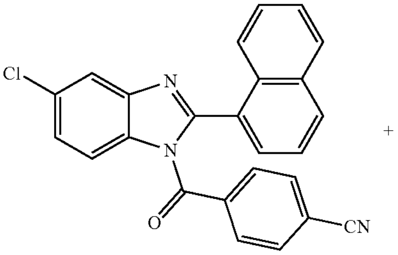

Isomer 1, Peak 1
Compound-688

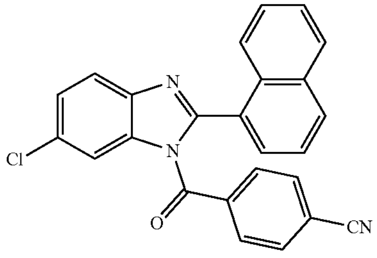

Isomer 2, peak 2
Compound-689

Steps 1 and 2 were performed as described for synthesis of Compound 535

Compound 688: LCMS—408.1 $(M)^+$ UPLC @ 254 nm=96.49% and @ 220 nm 92.76%. $^1H$ NMR (400 MHz, DMSO-d6) δ ppm 8.04 (d, J=1.75 Hz, 1H) 7.87 (d, J=8.77 Hz, 4H) 7.65 (d, J=7.02 Hz, 1H) 7.50-7.59 (m, 5H) 7.39 (d, J=7.02 Hz, 3H)

Compound 689: LCMS—408.1 $(M)^+$ UPLC @ 254 nm=98.97% and @ 220 nm=97.20%. $^1H$ NMR (400 MHz, DMSO-$d_6$) δ ppm 7.92-7.98 (m, 2H) 7.86 (d, J=8.33 Hz, 3H) 7.63 (d, J=6.58 Hz, 1H) 7.53-7.59 (m, 3H) 7.50 (d, J=7.89 Hz, 2H) 7.32-7.40 (m, 3H).

Compound 690

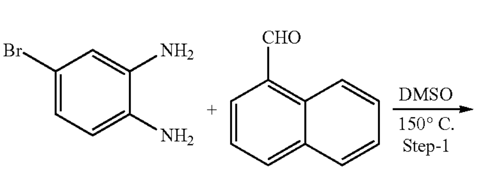

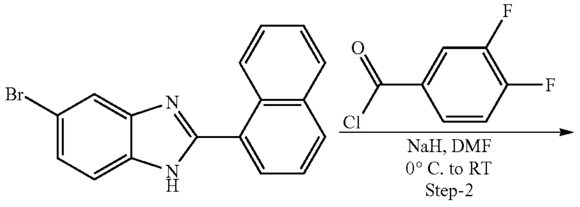

-continued

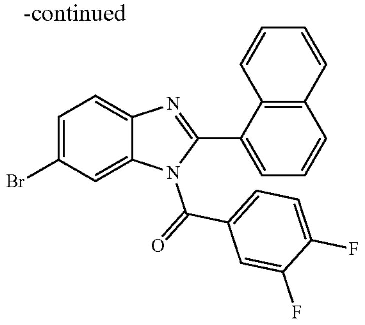

Isomer 2, peak 2
Compound-690

Step 1 was performed as described above for step 1 of synthesis of Compound 579

Step 2 was performed as described above for step 2 of synthesis of Compound 535

Compound 690: LCMS—463.2 $(M)^+$ UPLC @ 254 nm=98.22% and @ 220 nm 96.19%. $^1$H NMR (400 MHz, DMSO-$d_6$) δ ppm 8.04 (d, J=1.75 Hz, 1H) 7.87-7.94 (m, 4H) 7.68 (dd, J=8.55, 1.97 Hz, 1H) 7.63 (d, J=6.58 Hz, 1H) 7.52-7.58 (m, 3H) 7.38-7.43 (m, 1H) 7.28 (br. s., 1H) 7.04 (d, J=10.09 Hz, 1H).

Compound 691

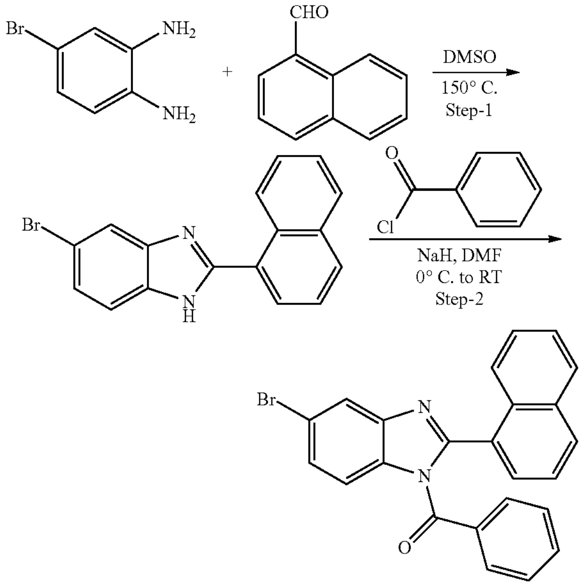

Isomer 1, Peak 1
Compound-691

Step 1 was performed as described above for step 1 of synthesis of Compound 579

Step 2 was performed as described above for step 2 of synthesis of Compound 535

Compound 691: LCMS—427.1 $(M)^+$ UPLC @ 254 nm=99.38% and @ 220 nm 98.53%. $^1$H NMR (400 MHz, DMSO-$d_6$) δ ppm 8.16 (d, J=1.32 Hz, 1H) 8.03 (d, J=9.21 Hz, 1H) 7.85-7.92 (m, 2H) 7.49-7.64 (m, 7H) 7.33-7.43 (m, 2H) 7.10 (t, J=7.89 Hz, 2H).

Compound 692

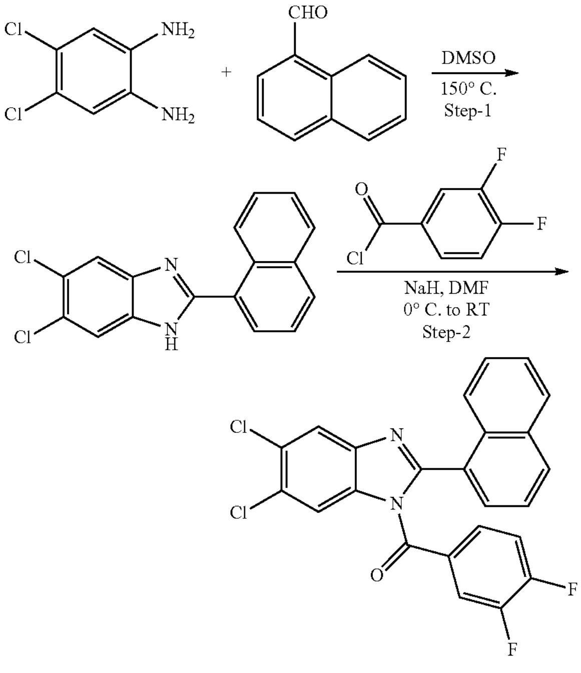

Compound-692

Step 1 was performed as described above for step 1 of synthesis of Compound 579

Step 2 was performed as described above for step 2 of synthesis of Compound 535

Compound 692: LCMS—453.2 $(M)^+$ UPLC @ 254 nm=95.86% and @ 220 nm 88.79%. $^1$H NMR (400 MHz, DMSO-$d_6$) δ ppm 8.29 (s, 1H) 8.08 (s, 1H) 7.91 (d, J=7.89 Hz, 3H) 7.64 (d, J=7.45 Hz, 1H) 7.51-7.59 (m, 3H) 7.41 (t, J=7.67 Hz, 1H) 7.29 (br. s., 1H) 7.05 (d, J=10.09 Hz, 1H).\

Compound 693

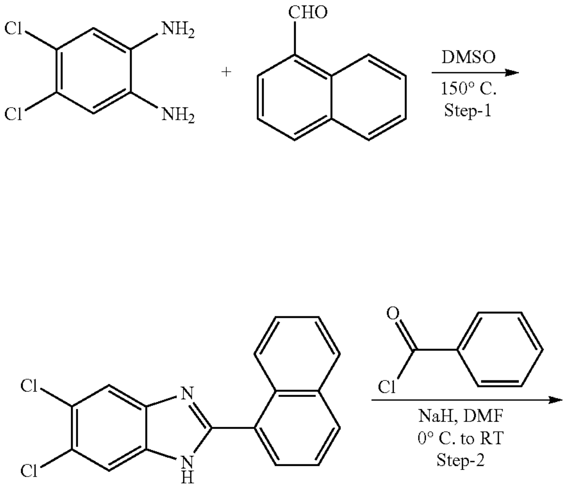

-continued

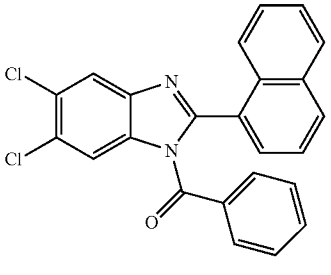

Compound-693

Step 1 was performed as described above for step 1 of synthesis of Compound 579

Step 2 was performed as described above for step 2 of synthesis of Compound 535

Compound 693: LCMS—417.1 $(M)^+$ UPLC @ 254 nm=97.48% and @ 220 nm 69.25%. $^1$H NMR (400 MHz, DMSO-$d_6$) δ ppm 8.28 (s, 1H) 8.03 (d, J=8.33 Hz, 1H) 7.86-7.91 (m, 2H) 7.84 (s, 1H) 7.62 (d, J=7.45 Hz, 1H) 7.56 (t, J=5.92 Hz, 2H) 7.48-7.53 (m, 2H) 7.30-7.41 (m, 2H) 7.07 (t, J=7.67 Hz, 2H).

Compound 694 and Compound 695

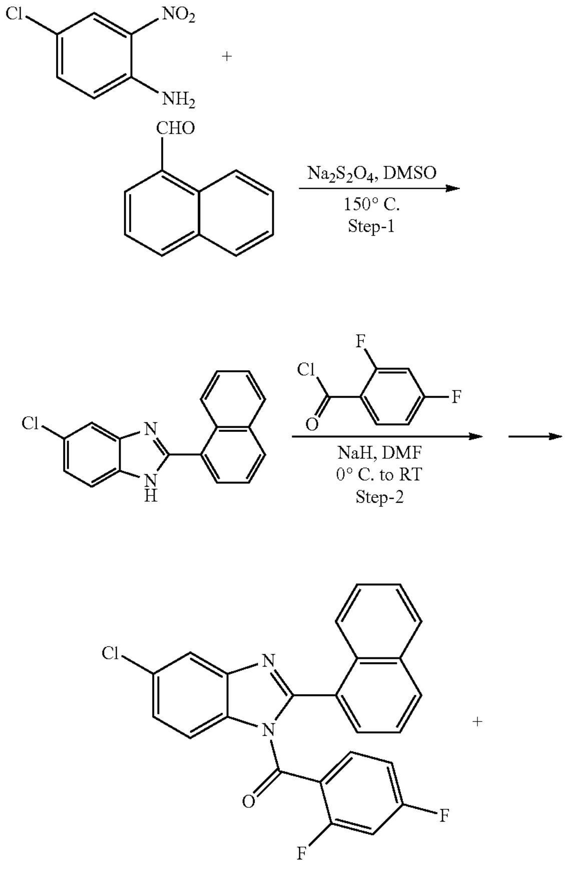

Isomer 1, Peak 1
Compound-694

-continued

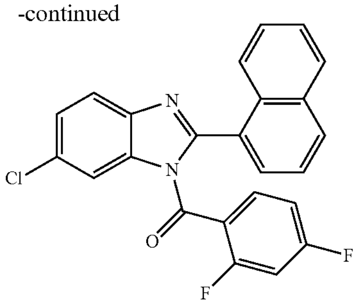

Isomer 2, Peak 2
Compound-695

Steps 1 and 2 were performed as described for synthesis of Compound 535

Compound 694: LCMS—419.1 $(M)^+$ UPLC @ 254 nm=99.70% and @ 220 nm 98.99% $^1$H NMR (400 MHz, DMSO-$d_6$) δ ppm 8.00-8.05 (m, 2H) 7.90 (d, J=8.33 Hz, 2H) 7.78-7.82 (m, 1H) 7.66 (d, J=7.02 Hz, 1H) 7.53-7.61 (m, 3H) 7.38-7.45 (m, 2H) 6.79 (t, J=9.65 Hz, 1H) 6.59 (t, J=7.67 Hz, 1H)

Compound 695: LCMS—419.1 $(M)^+$ UPLC @ 254 nm=99.29% and @ 220 nm=98.48%. $^1$H NMR (400 MHz, DMSO-$d_6$) δ ppm 8.07 (s, 1H) 7.95 (d, J=8.33 Hz, 1H) 7.90 (d, J=8.33 Hz, 2H) 7.79 (br. s., 1H) 7.65 (d, J=6.58 Hz, 1H) 7.54-7.61 (m, 3H) 7.36-7.44 (m, 2H) 6.78 (d, J=10.09 Hz, 1H) 6.56 (br. s., 1H).

Compound 696

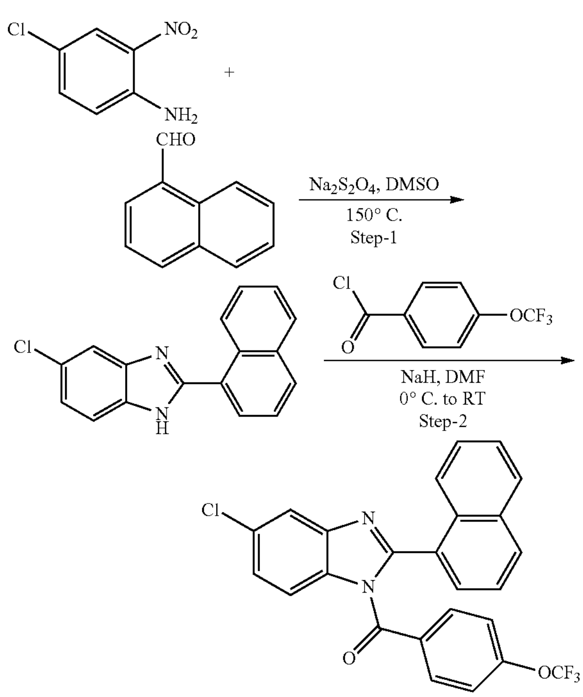

Peak 1, Isomer 1
Compound-696

Steps 1 and 2 were performed as described for synthesis of Compound 535

Compound 696: LCMS—467.2 $(M)^+$ UPLC @ 254 nm=99.22%, @ 220 nm=98.29%. $^1$H NMR (400 MHz, DMSO-d6) δ 8.03 (d, J=2.1 Hz, 1H), 7.86 (dd, J=15.8, 8.9, 2.3 Hz, 4H), 7.63 (d, J=7.1 Hz, 1H), 7.54 (dd, J=8.5, 6.3, 3.7 Hz, 5H), 7.37 (t, J=7.7 Hz, 1H), 6.89 (d, J=8.3 Hz, 2H).

Compound 697 and Compound 698

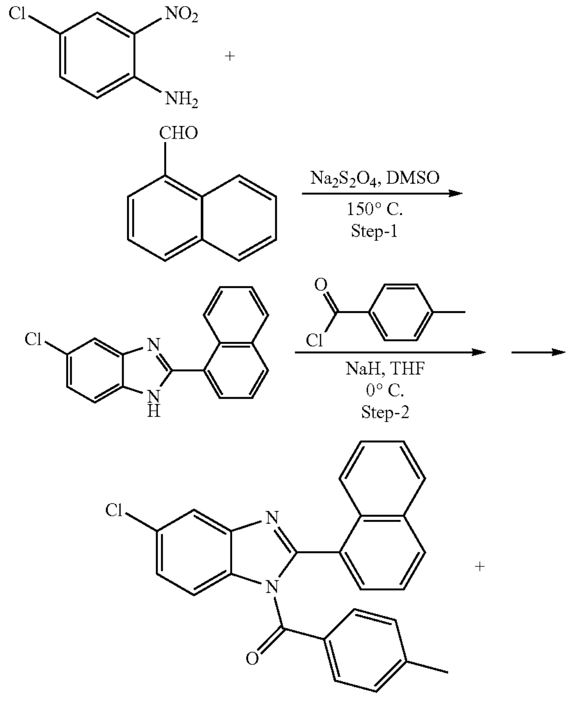

Isomer 1, Peak 1
Compound-697

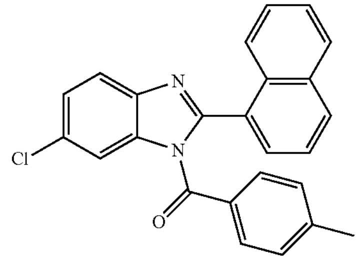

Isomer 2, Peak2
Compound-698

Steps 1 and 2 were performed as described for synthesis of Compound 535

Compound 697: LCMS—397.2 $(M)^+$ UPLC @ 254 nm=98.40%, @ 220 nm=98.56%. $^1$H NMR-1H NMR (400 MHz, DMSO-d6) δ 8.09-8.03 (m, 1H), 8.02 (s, 1H), 7.97-7.90 (m, 2H), 7.62 (d, J=7.1 Hz, 1H), 7.56 (dt, J=6.4, 3.5 Hz, 2H), 7.50 (d, J=7.9 Hz, 2H), 7.45 (d, J=1.9 Hz, 3H), 7.01 (d, J=7.9 Hz, 2H), 2.21 (s, 3H).

Compound 698: LCMS—397.2 $(M)^+$ UPLC @ 254 nm=98.05%, @ 220 nm=98.76%. $^1$H NMR-1H NMR (400 MHz, DMSO-d6) δ 8.08-8.01 (m, 1H), 7.97-7.88 (m, 3H), 7.61 (d, J=6.9 Hz, 1H), 7.58-7.48 (m, 4H), 7.45 (dd, J=12.0, 7.8 Hz, 3H), 6.98 (d, J=7.9 Hz, 2H), 2.20 (s, 3H).

Compound 699 and Compound 700

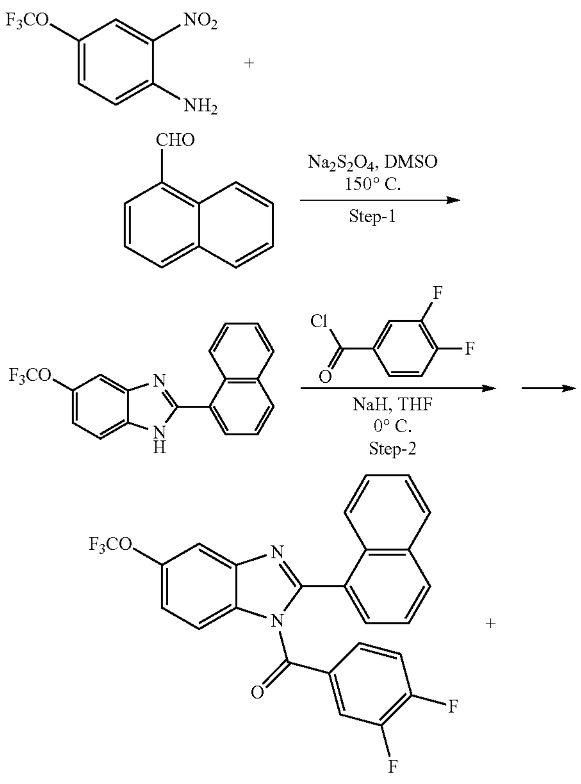

Isomer 1, Peak 1
Compound-699

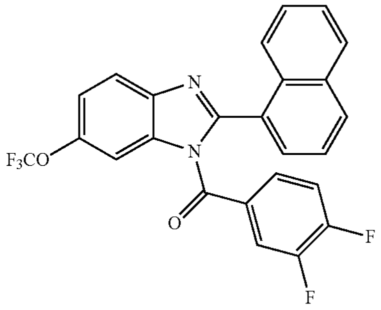

Isomer 2, Peak2
Compound-700

Steps 1 and 2 were performed as described for synthesis of Compound 535

Compound 699: LCMS—469.1 $(M+H)^+$ UPLC @ 254 nm=97.91%, @ 220 nm=94.54%. $^1$H NMR (400 MHz, DMSO-d6) δ 8.01-7.87 (m, 5H), 7.75-7.53 (m, 4H), 7.53-7.46 (m, 1H), 7.42 (t, J=7.7 Hz, 1H), 7.34 (d, J=4.8 Hz, 1H), 7.09 (q, J=8.7 Hz, 1H).

Compound 700: LCMS—469.2 $(M+H)^+$ UPLC @ 254 nm=98.64%, @ 220 nm=97.28%. $^1$H NMR (400 MHz, DMSO-d6) δ 8.04 (d, J=8.7 Hz, 1H), 7.91 (dt, J=8.6, 4.9 Hz, 3H), 7.83 (s, 1H), 7.64 (d, J=7.0 Hz, 1H), 7.60-7.45 (m, 4H), 7.42 (q, J=7.5 Hz, 1H), 7.30 (t, J=5.8 Hz, 1H), 7.05 (p, J=10.4, 9.0 Hz, 1H).

Compound 701

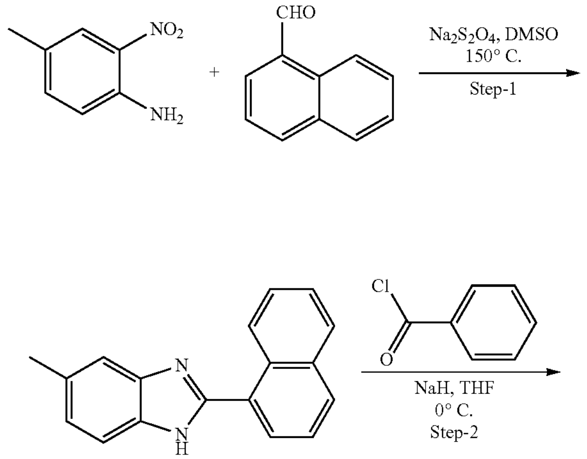

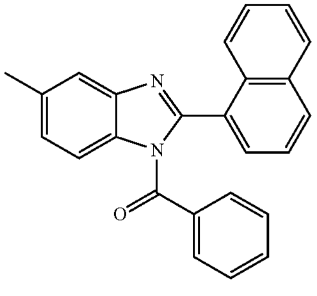

Isomer 1, Peak 1
Compound-701

Steps 1 and 2 were performed as described for synthesis of Compound 535

Compound 701: LCMS—363.2 $(M+H)^+$ UPLC @ 254=94.72%, @ 220=85.92% $^1$H NMR (400 MHz, DMSO-$d_6$) δ 8.07-7.98 (m, 1H), 7.94 (d, J=7.6 Hz, 1H), 7.92-7.68 (m, 3H), 7.66-7.21 (m, 9H), 7.16-7.04 (m, 1H), 2.45 (s, 3H).

Compound 702

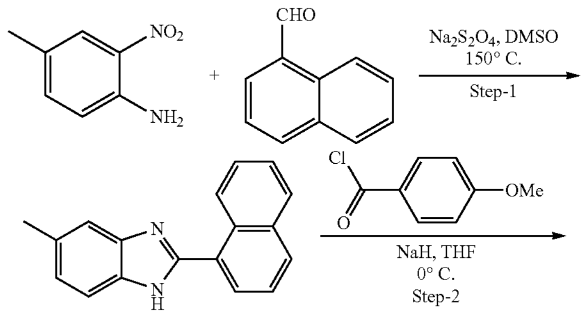

-continued

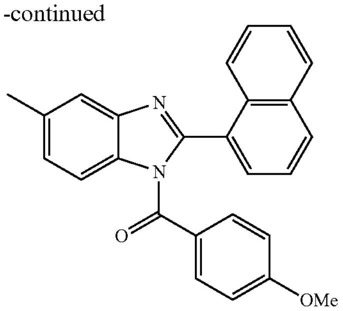

Isomer 1, Peak 1
Compound-702

Steps 1 and 2 were performed as described for synthesis of Compound 535

Compound 702: LCMS—393.2 $(M+H)^+$ UPLC @ 254 nm=98.33% @220 nm=98.36% $^1$H NMR (400 MHz, DMSO-$d_6$) δ 8.12-8.02 (m, 1H), 7.93 (t, J=8.7 Hz, 2H), 7.57 (ddd, J=18.0, 7.1, 4.0 Hz, 5H), 7.45 (q, J=8.0 Hz, 2H), 7.24 (dd, J=25.8, 9.5 Hz, 2H), 6.74 (dd, J=16.3, 8.7 Hz, 2H), 3.71 (d, J=8.1 Hz, 3H), 2.43 (s, 3H).

Compound 703

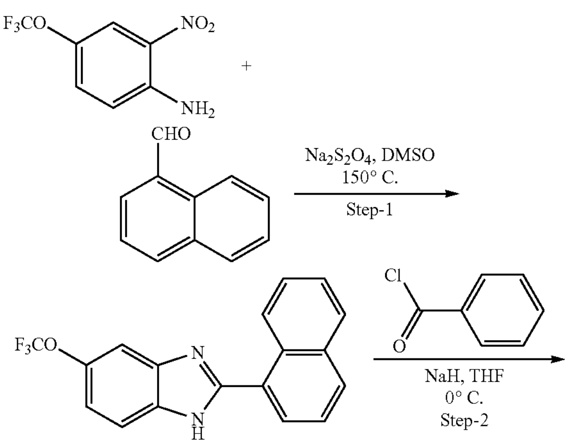

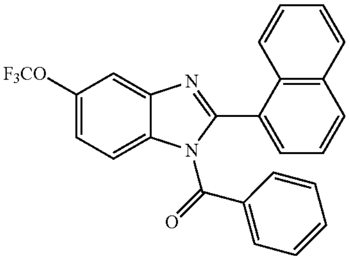

Isomer 1, Peak 1
Compound-703

Steps 1 and 2 were performed as described for synthesis of Compound 535

Compound 703: LCMS—433.2 $(M+H)^+$ UPLC @ 254 nm=97.55%, @ 220 nm=92.97%. $^1$H NMR (400 MHz, DMSO-$d_6$) δ ppm 8.03-8.07 (m, 1H) 7.97 (s, 1H) 7.86-7.91 (m, 2H) 7.69 (d, J=8.77 Hz, 1H) 7.62 (d, J=6.14 Hz, 1H), 7.51-7.58 (m, 4H) 7.47 (d, J=8.77 Hz, 1H) 7.41 (d, J=7.89 Hz, 1H) 7.33-7.36 (m, 1H) 7.10 (t, J=7.67 Hz, 2H).

Compound 704

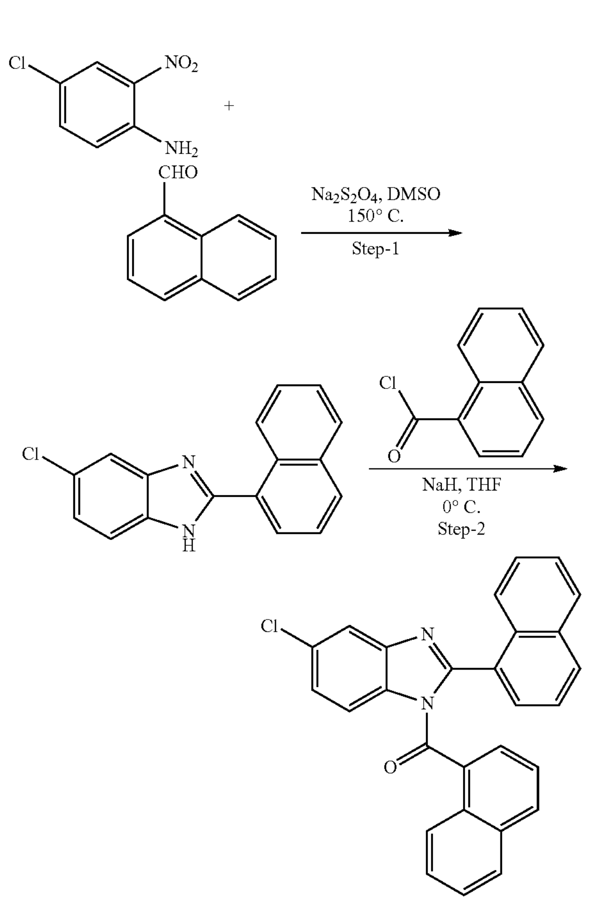

Isomer 1, Peak 1
Compound-704

Steps 1 and 2 were performed as described for synthesis of Compound 535

Compound 704: LCMS—432.1 $(M)^+$ UPLC @ 254 nm=99.68%, @ 220 nm=99.96% $^1H$ NMR (400 MHz, DMSO-d6) δ 8.04 (s, 1H), 7.92 (q, J=8.9 Hz, 3H), 7.79-7.62 (m, 3H), 7.50 (tt, J=22.1, 6.9 Hz, 8H), 6.91 (t, J=7.6 Hz, 1H), 6.84 (t, J=7.9 Hz, 1H).

Compound 763 and Compound 789

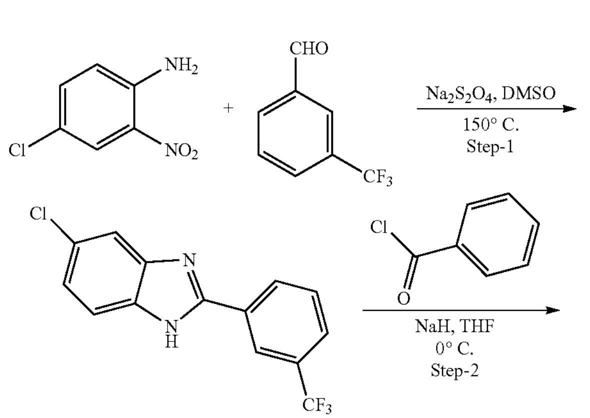

-continued

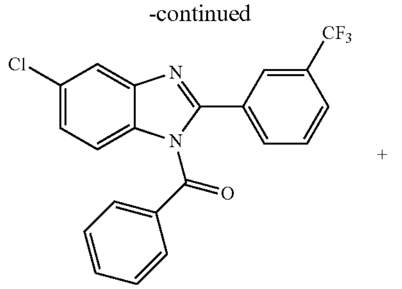

Isomer1, Peak 1
Compound-763

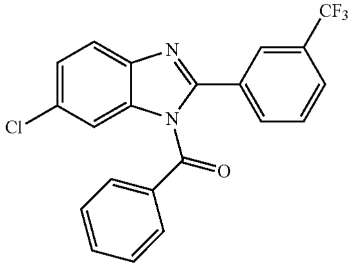

Isomer2, peak 2
Compound-789

Steps 1 and 2 were performed as described for synthesis of Compound 535

Compound 763: LCMS—401.1$(M)^+$ UPLC @ 254 nm=98.75%, @ 220 nm=99.54%. $^1H$ NMR (400 MHz, DMSO-d6) δ 8.02-7.96 (m, 1H), 7.89 (d, J=11.1 Hz, 2H), 7.72 (t, J=6.7 Hz, 3H), 7.62-7.42 (m, 4H), 7.37 (t, J=7.7 Hz, 2H).

Compound 789: LCMS—401.3 UPLC $(M)^+$@ 254 nm=93.56%, @ 220 nm=97.28%. $^1H$ NMR (400 MHz, DMSO-$d_6$) δ ppm 7.94-7.84 (m, 3H), 7.70 (t, J=7.3 Hz, 3H), 7.53 (ddd, J=21.8, 7.2, 2.9 Hz, 4H), 7.36 (t, J=7.7 Hz, 2H).

Compound 764 and Compound 765

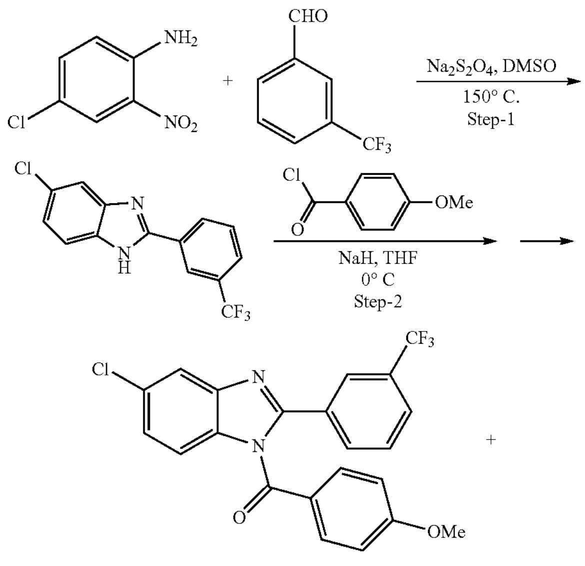

Isomer1, Peak 1
Compound-764

-continued

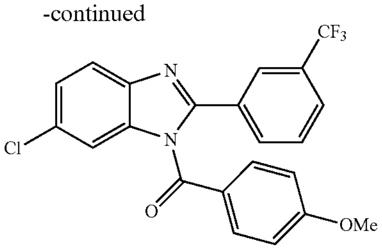

Isomer2, Peak 2
Compound-765

Steps 1 and 2 were performed as described for synthesis of Compound 535

Compound 764: LCMS—431.2 $(M)^+$ UPLC @ 254 nm=99.06%, @ 220 nm=98.75%. $^1H$ NMR (400 MHz, DMSO-$d_6$) δ ppm 8.00-7.91 (m, 2H), 7.89 (d, J=7.8 Hz, 1H), 7.78 (d, J=8.3 Hz, 3H), 7.62 (t, J=7.8 Hz, 1H), 7.41 (dd, J=8.8, 2.1 Hz, 1H), 7.36 (d, J=8.8 Hz, 1H), 6.98 (d, J=8.4 Hz, 2H), 3.81 (s, 3H).

Compound 765: LCMS—431.4 UPLC $(M)^+$@ 254 nm=93.56%, @ 220 nm=97.56%. $^1H$ NMR (400 MHz, DMSO-$d_6$) δ ppm 7.94-7.84 (m, 3H), 7.80-7.72 (m, 3H), 7.60 (t, J=7.8 Hz, 1H), 7.47 (dd, J=8.4, 2.2 Hz, 1H), 7.42 (d, J=2.1 Hz, 1H), 6.96 (d, J=8.5 Hz, 2H), 3.81 (s, 3H).

Compound 766

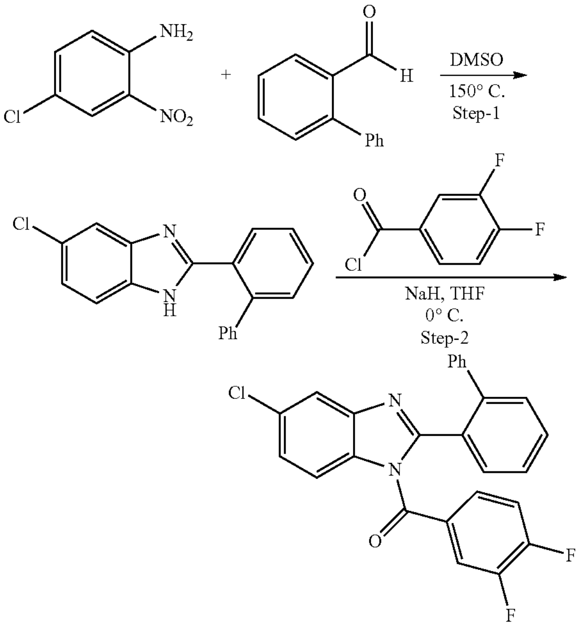

Isomer1, Peak 1
Compound-766

Steps 1 and 2 were performed as described for synthesis of Compound 535

Compound 766: LCMS—445.2 $(M)^+$ UPLC @ 254 nm=95.7%, @ 220 nm=93.29%. $^1H$ NMR (400 MHz, DMSO-$d_6$) δ ppm δ 7.97 (s, 1H), 7.82-7.73 (m, 1H), 7.59-7.47 (m, 2H), 7.47-7.08 (m, 9H), 6.92 (d, J=7.0 Hz, 2H).

Compound 767

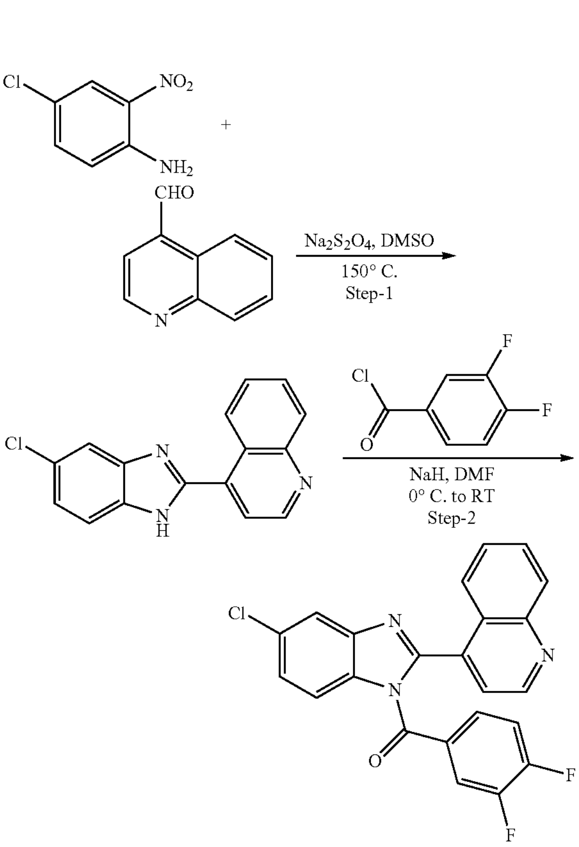

Isomer 1, peak 1
Compound-767

Steps 1 and 2 were performed as described for synthesis of Compound 535

Compound 767: LCMS: 420.2 $(M)^+$ UPLC @ 254 nm=97.49% and @ 220 nm 95.27%. $^1H$ NMR (400 MHz, DMSO-$d_6$) δ ppm 8.84 (d, J=3.95 Hz, 1H) 8.02-8.10 (m, 3H) 7.77-7.85 (m, 2H) 7.64-7.75 (m, 3H) 7.55 (dd, J=8.99, 1.97 Hz, 1H) 7.50 (br. s., 1H) 7.19-7.28 (m, 1H).

Compound 770

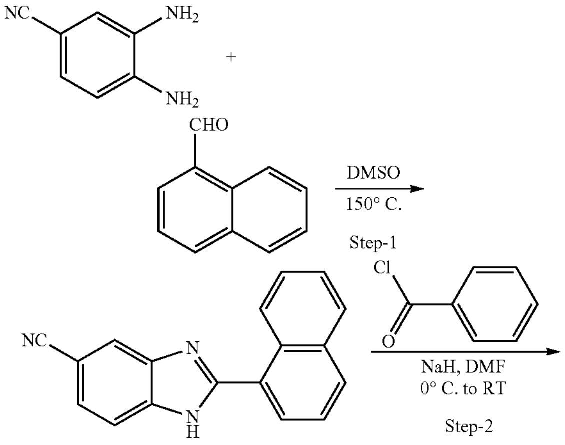

-continued

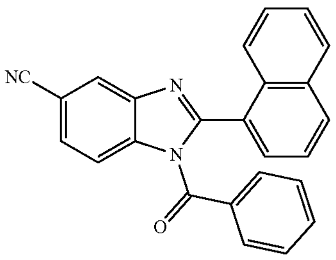

Isomer 1, peak 1
Compound-770

Step 1 was performed as described for step 1 of synthesis of Compound 579

Step 2 was performed as described for step 2 of synthesis of Compound 535

Compound 770: LCMS: 374.3 $(M+H)^+$ UPLC @ 254 nm=99.53% and @ 220 nm 98.26%. $^1H$ NMR (400 MHz, DMSO-$d_6$) δ ppm 8.53 (d, J=0.88 Hz, 1H) 8.06 (d, J=9.21 Hz, 1H) 7.90 (d, J=7.89 Hz, 2H) 7.83-7.88 (m, 1H) 7.72 (d, J=8.33 Hz, 1H) 7.65 (d, J=6.14 Hz, 1H) 7.54-7.60 (m, 4H) 7.34-7.45 (m, 2H) 7.12 (t, J=7.89 Hz, 2H).

Compound 771 and Compound 772

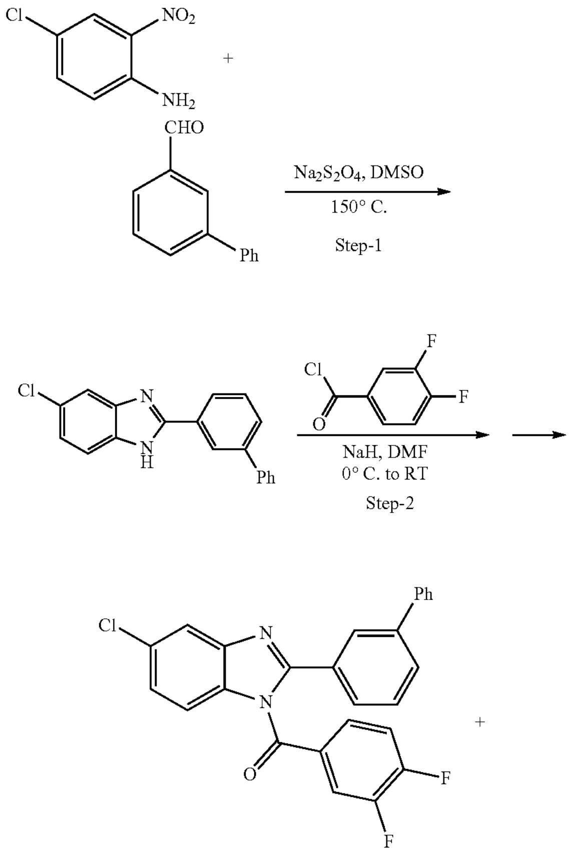

Isomer 1, peak 1
Compound-771

-continued

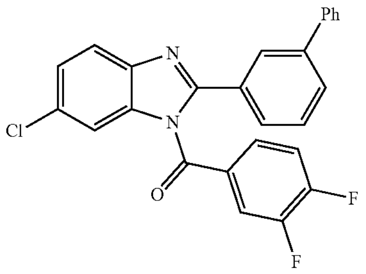

Isomer 2, peak 2
Compound-772

Steps 1 and 2 were performed as described for synthesis of Compound 535

Compound 771: LCMS—445.3 $(M)^+$ UPLC @ 254 nm=98.17% and @ 220 nm 99.25% $^1H$ NMR (400 MHz, DMSO-$d_6$) δ ppm 7.98 (d, J=2.19 Hz, 1H) 7.89 (br. s., 1H) 7.79 (s, 1H) 7.62-7.70 (m, 3H) 7.53-7.62 (m, 3H) 7.36-7.52 (m, 6H)

Compound 772: LCMS—445.3 $(M)^+$ UPLC @ 254 nm=99.15% and @ 220 nm=99.56%. $^1H$ NMR (400 MHz, DMSO-$d_6$) δ ppm 7.90 (d, J=8.33 Hz, 1H) 7.84 (d, J=7.89 Hz, 1H) 7.77 (s, 2H) 7.56-7.68 (m, 4H) 7.44-7.55 (m, 4H) 7.31-7.44 (m, 3H)

Compound 773 and Compound 774

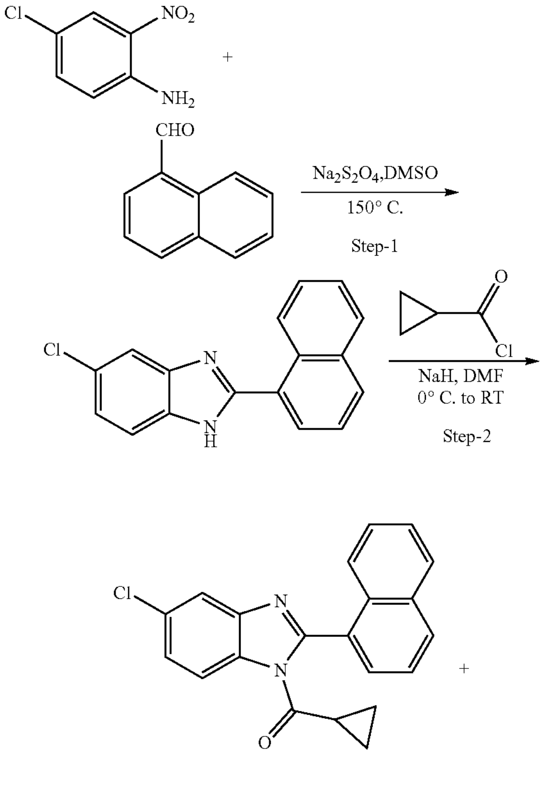

Isomer 1, peak 1
Compound-773

-continued

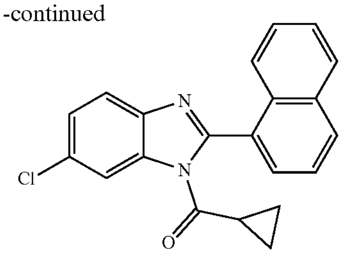

Isomer 2, peak 2
Compound-774

Steps 1 and 2 were performed as described for synthesis of Compound 535

Compound 773: LCMS—347.1 $(M)^+$ UPLC @ 220 nm 94.37%. 1H NMR (400 MHz, DMSO-$d_6$) δ 8.17 (d, J=8.3 Hz, 1H), 8.10 (d, J=3.8 Hz, 1H), 8.07 (d, J=3.2 Hz, 1H), 7.95 (s, 1H), 7.87 (d, J=7.1 Hz, 1H), 7.82 (d, J=8.2 Hz, 1H), 7.74-7.64 (m, 1H), 7.65-7.54 (m, 2H), 7.52 (dd, J=8.7, 2.1 Hz, 1H), 1.47 (dtt, J=12.3, 8.2, 4.8 Hz, 1H), 1.23 (d, J=4.0 Hz, 1H), 0.88 (h, J=5.0, 4.5 Hz, 1H), 0.84-0.72 (m, 1H), 0.51 (dq, J=8.0, 4.2 Hz, 1H).

Compound 774: LCMS—347.2 $(M)^+$ UPLC @ 220 nm=94.92%. $^1H$ NMR (400 MHz, DMSO-$d_6$) δ 8.17 (d, J=8.3 Hz, 1H), 8.10 (t, J=2.2 Hz, 1H), 8.07 (s, 1H), 7.87 (dd, J=8.0, 3.4 Hz, 1H), 7.83 (d, J=8.3 Hz, 1H), 7.69 (t, J=7.7 Hz, 1H), 7.63 (t, J=7.4 Hz, 1H), 7.60-7.54 (m, 2H), 7.52 (dd, J=8.5, 2.2 Hz, 1H), 1.43 (tt, J=8.0, 4.5 Hz, 1H), 1.23 (d, J=4.0 Hz, 1H), 0.88 (h, J=5.5, 4.9 Hz, 2H), 0.49 (dq, J=7.8, 4.1 Hz, 1H).

Compound 775 and Compound 776

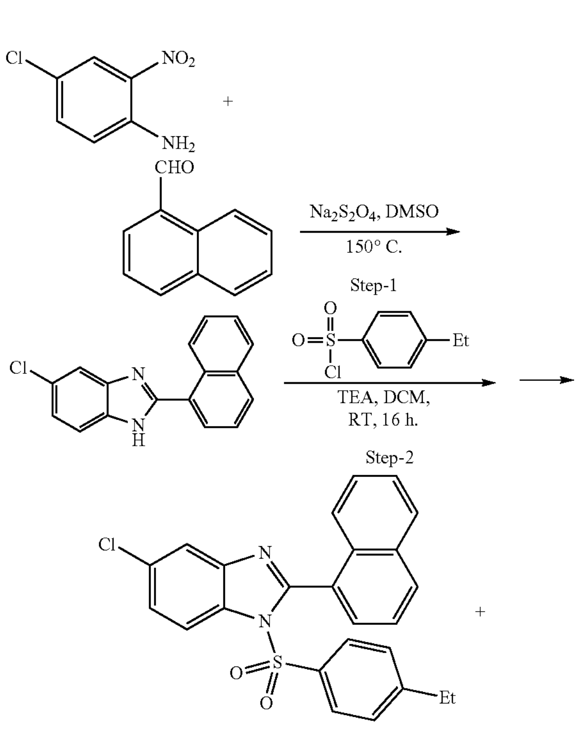

Isomer 1, peak 1
Compound-775

-continued

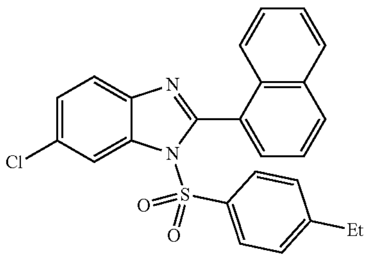

Isomer 2, peak 2
Compound-776

Steps 1 and 2 were performed as described for synthesis of Compound 535

Compound 775: LCMS—447.3 $(M)^+$ UPLC @ 254 nm=96.10%, @ 220 nm=99.05%. $^1H$ NMR (400 MHz, DMSO-$d_6$) δ ppm 8.19 (d, J=8.77 Hz, 2H), 8.03 (d, J=8.33 Hz, 1H), 7.96 (s, 1H), 7.58-7.71 (m, 3H), 7.50-7.55 (m, 1H), 7.25-7.36 (m, 3H), 7.17 (d, J=7.89 Hz, 3H), 2.52-2.59 (m, 2H), 1.07 (t, J=7.67 Hz, 3H).

Compound 776: LCMS—447.3 $(M)^+$ UPLC @ 254 nm=93.64%, @ 220 nm=98.20%. $^1H$ NMR (400 MHz, DMSO-$d_6$) δ ppm 8.12-8.23 (m, 2H), 8.02 (d, J=7.89 Hz, 1H), 7.88 (d, J=8.77 Hz, 1H), 7.49-7.69 (m, 4H), 7.30 (d, J=8.33 Hz, 3H), 7.07-7.19 (m, 3H), 2.53-2.59 (m, 2H), 1.07 (t, J=7.45 Hz, 3H).

Compound 777 and Compound 778

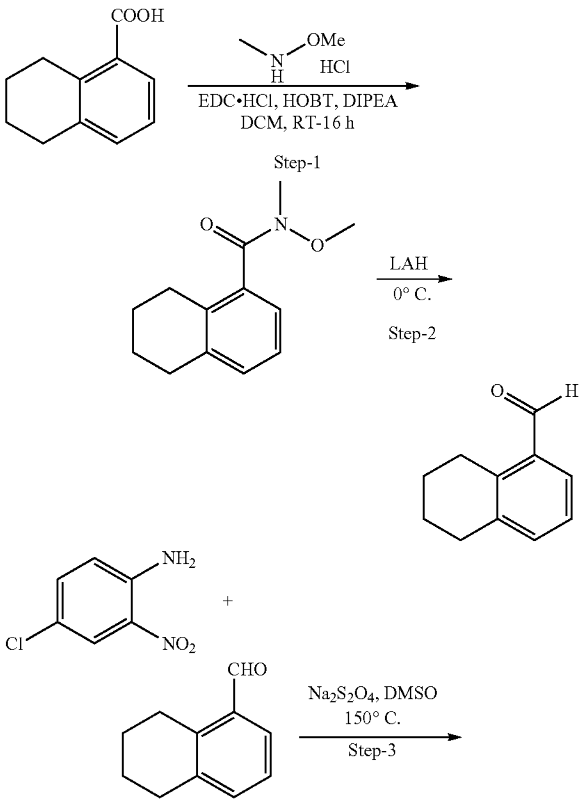

-continued

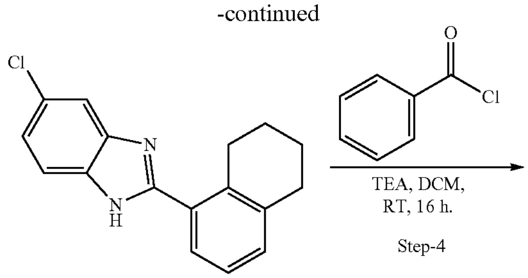

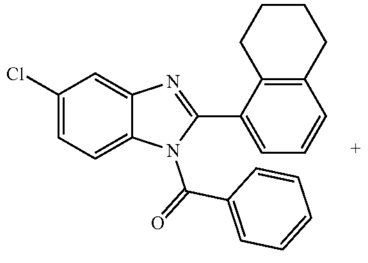

Isomer1-peak1
Compound-777

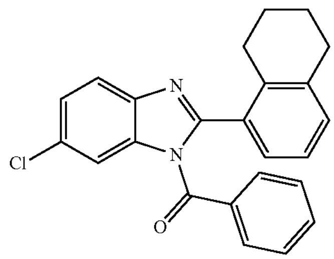

Isomer2-peak2
Compound-778

Step 1: To a stirred solution of 5,6,7,8-tetrahydronaphthalene-1-carboxylic acid (1 g, 5.675 mmol) in DCM (15 mL) was added N,O-dimethylhydroxylamine hydrochloride (608 mg, 6.242 mmol) followed by the addition of EDC·HCl (2.2 g, 11.35 mmol), HOBT (1.53 g, 11.35 mmol) followed by addition of DIPEA (5 mL, 28.37 mmol, 5.0 eq) under nitrogen atmosphere and the reaction mixture was stirred at rt for 16 h. After 16 h reaction was monitored by TLC and LCMS. After completion of reaction, the reaction mixture was diluted with DCM (200 mL) and washed with water (2×100 mL). The organic layer was washed with brine solution, separated and dried over sodium sulphate, concentrated under vacuo to yield crude product which was purified by flash chromatography (elution 0-20% EtOAc in hexane) to afford N-methoxy-N-methyl-5, 6, 7, 8-tetrahydronaphthalene-1-carboxamide (800 mg) as a yellow solid.

Step 2: N-methoxy-N-methyl-5,6,7,8-tetrahydronaphthalene-1-carboxamide (800 mg, 3.6 mmol) was dissolved in dry THF (12 mL) under nitrogen atmosphere. To the mixture was added (1.67 mL, 4.017 mmol) a solution of LAH in THF (2.5M) dropwise. The reaction was quenched after half an hour after by addition of 0.5M potassium hydrogen sulfate aqueous solution. The mixture was extracted with ethyl acetate and the ethyl acetate layer was washed three times with brine and dried over anhydrous sodium sulfate, concentrate under reduced pressure to yield crude product which was purified by flash chromatography (elution 0-20% EtOAc in hexane) to afford 5,6,7,8-tetrahydronaphthalene-1-carbaldehyde (438 mg) as a yellow oil.

Steps 3 and 4 were performed as described for Compound 490

Compound 777: LCMS—387.1 $(M)^+$ UPLC @ 254 nm=99.61%, @ 220 nm=99.86%. $^1$H NMR (400 MHz, DMSO-$d_6$) δ ppm 7.92 (d, J=1.75 Hz, 1H), 7.63 (d, J=7.02 Hz, 2H), 7.45-7.58 (m, 2H), 7.37-7.45 (m, 1H), 7.25-7.37 (m, 2H), 7.08 (d, J=7.02 Hz, 1H), 6.90-7.01 (m, 2H), 2.66 (d, J=15.35 Hz, 4H), 1.67 (br. s., 4H).

Compound 778: LCMS—387.1 $(M)^+$ UPLC @ 254 nm=99.88%, @ 220 nm=99.81%. $^1$H NMR (400 MHz, DMSO-$d_6$) δ ppm 7.85 (d, J=8.77 Hz, 1H), 7.62 (d, J=7.45 Hz, 2H), 7.54 (br. s., 1H), 7.43-7.54 (m, 2H), 7.26-7.37 (m, 2H), 7.01-7.12 (m, 1H), 6.87-7.01 (m, 2H), 2.66 (d, J=18.86 Hz, 4H), 1.66 (br. s., 4H).

Compound 779 and Compound 780

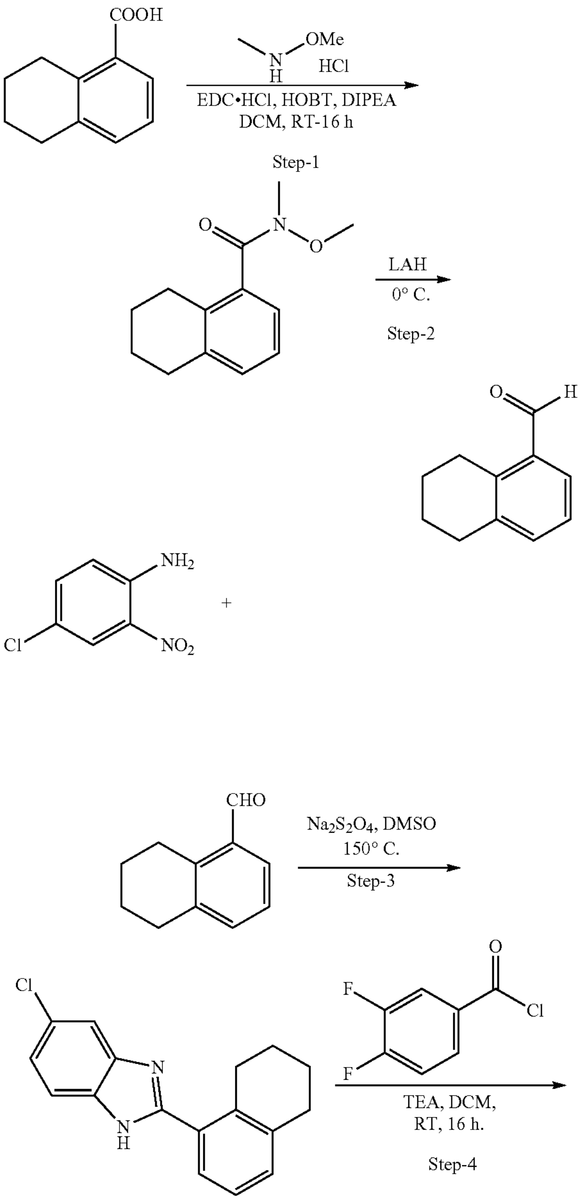

-continued

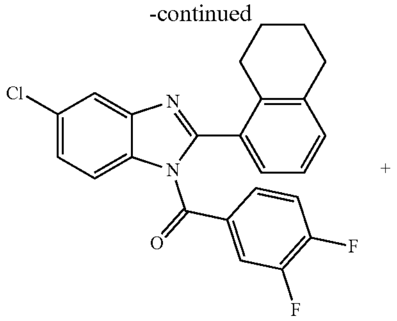

Isomer1-peak1
Compound-779

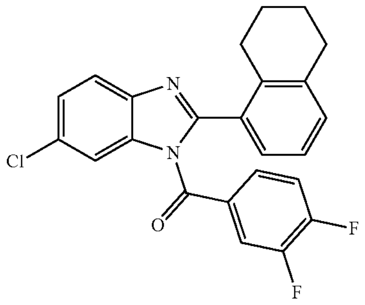

Isomer2-peak2
Compound-780

Steps 1-4 were performed as described for Compound 777

Compound 779: LCMS—423.3 $(M)^+$ UPLC @ 254 nm=99.33%, @ 220 nm=98.98%. $^1$H NMR (400 MHz, DMSO-$d_6$) δ ppm 7.85-7.99 (m, 1H), 7.73-7.84 (m, 2H), 7.48-7.61 (m, 2H), 7.41-7.48 (m, 1H), 7.32-7.41 (m, 1H), 7.08 (d, J=7.02 Hz, 1H), 6.96 (t, J=7.45 Hz, 1H), 2.65 (br. s., 4H), 1.67 (br. s., 4H).

Compound 780: LCMS—423.3 $(M)^+$ UPLC @ 254 nm=98.57%, @ 220 nm=98.17%. $^1$H NMR (400 MHz, DMSO-$d_6$) δ 7.76-7.92 (m, 2H), 7.66-7.76 (m, 1H), 7.45-7.59 (m, 2H), 7.32-7.43 (m, 1H), 7.06 (d, ppm J=7.45 Hz, 1H), 7.00-7.03 (m, 1H), 6.87-6.98 (m, 1H), 2.64 (br. s., 4H), 1.66 (br. s., 4H).

Compound 781 and Compound 782

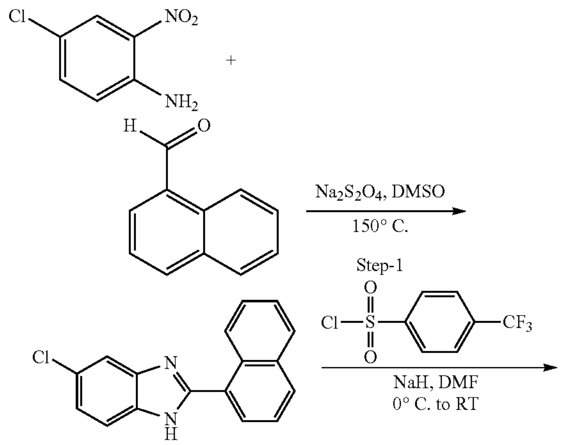

-continued

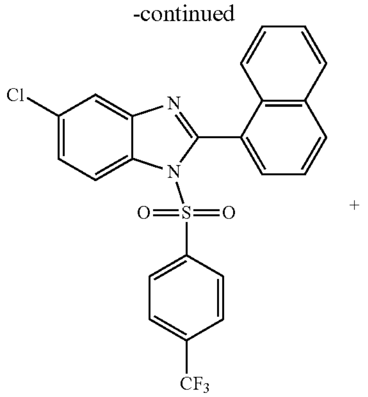

Peak1, Isomer 1
Compound-781

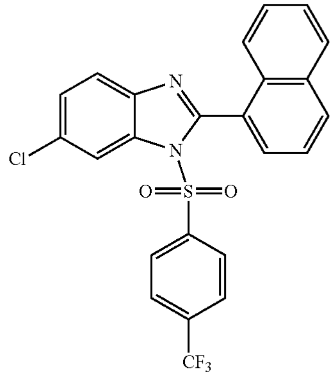

Peak2, Isomer 2
Compound-782

Steps 1 and 2 were performed as described for Compound 631

Compound 781: LCMS—487.1 $(M)^+$ UPLC @ 254 nm=99.88%, @ 220 nm=99.79%. $^1$H NMR (400 MHz, DMSO-$d_6$) δ ppm: 8.19 (d, J=7.89 Hz, 1H), 8.22 (d, J=8.77 Hz, 1H), 7.92-8.06 (m, 2H), 7.59-7.81 (m, 5H), 7.43-7.59 (m, 3H), 7.25 (t, J=7.67 Hz, 1H), 7.08 (d, J=8.77 Hz, 1H).

Compound 782: LCMS—487.0 $(M)^+$ UPLC @ 254 nm=99.30%, @ 220 nm=99.12%. $^1$H NMR (400 MHz, DMSO-$d_6$) δ ppm: 8.19-8.29 (m, 1H), 8.18 (s, 1H), 7.99 (d, J=7.89 Hz, 1H), 7.92 (d, J=8.33 Hz, 1H), 7.66-7.72 (m, 2H), 7.59-7.66 (m, 3H), 7.56 (d, 2H), 7.48-7.55 (s, 1H), 7.39-7.48 (m, 1H), 7.02 (d, J=8.33 Hz, 1H).

Compound 783 and Compound 784

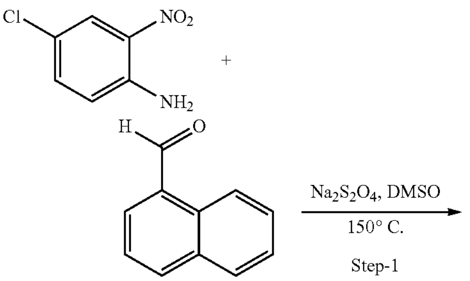

-continued

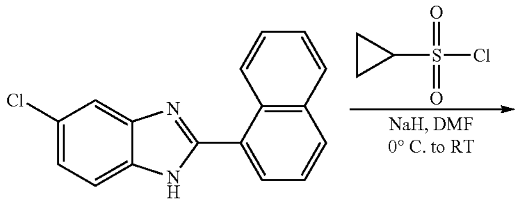

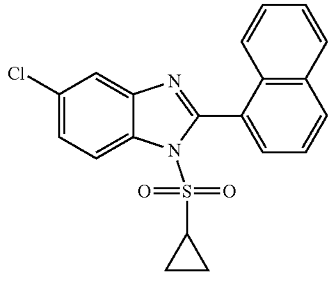

+

Peak1, Isomer 1
Compound-783

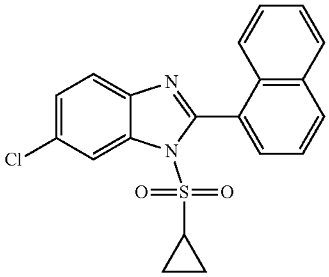

Peak2, Isomer 2
Compound-784

Steps 1 and 2 were performed as described for Compound 631

Compound 783: LCMS—383.1 $(M)^+$@ 254 nm=98.83% 1H NMR (400 MHz, DMSO-$d_6$) δ 8.16 (d, J=8.3 Hz, 1H), 8.09-7.96 (m, 3H), 7.82 (d, J=7.0 Hz, 1H), 7.69-7.48 (m, 5H), 3.07 (td, J=7.6, 3.8 Hz, 1H), 0.99 (s, 4H)

Compound 784: LCMS—383.2 $(M)^+$ @254 nm=98.40 1H NMR (400 MHz, DMSO-$d_6$) δ 8.16 (d, J=8.2 Hz, 1H), 8.09-7.99 (m, 2H), 7.92 (d, J=8.6 Hz, 1H), 7.82 (d, J=7.0 Hz, 1H), 7.65 (t, J=7.7 Hz, 1H), 7.62-7.47 (m, 4H), 3.17 (td, J=7.5, 3.8 Hz, 1H), 1.2-0.80 (m, 4H).

Compound 785 and Compound 786

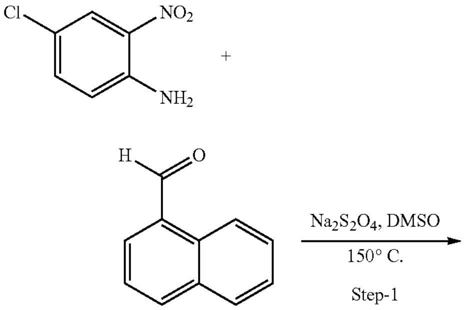

-continued

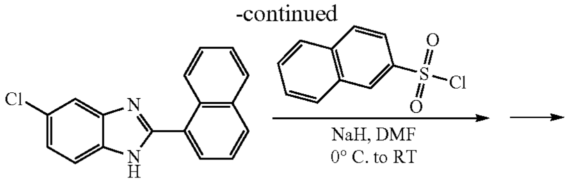

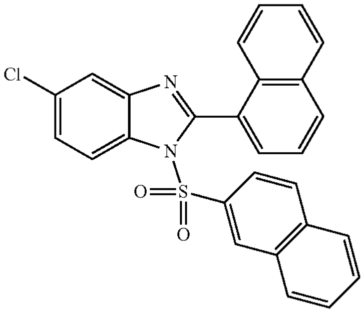

+

Peak1, Isomer 1
Compound-785

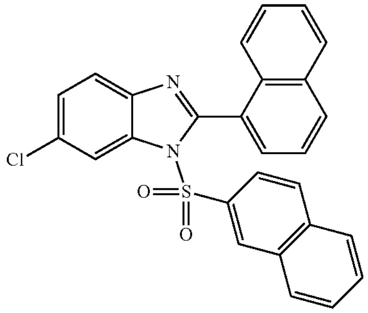

Peak2, Isomer 2
Compound-786

Steps 1 and 2 were performed as described for Compound 631

Compound 785: LCMS—469.1 $(M)^+$ @254 nm=97.97%. $^1$H NMR (400 MHz, DMSO-d6) δ 8.27 (d, J=8.8 Hz, 1H), 8.17 (dd, J=7.8, 1.9 Hz, 1H), 8.01 (d, J=2.2 Hz, 1H), 7.93 (ddd, J=11.0, 6.7, 2.2 Hz, 4H), 7.82 (d, J=8.2 Hz, 1H), 7.78-7.55 (m, 5H), 7.41 (dd, J=8.8, 2.1 Hz, 1H), 7.32 (dq, J=9.0, 5.0, 4.5 Hz, 1H), 7.10 (d, J=4.0 Hz, 2H)

Compound 786: LCMS—469.1 $((MH)^+$@ 254 nm=99.89% $^1$H NMR (400 MHz, DMSO-d6) δ 8.25 (s, 1H), 8.17-8.10 (m, 1H), 7.89 (q, J=17.9, 9.8 Hz, 5H), 7.78 (s, 1H), 7.75-7.51 (m, 5H), 7.41 (d, J=8.6 Hz, 1H), 7.29-7.22 (m, 1H), 7.02 (s, 2H).

Compound 787

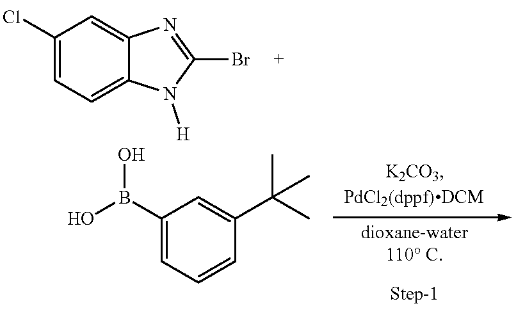

-continued

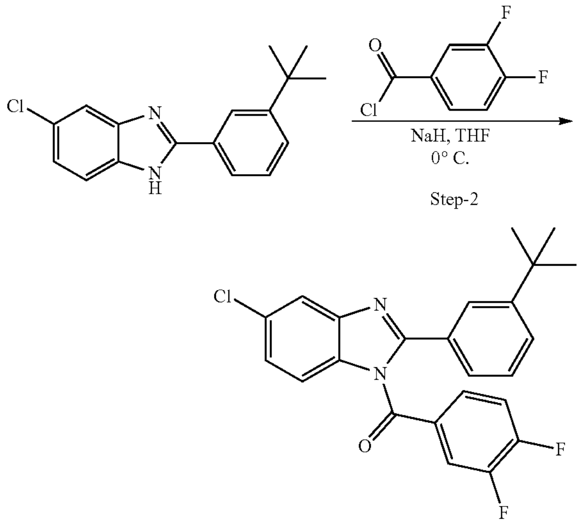

Isomer 1, peak 1
Compound-787

Step 1: To a solution of 2-bromo-5-chloro-1H-benzimidazole (1 g, 4.36 mmol), (3-tert-butylphenyl)boronic acid (932 mg, 5.24 mmol) in dioxane:water (20:4 mL) was added $K_2CO_3$ (924 mg, 8.72 mmol). The reaction mixture was purged with nitrogen for five minutes. $PdCl_2$(dppf)·dcm (354 mg, 0.436 mmol, 0.1 eq) was added and it was purged again for additional five minutes followed by heating at 110° C. for 16 hours. After completion of reaction, the reaction mixture was diluted with water and extracted with ethyl acetate (50 mL×2). The combined organic layer was washed with water (50 mL), brine solution (50 mL), dried over anhydrous sodium sulfate and concentrated under reduced pressure to afford crude product, which was purified by flash chromatography (elution 0-20% EtOAc in hexane) to afford the desired Compound: (650 mg) as a yellow solid.

Step 2: was performed as described above for step 2 of synthesis of Compound 535

Compound 787: LCMS—425 $(M)^+$ UPLC @ 254 nm=99.18%, @ 220 nm=97.18%. $^1H$ NMR (400 MHz, DMSO-$d_6$) δ ppm 7.96 (d, J=2.1 Hz, 1H), 7.86-7.73 (m, 2H), 7.58 (dd, J=9.1, 4.5 Hz, 1H), 7.50-7.43 (m, 2H), 7.43-7.32 (m, 3H), 7.25 (t, J=7.7 Hz, 1H), 1.19 (s, 9H).

Compound 788

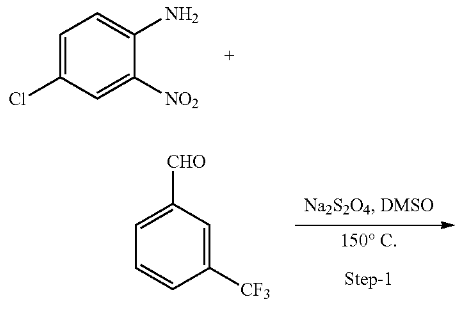

-continued

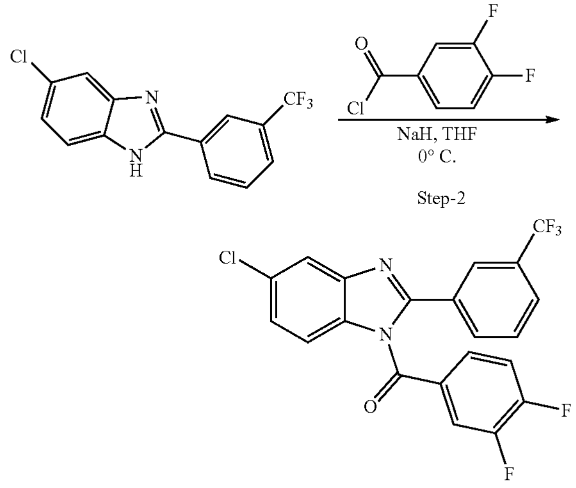

Isomer 1, peak 1
Compound-788

Steps 1 and 2 were performed as described for Compound 535

Compound 788: LCMS—437.2 (M)+ UPLC @ 254 nm=99.98%, @ 220 nm=98.81%. $^1H$ NMR (400 MHz, DMSO-$d_6$) δ ppm 7.99 (d, J=2.1 Hz, 1H), 7.92-7.82 (m, 3H), 7.75 (d, J=8.0 Hz, 1H), 7.71 (d, J=8.7 Hz, 1H), 7.66-7.54 (m, 2H), 7.49 (dd, J=8.7, 2.1 Hz, 1H), 7.42 (dt, J=10.3, 8.2 Hz, 1H).

Compound 789

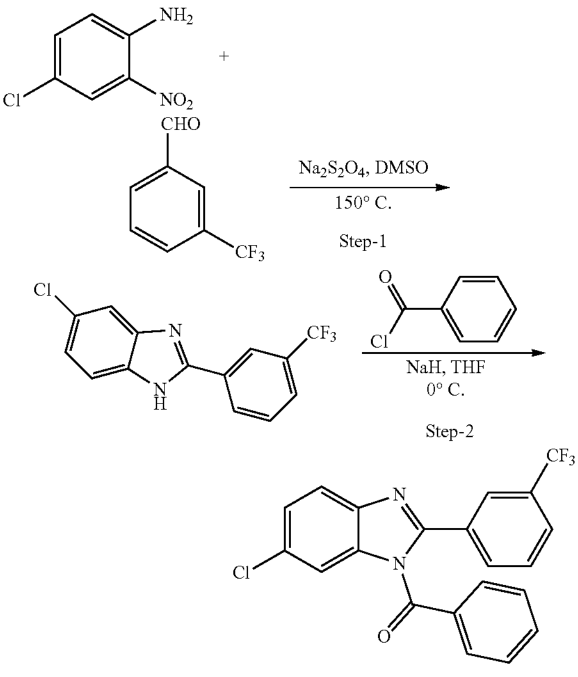

Isomer 2, peak 2
Compound-789

Steps 1 and 2 were performed as described for Compound 535

Compound 789: LCMS—401.3 (M)+UPLC @ 254 nm=97.28%, @ 220 nm=93.56%. $^{1}H$ NMR (400 MHz, DMSO-$d_6$) δ ppm 7.94-7.83 (m, 3H), 7.70 (t, J=7.3 Hz, 3H), 7.53 (ddd, J=21.8, 7.2, 2.9 Hz, 4H), 7.36 (t, J=7.7 Hz, 2H).

Compound 790

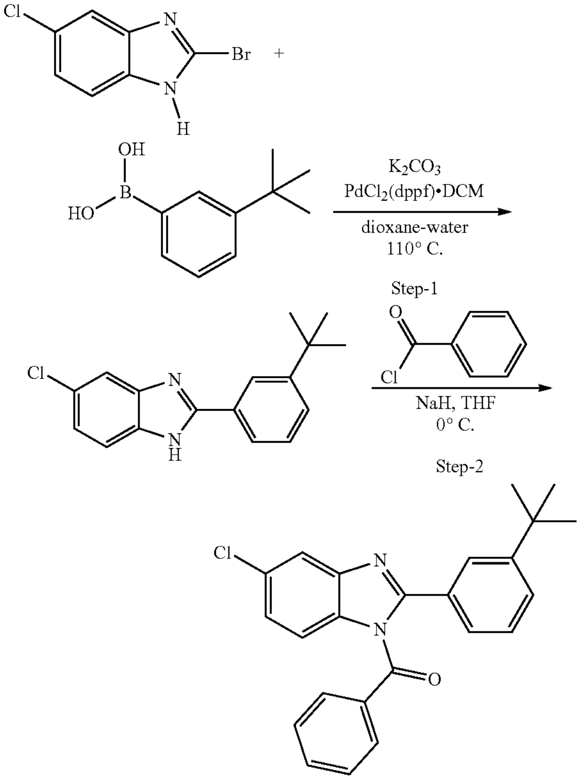

Isomer 1, peak 1
Compound-790

Steps 1 and 2 were performed as described for Compound 787

Compound 790: LCMS—389.4 $(M)^+$ UPLC @ 254 nm=97.92%, @ 220 nm=96.37%. $^{1}H$ NMR (400 MHz, DMSO-$d_6$) δ ppm 7.96 (d, J=2.2 Hz, 1H), 7.68 (d, J=7.6 Hz, 2H), 7.60-7.50 (m, 2H), 7.49-7.39 (m, 3H), 7.36 (t, J=7.7 Hz, 3H), 7.26 (t, J=7.7 Hz, 1H), 1.17 (s, 9H).

Compound 791

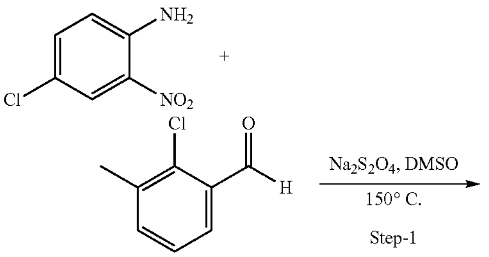

-continued

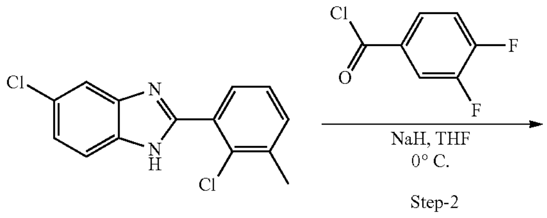

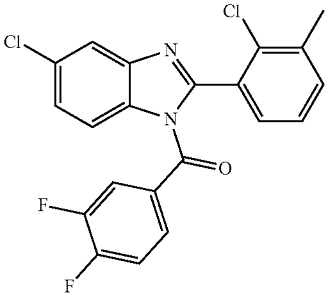

Isomer 1, peak 1
Compound-791

Steps 1 and 2 were performed as described for Compound 535

Compound 791: LCMS—417.1 $(M)^+$ UPLC @ 220 nm=95.86% $^{1}H$ NMR (400 MHz, DMSO-$d_6$) δ ppm 7.98 (d, J=2.1 Hz, 1H), 7.81 (ddd, J=10.4, 7.7, 2.2 Hz, 1H), 7.76 (d, J=8.7 Hz, 1H), 7.59 (d, J=10.0 Hz, 1H), 7.55-7.47 (m, 2H), 7.46-7.32 (m, 2H), 7.29 (t, J=7.5 Hz, 1H), 2.18 (s, 3H).

Compound 792

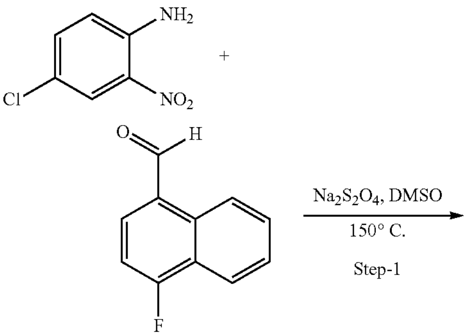

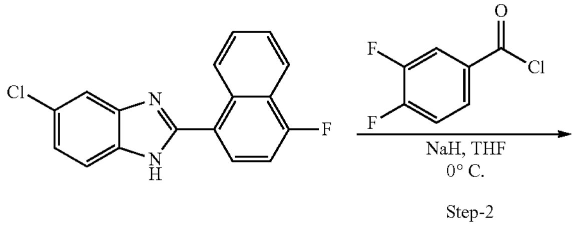

-continued

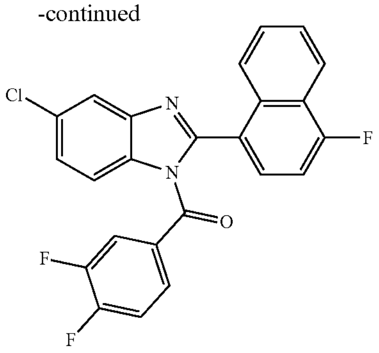

Isomer 1, peak 1
Compound-792

Steps 1 and 2 were performed as described for Compound 535

Compound 792: LCMS—437.1 $(M)^+$ LCMS @ 220 nm=98.17%. $^1H$ NMR (400 MHz, DMSO-$d_6$) δ ppm 8.07-7.97 (m, 2H), 7.95 (d, J=8.5 Hz, 1H), 7.87 (d, J=2.1 Hz, 1H), 7.68 (dq, J=8.6, 5.3, 4.8 Hz, 3H), 7.57 (td, J=8.4, 2.3 Hz, 2H), 7.32 (d, J=8.8 Hz, 1H), 7.26 (dd, J=10.4, 8.0 Hz, 1H), 7.16-7.05 (m, 1H).

Compound 848 and Compound 849

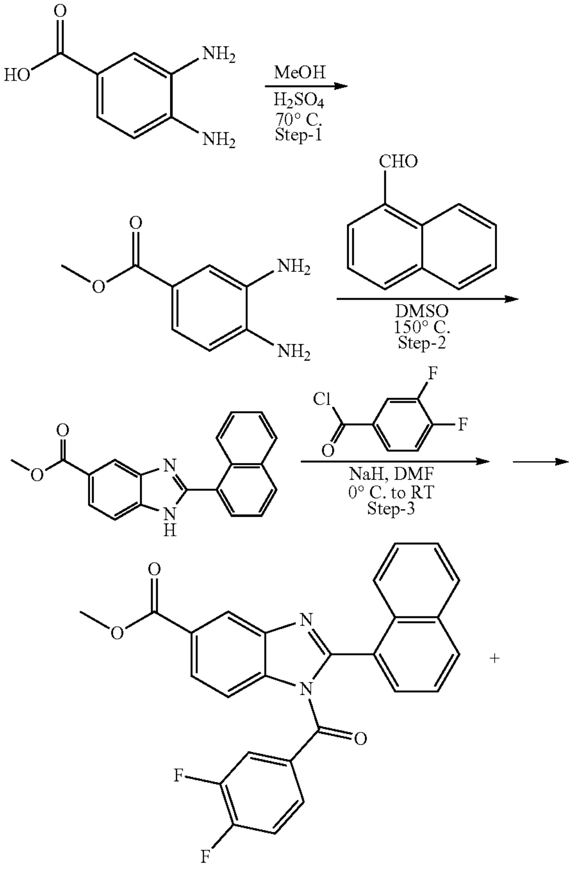

Peak1, Isomer 1
Compound-848

-continued

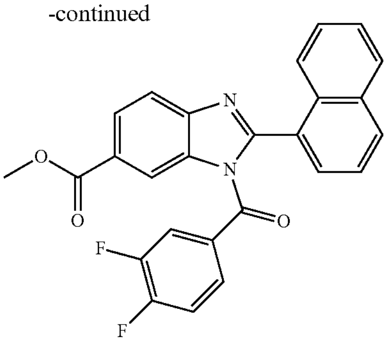

Peak 2, Isomer 2
Compound-849

Step 1: To a stirred solution of 3,4-diaminobenzoic acid (1.0 g, 6.57 mmol) in methanol (20 mL) at 0° C. was added concentrated sulphuric acid (20.0 mL) and the reaction mixture was refluxed at 70° C. for 4 hours. After completion, the reaction mixture was cooled and basified using saturated solution of sodium bicarbonate. The aqueous layer was extracted with DCM. The organic layer was dried under vacuum to give crude Compound. The crude Compound was washed with ether to give desired product methyl-3,4-diaminobenzoate (0.9 g) as an off-white solid.

Step 2 was performed as described above for step 1 of synthesis of Compound 579

Step 3 was performed as described above for step 2 of synthesis of Compound 535

Compound 848: LCMS—443.3$(M+H)^+$ UPLC @ 254 nm=97.79% and @ 220 nm 95.94% $^1H$ NMR (400 MHz, DMSO-$d_6$) δ ppm 7.90 (d, J=8.33 Hz, 1H) 7.84 (d, J=7.89 Hz, 1H) 7.77 (s, 2H) 7.56-7.68 (m, 3H) 7.44-7.55 (m, 3H) 7.31-7.44 (m, 3H), 3.93 (s, 3H)

Compound 849: LCMS—443.3$(M+H)^+$ UPLC @ 254 nm=97.51% and @ 220 nm=95.80%. $^1H$ NMR (400 MHz, DMSO-$d_6$) δ ppm 8.46 (d, J=1.75 Hz, 1H) 8.10 (dd, J=8.77, 1.75 Hz, 1H) 7.89-7.98 (m, 4H) 7.53-7.70 (m, 4H) 7.41-7.47 (m, 1H) 7.35 (br. s., 1H) 7.10 (d, J=10.09 Hz, 1H) 3.94 (s, 3H).

Compound 850 and Compound 851

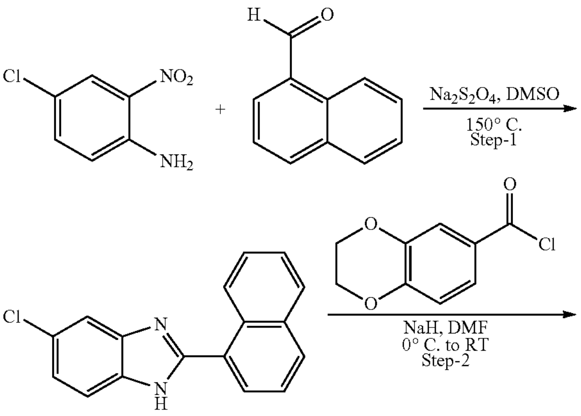

-continued

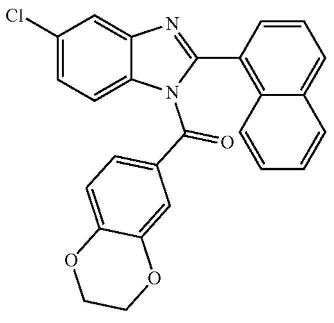

+

Peak1, Isomer 1
Compound-850

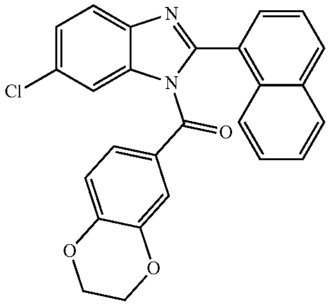

Peak 2, Isomer 2
Compound-851

Steps 1 and 2 were performed as described for Compound 535

Compound 850: LCMS—441.3 $(M)^+$ UPLC @ 254 nm=91.40% and @ 220 nm 91.30%. $^1$H NMR (400 MHz, DMSO-$d_6$) δ ppm 7.93-8.06 (m, 4H) 7.60 (d, J=6.14 Hz, 1H) 7.53-7.57 (m, 2H) 7.43-7.52 (m, 3H) 7.03-7.09 (m, 2H) 6.64 (d, J=8.33 Hz, 1H) 4.20 (br. s., 2H) 4.08 (br. s., 2H)

Compound 851: LCMS—441.3 $(M)^+$ UPLC @ 254 nm=99.83% and @ 220 nm=99.66%. $^1$H NMR (400 MHz, DMSO-$d_6$) δ ppm 8.00-8.04 (m, 1H) 7.90-7.98 (m, 4H) 7.52-7.60 (m, 3H) 7.50 (dd, J=8.55, 1.97 Hz, 1H) 7.41-7.47 (m, 1H) 7.01-7.08 (m, 2H) 6.61 (s, 1H) 4.18 (br. s., 2H) 4.06 (br. s., 2H).

Compound 852 and Compound 853

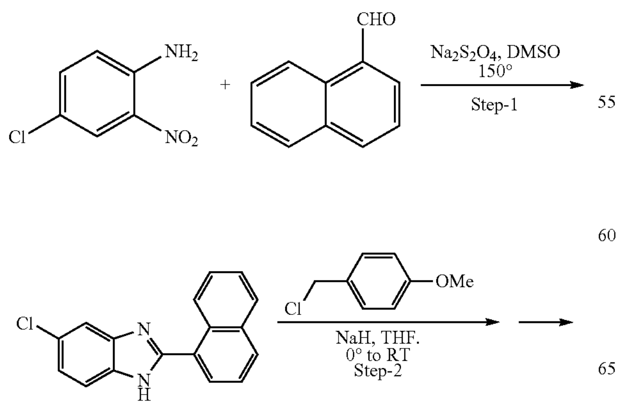

-continued

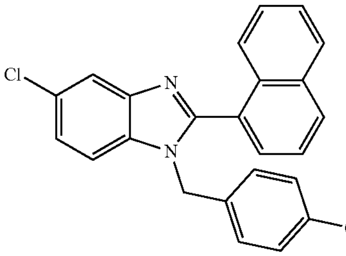

+

Peak1-Isomer1
Compound-852

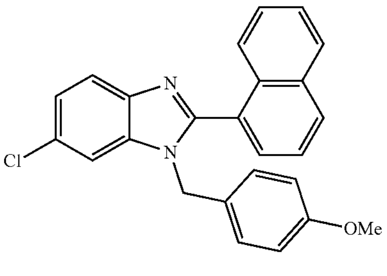

Peak2-Isomer2
Compound-853

Steps 1 and 2 were performed as described for Compound 533

Compound 852: LCMS—399.3 $(M)^+$ UPLC @ 254 nm=99.34%, @ 220 nm=99.86%. $^1$H NMR (400 MHz, DMSO-$d_6$) δ ppm 8.18 (d, J=7.89 Hz, 1H), 8.08 (d, J=7.89 Hz, 1H), 7.85 (s, 1H), 7.75 (d, J=7.02 Hz, 1H), 7.69 (d, 2H), 7.58-7.67 (m, 2H), 7.54 (d, J=7.02 Hz, 1H), 7.35 (d, J=9.21 Hz, 1H), 6.79 (m, J=8.33 Hz, 2H), 6.70 (m, J=8.77 Hz, 2H), 5.26 (s, 2H), 3.62 (s, 3H).

Compound 853: LCMS—399.3 $(M)^+$ UPLC @ 254 nm=99.08%, @ 220 nm=99.07%. $^1$H NMR (400 MHz, DMSO-$d_6$) δ ppm 8.16 (d, J=7.89 Hz, 1H), 8.07 (d, J=7.89 Hz, 1H), 7.76-7.89 (m, 1H), 7.72 (d, J=6.14 Hz, 2H), 7.62-7.69 (m, 2H), 7.60 (d, J=7.89 Hz, 1H), 7.44-7.55 (m, 1H), 7.32 (d, J=7.02 Hz, 1H), 6.78 (m, J=8.33 Hz, 2H), 6.70 (m, J=8.33 Hz, 2H), 5.25 (s, 2H), 3.62 (s, 3H).

Compound 854

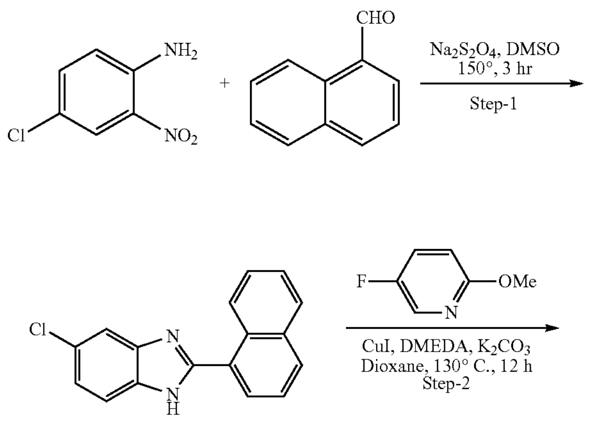

-continued

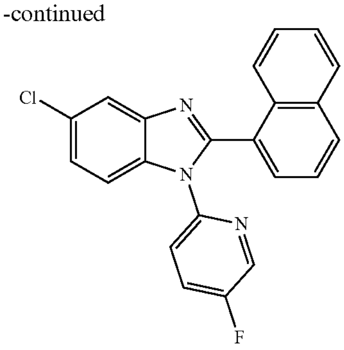

Isomer 1, peak 1
Compound-854

Step 1 was performed as described above for synthesis of Compound 494

Step 2: To a stirred solution of 5-chloro-2-(naphthalen-1-yl)-1H-benzo[d]imidazole (200 mg, 0.719 mmol) and 2-bromo-5-fluoropyridine (150 mg, 0.863 mmol) in (3 mL) of dioxane were added potassium carbonate (200 mg, 1.438 mmol) and the resulting mixture was purged with nitrogen for 10 min Copper iodide (27.4 mg, 0.143 mmol), and N,N'-dimethylethylenediamine (DMEDA) (0.03 mL, 0.287 mmol) were added to the reaction mixture and it was again purged with nitrogen for 10 min followed by stirring at 130° C. overnight. After completion of reaction, the reaction mixture was diluted with water and extracted with EtOAc (250 mL×2). The combined organic layers were washed with water (250 mL) brine solution (250 mL), dried over anhydrous sodium sulphate and concentrated under reduced pressure to afford crude product, which was purified by flash chromatography (Peak 1) 5-chloro-1-(5-fluoropyridin-2-yl)-2-(naphthalen-1-yl)-1H-benzo[d]imidazole (4 mg) as a yellow solid.

Compound 854: LCMS—374.2 $(M)^+$ UPLC @ 254 nm=93.25%, @ 220 nm=98.79%. $^1$H NMR (400 MHz, DMSO-$d_6$) δ ppm 8.53 (s, J=3.07 Hz, 1H), 8.06 (dd, J=6.36, 2.41 Hz, 2H), 7.87-8.02 (m, 2H), 7.76 (dd, J=8.33, 3.07 Hz, 2H), 7.57-7.65 (m, 2H), 7.43-7.57 (m, 2H), 7.32 (dd, J=8.99, 4.17 Hz, 2H).

Compound 855 and Compound 856

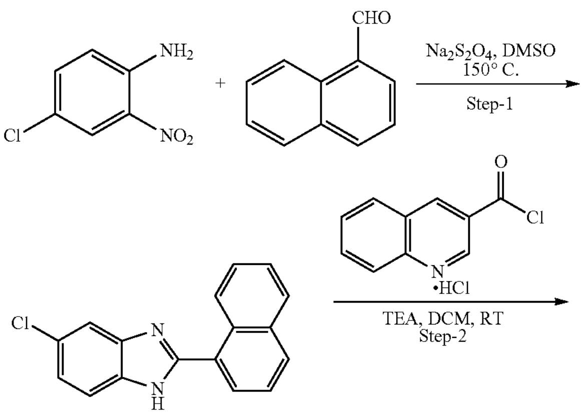

-continued

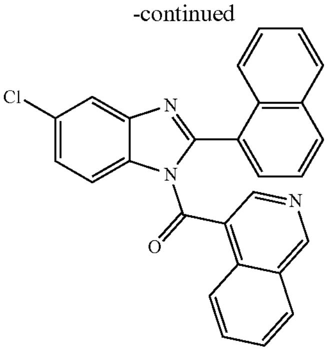

+

Isomer1-Peak1
Compound-855

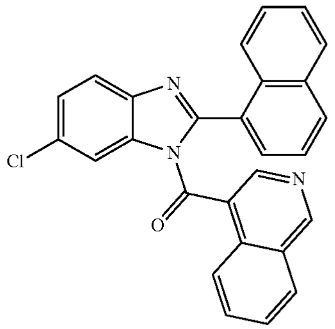

Isomer2-Peak2
Compound-856

Steps 1 and 2 were performed as described for Compound 529

Compound 855: LCMS—434.2 $(M)^+$ UPLC @ 254 nm=97.93%, @ 220 nm=95.59%. $^1$H NMR (400 MHz, DMSO-$d_6$) δ ppm 8.75 (d, J=2.19 Hz, 1H), 8.52 (d, J=1.75 Hz, 1H), 8.07 (d, J=1.75 Hz, 1H), 8.01 (d, J=8.33 Hz, 1H), 7.94 (d, J=8.77 Hz, 1H), 7.80-7.84 (m, 1H), 7.74-7.78 (m, 1H), 7.65-7.72 (m, 2H), 7.47-7.62 (m, 6H), 7.18-7.23 (m, 1H).

Compound 856: LCMS—434.3 $(M)^+$ UPLC @ 254 nm=98.91%, @ 220 nm=97.74%. $^1$H NMR (400 MHz, DMSO-$d_6$) δ ppm 8.71 (s, 1H), 8.47 (s, 1H), 7.97-8.04 (m, 3H), 7.78-7.83 (m, 1H), 7.75 (d, J=6.14 Hz, 1H), 7.57-7.69 (m, 4H), 7.43-7.55 (m, 4H), 7.18 (t, J=7.89 Hz, 1H).

Compound 857 and Compound 858

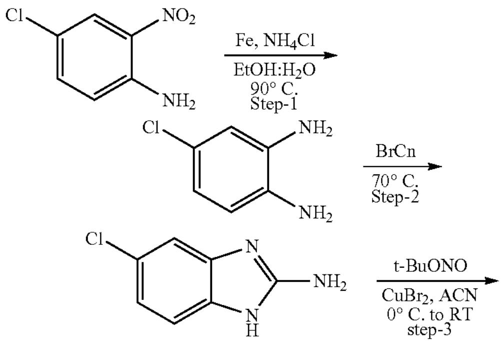

-continued

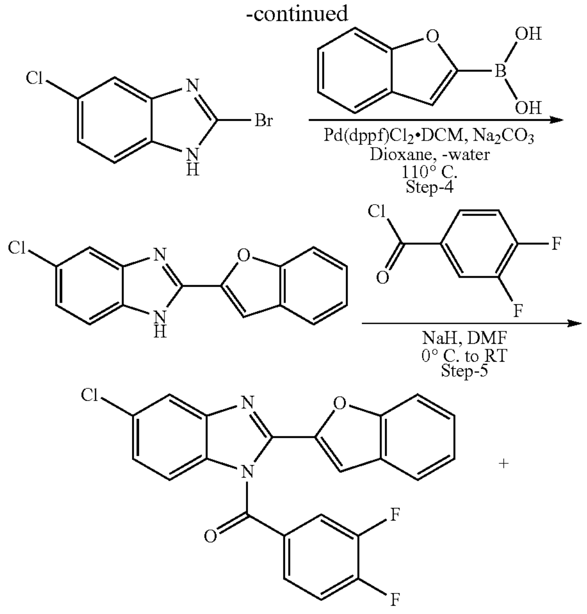

Isomer 1, peak 1
Compound-857

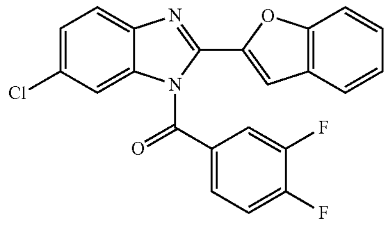

Isomer 2, peak 2
Compound-858

Steps 1-5 were performed as described for Compounds 588 and 584

Compound 857: LCMS—409.3 $(M)^+$ UPLC @ 254 nm=99.01%, @ 220 nm=99.30%. $^1$H NMR (400 MHz, DMSO-$d_6$) δ ppm 8.04-8.11 (m, 1H) 8.01 (d, J=1.75 Hz, 1H) 7.71 (d, J=7.45 Hz, 2H) 7.63 (s, 1H) 7.53-7.57 (m, 1H) 7.44-7.50 (m, 2H) 7.43 (s, 1H) 7.38 (t, J=7.24 Hz, 1H) 7.27-7.33 (m, 1H).

Compound 858: LCMS—409.3 $(M)^+$ UPLC @ 254 nm=96.56%, @ 220 nm=97.53% $^1$H NMR (400 MHz, DMSO-$d_6$) δ ppm 8.01-8.08 (m, 1H) 7.93 (d, J=8.33 Hz, 1H) 7.70 (d, J=7.45 Hz, 2H) 7.65 (d, J=2.19 Hz, 1H) 7.61 (s, 1H) 7.53 (dd, J=8.33, 2.19 Hz, 1H) 7.39-7.49 (m, 2H) 7.34-7.39 (m, 1H) 7.26-7.32 (m, 1H).

Compound 859

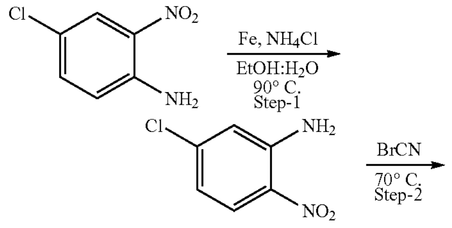

-continued

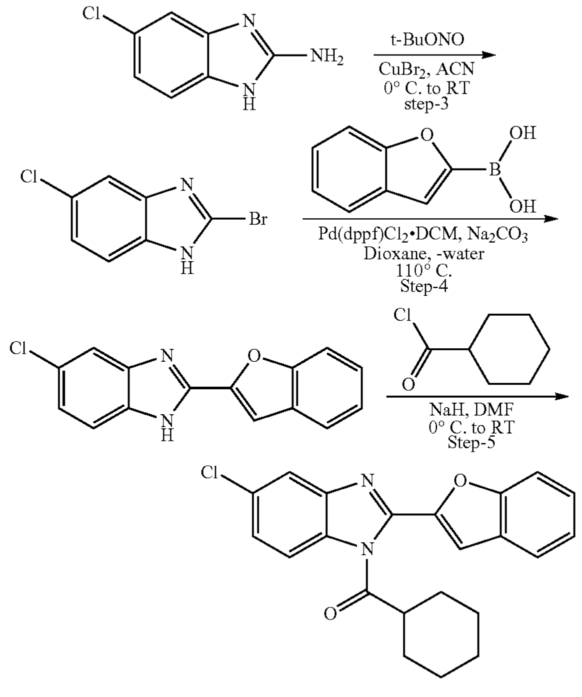

Isomer 1, peak 1
Compound-859

Steps 1-5 were performed as described for Compounds 588 and 584

Compound 859: LCMS—379.3 $(M)^+$ UPLC @ 254 nm=97.72%, @ 220 nm=97.66%. $^1$H NMR (400 MHz, DMSO-$d_6$) δ ppm 7.95 (d, J=1.75 Hz, 1H) 7.86 (dd, J=8.11, 3.73 Hz, 2H) 7.69-7.78 (m, 2H) 7.47-7.55 (m, 2H) 7.36-7.44 (m, 1H), 2.67 (m, 1H) 1.90 (d, J=10.96 Hz, 2H) 1.64 (d, J=13.59 Hz, 2H) 1.50 (d, J=9.21 Hz, 2H) 1.21 (d, J=15.79 Hz, 2H) 0.87-0.99 (m, 2H).

Compound 860

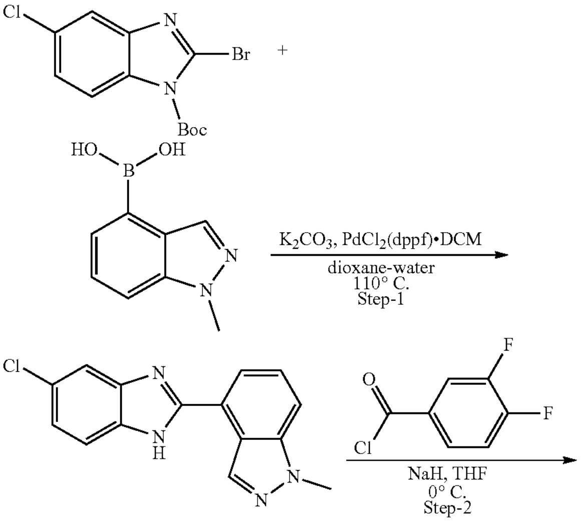

-continued

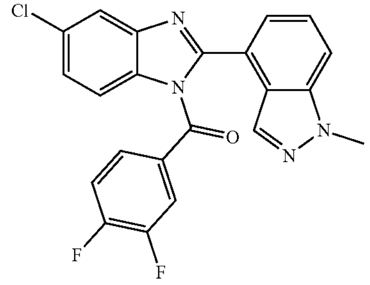

Isomer 1, peak 1
Compound-860

Steps 1-2 were performed as described for synthesis of Compound 787

LCMS—423.3 $(M)^+$ UPLC @ 254 nm=95.39%, @ 220 nm=94.01%.

$^1$H NMR (400 MHz, DMSO-$d_6$) δ ppm 8.14 (s, 1H), 8.02 (s, 1H), 7.89-7.79 (m, 1H), 7.70 (d, J=8.4 Hz, 1H), 7.58 (t, J=8.4 Hz, 1H), 7.46 (d, J=8.4 Hz, 1H), 7.34 (q, J=8.8, 8.0 Hz, 3H), 7.26 (d, J=7.1 Hz, 1H), 4.06 (s, 3H).

Compound 861 and Compound 862

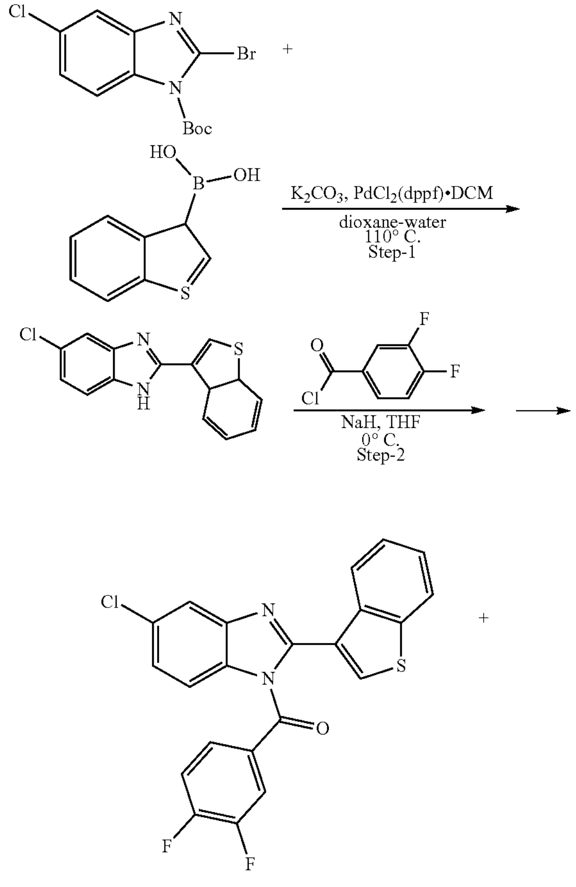

Isomer1, Peak1
Compound-861

-continued

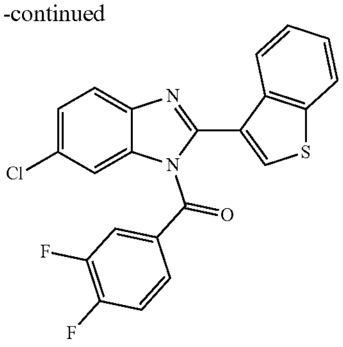

Isomer2, Peak 2
Compound-862

Steps 1 and 2 were performed as described for synthesis of Compound 787

Compound 861: LCMS—425.1 $(M)^+$ UPLC @ 254 nm=99.44%, @ 220 nm=99.88%. $^1$H NMR (400 MHz, DMSO-$d_6$) δ 8.11-7.96 (m, 4H), 7.78 (d, J=8.7 Hz, 1H), 7.72 (ddd, J=10.1, 7.6, 2.2 Hz, 1H), 7.54-7.39 (m, 4H), 7.25 (dt, J=10.5, 8.1 Hz, 1H).

Compound 862: LCMS—425.1 $(M)^+$ UPLC @ 254 nm=99.59%, @ 220 nm=99.38%. $^1$H NMR (400 MHz, DMSO-$d_6$) δ 8.09-8.01 (m, 2H), 7.98 (d, J=7.9 Hz, 1H), 7.94 (d, J=8.5 Hz, 1H), 7.85 (d, J=2.1 Hz, 1H), 7.67 (ddd, J=10.2, 7.7, 2.1 Hz, 1H), 7.54 (dd, J=8.5, 2.1 Hz, 1H), 7.45 (dq, J=14.6, 7.4 Hz, 3H), 7.22 (dt, J=10.4, 8.1 Hz, 1H).

Compound 863

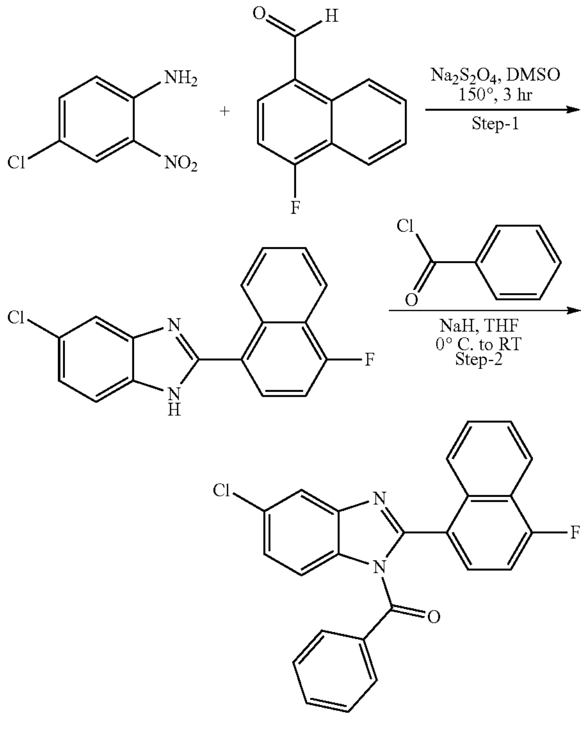

Isomer 1, Peak 1
Compound-863

Steps 1 and 2 were performed as described for synthesis of Compound 535

Compound 863: LCMS—401.2(M)$^+$ UPLC @ 254 nm=99.95%, @ 220 nm=99.82%. $^1$H NMR (401 MHz, DMSO-$d_6$) δ ppm 8.08 (d, J=7.9 Hz, 1H), 8.05-7.97 (m, 2H), 7.72-7.60 (m, 4H), 7.53-7.46 (m, 3H), 7.36 (t, J=7.5 Hz, 1H), 7.24 (dd, J=10.5, 8.0 Hz, 1H), 7.09 (t, J=7.6 Hz, 2H).

Compound 864 and Compound 865

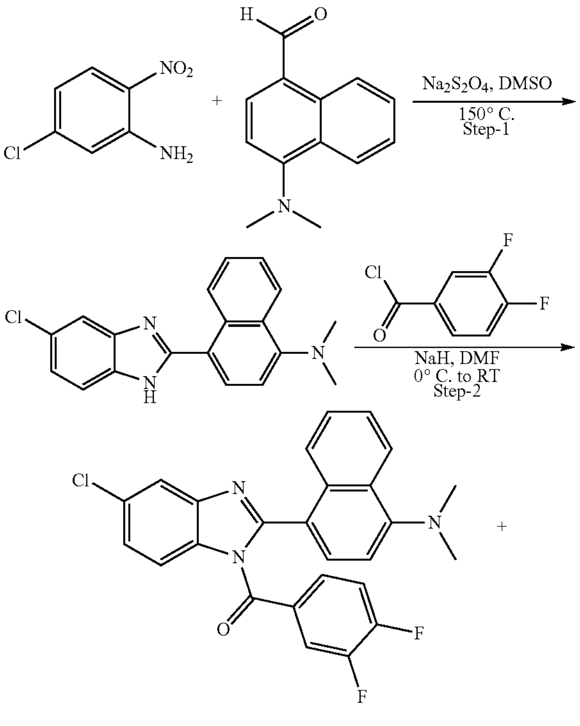

Peak1, Isomer 1
Compound-864

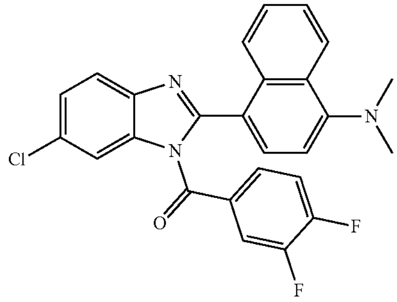

Peak 2, Isomer 2
Compound-865

Steps 1 and 2 were performed as described for synthesis of Compound 535

Compound 864: LCMS—322.3 (fragment; benzimidazole core) UPLC @ 254 nm=99.70% and @ 220 nm 97.70% $^1$H NMR (400 MHz, DMSO-$d_6$) δ ppm 8.02-8.06 (m, 1H) 8.00 (d, J=1.75 Hz, 1H) 7.92 (d, J=8.77 Hz, 1H) 7.77-7.81 (m, 1H) 7.49-7.57 (m, 4H) 7.41 (br. s., 1H) 7.15 (br. s., 1H) 6.99 (d, J=10.96 Hz, 1H) 6.94 (d, J=8.33 Hz, 1H) 2.78 (s, 6H)

Compound 865: LCMS—322.3 (fragment; benzimidazole core) UPLC @ 254 nm=91.49% and @ 220 nm=92.38%. $^1$H NMR (400 MHz, DMSO-d6) δ ppm 8.05 (br. s., 1H) 7.98 (s, 1H) 7.93 (d, J=8.77 Hz, 1H) 7.76 (br. s., 1H) 7.48-7.58 (m, 3H) 7.37 (br. s., 1H) 7.14 (br. s., 2H) 6.89-7.01 (m, 2H) 2.77 (s, 6H).

Compound 866

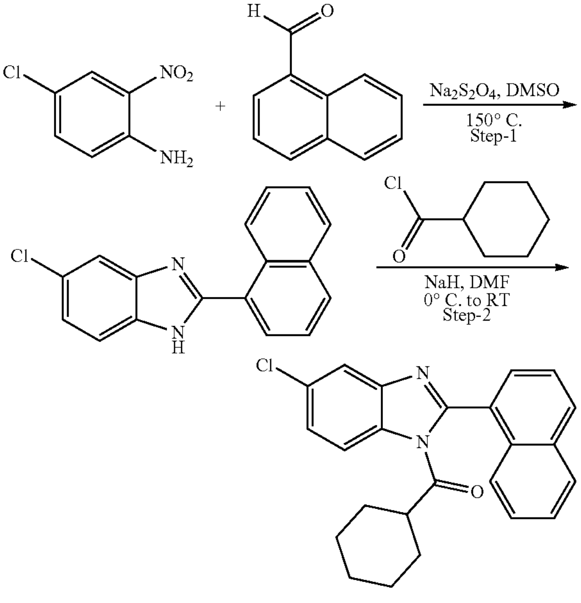

Peak 1, Isomer 1
Compound-866

Steps 1-2 were performed as described for synthesis of Compound 535

Compound 866: LCMS—389.3 (M)$^+$ UPLC @ 254 nm=99.26% and @ 220 nm 98.82%. $^1$H NMR (400 MHz, DMSO-$d_6$) δ ppm 8.24 (d, J=8.33 Hz, 1H) 8.13 (dd, J=8.33, 5.26 Hz, 2H) 7.93-7.96 (m, 1H) 7.88 (d, J=7.02 Hz, 1H) 7.71 (t, J=7.45 Hz, 1H) 7.64 (d, J=4.38 Hz, 2H) 7.58 (d, J=7.45 Hz, 1H) 7.51-7.56 (m, 1H) 1.95-2.04 (m, 1H) 1.35 (d, J=12.28 Hz, 4H) 1.21-1.30 (m, 2H) 1.09-1.21 (m, 3H) 0.90 (d, J=13.15 Hz, 1H).

Compound 867 and Compound 868

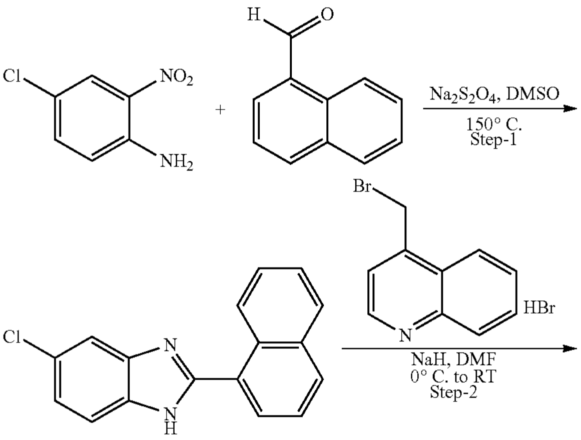

-continued

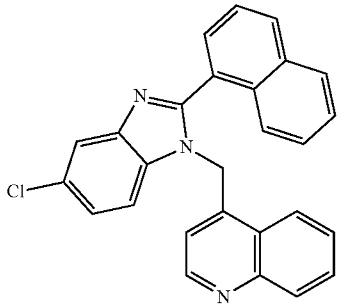

+

Peak1, Isomer 1
Compound-867

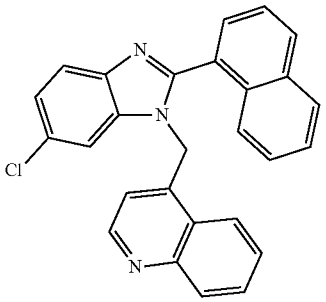

Peak 2, Isomer2
Compound-868

Steps 1-2 were performed as described for synthesis of Compound 535

Compound 867: LCMS—420.3 $(M)^+$ UPLC @ 254 nm=98.40% and @ 220 nm 99.35%. $^1H$ NMR (400 MHz, DMSO-d6) δ ppm 8.63 (d, J=4.39 Hz, 1H) 7.78-8.04 (m, 7H) 7.74 (br. s., 1H) 7.63 (d, J=6.58 Hz, 1H) 7.55 (d, J=7.45 Hz, 2H) 7.45-7.52 (m, 2H) 7.38 (d, J=9.21 Hz, 1H) 6.54 (br. s., 1H) 5.96 (s, 2H)

Compound 868: LCMS—420.3 $(M)^+$ UPLC @ 254 nm=99.92% and @ 220 nm=99.66%. $^1H$ NMR (400 MHz, DMSO-$d_6$) δ ppm 8.62 (d, J=4.38 Hz, 1H) 8.04 (d, J=8.33 Hz, 1H) 7.91-8.00 (m, 4H) 7.84 (d, J=8.33 Hz, 1H) 7.73 (d, J=8.33 Hz, 1H) 7.47-7.66 (m, 6H) 7.35 (d, J=10.52 Hz, 1H) 6.57 (d, J=4.82 Hz, 1H) 5.96 (s, 2H).

Compound 869 and Compound 870

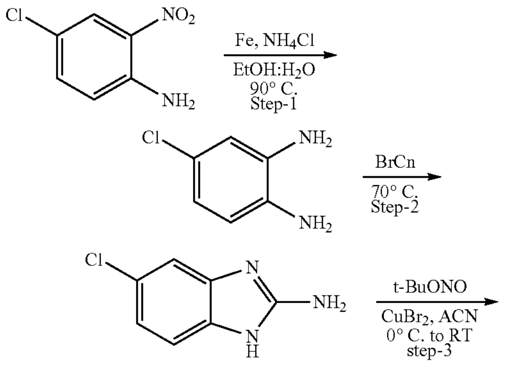

-continued

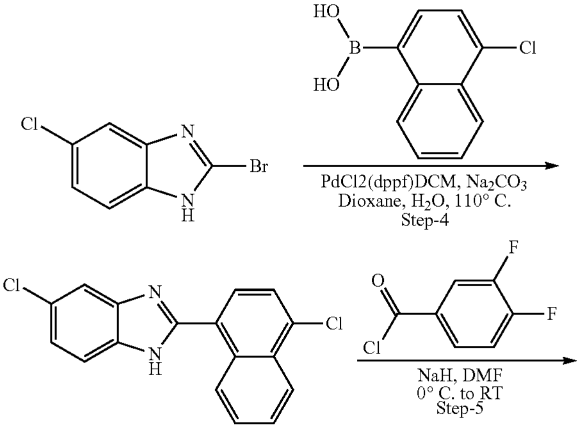

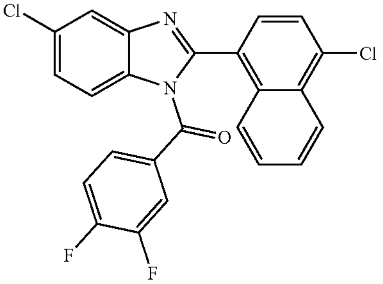

+

Isomer 1, peak 1
Compound-869

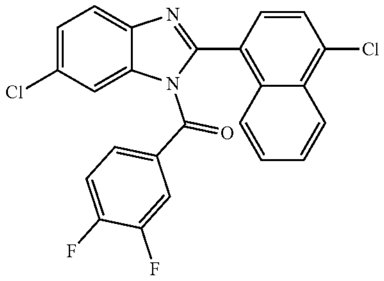

Isomer 2, peak 2
Compound-870

Steps 1-5 were performed as described for synthesis of Compound 590

Compound 869: LCMS—453.2$(M)^+$ UPLC @ 254 nm=99.32% and @ 220 nm 98.61% $^1H$ NMR (400 MHz, DMSO-$d_6$) δ ppm 8.19 (d, J=8.33 Hz, 1H) 7.98-8.05 (m, 2H) 7.71-7.79 (m, 2H) 7.58-7.71 (m, 4H) 7.53 (dd, J=8.77, 2.19 Hz, 1H) 7.35 (br. s., 1H) 7.10-7.19 (m, 1H)

Compound 870: LCMS—453.2$(M)^+$ UPLC @ 254 nm=99.66% and @ 220 nm=99.21%. $^1H$ NMR (400 MHz, DMSO-$d_6$) δ ppm 8.18 (d, J=8.33 Hz, 1H) 8.00 (d, J=7.89 Hz, 1H) 7.96 (d, J=8.77 Hz, 1H) 7.86 (d, J=1.75 Hz, 1H) 7.66-7.77 (m, 2H) 7.61-7.66 (m, 2H) 7.57 (dd, J=8.55, 1.97 Hz, 2H) 7.31 (br. s., 1H) 7.06-7.15 (m, 1H).

Compound 871 and Compound 872

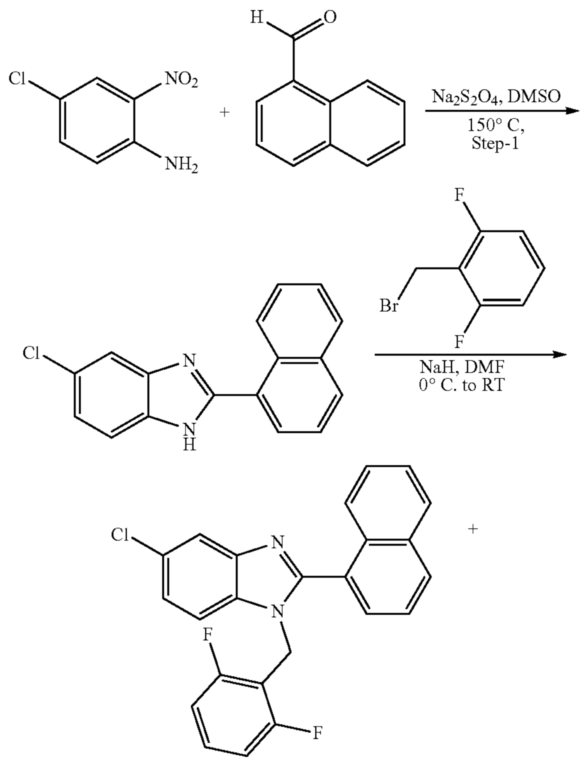

Peak1, Isomer 1
Compound-871

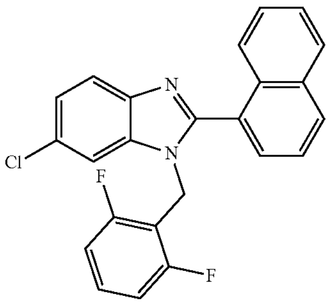

Peak2, Isomer 2
Compound-872

Steps 1 and 2 were performed as described for synthesis of Compound 533

Compound 871: LCMS—405.3 $(M)^+$ UPLC @ 254 nm=99.74% and @ 220 nm 99.71%. $^1H$ NMR (400 MHz, DMSO-d6) δ 8.11 (d, J=8.1 Hz, 1H), 8.00 (d, J=8.2 Hz, 1H), 7.82 (d, J=2.1 Hz, 1H), 7.73-7.58 (m, 3H), 7.58-7.46 (m, 2H), 7.46-7.35 (m, 2H), 7.14 (ddd, J=14.9, 8.4, 6.5 Hz, 1H), 6.74 (t, J=8.2 Hz, 2H), 5.46 (s, 2H).

Compound 872: LCMS—401.2 $(M)^+$ UPLC @ 254 nm=99.91% and @ 220 nm=99.71%. $^1H$ NMR (400 MHz, DMSO-d6) δ 8.10 (d, J=8.1 Hz, 1H), 7.99 (d, J=8.2 Hz, 1H), 7.81 (d, J=2.3 Hz, 1H), 7.76 (d, J=8.5 Hz, 1H), 7.66 (d, J=7.0 Hz, 1H), 7.60 (t, J=7.6 Hz, 1H), 7.52 (ddd, J=8.3, 6.5, 1.5 Hz, 1H), 7.47-7.29 (m, 3H), 7.12 (ddd, J=15.0, 8.5, 6.7 Hz, 1H), 6.72 (t, J=8.2 Hz, 2H), 5.46 (s, 2H).

Compound 874

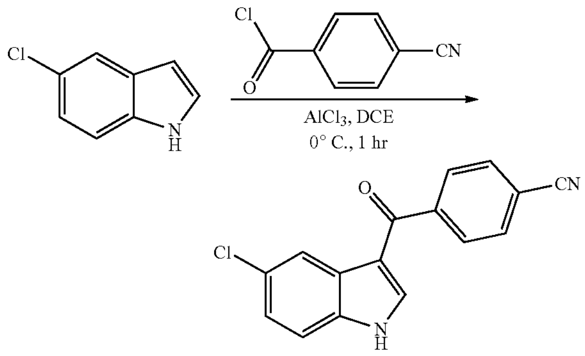

Compound-874

Step 1 was performed as described for synthesis of Compound 359

Compound 874: LCMS: 281.2 $(M)^+$ UPLC @ 254=99.92%, @ 220=99.82% $^1H$ NMR (400 MHz, DMSO-$d_6$) δ ppm 12.38 (br. s., 1H) 8.24 (s, 1H) 8.06 (s, 1H) 8.02 (d, J=7.89 Hz, 2H) 7.93 (d, J=8.33 Hz, 2H) 7.56 (d, J=8.77 Hz, 1H) 7.32 (dd, J=8.77, 2.19 Hz, 1H).

Compound 875

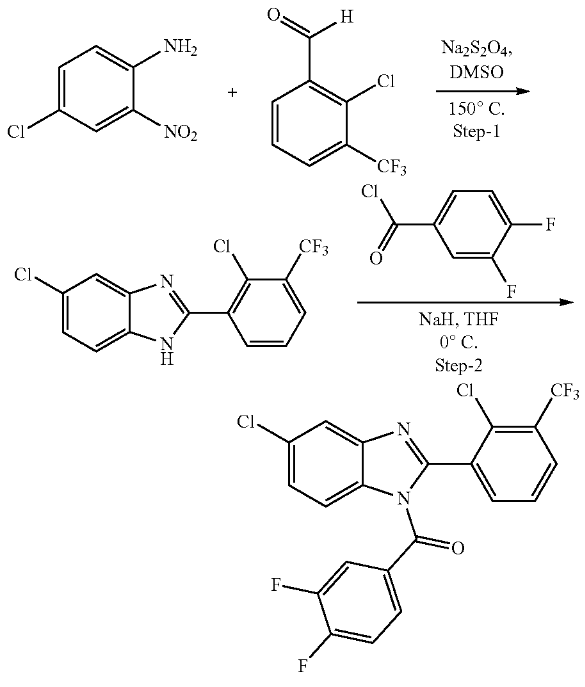

Peak1, Isomer 1
Compound-875

Steps 1 and 2 were performed as described for synthesis of Compound 535

Compound 875: LCMS—471.2 $(M)^+$ UPLC @ 254 nm=97.03%, @ 220 nm=83.96%. $^1H$ NMR (400 MHz, DMSO-$d_6$) δ ppm δ 8.06-7.99 (m, 2H), 7.94-7.83 (m, 2H), 7.74 (d, J=8.7 Hz, 1H), 7.63 (q, J=9.9, 8.9 Hz, 2H), 7.54 (dd, J=8.9, 2.1 Hz, 1H), 7.41 (q, J=8.9 Hz, 1H).

Compound 876 and Compound 877

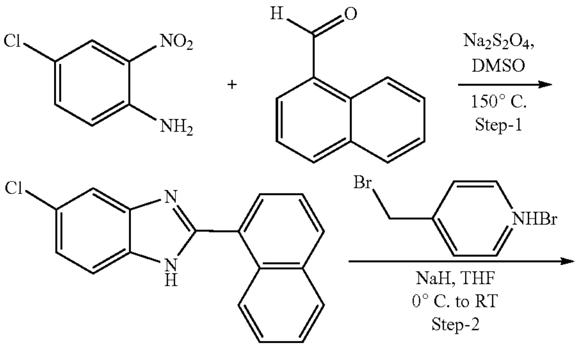

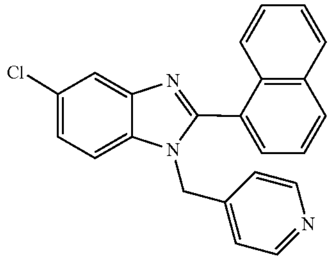

+

Peak 1, Isomer1
Compound-876

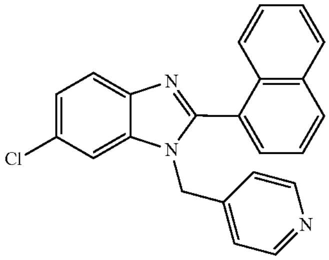

Peak 2, Isomer2
Compound-877

Steps 1 and 2 were performed as described for synthesis of Compound 533

Compound 876: LCMS—370.2 $(M)^+$ UPLC @ 254 nm=96.14%, @ 220 nm=95.83% $^1$H NMR (400 MHz, DMSO-d6) δ 8.37-8.30 (m, 2H), 8.13 (d, J=8.2 Hz, 1H), 8.04 (d, J=8.2 Hz, 1H), 7.83 (d, J=8.6 Hz, 1H), 7.75 (d, J=2.1 Hz, 1H), 7.73-7.64 (m, 2H), 7.60 (q, J=7.9 Hz, 2H), 7.51 (t, J=7.6 Hz, 1H), 7.36 (dd, J=8.6, 2.1 Hz, 1H), 6.81 (d, J=5.5 Hz, 2H), 5.39 (s, 2H).

Compound 877: LCMS—370.1 UPLC $(M)^+$ @ 254 nm=97.97%, @ 220 nm=98.11%. $^1$H NMR (400 MHz, DMSO-d6) δ 8.37-8.30 (m, 2H), 8.14 (d, J=8.0 Hz, 1H), 8.04 (d, J=8.1 Hz, 1H), 7.90 (d, J=2.0 Hz, 1H), 7.74-7.65 (m, 2H), 7.65-7.47 (m, 4H), 7.36 (dd, J=8.6, 2.1 Hz, 1H), 6.83 (d, J=5.5 Hz, 2H), 5.39 (s, 2H).

Compound 881

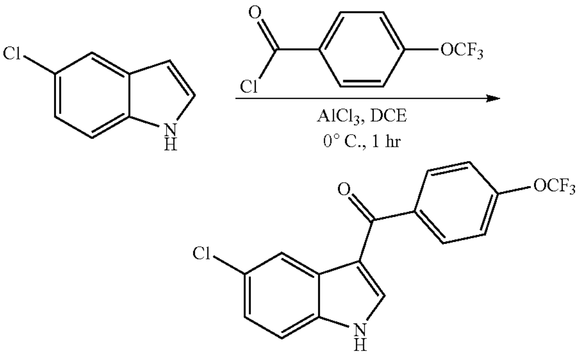

Compound-881

Step 1 was performed as described for step 2 of synthesis of Compound 359

Compound 881: LCMS—340.2 $(M)^+$ UPLC @ 254=99.64%, @ 220=99.89% $^1$H NMR (400 MHz, DMSO-$d_6$) δ ppm 12.32 (br. s., 1H) 8.24 (d, J=2.19 Hz, 1H) 8.10 (s, 1H) 7.91-7.99 (m, 2H) 7.54 (t, J=8.99 Hz, 3H) 7.30 (dd, J=8.33, 2.19 Hz, 1H).

Compound 882

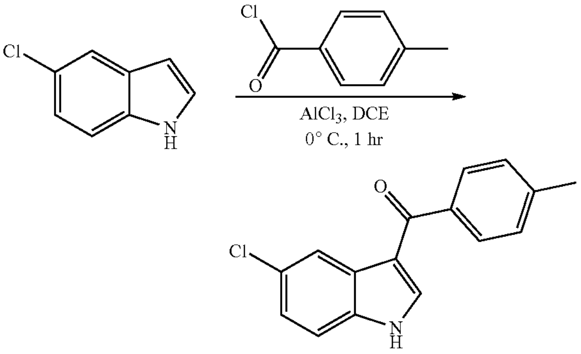

Compound-882

Step 1 was performed as described for step 2 of synthesis of Compound 359

Compound 882: LCMS—270.1 (M)+UPLC @220=96.0% $^1$H NMR (400 MHz, DMSO-$d_6$) δ ppm 12.19 (br. s., 1H) 8.21 (d, J=1.75 Hz, 1H) 8.02 (s, 1H) 7.70 (m, J=7.89 Hz, 2H) 7.52 (d, J=8.77 Hz, 1H) 7.34 (m, J=7.89 Hz, 2H) 7.26 (dd, J=8.33, 2.19 Hz, 1H) 2.39 (s, 3H).

Compound 883

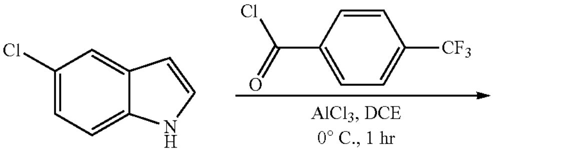

-continued

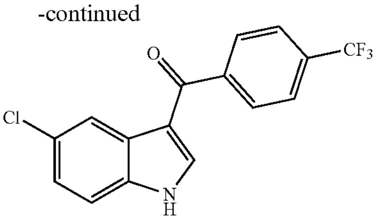

Compound-883

Step 1 was performed as described for step 2 of synthesis of Compound 359

Compound 883: LCMS—324.1 (M)+UPLC @220=94.83% $^1$H NMR (400 MHz, DMSO-$d_6$) δ ppm 12.38 (br. s., 1H) 8.25 (d, J=2.19 Hz, 1H) 8.10 (s, 1H) 7.98 (d, J=7.89 Hz, 2H) 7.91 (d, J=8.33 Hz, 2H) 7.56 (d, J=8.77 Hz, 1H) 7.31 (dd, J=8.77, 2.19 Hz, 1H).

Compound 884

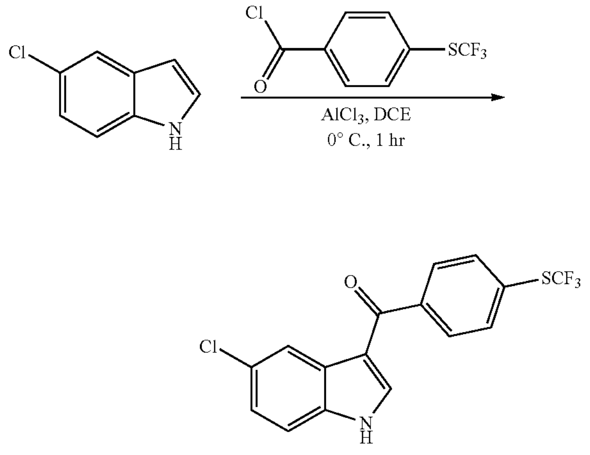

Compound-884

Step 1 was performed as described for step 2 of synthesis of Compound 359

Compound 884: LCMS—356.1 (M)+UPLC @220=99.38% $^1$H NMR (400 MHz, DMSO-$d_6$) δ ppm 12.32 (br. s., 1H) 8.24 (d, J=2.19 Hz, 1H) 8.09 (s, 1H) 7.85-7.93 (m, 3H) 7.56 (d, J=8.33 Hz, 2H) 7.31 (dd, J=8.77, 2.19 Hz, 1H).

Compound 885

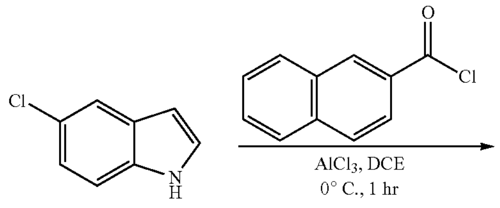

-continued

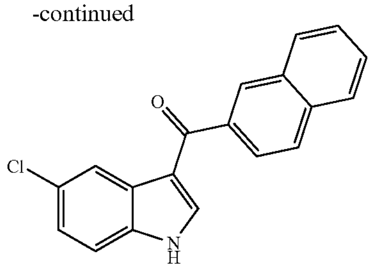

Compound-885

Step 1 was performed as described for step 2 of synthesis of Compound 359

Compound 885: LCMS—306.1 (M)+UPLC @220=99.18% $^1$H NMR (400 MHz, DMSO-$d_6$) δ ppm 12.32 (br. s., 1H) 8.43 (s, 1H) 8.28 (d, J=2.19 Hz, 1H) 8.11-8.17 (m, 2H) 8.07 (d, J=8.77 Hz, 1H) 8.03 (d, J=7.45 Hz, 1H) 7.88 (dd, J=8.33, 1.75 Hz, 1H) 7.60-7.69 (m, 2H) 7.57 (d, J=8.77 Hz, 1H) 7.29 (dd, J=8.55, 1.97 Hz, 1H).

Compound 886

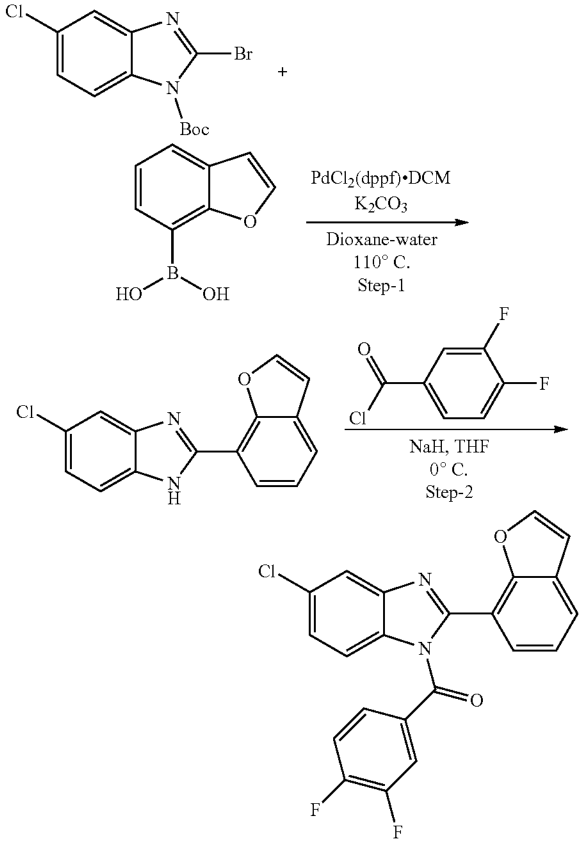

Isomer 1, peak 1
Compound-886

Steps 1 and 2 were performed as described for synthesis of Compound 787

Compound 886: LCMS—409.3 (M)$^+$ UPLC @ 254 nm=97.18%, @ 220 nm=99.18%. $^1$H NMR (400 MHz, DMSO-$d_6$) δ ppm 8.02 (s, 1H) 7.96 (s, 1H) 7.83 (d, J=8.77

Hz, 1H) 7.64-7.74 (m, 3H) 7.52 (d, J=8.77 Hz, 1H) 7.40 (br. s., 1H) 7.33 (t, J=7.67 Hz, 1H) 7.14-7.24 (m, 1H) 6.92 (d, J=1.75 Hz, 1H).

Compound 887 and Compound 888

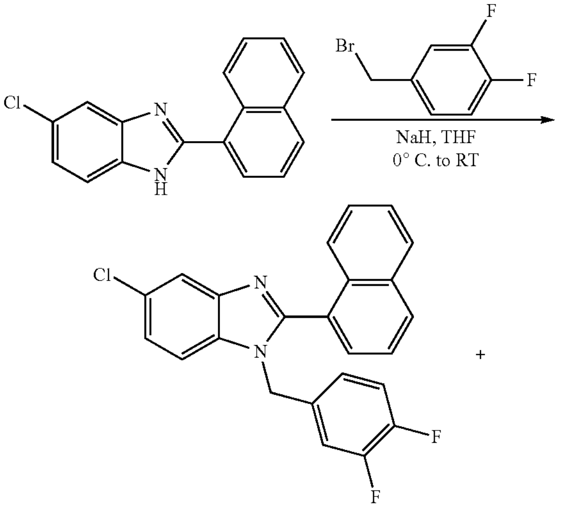

Isomer 1, Peak-1
Compound-887

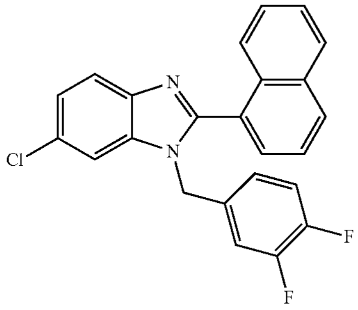

Isomer 2, Peak-2
Compound-888

Step 1 was performed as described for synthesis of Compound 533

Compound 887: LCMS—405.3 (M)+UPLC @ 254 nm=98.93%, @ 220 nm=99.36% $^{1}$H NMR (400 MHz, Methanol-d4) δ 8.13 (dd, J=7.5, 2.0 Hz, 1H), 8.01 (d, J=8.2 Hz, 1H), 7.76 (d, J=8.6 Hz, 1H), 7.69-7.61 (m, 2H), 7.61-7.53 (m, 1H), 7.49 (dd, J=5.8, 1.5 Hz, 2H), 7.44-7.32 (m, 1H), 7.00 (dt, J=10.5, 8.3 Hz, 2H), 6.72-6.56 (m, 2H), 5.26 (s, 2H).

Compound 888: LCMS—405.3 (M)+UPLC @ 254 nm=98.78%, @ 220 nm=98.94%. $^{1}$H NMR (400 MHz, Methanol-d4) δ 8.13 (dd, J=7.7, 1.9 Hz, 1H), 8.01 (d, J=8.2 Hz, 1H), 7.79 (d, J=1.9 Hz, 1H), 7.68-7.60 (m, 2H), 7.60-7.54 (m, 2H), 7.54-7.44 (m, 2H), 7.39 (dd, J=8.7, 2.0 Hz, 1H), 7.00 (dt, J=10.4, 8.4 Hz, 1H), 6.70 (ddd, J=10.8, 7.6, 2.2 Hz, 1H), 6.64-6.55 (m, 1H), 5.28 (s, 2H).

Compound 889

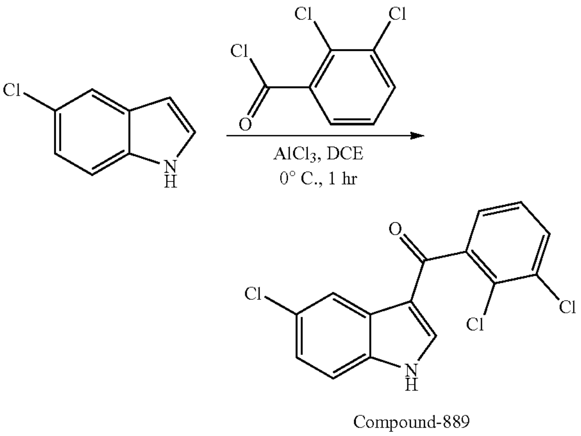

Compound-889

Step 1 was performed as described for step 2 of synthesis of Compound 359

Compound 889: LCMS: 324.1 $(M)^+$ UPLC @ 254=99.95%, @ 220=99.84% $^{1}$H NMR (400 MHz, DMSO-$d_6$) δ ppm 12.37 (br. s., 1H) 8.16 (s, 1H) 7.80-7.86 (m, 1H) 7.76-7.80 (m, 1H) 7.46-7.57 (m, 3H) 7.32 (dd, J=8.77, 2.19 Hz, 1H)

Compound 890

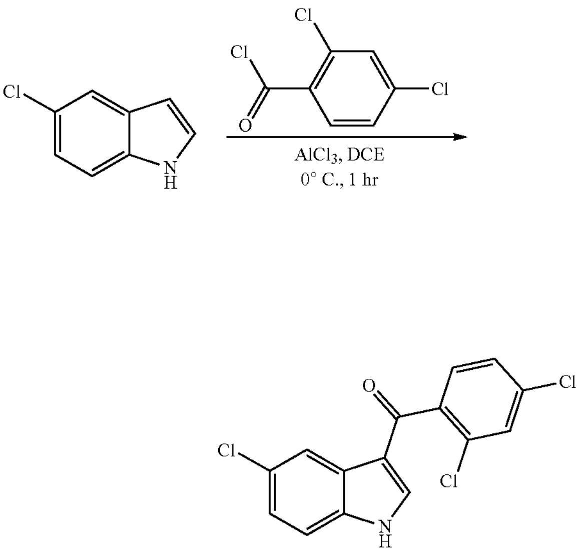

Compound-890

Step 1 was performed as described for step 2 of synthesis of Compound 359

Compound 890: LCMS: 324.2 $(M)^+$ UPLC @ 254=99.44%, @ 220=99.58% $^{1}$H NMR (400 MHz, DMSO-$d_6$) δ ppm 12.37 (br. s., 1H) 8.16 (d, J=1.75 Hz, 1H) 7.84 (s, 1H) 7.78 (s, 1H) 7.48-7.60 (m, 3H) 7.31 (dd, J=8.55, 1.97 Hz, 1H).

Compound 891

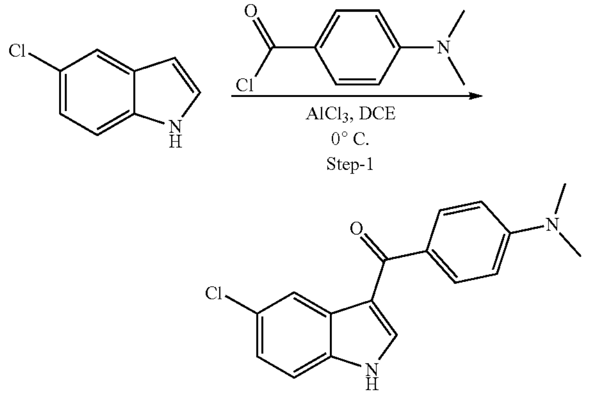

Compound-891

Step 1 was performed as described for step 2 of synthesis of Compound 359

Compound 891: LCMS—299.1 $(M)^+$ UPLC:—At 254 nm: 96.76%, At 220 nm: 96.34%. $^1$H NMR (400 MHz, DMSO-$d_6$) δ ppm 12.07 (br. s., 1H) 8.17 (d, J=1.75 Hz, 1 H) 8.02 (d, J=2.63 Hz, 1H) 7.75 (m, J=9.21 Hz, 2H) 7.52 (d, J=8.33 Hz, 1H) 7.21-7.28 (m, 1H) 6.79 (m, J=9.21 Hz, 2H) 3.03 (s, 6H).

Compound 892

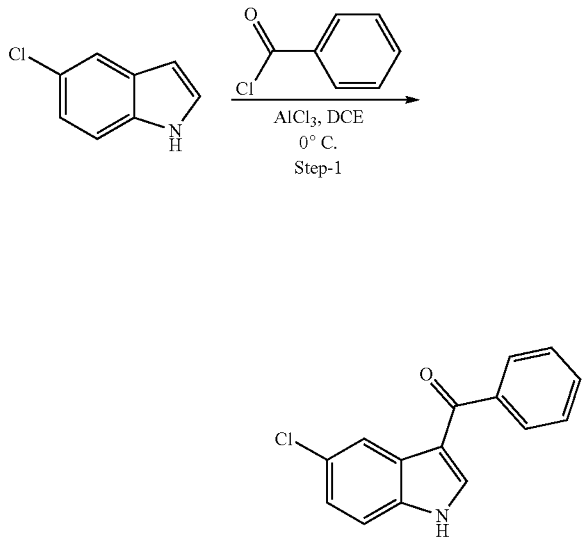

Compound-892

Step 1 was performed as described for step 2 of synthesis of Compound 359

Compound 892: LCMS—256.2 $(M)^+$ UPLC:—At 255 nm 99.84%, At 220 nm: 99.85%. $^1$H NMR (400 MHz, DMSO-$d_6$) δ ppm 12.26 (br. s., 1H) 8.24 (d, J=2.19 Hz, 1H) 8.04 (s, 1H) 7.80 (d, J=7.02 Hz, 2H) 7.44-7.69 (m, 4H) 7.29 (dd, J=8.99, 1.97 Hz, 1H).

Compound 893

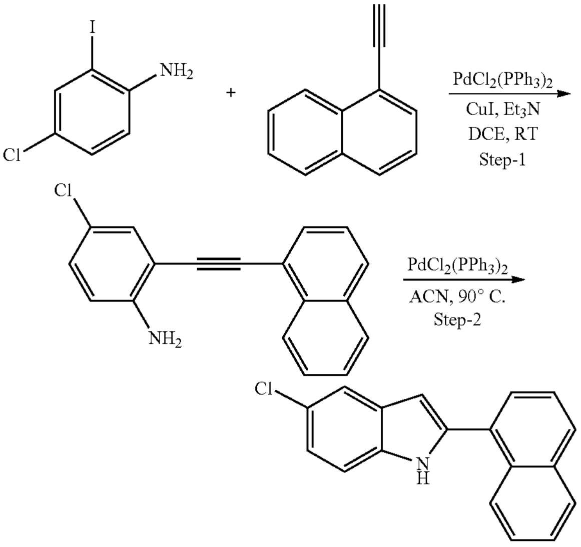

Compound-893

Step 1: To a solution of 4-chloro-2-iodoaniline (0.200 g, 0.78 mmol) and 1-ethynylnaphthalene (0.179 g, 1.18 mmol) in dichloroethane (10.0 ml), triethylamine (0.4 mL, 3.15 mmol) was added. The reaction mixture was purged with nitrogen. After few minutes of purging, copper(I) iodide (0.004 g, 0.023 mmol) and bis(triphenylphosphine)palladium(II) dichloride (0.017 g, 0.023 mmol) was added. The reaction mixture was purged again for few more minutes and then the reaction mixture was stirred at RT for 4 hours. After completion of reaction, the reaction mixture was diluted with water and extracted with ethyl acetate (50 mL×2). The combined organic layer was washed with water (50 mL), brine solution (50 mL), dried over anhydrous sodium sulfate and concentrated under reduced pressure to afford crude product, which was purified by flash chromatography (elution 0-30% EtOAc in hexane) to afford the desired Compound: 4-chloro-2-(naphthalen-1-ylethynyl)aniline (0.200 g) as a off white solid.

Step 2: A solution of 4-chloro-2-(naphthalen-1-ylethynyl) aniline (0.200 g, 0.72 mmol) in ACN (8.0 mL) was purged with nitrogen for five minutes. Bis(triphenylphosphine)palladium(II) dichloride (0.019 g, 0.027 mmol) was added to the reaction mixture and it was purged with $N_2$ for additional five minutes. The reaction mixture was stirred at 90° C. for 4 hours. After completion of reaction, the reaction mixture was diluted with water and extracted with ethyl acetate (50 mL×2). The combined organic layer was washed with water (50 mL), brine solution (50 mL), dried over anhydrous sodium sulfate and concentrated under reduced pressure to afford crude product, which was purified by flash (0-30% EtOAc in hexane) to afford the desired Compound: 5-chloro-2-(naphthalen-1-yl)-1H-indole (0.115 g) as an off-white solid.

Compound 893: LCMS—278.2 $(M)^+$ UPLC:—At 254 nm: 99.93%, At 220 nm: 99.38%. $^1$H NMR (400 MHz, DMSO-$d_6$) δ ppm 11.79 (br. s., 1H) 8.27 (dd, J=6.14, 3.51 Hz, 1H) 7.97-8.08 (m, 2H) 7.68-7.74 (m, 1H) 7.54-7.68 (m, 4H) 7.45 (d, J=8.77 Hz, 1H) 7.14 (dd, J=8.77, 2.19 Hz, 1H), 6.74 (d, J=1.75 Hz, 1H).

Compound 894

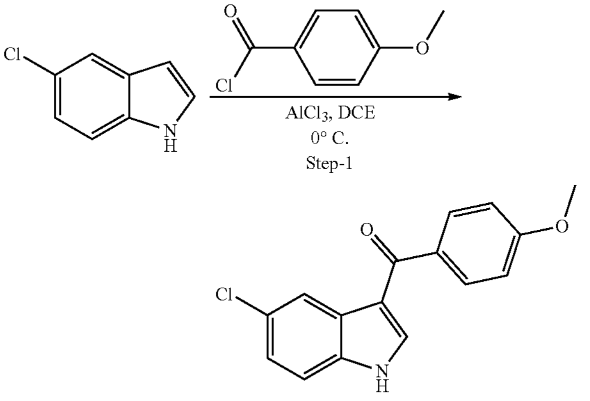

Compound-894

Step 1 was performed as described for step 2 of synthesis of Compound 359

Compound 894: LCMS—286.2 $(M)^+$ UPLC: @ 254 nm: 99.42%, @ 220 nm: 99.55%. $^1H$ NMR (400 MHz, DMSO-$d_6$) δ ppm 12.19 (br. s., 1H) 8.21 (d, J=1.75 Hz, 1H) 8.05 (s, 1H) 7.82 (m, J=8.77 Hz, 2H) 7.54 (d, J=8.33 Hz, 1H) 7.27 (dd, J=8.77, 1.75 Hz, 1H) 7.08 (m, J=8.77 Hz, 2H) 3.86 (s, 3H).

Compound 895

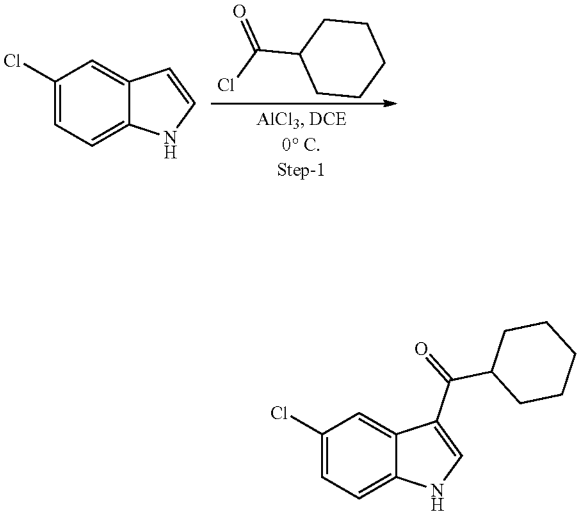

Compound-895

Step 1 was performed as described for step 2 of synthesis of Compound 359

Compound 895: LCMS—262.2 $(M)^+$ UPLC:—@ 254 nm: 99.85%, @ 220 nm: 99.91% $^1H$ NMR (400 MHz, DMSO-d6) δ 12.10 (s, 1H), 8.44 (s, 1H), 8.18 (d, J=2.2 Hz, 1H), 7.47 (d, J=8.6 Hz, 1H), 7.22 (dd, J=8.6, 2.2 Hz, 1H), 3.17 (qt, J=6.6, 2.9 Hz, 1H), 1.91-1.58 (m, 5H), 1.41 (tt, J=8.8, 3.3 Hz, 4H), 1.27-1.07 (m, 1H).

Compound 972

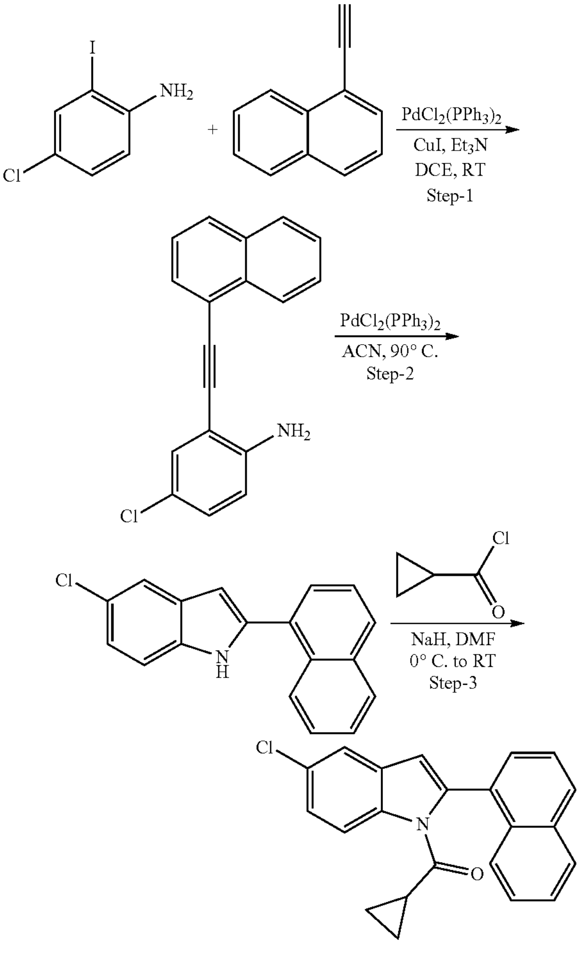

Compound-972

Steps 1 and 2 were performed as described for synthesis of Compound 893

Step 3 was performed as described for synthesis of Compound 535

Compound 972: LCMS—346.3 $(M)^+$ UPLC @ 254 nm=96.78% and @ 220 nm 96.44%. $^1H$ NMR (400 MHz, DMSO-$d_6$) δ ppm 8.19 (d, J=8.77 Hz, 1H) 8.05 (t, J=7.67 Hz, 2H) 7.78 (d, J=2.19 Hz, 1H) 7.75-7.50 (m, 5H) 7.40 (dd, J=8.77, 2.19 Hz, 1H), 6.93 (s, 1H), 1.41-1.32 (m, 1H) 1.27-1.22 (m, 1H) 0.95-0.80 (m, 2H), 0.50 (br. s., 1H).

Compound 973

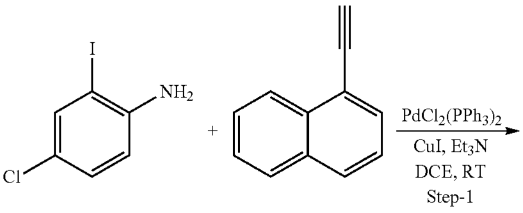

-continued

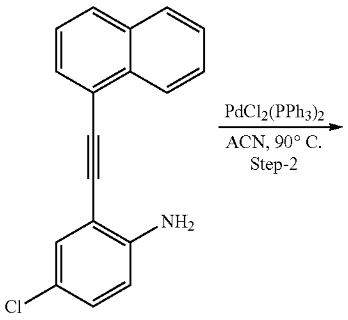

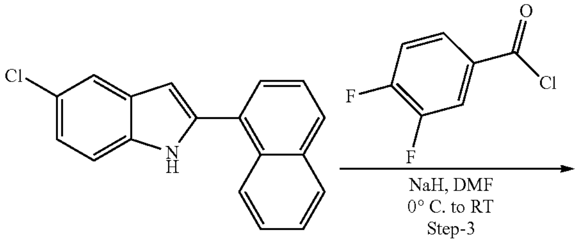

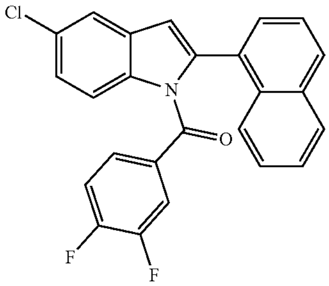

Compound-973

Steps 1 and 2 were performed as described for synthesis of Compound 893

Step 3 was performed as described for synthesis of Compound 535

Compound 973: LCMS—418.3 $(M)^+$ UPLC @ 254 nm=99.91% and @ 220 nm 99.74%. $^1H$ NMR (400 MHz, DMSO-$d_6$) δ ppm 7.95 (d, J=8.77 Hz, 1H) 7.83-7.88 (m, 2H) 7.79 (d, J=7.89 Hz, 1H) 7.70-7.74 (m, 1H) 7.48-7.56 (m, 3H) 7.43 (dd, J=8.77, 2.19 Hz, 2H) 7.39 (d, J=7.89 Hz, 1H) 7.32 (br. s., 1H) 7.09 (br. s., 1H) 6.97 (d, J=10.09 Hz, 1H).

Compound 1328

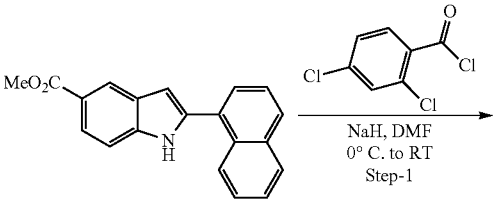

-continued

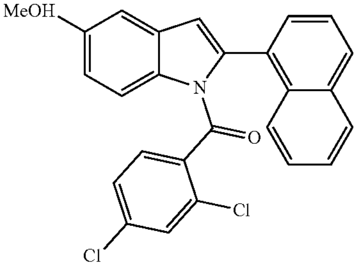

Peak-1
Compound-1328

Step 1 was performed as described for synthesis of Compound 535

Compound 1328: LCMS—$(M)^+$ (475.2) 97.65% @220 nm $^1H$ NMR (400 MHz, DMSO-$d_6$) δ ppm 8.45 (s, 1H), 8.26-8.13 (m, 1H), 7.94-7.85 (m, 2H), 7.79 (d, J=8.77 Hz, 1H), 7.76 (d, J=8.77 Hz, 1H), 7.71-7.62 (m, 1H), 7.62-7.46 (m, 2H), 7.41 (t, J=7.67 Hz, 1H), 7.24 (d, J=7.02 Hz, 1H), 7.13 (br. s., 1H), 6.74 (br. s., 1H), 3.94 (s, 3H).

Compound 1329 and Compound 1330

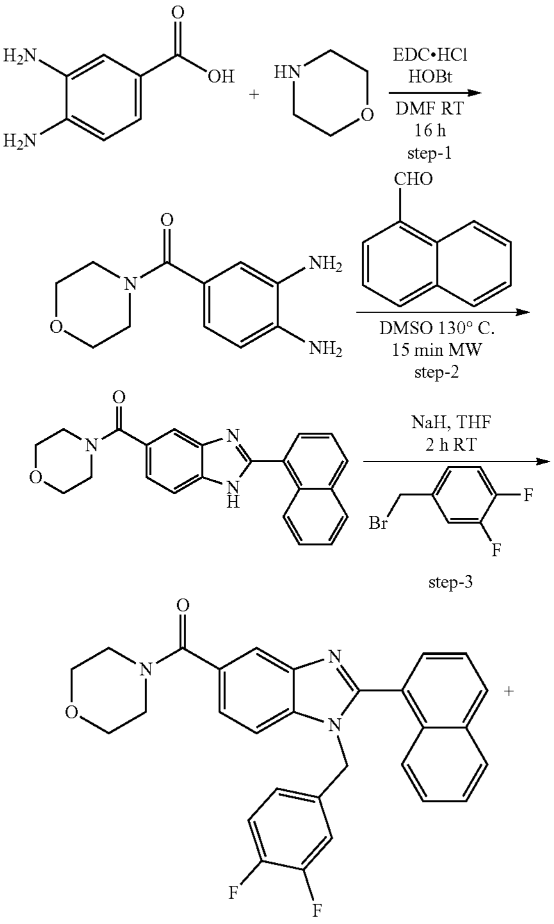

Compound-1329
Peak-1 isomer-1

-continued

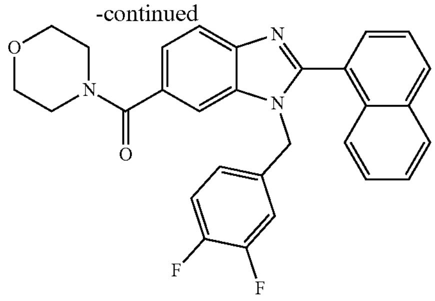

Compound-1300
Peak-2 isomer-2

Step 1: To a stirred solution of 3,4-diaminobenzoic acid (2.0 g, 13.15 mmol) in DMF (10 mL) was added EDC·HCl (3.7 g, 19.72 mmol) and HOBT (2.66 g, 19.22 mmol). The resultant reaction mixture was allowed to stir for 10 min followed by addition of morpholine (1.4 mL, 15.78 mmol) and then stirring for 16 h at RT. After completion of reaction, the reaction mixture was diluted with water (20 ml) and extracted with (10% methanol in DCM). The combined organic layer was dried over anhydrous sodium sulfate filtered and concentrated under reduced pressure to obtain desired product which was directly used for next step.

Steps 2 and 3 were performed as described for synthesis of Compounds 579 and 533

Compound 1329: LCMS—484.2$(M+H)^+$ @ 220 nm=97.66% $^1$H NMR (400 MHz, DMSO-d6) δ 8.16 (d, J=8.2 Hz, 1H), 8.06 (d, J=8.2 Hz, 1H), 7.84 (d, J=8.2 Hz, 1H), 7.77-7.69 (m, 2H), 7.69-7.54 (m, 3H), 7.50 (t, J=7.6 Hz, 1H), 7.37 (dd, J=8.3, 1.5 Hz, 1H), 7.19 (dt, J=10.6, 8.5 Hz, 1H), 6.97-6.79 (m, 2H), 5.35 (s, 2H), 3.59 (br.s., 8H).

Compound 1330: LCMS—484.1$(M+H)^+$ @ 220 nm=99.87% $^1$H NMR (400 MHz, DMSO-d6) δ 8.16 (d, J=8.2 Hz, 1H), 8.06 (d, J=8.2 Hz, 1H), 7.84 (d, J=1.4 Hz, 1H), 7.77-7.55 (m, 5H), 7.50 (t, J=7.6 Hz, 1H), 7.39 (dd, J=8.2, 1.6 Hz, 1H), 7.19 (dt, J=10.7, 8.4 Hz, 2H), 6.95-6.82 (m, 1H), 5.33 (s, 2H), 3.64 (s, 8H).

Compound 1336 and Compound 1337

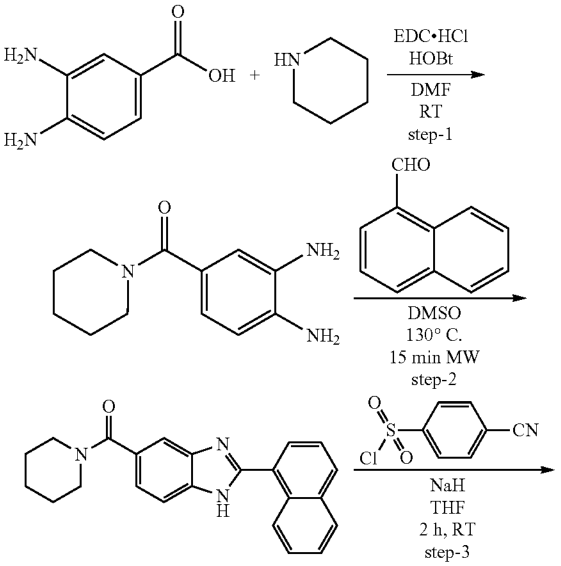

-continued

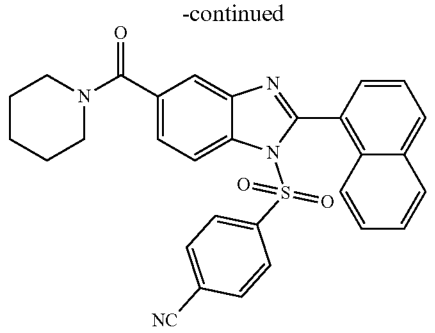

+

Compound-1336
Peak-1 isomer-1

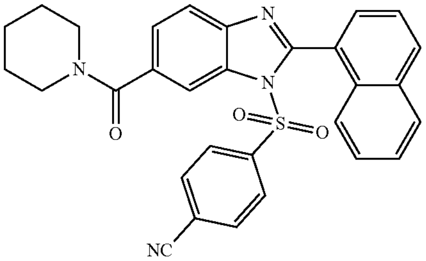

Compound-1337
Peak-2 isomer-2

Steps 1 and 2 were performed as described for synthesis of Compound 1329

Compound 1336: LCMS—521.1$(M+H)^+$ @ 220 nm=99.82% $^1$H NMR-(400 MHz, DMSO-d6) δ 8.24 (d, J=8.5 Hz, 1H), 8.18 (dt, J=7.2, 3.7 Hz, 1H), 8.03 (d, J=8.3 Hz, 1H), 7.85 (d, J=1.6 Hz, 1H), 7.82-7.75 (m, 2H), 7.66 (q, J=3.4, 2.8 Hz, 2H), 7.62-7.50 (m, 4H), 7.34 (t, J=7.6 Hz, 1H), 7.17 (d, J=8.5 Hz, 1H), 3.59 (br.s., 4H), 1.68-1.5(m, 6H).

Compound 1337: LCMS—521.2$(M+H)^+$ @ 220 nm=99.39% $^1$H NMR-400 MHz, DMSO-d6) δ 8.27-8.15 (m, 1H), 8.13 (s, 1H), 8.03 (d, J=8.3 Hz, 1H), 7.92 (d, J=8.2 Hz, 1H), 7.77 (d, J=7.9 Hz, 2H), 7.71-7.62 (m, 2H), 7.54 (t, J=7.6 Hz, 4H), 7.34 (t, J=7.7 Hz, 1H), 7.18 (d, J=8.4 Hz, 1H), 3.63 (br.s, 4H), 1.67 (d, J=7.7 Hz, 2H), 1.62-1.50 (m, 4H).

Compound 1338 and Compound 1339

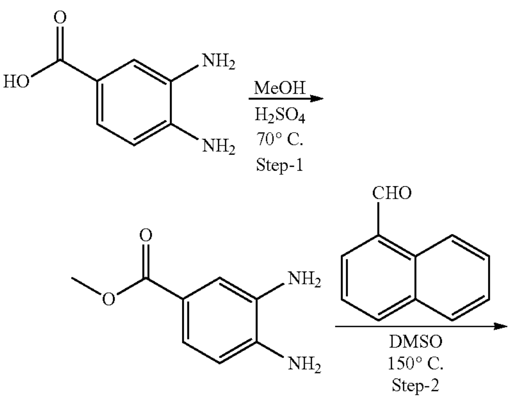

-continued

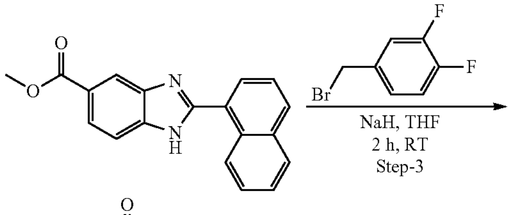

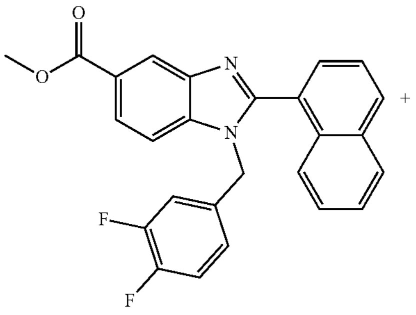

Compound-1338
Peak-1 isomer-1

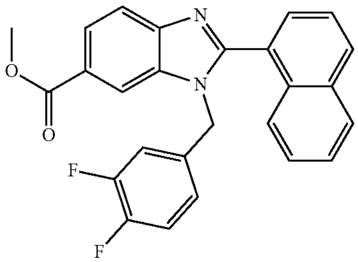

Compound-1339
Peak-2 isomer-2

Steps 1 and 2 were performed as described for synthesis of Compound 848

Step 3 was performed as described for synthesis of Compound 533

Compound 1338: LCMS—429.0 $(M+H)^+$ @ 220 nm=98.3% $^1H$ NMR (400 MHz, DMSO-d6) δ ppm 8.26 (s, 1H), 8.16 (d, J=8.33 Hz, 1H), 8.06 (d, J=8.33 Hz, 1H), 7.96 (d, J=8.77 Hz, 1H), 7.90 (d, J=8.33 Hz, 1H), 7.74 (d, J=7.02 Hz, 1H), 7.69-7.55 (m, 3H), 7.53-7.47 (m, 1H), 7.24-7.14 (m, 1H), 6.91-6.84 (m, 1H), 6.65 (br. s., 1H), 5.43 (s, 2H), 3.88 (s, 3H).

Compound 1339: LCMS—429.0 $(M+H)^+$ @ 220 nm=97.5% $^1H$ NMR (400 MHz, DMSO-d6) δ 8.39 (d, J=1.7 Hz, 1H), 8.17 (d, J=8.3 Hz, 1H), 8.06 (d, J=8.5 Hz, 1H), 7.97 (dd, J=8.5, 1.6 Hz, 1H), 7.75 (dd, J=7.8, 3.7 Hz, 2H), 7.66 (t, J=7.6 Hz, 1H), 7.59 (dt, J=7.6, 3.0 Hz, 2H), 7.49 (dd, J=8.7, 6.4 Hz, 1H), 7.18 (dt, J=10.7, 8.4 Hz, 1H), 6.87 (ddd, J=11.2, 8.0, 2.2 Hz, 1H), 6.63 (dt, J=7.2, 3.0 Hz, 1H), 5.36 (s, 2H), 3.90 (s, 3H).

Compound 1340 and Compound 1341

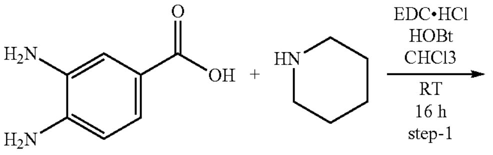

-continued

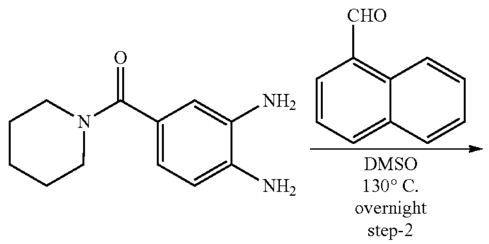

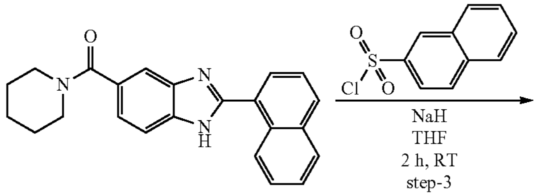

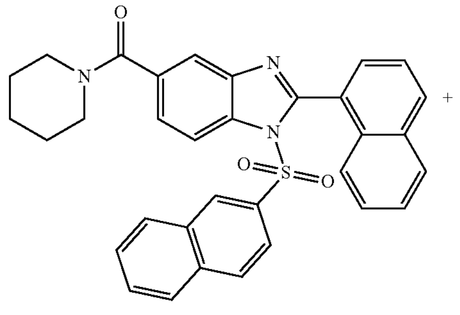

Compound-1340
Peak-1 isomer-1

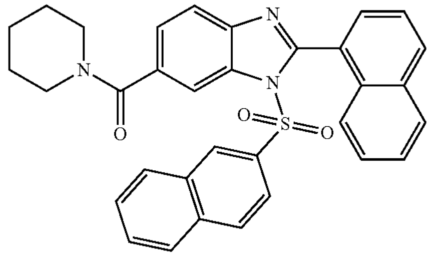

Compound-1341
Peak-2 isomer-2

Steps 1-3 were performed as described for synthesis of Compound 1329

Compound 1340: LCMS—546.2 $(M+H)^+$ @ 220 nm=98.5% $^1H$ NMR (400 MHz, DMSO-d6) δ 8.18 (d, J=7.4 Hz, 2H), 8.12 (d, J=2.1 Hz, 1H), 7.98-7.91 (m, 3H), 7.87 (dd, J=8.4, 6.3 Hz, 2H), 7.76-7.69 (m, 2H), 7.65 (q, J=7.7 Hz, 2H), 7.48 (dd, J=8.1, 1.5 Hz, 1H), 7.42 (dd, J=8.8, 2.1 Hz, 1H), 7.36 (ddd, J=8.1, 6.4, 1.6 Hz, 1H), 7.21-7.12 (m, 2H), 3.66 (s, 4H), 1.63 (s, 6H).

Compound 1341: LCMS—546.2 $(M+H)^+$ @ 220 nm=99.3% $^1H$ NMR (400 MHz, DMSO-$d_6$) δ 8.31 (d, J=8.5 Hz, 1H), 8.17 (dd, J=7.0, 2.5 Hz, 1H), 8.03 (d, J=2.1 Hz, 1H), 7.97-7.89 (m, 3H), 7.88-7.78 (m, 2H), 7.72 (t, J=7.5 Hz, 2H), 7.68-7.59 (m, 2H), 7.58 (dd, J=8.4, 1.6 Hz, 1H), 7.46 (dd, J=8.8, 2.1 Hz, 1H), 7.33 (ddd, J=8.2, 5.6, 2.4 Hz, 1H), 7.11 (d, J=5.4 Hz, 2H), 3.61 (s, 4H), 1.58 (d, J=38.2 Hz, 6H).

Compound 1342

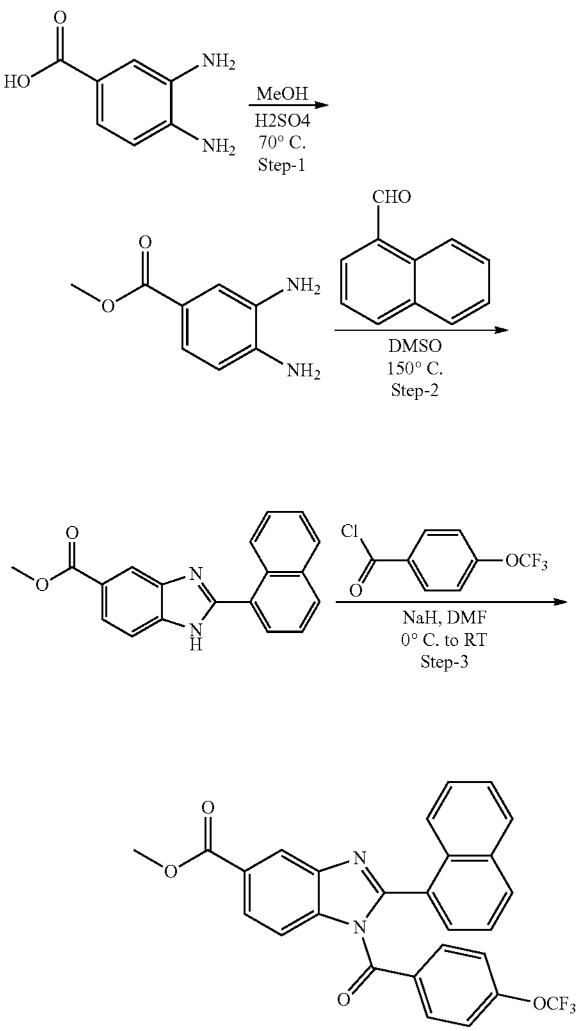

Peak 1, isomer 1
Compound-1342

Steps 1 and 2 were performed as described for synthesis of Compounds 848 and 535

Compound 1342: $^1$H NMR: $^1$H NMR (400 MHz, DMSO-$d_6$) δ ppm 8.46 (s, 1H), 8.11 (d, J=8.33 Hz, 1H), 8.04-7.78 (m, 4H), 7.66 (d, J=6.14 Hz, 1H), 7.56 (d, J=8.77 Hz, 4H), 7.39 (t, J=7.67 Hz, 1H), 6.91 (d, J=8.77 Hz, 2H), 3.94 (s, 3H).

Compound 1356 and Compound 1357

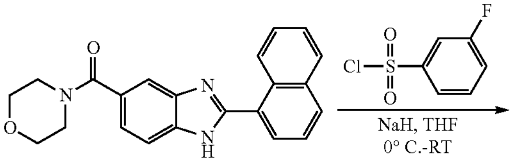

-continued

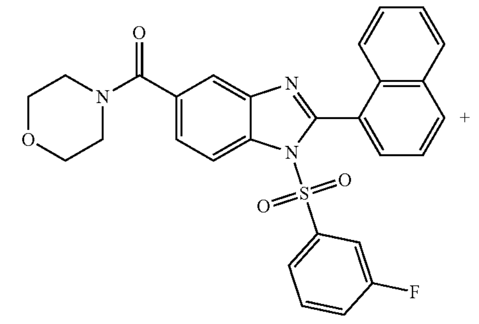

Compound-1356
Peak-1 isomer-1

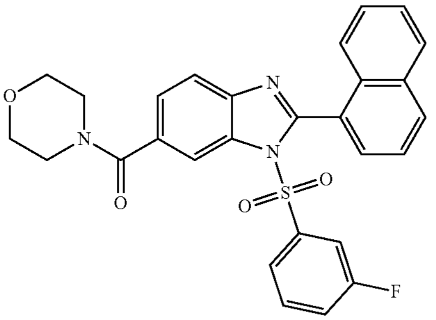

Compound-1357
Peak-2 isomer-2

Step 1 was performed as described for synthesis of Compound 132

Compound 1356: LCMS—$(M+H)^+$516.5, 98.45% @220 nm 98.71% @254 nm $^1$H NMR: 8.23-8.16 (m, 2H), 8.04 (d, J=8.2 Hz, 1H), 7.92 (d, J=8.2 Hz, 1H), 7.73-7.62 (m, 2H), 7.55 (t, J=7.5 Hz, 2H), 7.50-7.38 (m, 2H), 7.36 (dd, J=8.9, 6.5 Hz, 2H), 7.27-7.16 (m, 2H), 3.91-3.37 (m, 8H).

Compound 1357: LCMS—$(M+H)^+$ 516.5, 94.45% @220 nm 95.47% @254 nm NMR: 8.26 (d, J=8.5 Hz, 1H), 8.19 (dt, J=7.4, 3.6 Hz, 1H), 8.04 (d, J=8.4 Hz, 1H), 7.91 (d, J=1.4 Hz, 1H), 7.73-7.50 (m, 5H), 7.45 (t, J=6.3 Hz, 2H), 7.40-7.30 (m, 2H), 7.24-7.11 (m, 1H), 3.80-3.40 (m, 8H).

Compound 1358 and Compound 1359

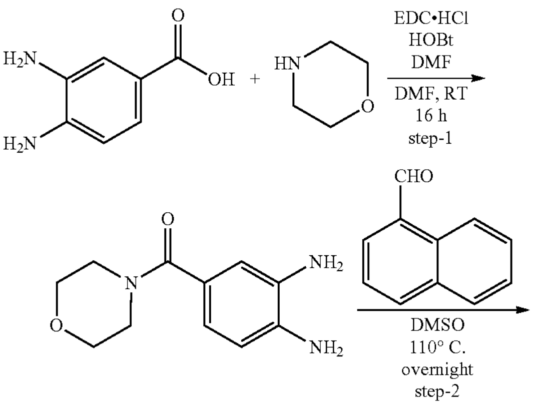

-continued

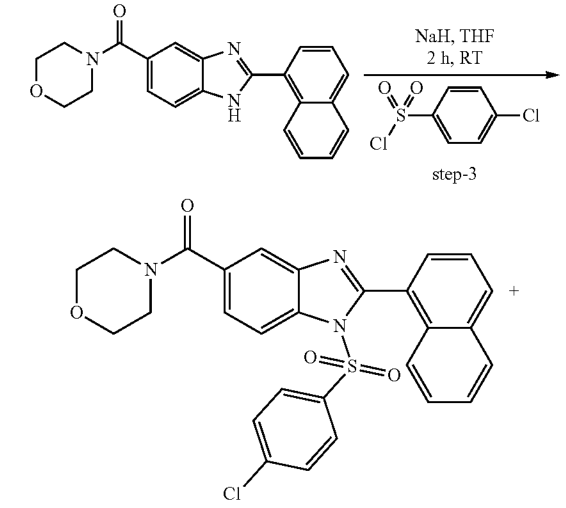

Compound-1358
Peak-1 isomer-1

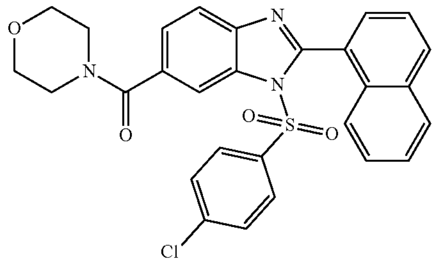

Compound-1359
Peak-2 isomer-2

Steps 1-3 were performed as described for synthesis of Compound 1329

Compound 1358: LCMS—532.5(M)$^+$ @ 254 nm=96.04% @ 220 nm=96.73% $^1$H NMR-(400 MHz, DMSO-d6) δ 8.23-8.14 (m, 2H), 8.03 (d, J=8.2 Hz, 1H), 7.92 (d, J=8.2 Hz, 1H), 7.71-7.62 (m, 2H), 7.60-7.50 (m, 2H), 7.44-7.30 (m, 5H), 7.18 (d, J=8.5 Hz, 1H), 3.66 (s, 8H).

Compound 1359: LCMS—532.4 (M)$^+$@ 254 nm=98.52% @ 220 nm=97.41% $^1$H NMR-(400 MHz, DMSO-d6) δ 8.24 (d, J=8.5 Hz, 1H), 8.19 (dt, J=7.0, 3.6 Hz, 1H), 8.03 (d, J=8.2 Hz, 1H), 7.91 (d, J=1.5 Hz, 1H), 7.71-7.50 (m, 4H), 7.46-7.30 (m, 5H), 7.17 (d, J=8.4 Hz, 1H), 3.55 (d, J=65.4 Hz, 8H).

Compound 1360

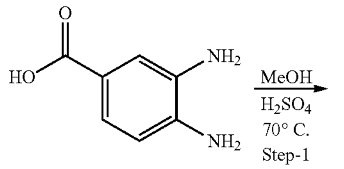

-continued

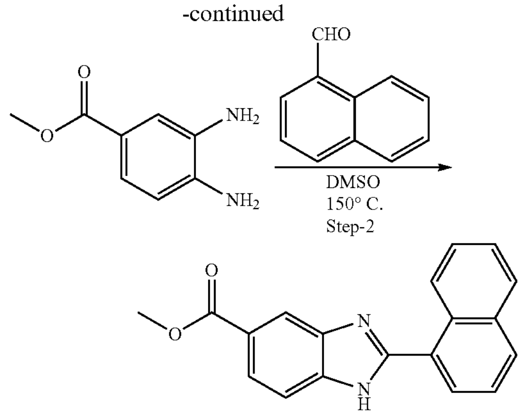

Compound-1360

Steps 1 and 2 were performed as described for synthesis of Compound 848

Compound 1360: LCMS—303.2(M+H)$^+$ 96.41 @220 NM 97.62 @ 254 nm $^1$H NMR (400 MHz, DMSO-d6) δ 13.29 (s, 1H), 9.02 (d, J=8.0 Hz, 1H), 8.37 (s, 1H), 8.21-8.08 (m, 1H), 8.09-7.97 (m, 2H), 7.92 (dd, J=8.2, 1.6 Hz, 1H), 7.86 (d, J=2.6 Hz, 1H), 7.74-7.57 (m, 3H), 3.88 (s, 3H).

Compound 1361 and Compound 1362

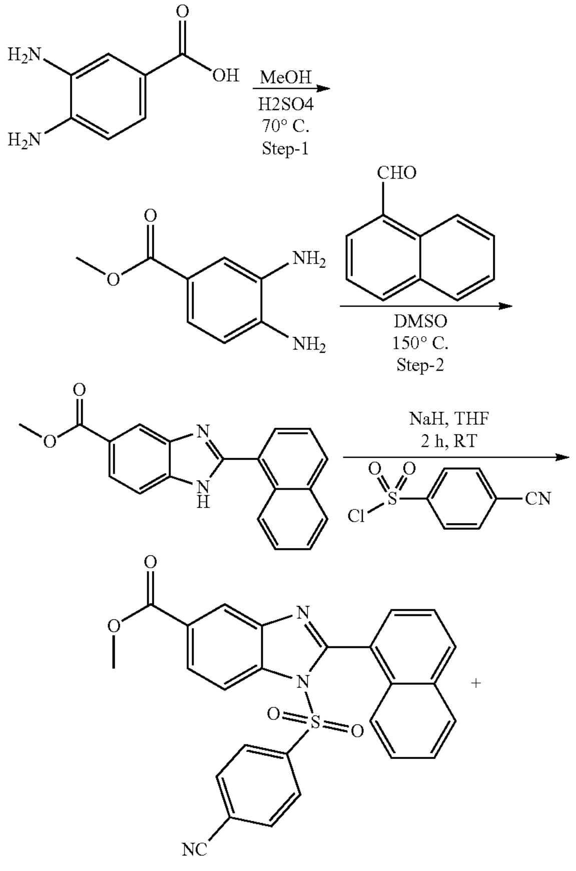

Compound-1361
Peak-1 isomer-1

-continued

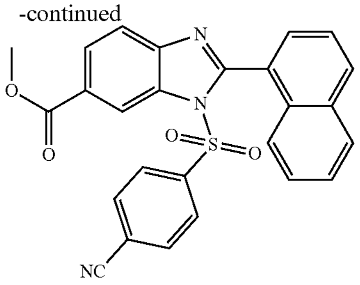

Compound-1362
Peak-2 isomer-2

Steps 1 and 3 were performed as described for synthesis of Compounds 848 and 631

Compound 1361: LCMS—468.4 $(M+H)^+$ @ 254 nm=97.62% @ 220 nm=96.41% $^1$H NMR (400 MHz, Chloroform-d) δ 8.98 (d, J=1.6 Hz, 1H), 8.22 (dd, J=8.4, 1.6 Hz, 1H), 8.08 (d, J=8.1 Hz, 1H), 7.90 (t, J=8.3 Hz, 2H), 7.75-7.66 (m, 1H), 7.63 (t, J=7.7 Hz, 1H), 7.50 (t, J=7.5 Hz, 1H), 7.34-7.27 (m, 3H), 7.26 (br.s, 1H), 7.22 (dd, J=8.6, 6.9 Hz, 1H), 7.06 (d, J=8.5 Hz, 1H), 4.04 (s, 3H).

Compound 1362: LCMS—468.4 $(M+H)^+$ @ 254 nm=96.54% @ 220 nm=94.2% 1H NMR (400 MHz, Chloroform-d) δ 8.53 (d, J=1.6 Hz, 1H), 8.34 (d, J=8.7 Hz, 1H), 8.25 (dd, J=8.7, 1.6 Hz, 1H), 8.06 (t, J=10.0 Hz, 2H), 7.90 (d, J=8.4 Hz, 2H), 7.69 (d, J=7.2 Hz, 1H), 7.62 (t, J=7.6 Hz, 1H), 7.49 (dd, J=8.4, 6.7 Hz, 1H), 7.26 (s, 2H), 7.24-7.17 (m, 1H), 7.04 (d, J=8.4 Hz, 1H), 4.00 (s, 3H).

Compound 1363 and Compound 1389

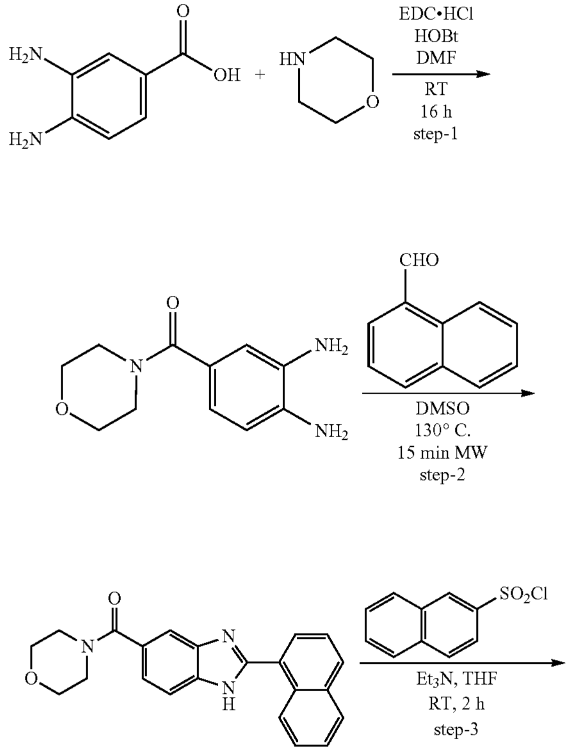

-continued

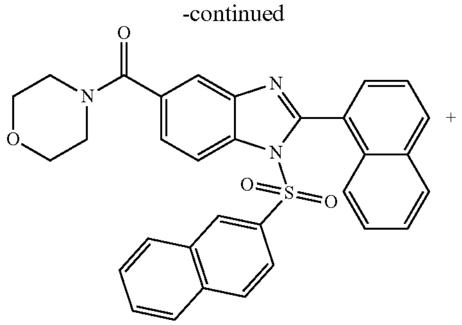

Compound-1363
Peak-1 isomer-1

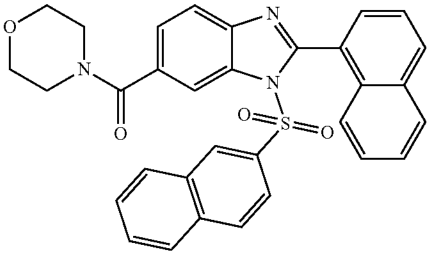

Compound-1389
Peak-2 isomer-2

Steps 1-3 were performed as described for synthesis of Compound 1329

Compound 1363: LCMS—548.5 $(M+H)^+$@ 254 nm=97.17% @ 220 nm=93.39% $^1$H NMR (400 MHz, DMSO-d6) δ 8.24 (s, 1H), 8.17 (d, J=8.1 Hz, 1H), 8.12 (d, J=2.2 Hz, 1H), 8.00-7.76 (m, 5H), 7.68 (dq, J=22.6, 7.5 Hz, 4H), 7.52 (d, J=8.2 Hz, 1H), 7.43 (dd, J=8.6, 2.2 Hz, 1H), 7.35 (ddd, J=8.2, 6.1, 1.8 Hz, 1H), 7.24-7.08 (m, 2H), 3.80-3.45 (m, 8H).

Compound 1389: LCMS—548.5 $(M+H)^+$@ 254 nm=99.42% @ 220 nm=99.49% $^1$H NMR (400 MHz, DMSO-d6) δ 8.32 (d, J=8.5 Hz, 1H), 8.17 (dt, J=7.3, 3.6 Hz, 1H), 8.04 (d, J=2.1 Hz, 1H), 7.94 (dd, J=8.9, 2.8 Hz, 3H), 7.88 (d, J=1.6 Hz, 1H), 7.84 (d, J=8.2 Hz, 1H), 7.75-7.68 (m, 1H), 7.69-7.54 (m, 4H), 7.46 (dd, J=8.8, 2.1 Hz, 1H), 7.33 (dq, J=8.9, 4.9, 4.5 Hz, 1H), 7.11 (d, J=3.9 Hz, 2H), 3.78-3.37 (m, 8H).

Compound 1364 and Compound 1365

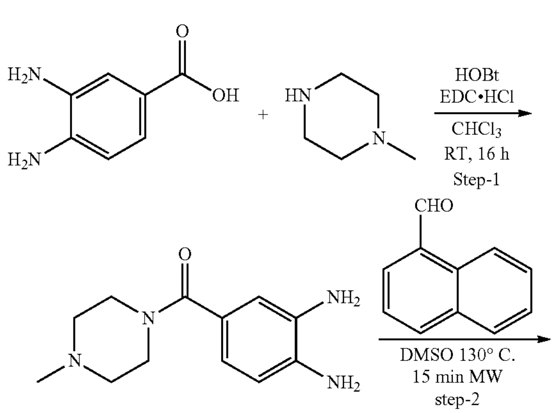

-continued

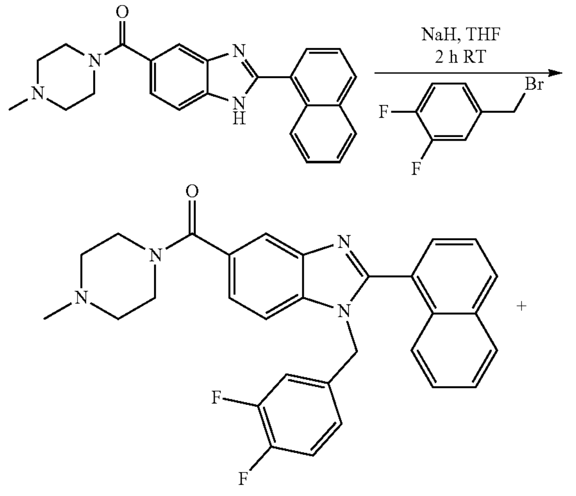

Compound-1364
Peak-1 isomer-1

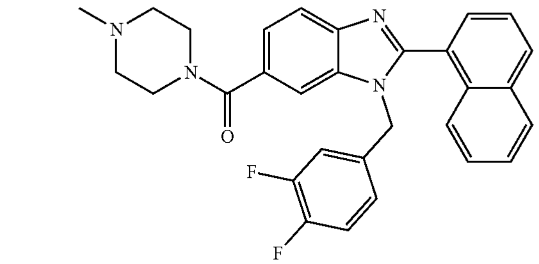

Compound-1365
Peak-2 isomer-2

Steps 1-3 were performed as described for synthesis of Compound 1329

Compound 1364: LCMS—497.5 $(M+H)^+$ UPLC @ 254 nm=96.82%, @ 220 nm=96.29%. $^1H$ NMR (400 MHz, Chloroform-d) δ 8.04 (dd, J=7.24, 1.97 Hz, 1H) 7.90-7.98 (m, 2H) 7.67 (d, J=7.89 Hz, 1H) 7.53-7.60 (m, 3H) 7.46-7.52 (m, 2H) 7.39-7.45 (m, 1H) 6.94-7.03 (m, 1H) 6.60-6.69 (m, 2H) 5.17 (s, 2H), 4.01-3.67(br. s., 4H) 2.73 (br. s., 3H) 2.51-2.48(br. s., 4H)

Compound 1365: LCMS—497.5 (M+H)+UPLC @ 254 nm=96.66%, @ 220 nm=97.12% $^1H$ NMR (400 MHz, Chloroform-d) δ 8.04 (dt, J=7.2, 3.7 Hz, 1H), 7.96 (d, J=7.4 Hz, 2H), 7.67 (d, J=8.3 Hz, 1H), 7.61-7.51 (m, 3H), 7.48 (ddd, J=8.2, 6.6, 1.3 Hz, 1H), 7.43 (dd, J=8.4, 1.6 Hz, 1H), 7.35 (d, J=8.3 Hz, 1H), 6.98 (dt, J=9.8, 8.2 Hz, 1H), 6.75-6.54 (m, 2H), 5.17 (s, 2H), 3.95 (s, 4H), 2.83 (s, 4H), 2.62 (s, 3H).

Compound 1366 and Compound 1367

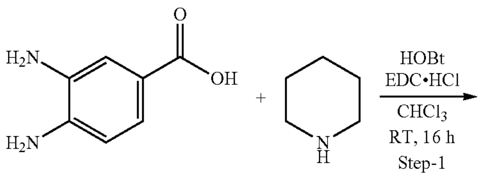

-continued

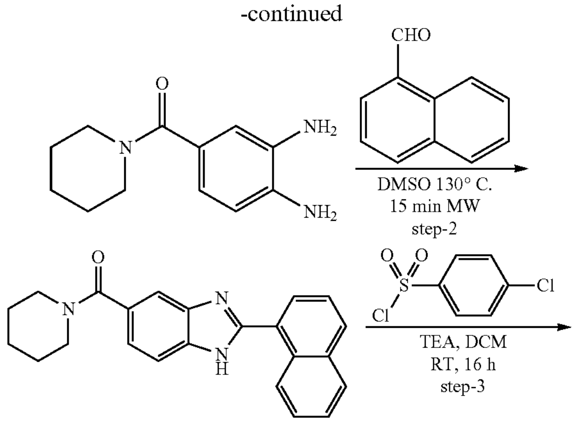

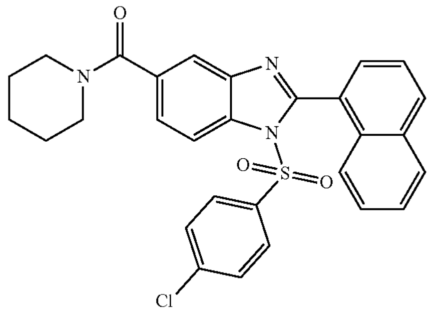

+

Compound-1366
Peak-1 isomer-1

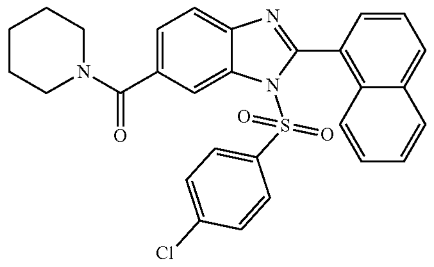

Compound-1367
Peak-2 isomer-2

Steps 1-3 were performed as described for synthesis of Compound 1329

Compound 1366: LCMS—530.5 $(M)^+$ UPLC @ 254 nm=98.61%, @ 220 nm=98.51% $^1H$ NMR (400 MHz, DMSO-d6) δ 8.18 (dt, J=7.6, 3.7 Hz, 1H), 8.11 (s, 1H), 8.03 (d, J=8.3 Hz, 1H), 7.91 (d, J=8.2 Hz, 1H), 7.68 (q, J=4.5 Hz, 2H), 7.54 (q, J=8.5, 8.0 Hz, 2H), 7.39 (s, 4H), 7.33 (d, J=7.4 Hz, 1H), 7.19 (d, J=8.5 Hz, 1H), 3.66 (s, 4H), 1.66 (s, 3H), 1.60-1.43 (m, 3H).

Compound 1367: LCMS—530.5 $(M)^+$ UPLC @ 254 nm=99.40%, @ 220 nm=98.80%. $^1H$ NMR (400 MHz, DMSO-d6) δ 8.26-8.15 (m, 2H), 8.03 (d, J=8.2 Hz, 1H), 7.84 (d, J=1.5 Hz, 1H), 7.66 (q, J=3.6, 3.1 Hz, 2H), 7.61-7.50 (m, 2H), 7.41 (s, 4H), 7.34 (t, J=7.6 Hz, 1H), 7.18 (d, J=8.4 Hz, 1H), 3.62 (br. s., 4H), 1.64 (q, J=5.3 Hz, 3H), 1.54 (s, 3H).

Compound 1368 and Compound 1369

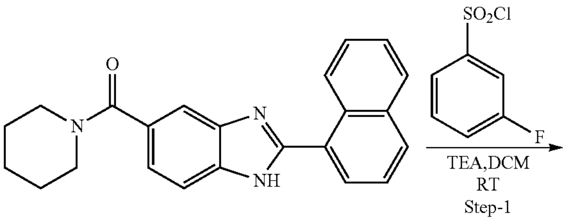

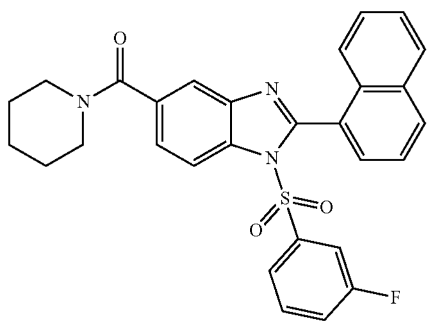

Compound-1368
Peak-1 isomer-1

+

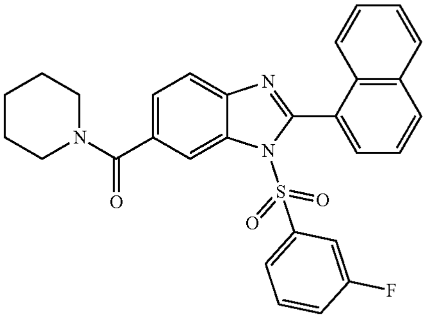

Compound-1369
Peak-2 isomer-2

Step 1 was performed as described for synthesis of Compound 1329

Compound 1368—LCMS: 514.5 (M+H)+98.48% @220 nm 99.43% @254 nm $^1$H NMR (400 MHz, DMSO-d6) δ 8.20 (d, J=7.8 Hz, 1H), 8.16-8.11 (m, 1H), 8.04 (d, J=8.2 Hz, 1H), 7.91 (d, J=8.2 Hz, 1H), 7.74-7.63 (m, 2H), 7.59-7.49 (m, 2H), 7.44 (t, J=6.0 Hz, 2H), 7.35 (q, J=6.5, 5.1 Hz, 2H), 7.24 (d, J=8.5 Hz, 1H), 7.18-7.12 (m, 1H), 3.66 (s, 4H), 1.59 (d, J=51.8 Hz, 6H).

Compound 1369:-1369-LCMS:514.5 (M+H)$^+$94.08% @220 nm 95.90% @254 nm $^1$H NMR (400 MHz, DMSO-d6) δ 8.25 (d, J=8.5 Hz, 1H), 8.19 (dt, J=7.2, 3.6 Hz, 1H), 8.04 (d, J=8.4 Hz, 1H), 7.84 (d, J=1.6 Hz, 1H), 7.67 (q, J=4.0 Hz, 2H), 7.61-7.50 (m, 2H), 7.50-7.40 (m, 2H), 7.40-7.29 (m, 2H), 7.21 (d, J=8.5 Hz, 1H), 7.15 (dd, J=8.1, 2.5 Hz, 1H), 3.64 (d, J=17.0 Hz, 4H), 1.57 (dd, J=41.2, 10.9 Hz, 6H).

Compound 1370

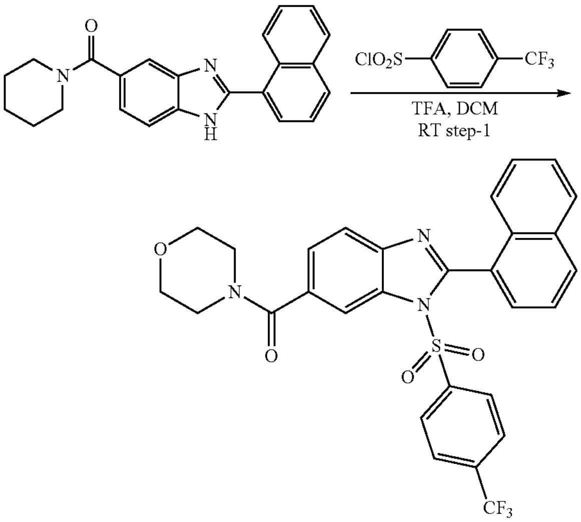

Compound-1370
Peak-2 isomer-2

Step 1 was performed as described for synthesis of Compound 1329

Compound 1370-LCMS: 566.4 (M+H)$^+$ 95.17% @220 nm 97.06% @254 nm $^1$H NMR (400 MHz, DMSO-d6) δ 8.27 (d, J=8.5 Hz, 1H), 8.19 (dd, J=7.4, 2.1 Hz, 1H), 8.00 (d, J=8.3 Hz, 1H), 7.92 (d, J=1.5 Hz, 1H), 7.73-7.67 (m, 2H), 7.68-7.62 (m, 3H), 7.59 (d, J=8.3 Hz, 2H), 7.50 (t, J=7.5 Hz, 1H), 7.25 (t, J=7.7 Hz, 1H), 7.09 (d, J=8.5 Hz, 1H), 3.81 (br.s., 8H)

Compound 1384

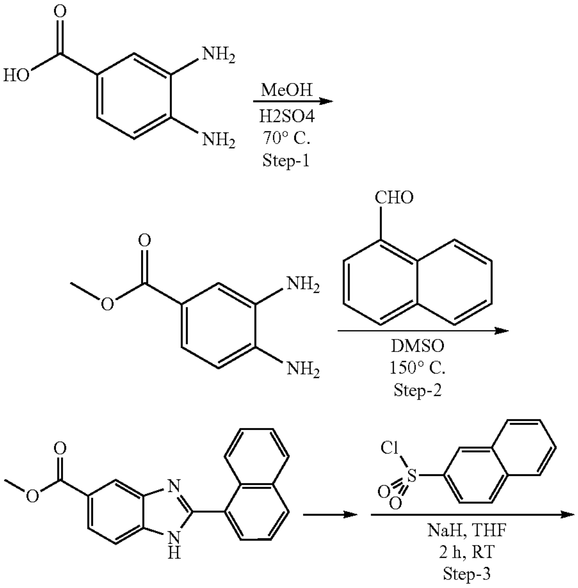

-continued

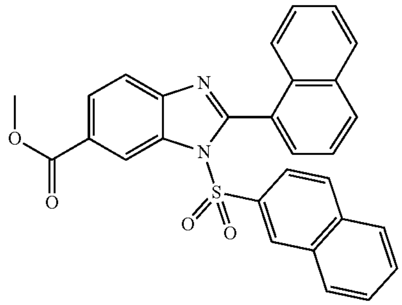

Peak2, Isomer 2
Compound-1384

Step 1 was performed as described for synthesis of Compounds 848 and 631

Compound 1384: LCMS: 493.4 $(M+H)^+$ 88.82% @220 nm 96.31% @254 nm $^1H$ NMR (400 MHz, DMSO-d6) δ 8.41 (d, J=8.7 Hz, 1H), 8.36 (s, 1H), 8.18 (dd, J=8.3, 4.2 Hz, 2H), 8.03 (s, 1H), 7.99-7.88 (m, 3H), 7.82 (d, J=8.4 Hz, 1H), 7.67 (dp, J=22.0, 7.2 Hz, 4H), 7.44 (d, J=8.7 Hz, 1H), 7.32 (dt, J=8.3, 3.9 Hz, 1H), 7.09 (d, J=4.0 Hz, 2H), 3.91 (s, 3H).

Compound 1385 and Compound 1386

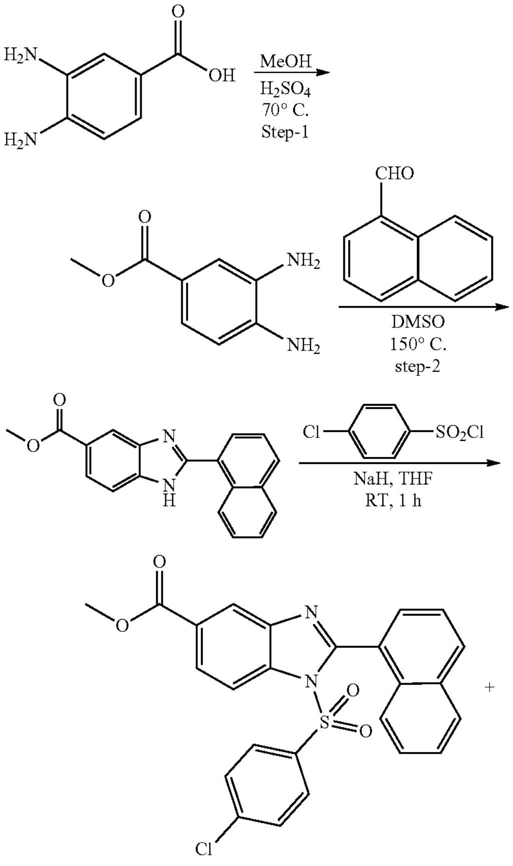

Compound-1385
Peak-1 isomer-1

-continued

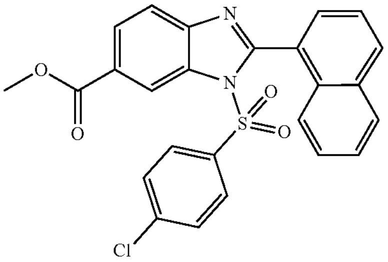

Compound-1386
Peak-2 isomer-2

Steps 1-3 were performed as described for synthesis of Compounds 848 and 527

Compound 1385: LCMS—477.1$(M+H)^+$ @ 220 nm=99.05% $^1H$ NMR (400 MHz, DMSO-$d_6$) δ 8.79 (d, J=1.6 Hz, 1H), 8.19 (q, J=4.1, 3.3 Hz, 1H), 8.14 (dd, J=8.5, 1.7 Hz, 1H), 8.01 (dd, J=10.1, 8.3 Hz, 2H), 7.66 (d, J=4.8 Hz, 2H), 7.53 (t, J=7.5 Hz, 1H), 7.39-7.23 (m, 5H), 7.09 (d, J=8.4 Hz, 1H), 3.97 (s, 3H).

Compound 1386: LCMS—477.1$(M+H)^+$ @ 220 nm=99.5% $^1H$ NMR (400 MHz, DMSO-$d_6$) δ 8.39 (d, J=1.7 Hz, 1H), 8.33 (d, J=8.7 Hz, 1H), 8.24-8.14 (m, 2H), 8.03 (d, J=8.2 Hz, 1H), 7.68 (q, J=4.1 Hz, 2H), 7.55 (t, J=7.5 Hz, 1H), 7.39 (d, J=1.9 Hz, 4H), 7.33 (d, J=7.4 Hz, 1H), 7.16 (d, J=8.4 Hz, 1H), 3.93 (s, 3H).

Compound 1387 and Compound 1388

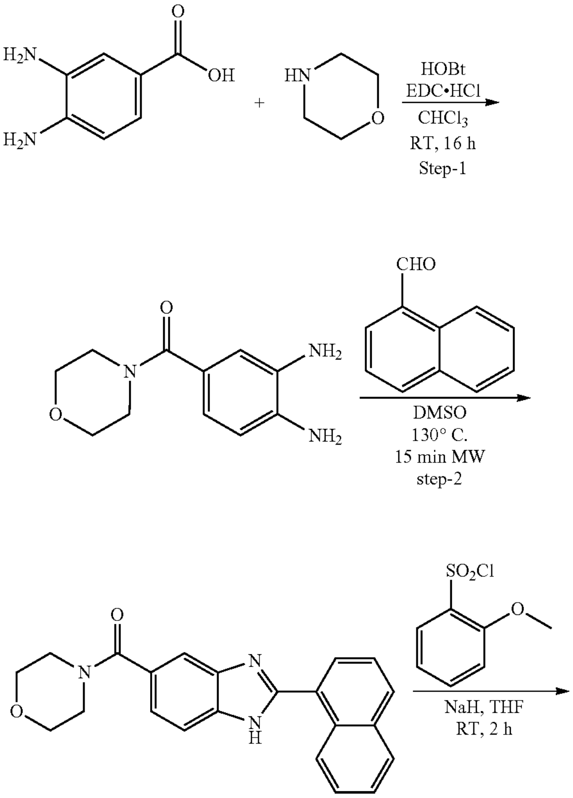

-continued

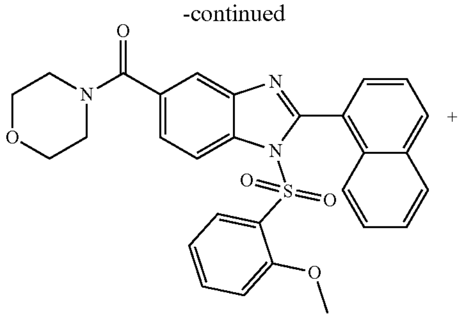

Compound-1387
Peak-1 isomer-1

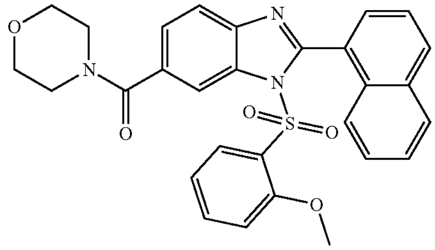

Compound-1388
Peak-2 isomer-2

Steps 1-3 were performed as described for synthesis of Compound 1329

Compound 1387: LCMS—527.59 (M+H)$^+$@ 200 nm=92.0% @ 254 nm=95.1% $^1$H NMR (400 MHz, Chloroform-d) δ 8.36 (d, J=1.4 Hz, 1H), 7.92 (dd, J=11.0, 8.0 Hz, 2H), 7.77 (t, J=7.0 Hz, 1H), 7.52 (d, J=8.0 Hz, 1H), 7.49-7.31 (m, 4H), 7.17 (d, J=4.0 Hz, 2H), 6.94 (dd, J=8.0, 1.7 Hz, 1H), 6.69 (d, J=8.4 Hz, 1H), 6.44 (q, J=9.0, 8.4 Hz, 1H), 3.76 (s, 8H), 3.55 (s, 3H).

Compound 1388: LCMS—527.59 (M+H)$^+$@ 200 nm=93.3% @ 254 nm=95.99% $^1$H NMR (400 MHz, Chloroform-d) δ 8.29 (d, J=8.5 Hz, 1H), 7.96-7.87 (m, 2H), 7.77 (d, J=8.2 Hz, 1H), 7.57 (dd, J=8.5, 1.6 Hz, 1H), 7.51-7.43 (m, 2H), 7.36 (ddd, J=8.1, 4.9, 3.0 Hz, 1H), 7.24-7.13 (m, 3H), 6.97 (dd, J=8.0, 1.7 Hz, 1H), 6.65 (d, J=8.4 Hz, 1H), 6.42 (t, J=7.7 Hz, 1H), 3.76 (s, 8H), 3.51 (s, 3H).

Compound 1390 and Compound 1391

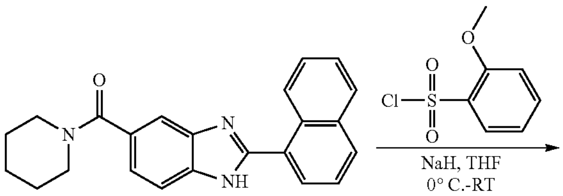

-continued

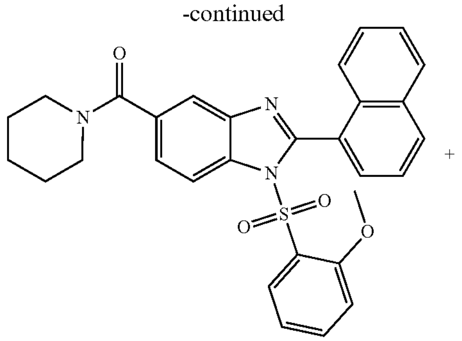

Compound-1390
Peak-1 isomer-1

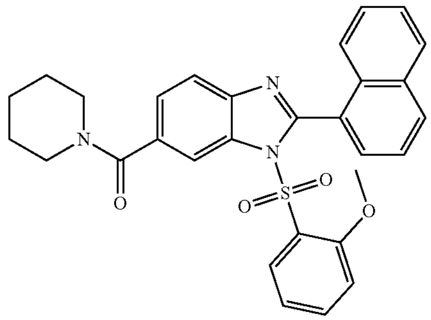

Compound-1391
Peak-2 isomer-2

Step 1 was performed as described for synthesis of Compounds 1329 and 631 Compound 1390: LCMS—(M+H)$^+$526.5, 96.43 @220 nm 97.46@ 254 nm $^1$H NMR (400 MHz, DMSO-d6) δ 8.07 (d, J=8.3 Hz, 1H), 8.03 (d, J=1.5 Hz, 1H), 7.91 (dd, J=13.9, 8.2 Hz, 2H), 7.58-7.37 (m, 5H), 7.29 (t, J=7.6 Hz, 1H), 7.17 (d, J=8.5 Hz, 1H), 7.05-6.93 (m, 2H), 6.62 (t, J=7.7 Hz, 1H), 3.62 (d, J=23.6 Hz, 4H), 3.50 (s, 3H), 1.65 (s, 2H), 1.56 (s, 4H).

Compound 1391: LCMS—(M+H)$^+$ 526.5, 91.79@220 nm 94.64@ 254 nm $^1$H NMR (400 MHz, DMSO-d6) δ 8.07 (dd, J=8.4, 5.1 Hz, 2H), 7.92 (d, J=8.3 Hz, 1H), 7.83 (d, J=1.6 Hz, 1H), 7.59-7.48 (m, 2H), 7.48-7.36 (m, 3H), 7.29 (t, J=7.6 Hz, 1H), 7.18 (d, J=8.4 Hz, 1H), 7.08-6.94 (m, 2H), 6.62 (t, J=7.7 Hz, 1H), 3.65 (d, J=21.4 Hz, 4H), 3.50 (s, 3H), 1.70-1.40 (m, 6H)

Compound 1392 and Compound 1392

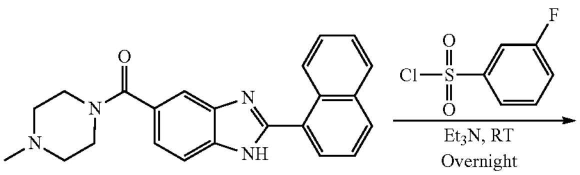

-continued

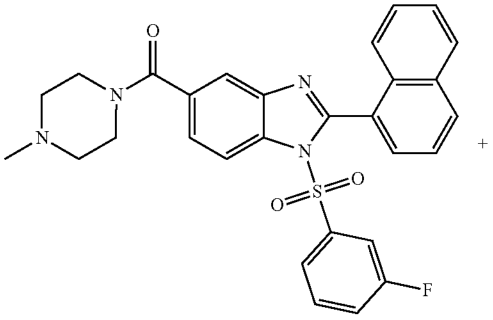

+

Compound-1392
Peak-1 isomer-1

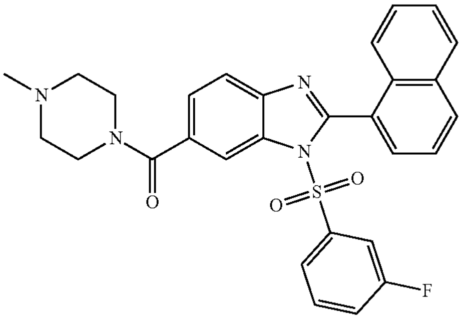

Compound-1393
Peak-2 isomer-2

Step 1 was performed as described for synthesis of Compounds 1329 and 631

Compound 1392: LCMS—$(M+H)^+$529.5, 95.94@220 nm 97.3@ 254 nm $^1$H NMR (400 MHz, Chloroform-d) δ 8.37 (d, J=1.5 Hz, 1H), 8.11-8.02 (m, 1H), 7.89 (dd, J=8.7, 1.9 Hz, 2H), 7.66-7.57 (m, 2H), 7.54 (dd, J=8.2, 1.5 Hz, 1H), 7.50-7.42 (m, 1H), 7.25-7.19 (m, 1H), 7.17-7.06 (m, 3H), 7.06-6.96 (m, 1H), 6.85 (dt, J=7.8, 2.1 Hz, 1H), 3.90 (d, J=55.7 Hz, 4H), 2.80 (s, 4H), 2.60 (s, 3H).

Compound 1393: LCMS: $(M+H)^+$ 529.5, 94.96@220 nm 95.9@ 254 nm $^1$H NMR (400 MHz, Chloroform-d) δ 8.33 (d, J=8.5 Hz, 1H), 8.10-8.02 (m, 1H), 7.93-7.82 (m, 2H), 7.69-7.52 (m, 3H), 7.46 (ddd, J=8.2, 6.6, 1.3 Hz, 1H), 7.25-7.20 (m, 1H), 7.17 (d, J=8.5 Hz, 1H), 7.11 (t, J=3.4 Hz, 2H), 7.07-6.98 (m, 1H), 6.96-6.85 (m, 1H), 3.79 (d, J=69.0 Hz, 4H), 2.65 (s, 4H), 2.47 (s, 3H).

Compound 1401 and Compound 1402

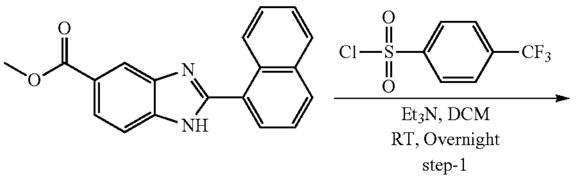

-continued

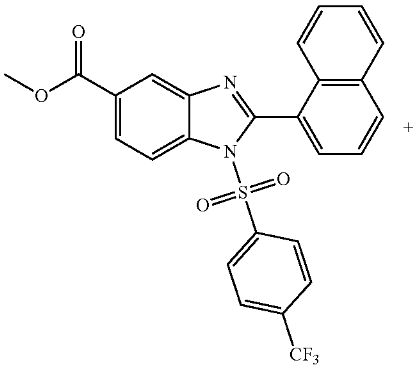

+

Compound-1401
Peak-1 isomer-1

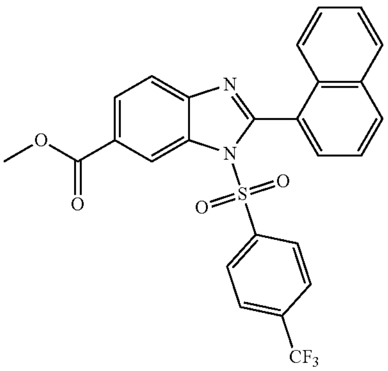

Compound-1402
Peak-2 isomer-2

Step 1 was performed as described for synthesis of Compound 527

Compound 1401: LCMS—511.4 $(M+H)^+$ UPLC @ 254 nm=99.48%, @ 220 nm=99.04%. $^1$H NMR (400 MHz, DMSO-d6) δ 8.85-8.79 (m, 1H), 8.22-8.11 (m, 2H), 8.00 (dd, J=10.4, 8.3 Hz, 2H), 7.73-7.63 (m, 2H), 7.57 (d, J=8.4 Hz, 2H), 7.48 (d, J=8.1 Hz, 3H), 7.20 (t, J=7.7 Hz, 1H), 7.01 (d, J=8.4 Hz, 1H), 3.97 (s, 3H).

Compound 1402: LCMS—511.4 (M+H)+UPLC @ 254 nm=99.54%, @ 220 nm=98.88%. $^1$H NMR (400 MHz, DMSO-d6) δ 8.40 (d, J=1.7 Hz, 1H), 8.36 (d, J=8.7 Hz, 1H), 8.26-8.15 (m, 2H), 8.00 (d, J=8.2 Hz, 1H), 7.77-7.67 (m, 2H), 7.66-7.55 (m, 4H), 7.49 (t, J=7.5 Hz, 1H), 7.29-7.22 (m, 1H), 7.08 (d, J=8.4 Hz, 1H), 3.93 (s, 3H).

Compound 1403 and Compound 1404

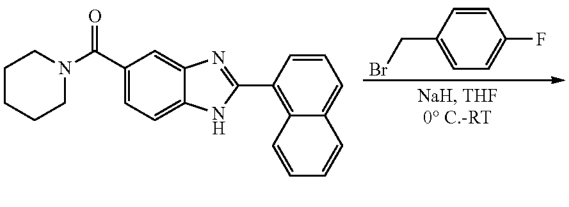

-continued

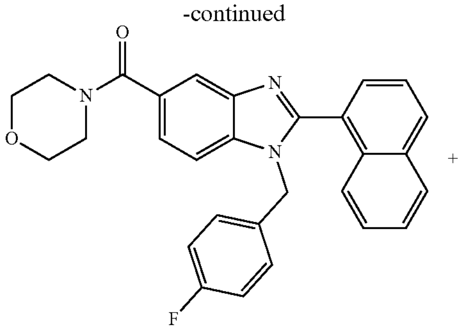

Peak1, Isomer 1
Compound-1403

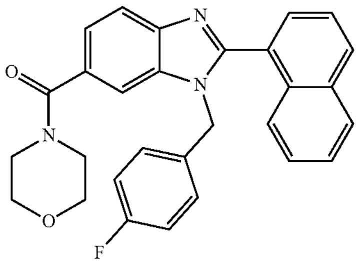

Peak2, Isomer2
Compound-1404

Step 1 was performed as described for synthesis of Compounds 1329 and 533

Compound 1403: LCMS—466.4 $(M+H)^+$ UPLC @ 254 nm=97.61%, @ 220 nm=97.84%. $^1$H NMR (400 MHz, DMSO-d6) δ 8.16 (d, J=8.2 Hz, 1H), 8.06 (d, J=8.2 Hz, 1H), 7.83 (d, J=8.3 Hz, 1H), 7.72 (d, J=6.9 Hz, 1H), 7.69-7.63 (m, 3H), 7.60 (t, J=7.4 Hz, 1H), 7.52 (t, J=7.5 Hz, 1H), 7.36 (d, J=8.3 Hz, 1H), 6.98 (t, J=8.7 Hz, 2H), 6.88 (dd, J=8.5, 5.4 Hz, 2H), 5.35 (s, 2H), 3.51 (d, J=53.3 Hz, 8H).

Compound 1404: LCMS—466.4 $(M+H)^+$ UPLC @ 254 nm=98.81%, @ 220 nm=99.01%. $^1$H NMR (400 MHz, DMSO-d6) δ 8.16 (d, J=8.1 Hz, 1H), 8.06 (d, J=8.2 Hz, 1H), 7.83 (s, 1H), 7.71 (d, J=6.9 Hz, 1H), 7.68-7.55 (m, 4H), 7.51 (t, J=7.6 Hz, 1H), 7.41-7.34 (m, 1H), 6.97 (t, J=8.9 Hz, 2H), 6.89 (dd, J=8.5, 5.4 Hz, 2H), 5.33 (s, 2H), 3.59 (d, J=30.9 Hz, 8H).

Compound 1405

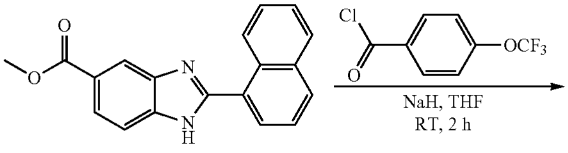

-continued

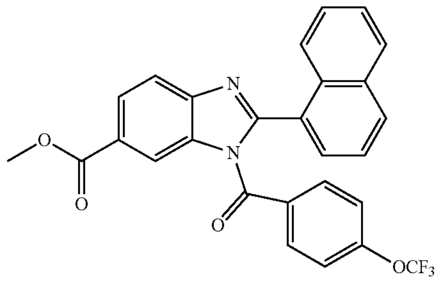

Isomer2, Peak 2
Compound 1405

Step 1 was performed as described for synthesis of Compound 535

Compound 1405: LCMS—491.2 $(M+H)^+$ 97.35% @ 220 nm $^1$H NMR (400 MHz, DMSO-d6) δ 8.46 (d, J=1.6 Hz, 1H), 8.11 (dd, J=8.5, 1.7 Hz, 1H), 8.03 (d, J=8.4 Hz, 1H), 7.95-7.89 (m, 1H), 7.85 (dd, J=8.4, 5.6 Hz, 2H), 7.66 (d, J=7.1 Hz, 1H), 7.55 (ddd, J=10.1, 6.3, 3.3 Hz, 4H), 7.38 (t, J=7.7 Hz, 1H), 6.89 (d, J=8.3 Hz, 2H), 3.91 (s, 3H).

Compound 1406 and Compound 1407

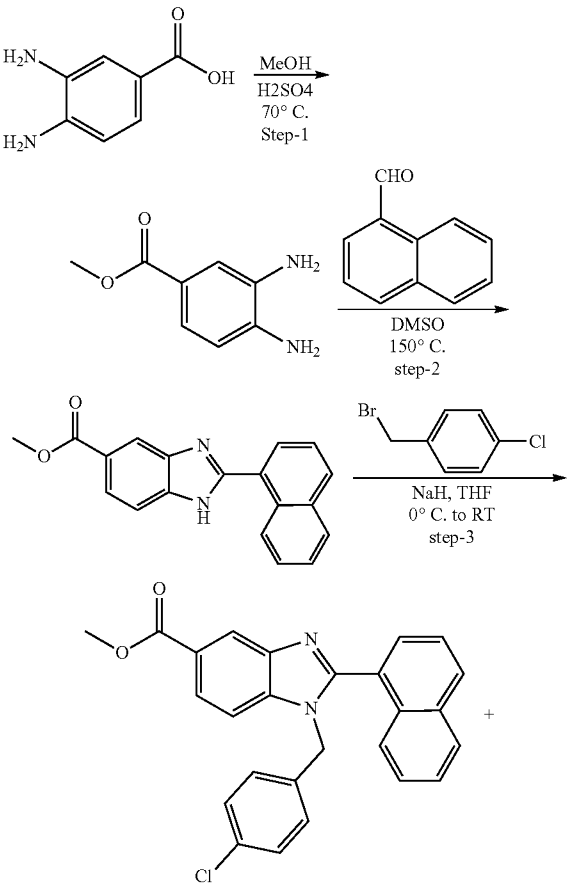

Compound-1406
Peak-1 isomer-1

-continued

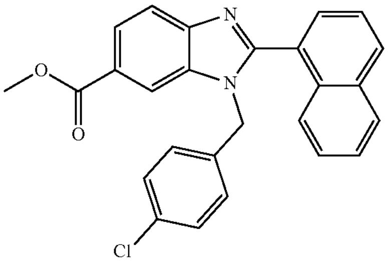

Compound-1407
Peak-2 isomer-2

Steps 1-3 were performed as described for synthesis of Compound 848

Compound 1406: LCMS—427.4 $(M+H)^+$ UPLC @ 254 nm=96.67%, @ 220 nm=98.01%. $^1H$ NMR (400 MHz, DMSO-d6) δ 8.19 (d, J=1.6 Hz, 1H), 8.16 (d, J=8.2 Hz, 1H), 8.06 (d, J=8.1 Hz, 1H), 7.98-7.86 (m, 2H), 7.75-7.55 (m, 4H), 7.51 (t, J=7.6 Hz, 1H), 7.22 (d, J=8.1 Hz, 2H), 6.85 (d, J=8.1 Hz, 2H), 5.43 (s, 2H), 3.87 (s, 3H).

Compound 1407: LCMS—427.4 $(M+H)^+$ UPLC @ 254 nm=98.05%, @ 220 nm=98.66%. $^1H$ NMR (400 MHz, DMSO-d6) δ 8.37 (d, J=1.6 Hz, 1H), 8.14 (d, J=8.2 Hz, 1H), 8.04 (d, J=8.1 Hz, 1H), 7.93 (dd, J=8.5, 1.6 Hz, 1H), 7.74-7.66 (m, 2H), 7.60 (dt, J=18.9, 7.4 Hz, 3H), 7.49 (dd, J=8.5, 6.7 Hz, 1H), 7.22-7.13 (m, 2H), 6.83 (d, J=8.1 Hz, 2H), 5.35 (s, 2H), 3.88 (s, 3H).

Compound 1408 and Compound 1409

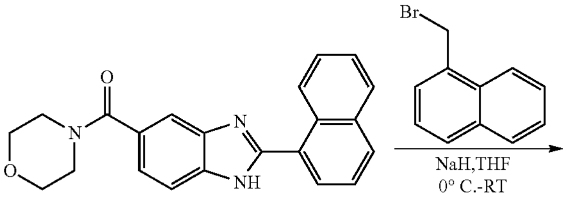

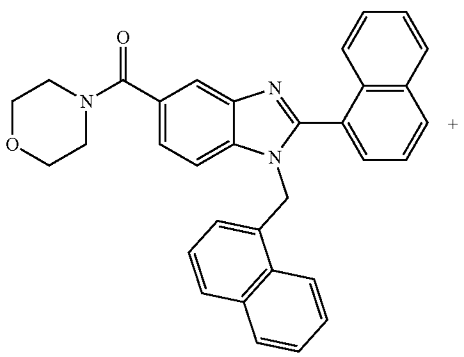

Compound-1408
Peak-1 isomer-1

-continued

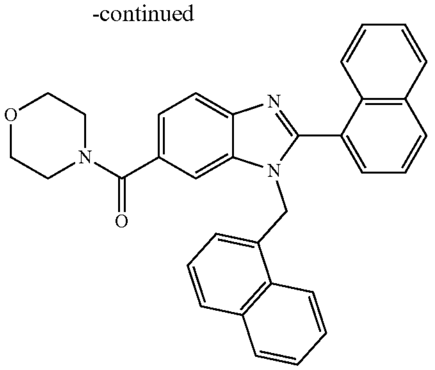

Compound-1409
Peak-2 isomer-2

Step 1 was performed as described for synthesis of Compounds 1329 and 533

Compound 1408: LCMS: 498.5 $(M+H)^+$96.19% @220 nm 96.40% @254 nm $^1H$ NMR (400 MHz, DMSO-d6) δ 8.06 (d, J=8.3 Hz, 1H), 8.03-7.97 (m, 1H), 7.88 (dd, J=11.6, 8.1 Hz, 4H), 7.75 (d, J=8.3 Hz, 1H), 7.68 (d, J=7.1 Hz, 1H), 7.63-7.47 (m, 5H), 7.43 (ddd, J=8.4, 6.8, 1.5 Hz, 1H), 7.37 (dd, J=8.2, 1.6 Hz, 1H), 7.27 (t, J=7.7 Hz, 1H), 6.65 (d, J=7.2 Hz, 1H), 5.91 (s, 2H), 3.52 (br.s, 8H).

Compound 1409: LCMS: 498.5 $(M+H)^+$99.22% @220 nm 99.09% @254 nm $^1H$ NMR (400 MHz, DMSO-d6) δ 8.03 (dd, J=21.5, 8.1 Hz, 2H), 7.92-7.82 (m, 4H), 7.71 (dd, J=30.8, 7.7 Hz, 2H), 7.62-7.47 (m, 5H), 7.42 (t, J=7.6 Hz, 1H), 7.33 (dd, J=8.4, 1.5 Hz, 1H), 7.27 (t, J=7.7 Hz, 1H), 6.68 (d, J=7.1 Hz, 1H), 5.89 (s, 2H), 3.74-3.52 (m, 8H).

Compound 1411 and Compound 1412

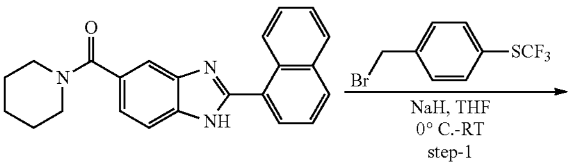

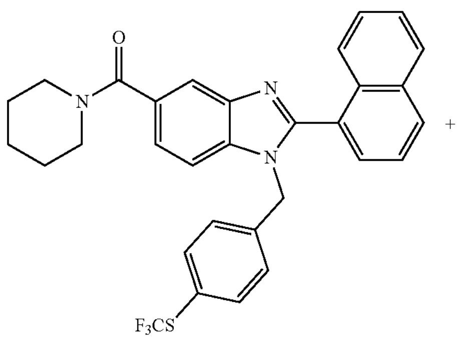

Compound-1411
Peak-1 isomer-1

-continued

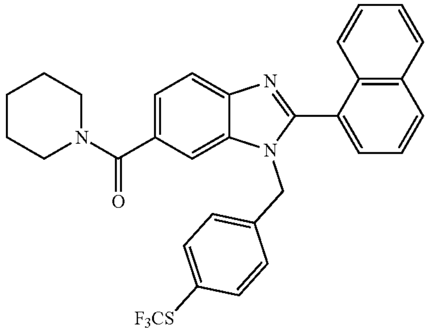

Compound-1412
Peak-2 isomer-2

Step 1 was performed as described for synthesis of Compounds 1329 and 533

Compound 1411: LCMS—546.5 $(M+H)^+$ 97.66% @220 nm 98.72% @254 nm $^1$H NMR (400 MHz, DMSO-d6) δ 8.14 (d, J=8.2 Hz, 1H), 8.05 (d, J=8.1 Hz, 1H), 7.84 (d, J=8.3 Hz, 2H), 7.70 (t, J=8.7 Hz, 2H), 7.64 (d, J=7.7 Hz, 1H), 7.62-7.56 (m, 2H), 7.49 (dd, J=7.7, 5.6 Hz, 2H), 7.32 (dd, J=8.4, 1.5 Hz, 1H), 7.00 (d, J=7.9 Hz, 2H), 5.45 (s, 2H), 3.56 (s, 4H), 1.49 (d, J=81.5 Hz, 6H).

Compound 1412: LCMS—546.5 $(M+H)^+$ 97.54% @220 nm 97.39% @254 nm $^1$H NMR Compound 1412 (400 MHz, DMSO-d6) δ 8.14 (d, J=8.1 Hz, 1H), 8.04 (d, J=8.2 Hz, 1H), 7.79 (d, J=1.5 Hz, 1H), 7.70 (d, J=7.0 Hz, 1H), 7.65 (d, J=2.7 Hz, 1H), 7.65-7.59 (m, 2H), 7.57 (d, J=7.7 Hz, 1H), 7.48 (t, J=7.6 Hz, 3H), 7.34 (dd, J=8.4, 1.5 Hz, 1H), 7.00 (d, J=8.0 Hz, 2H), 5.43 (s, 2H), 3.52 (d, J=45.9 Hz, 4H), 1.72-1.42 (m, 6H)

TABLE 1

Exemplary compounds of Formulae I, IA, IB, IC, ID, and IE

| No | Structure |
|---|---|
| 360 | 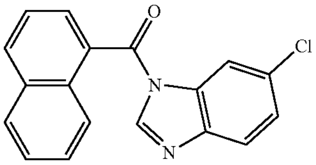 [SMILES: O=C(c1cccc2ccccc12)n1cnc2ccc(Cl)cc21] |
| 857 | 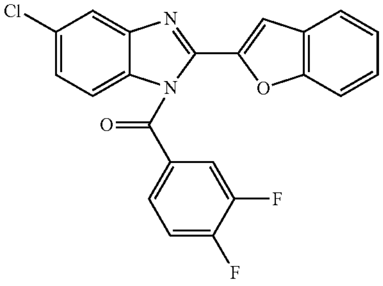 [SMILES: O=C(c1ccc(F)c(F)c1)n1c(-c2cc3ccccc3o2)nc2cc(Cl)ccc21] |
| 361 | 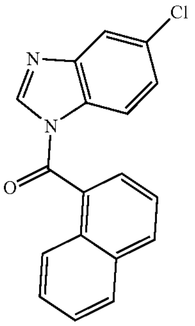 [SMILES: O=C(c1cccc2ccccc12)n1cnc2cc(Cl)ccc21] |
| 858 | 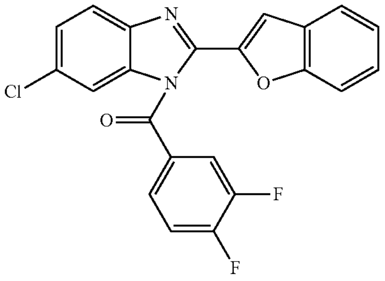 [SMILES: O=C(c1ccc(F)c(F)c1)n1c(-c2cc3ccccc3o2)nc2ccc(Cl)cc21] |
| 429 | 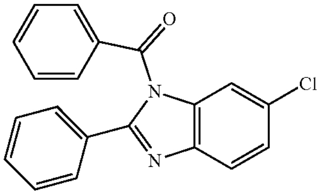 [SMILES: O=C(c1ccccc1)n1c(-c2ccccc2)nc2ccc(Cl)cc21] |
| 859 | 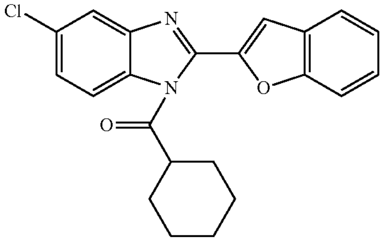 [SMILES: O=C(C1CCCCC1)n1c(-c2cc3ccccc3o2)nc2cc(Cl)ccc21] |
| 430 | 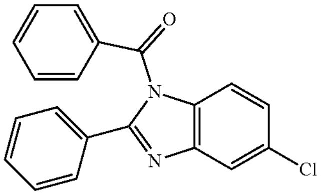 [SMILES: O=C(c1ccccc1)n1c(-c2ccccc2)nc2cc(Cl)ccc21] |
| 860 | 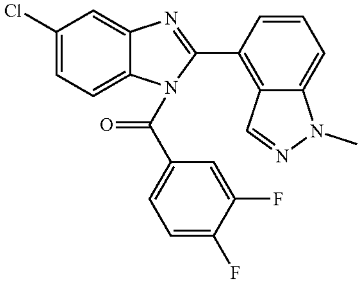 [SMILES: Cn1ncc2c(-c3nc4cc(Cl)ccc4n3C(=O)c3ccc(F)c(F)c3)cccc21] |

TABLE 1-continued
Exemplary compounds of Formulae I, IA, IB, IC, ID, and IE
| No | Structure |
|---|---|
| 431 | 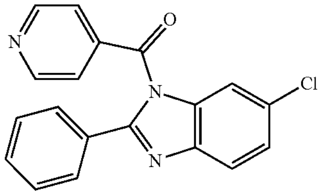 [SMILES: O=C(c1ccncc1)n1c(-c2ccccc2)nc2ccc(Cl)cc21] |
| 861 | 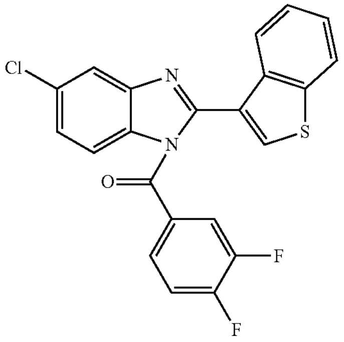 [SMILES: O=C(c1ccc(F)c(F)c1)n1c(-c2csc3ccccc23)nc2cc(Cl)ccc21] |
| 432 | 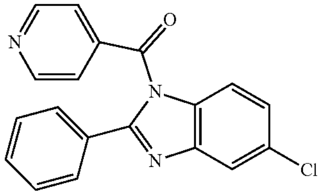 [SMILES: O=C(c1ccncc1)n1c(-c2ccccc2)nc2cc(Cl)ccc21] |
| 862 | 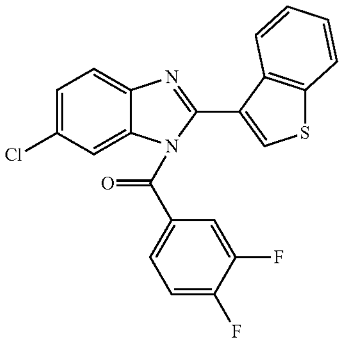 [SMILES: O=C(c1ccc(F)c(F)c1)n1c(-c2csc3ccccc23)nc2ccc(Cl)cc21] |
| 490 | 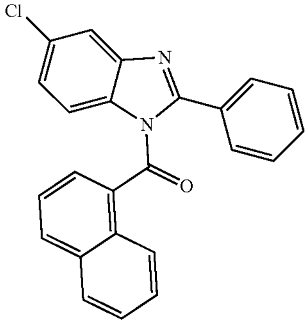 [SMILES: O=C(c1cccc2ccccc12)n1c(-c2ccccc2)nc2cc(Cl)ccc21] |
| 863 | 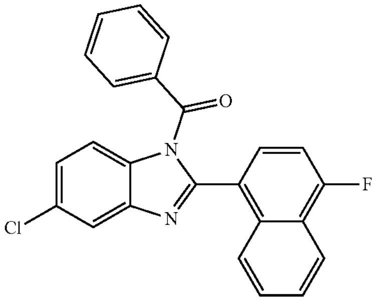 [SMILES: O=C(c1ccccc1)n1c(-c2ccc(F)c3ccccc23)nc2cc(Cl)ccc21] |
| 491 | 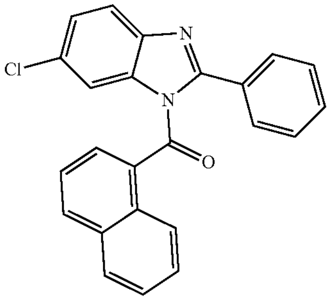 [SMILES: O=C(c1cccc2ccccc12)n1c(-c2ccccc2)nc2ccc(Cl)cc21] |
| 864 | 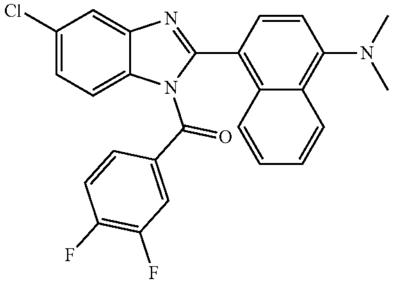 [SMILES: CN(C)c1ccc(-c2nc3cc(Cl)ccc3n2C(=O)c2ccc(F)c(F)c2)c2ccccc12] |
| 492 | 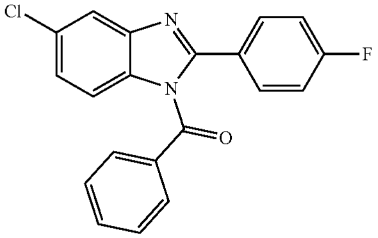 [SMILES: O=C(c1ccccc1)n1c(-c2ccc(F)cc2)nc2cc(Cl)ccc21] |
| 865 | 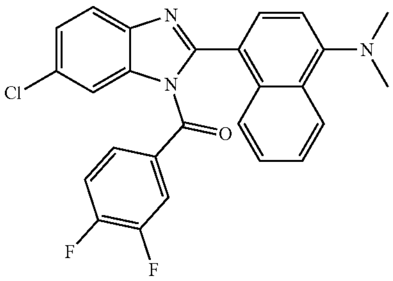 [SMILES: CN(C)c1ccc(-c2nc3ccc(Cl)cc3n2C(=O)c2ccc(F)c(F)c2)c2ccccc12] |

TABLE 1-continued
| Exemplary compounds of Formulae I, IA, IB, IC, ID, and IE | |
|---|---|
| No | Structure |
| 493 | 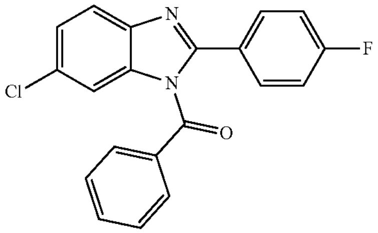 [SMILES: O=C(c1ccccc1)n1c(-c2ccc(F)cc2)nc2ccc(Cl)cc21] |
| 866 | 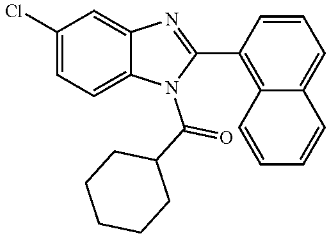 [SMILES: O=C(C1CCCCC1)n1c(-c2cccc3ccccc23)nc2cc(Cl)ccc21] |
| 494 | 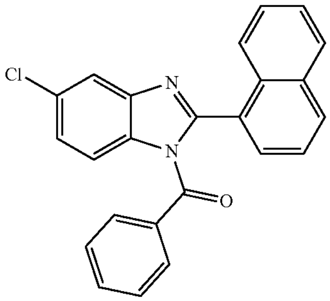 [SMILES: O=C(c1ccccc1)n1c(-c2cccc3ccccc23)nc2cc(Cl)ccc21] |
| 867 | 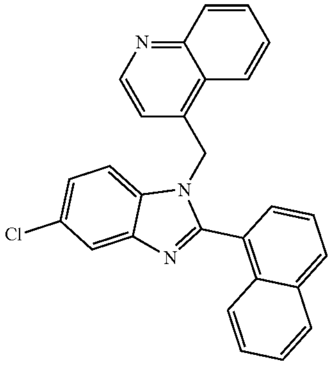 [SMILES: Clc1ccc2c(c1)nc(-c1cccc3ccccc13)n2Cc1ccnc2ccccc12] |
| 495 | 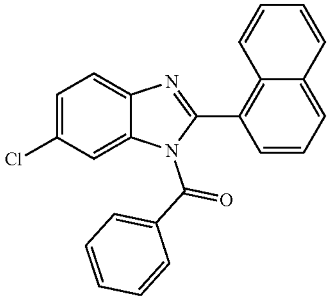 [SMILES: O=C(c1ccccc1)n1c(-c2cccc3ccccc23)nc2ccc(Cl)cc21] |
TABLE 1-continued
| Exemplary compounds of Formulae I, IA, IB, IC, ID, and IE | |
|---|---|
| No | Structure |
| 868 | 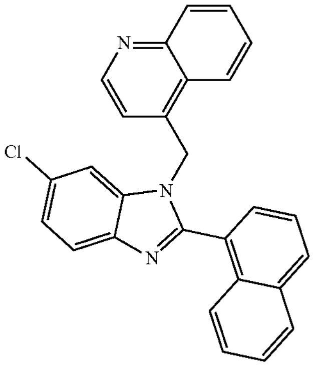 [SMILES: Clc1ccc2nc(-c3cccc4ccccc34)n(Cc3ccnc4ccccc34)c2c1] |
| 496 | 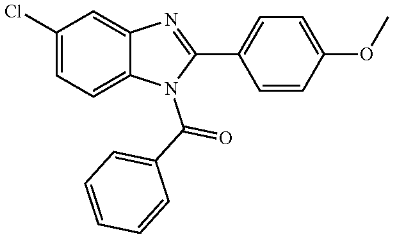 [SMILES: COc1ccc(-c2nc3cc(Cl)ccc3n2C(=O)c2ccccc2)cc1] |
| 869 | 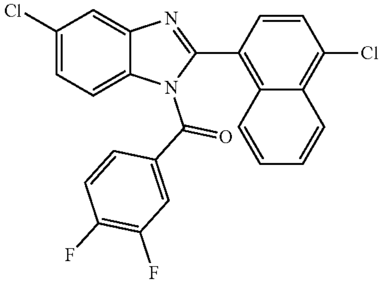 [SMILES: O=C(c1ccc(F)c(F)c1)n1c(-c2ccc(Cl)c3ccccc23)nc2cc(Cl)ccc21] |
| 497 | 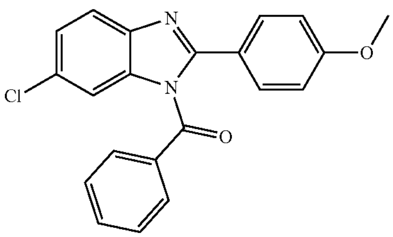 [SMILES: COc1ccc(-c2nc3ccc(Cl)cc3n2C(=O)c2ccccc2)cc1] |
| 870 | 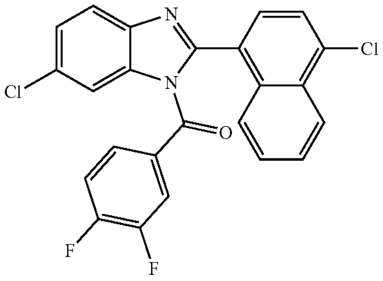 [SMILES: O=C(c1ccc(F)c(F)c1)n1c(-c2ccc(Cl)c3ccccc23)nc2ccc(Cl)cc21] |

TABLE 1-continued
| Exemplary compounds of Formulae I, IA, IB, IC, ID, and IE | |
|---|---|
| No | Structure |
| 527 | 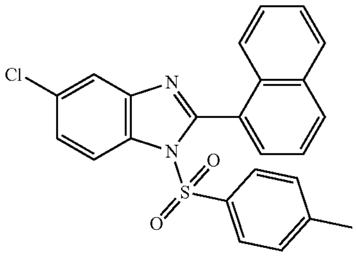 [SMILES: Cc1ccc(S(=O)(=O)n2c(-c3cccc4ccccc34)nc3cc(Cl)ccc32)cc1] |
| 871 | 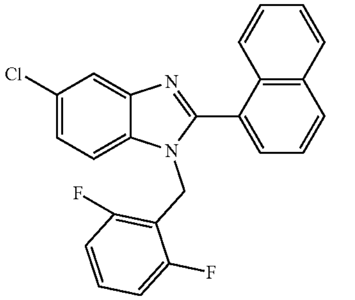 [SMILES: Fc1cccc(F)c1Cn1c(-c2cccc3ccccc23)nc2cc(Cl)ccc21] |
| 528 | 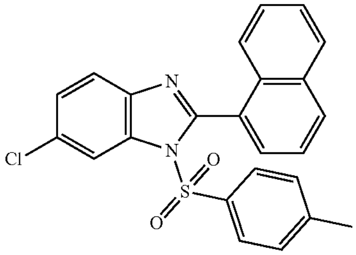 [SMILES: Cc1ccc(S(=O)(=O)n2c(-c3cccc4ccccc34)nc3ccc(Cl)cc32)cc1] |
| 872 | 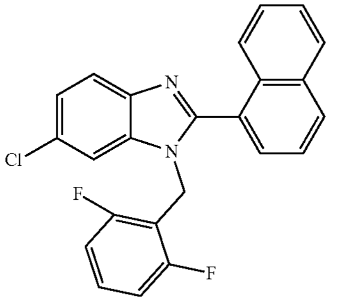 [SMILES: Fc1cccc(F)c1Cn1c(-c2cccc3ccccc23)nc2ccc(Cl)cc21] |
| 529 | 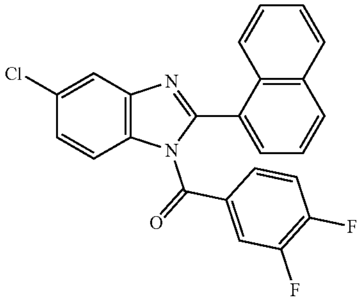 [SMILES: O=C(c1ccc(F)c(F)c1)n1c(-c2cccc3ccccc23)nc2cc(Cl)ccc21] |
TABLE 1-continued
| Exemplary compounds of Formulae I, IA, IB, IC, ID, and IE | |
|---|---|
| No | Structure |
| 875 | 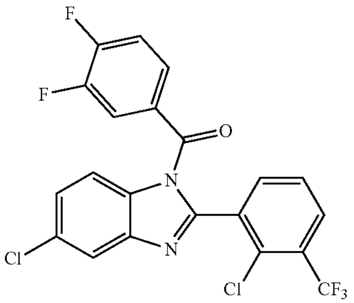 [SMILES: O=C(c1ccc(F)c(F)c1)n1c(-c2cccc(C(F)(F)F)c2Cl)nc2cc(Cl)ccc21] |
| 530 | 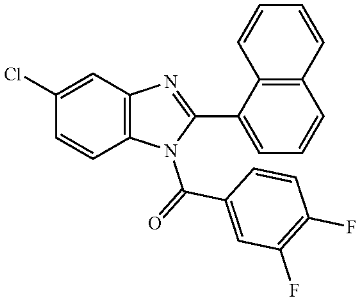 [SMILES: O=C(c1ccc(F)c(F)c1)n1c(-c2cccc3ccccc23)nc2cc(Cl)ccc21] |
| 876 | 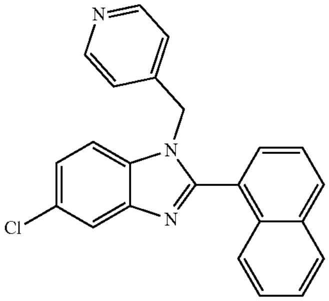 [SMILES: Clc1ccc2c(c1)nc(-c1cccc3ccccc13)n2Cc1ccncc1] |
| 533 | 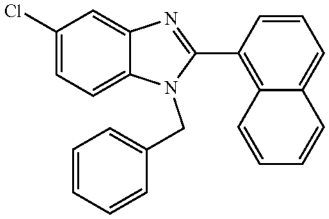 [SMILES: Clc1ccc2c(c1)nc(-c1cccc3ccccc13)n2Cc1ccccc1] |
| 877 | 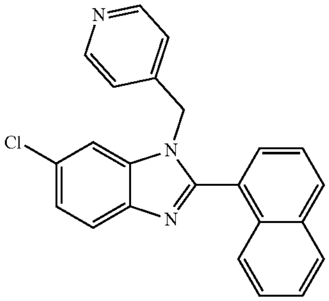 [SMILES: Clc1ccc2nc(-c3cccc4ccccc34)n(Cc3ccncc3)c2c1] |

TABLE 1-continued
| Exemplary compounds of Formulae I, IA, IB, IC, ID, and IE | |
|---|---|
| No | Structure |
| 534 | 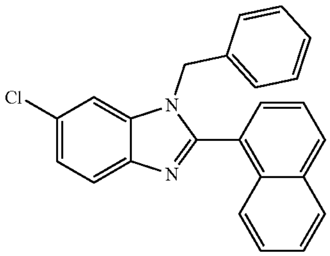 [SMILES: Clc1ccc2nc(-c3cccc4ccccc34)n(Cc3ccccc3)c2c1] |
| 886 | 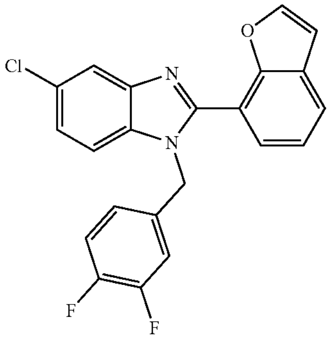 [SMILES: Fc1ccc(Cn2c(-c3cccc4ccoc34)nc3cc(Cl)ccc32)cc1F] |
| 535 | 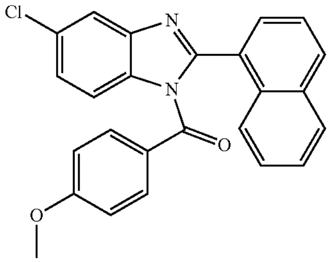 [SMILES: COc1ccc(C(=O)n2c(-c3cccc4ccccc34)nc3cc(Cl)ccc32)cc1] |
| 887 | 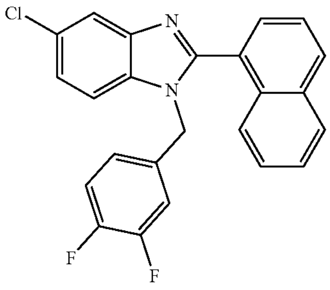 [SMILES: Fc1ccc(Cn2c(-c3cccc4ccccc34)nc3cc(Cl)ccc32)cc1F] |
| 536 | 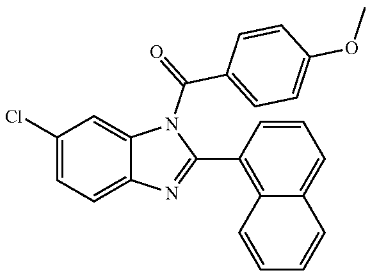 [SMILES: COc1ccc(C(=O)n2c(-c3cccc4ccccc34)nc3ccc(Cl)cc32)cc1] |
TABLE 1-continued
| Exemplary compounds of Formulae I, IA, IB, IC, ID, and IE | |
|---|---|
| No | Structure |
| 888 | 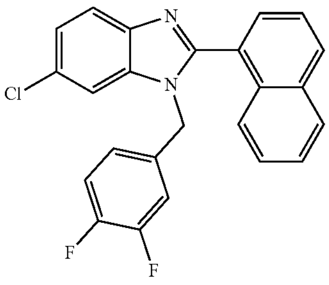 [SMILES: Fc1ccc(Cn2c(-c3cccc4ccccc34)nc3ccc(Cl)cc32)cc1F] |
| 579 | 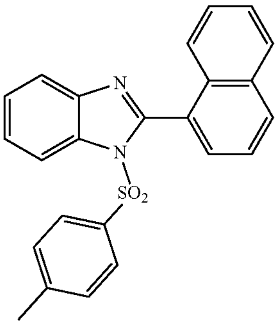 [SMILES: Cc1ccc(S(=O)(=O)n2c(-c3cccc4ccccc34)nc3ccccc32)cc1] |
| 1328 | 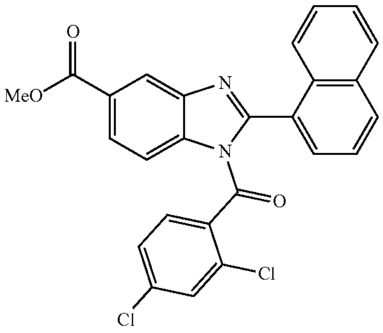 [SMILES: COC(=O)c1ccc2c(c1)nc(-c1cccc3ccccc13)n2C(=O)c1ccc(Cl)cc1Cl] |
| 580 | 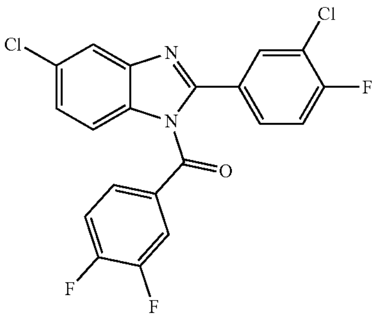 [SMILES: O=C(c1ccc(F)c(F)c1)n1c(-c2ccc(F)c(Cl)c2)nc2cc(Cl)ccc21] |

TABLE 1-continued
| Exemplary compounds of Formulae I, IA, IB, IC, ID, and IE | |
|---|---|
| No | Structure |
| 1329 | 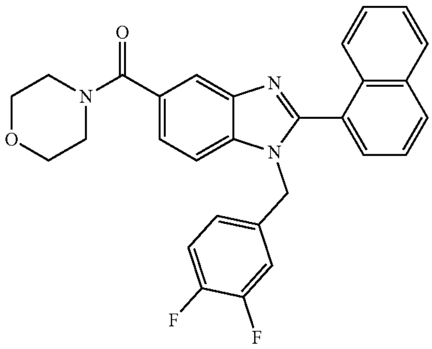 [SMILES: O=C(c1ccc2c(c1)nc(-c1cccc3ccccc13)n2Cc1ccc(F)c(F)c1)N1CCOCC1] |
| 581 | 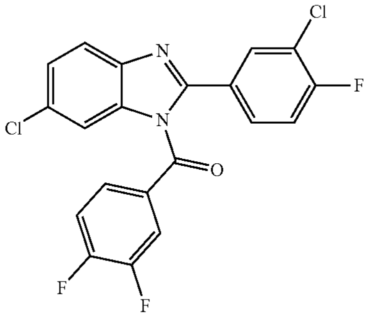 [SMILES: O=C(c1ccc(F)c(F)c1)n1c(-c2ccc(F)c(Cl)c2)nc2ccc(Cl)cc21] |
| 1330 | 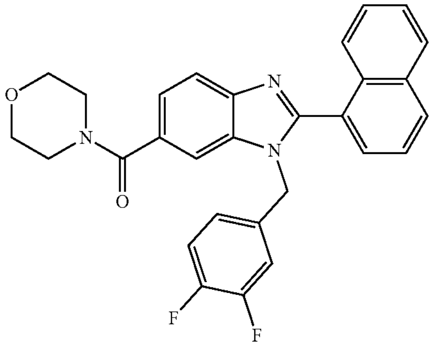 [SMILES: O=C(c1ccc2nc(-c3cccc4ccccc34)n(Cc3ccc(F)c(F)c3)c2c1)N1CCOCC1] |
| 582 | 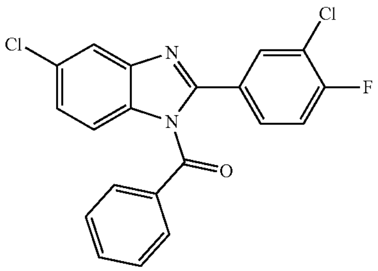 [SMILES: O=C(c1ccccc1)n1c(-c2ccc(F)c(Cl)c2)nc2cc(Cl)ccc21] |
TABLE 1-continued
| Exemplary compounds of Formulae I, IA, IB, IC, ID, and IE | |
|---|---|
| No | Structure |
| 1336 | 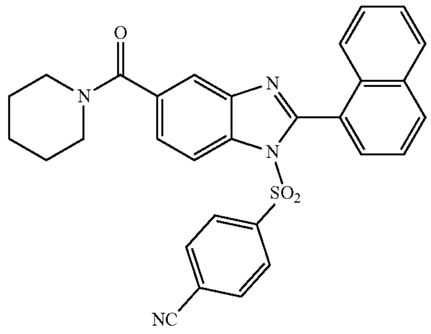 |
| 583 | 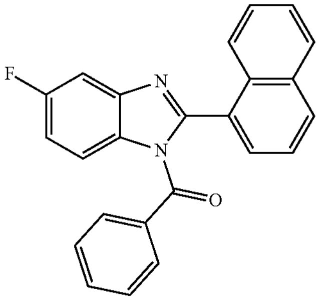 [SMILES: O=C(c1ccccc1)n1c(-c2cccc3ccccc23)nc2cc(F)ccc21] |
| 1337 | 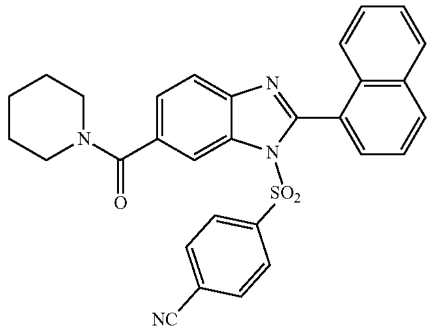 |
| 584 | 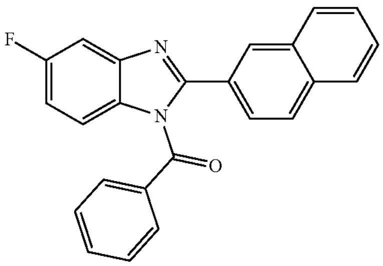 [SMILES: O=C(c1ccccc1)n1c(-c2ccc3ccccc3c2)nc2cc(F)ccc21] |

TABLE 1-continued
| Exemplary compounds of Formulae I, IA, IB, IC, ID, and IE | |
|---|---|
| No | Structure |
| 1338 | 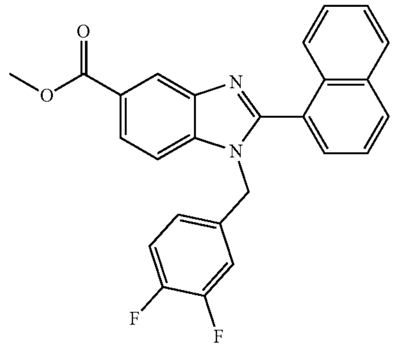 [SMILES: COC(=O)c1ccc2c(c1)nc(-c1cccc3ccccc13)n2Cc1ccc(F)c(F)c1] |
| 585 | 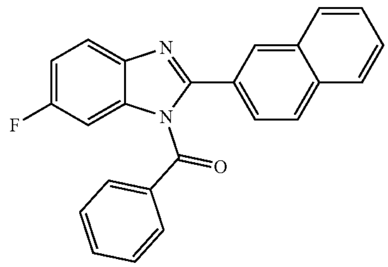 [SMILES: O=C(c1ccccc1)n1c(-c2ccc3ccccc3c2)nc2ccc(F)cc21] |
| 1339 | 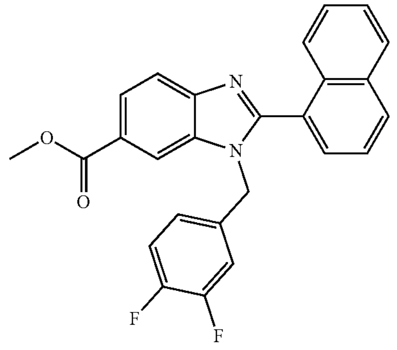 [SMILES: COC(=O)c1ccc2nc(-c3cccc4ccccc34)n(Cc3ccc(F)c(F)c3)c2c1] |
| 586 | 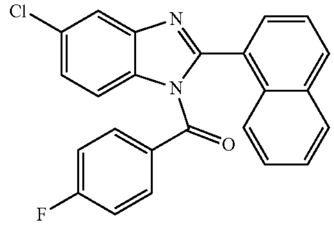 [SMILES: O=C(c1ccc(F)cc1)n1c(-c2cccc3ccccc23)nc2cc(Cl)ccc21] |
TABLE 1-continued
| Exemplary compounds of Formulae I, IA, IB, IC, ID, and IE | |
|---|---|
| No | Structure |
| 1340 | 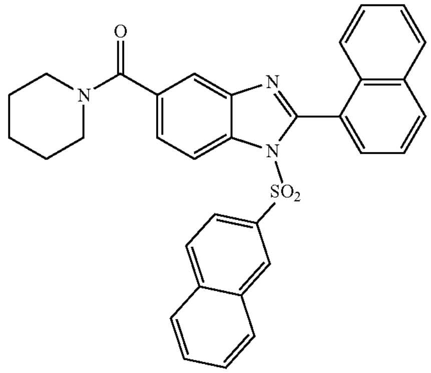 [SMILES: O=C(c1ccc2c(c1)nc(-c1cccc3ccccc13)n2S(=O)(=O)c1ccc2ccccc2c1)N1CCCCC1] |
| 587 | 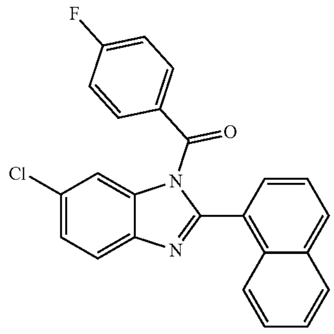 [SMILES: O=C(c1ccc(F)cc1)n1c(-c2cccc3ccccc23)nc2ccc(Cl)cc21] |
| 1341 | 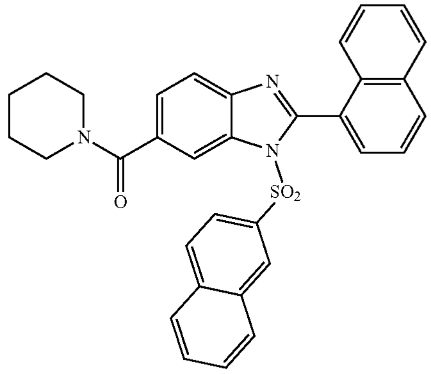 [SMILES: O=C(c1ccc2nc(-c3cccc4ccccc34)n(S(=O)(=O)c3ccc4ccccc4c3)c2c1)N1CCCCC1] |
| 588 | 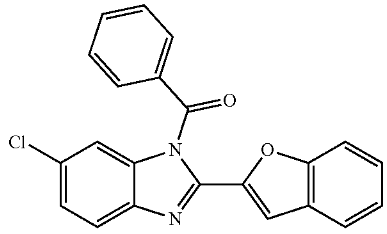 [SMILES: O=C(c1ccccc1)n1c(-c2cc3ccccc3o2)nc2ccc(Cl)cc21] |

TABLE 1-continued
| Exemplary compounds of Formulae I, IA, IB, IC, ID, and IE | |
|---|---|
| No | Structure |
| 1342 | 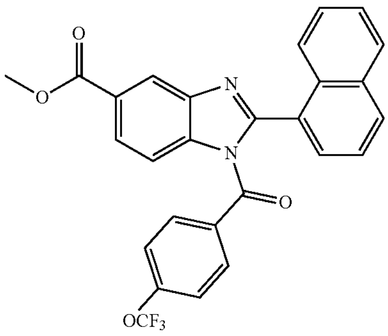 [SMILES: COC(=O)c1ccc2c(c1)nc(-c1cccc3ccccc13)n2C(=O)c1ccc(OC(F)(F)F)cc1] |
| 590 | 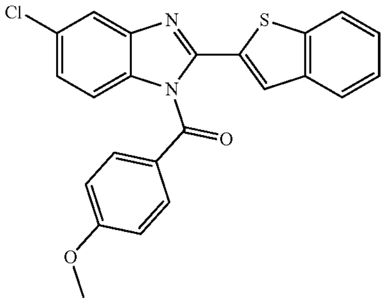 [SMILES: COc1ccc(C(=O)n2c(-c3cc4ccccc4s3)nc3cc(Cl)ccc32)cc1] |
| 1356 | 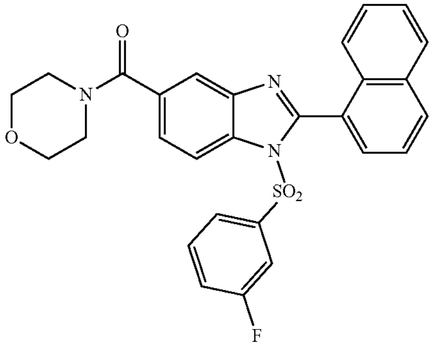 [SMILES: O=C(c1ccc2c(c1)nc(-c1cccc3ccccc13)n2S(=O)(=O)c1cccc(F)c1)N1CCOCC1] |
| 591 | 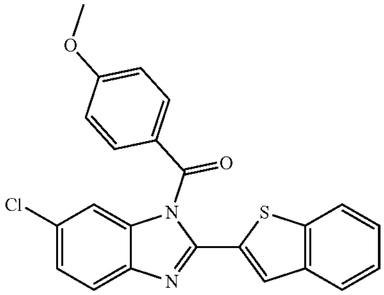 [SMILES: COc1ccc(C(=O)n2c(-c3cc4ccccc4s3)nc3ccc(Cl)cc32)cc1] |
TABLE 1-continued
| Exemplary compounds of Formulae I, IA, IB, IC, ID, and IE | |
|---|---|
| No | Structure |
| 1357 | 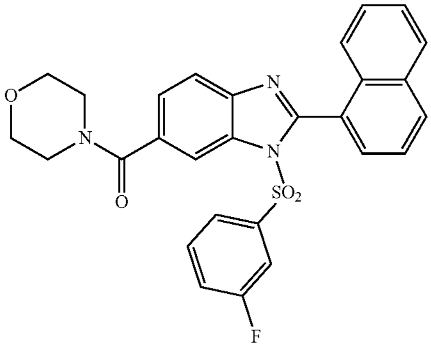 [SMILES: O=C(c1ccc2nc(-c3cccc4ccccc34)n(S(=O)(=O)c3cccc(F)c3)c2c1)N1CCOCC1] |
| 630 | 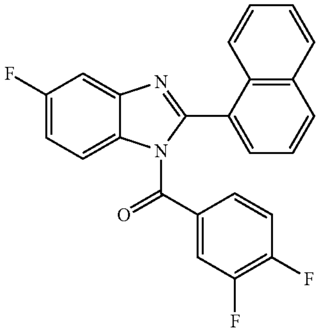 [SMILES: O=C(c1ccc(F)c(F)c1)n1c(-c2cccc3ccccc23)nc2cc(F)ccc21] |
| 1358 | 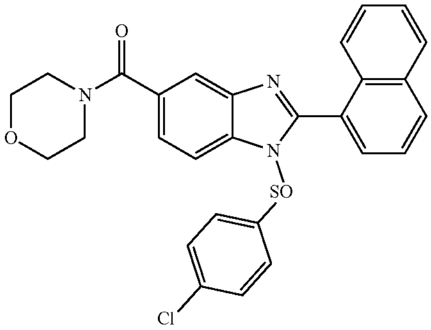 |
| 631 | 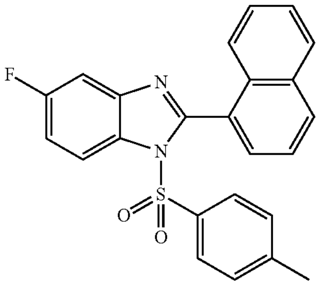 [SMILES: Cc1ccc(S(=O)(=O)n2c(-c3cccc4ccccc34)nc3cc(F)ccc32)cc1] |

TABLE 1-continued
Exemplary compounds of Formulae I, IA, IB, IC, ID, and IE
| No | Structure |
|---|---|
| 1359 | 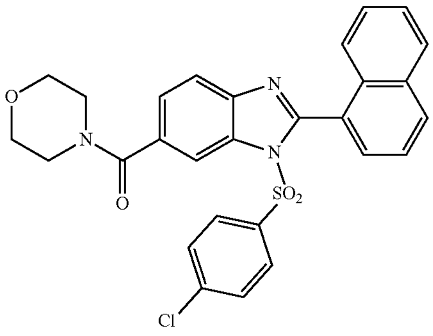 [SMILES: O=C(c1ccc2nc(-c3cccc4ccccc34)n(S(=O)(=O)c3ccc(Cl)cc3)c2c1)N1CCOCC1] |
| 632 | 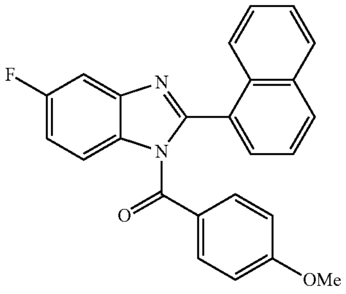 [SMILES: COc1ccc(C(=O)n2c(-c3cccc4ccccc34)nc3cc(F)ccc32)cc1] |
| 1360 | 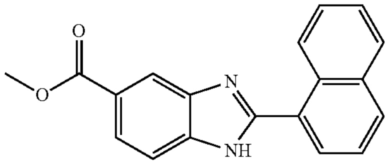 [SMILES: COC(=O)c1ccc2[nH]c(-c3cccc4ccccc34)nc2c1] |
| 633 | 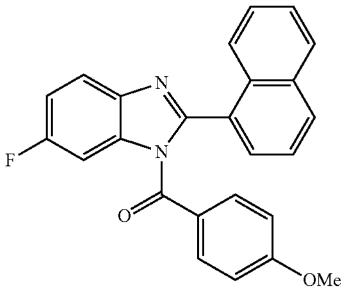 [SMILES: COc1ccc(C(=O)n2c(-c3cccc4ccccc34)nc3ccc(F)cc32)cc1] |
| 1361 | 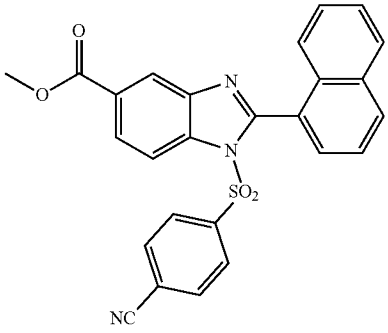 |
TABLE 1-continued
Exemplary compounds of Formulae I, IA, IB, IC, ID, and IE
| No | Structure |
|---|---|
| 634 | 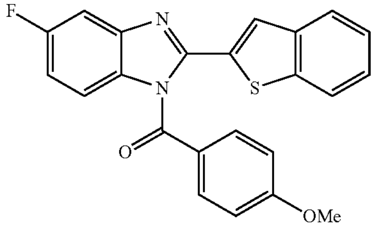 [SMILES: COc1ccc(C(=O)n2c(-c3cc4ccccc4s3)nc3cc(F)ccc32)cc1] |
| 1362 | 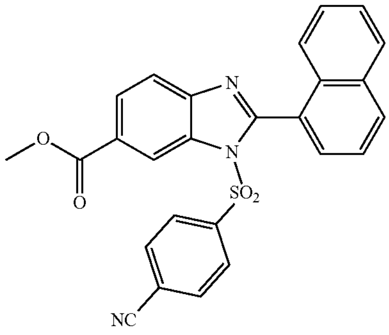 [SMILES: COC(=O)c1ccc2nc(-c3cccc4ccccc34)n(S(=O)(=O)c3ccc(C#N)cc3)c2c1] |
| 635 | 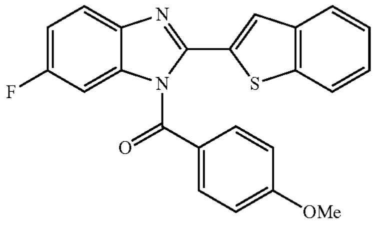 [SMILES: COc1ccc(C(=O)n2c(-c3cc4ccccc4s3)nc3ccc(F)cc32)cc1] |
| 1363 | 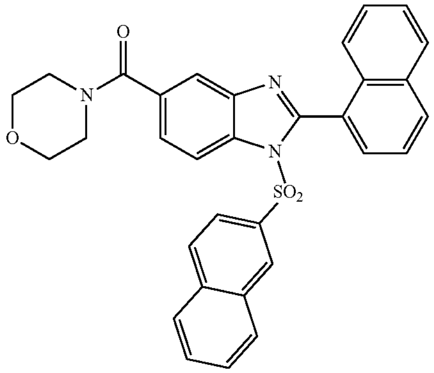 [SMILES: O=C(c1ccc2c(c1)nc(-c1cccc3ccccc13)n2S(=O)(=O)c1ccc2ccccc2c1)N1CCOCC1] |
| 636 | 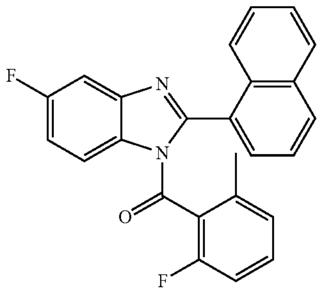 [SMILES: Cc1cccc(F)c1C(=O)n1c(-c2cccc3ccccc23)nc2cc(F)ccc21] |

TABLE 1-continued
| Exemplary compounds of Formulae I, IA, IB, IC, ID, and IE | |
|---|---|
| No | Structure |
| 1364 | 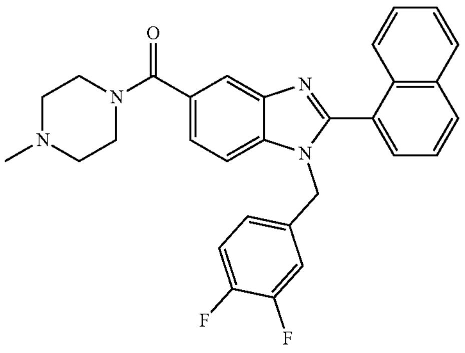 [SMILES: CN1CCN(C(=O)c2ccc3c(c2)nc(-c2cccc4ccccc24)n3Cc2ccc(F)c(F)c2)CC1] |
| 637 | 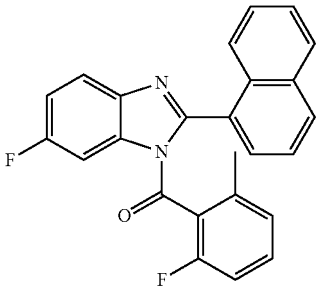 [SMILES: Cc1cccc(F)c1C(=O)n1c(-c2cccc3ccccc23)nc2ccc(F)cc21] |
| 1365 | 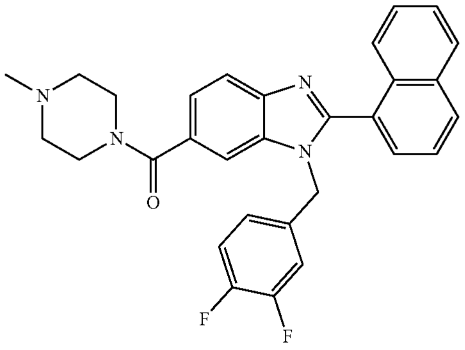 [SMILES: CN1CCN(C(=O)c2ccc3nc(-c4cccc5ccccc45)n(Cc4ccc(F)c(F)c4)c3c2)CC1] |
| 638 | 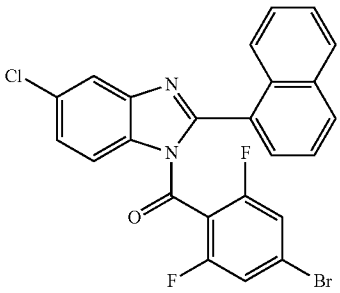 [SMILES: O=C(c1c(F)cc(Br)cc1F)n1c(-c2cccc3ccccc23)nc2cc(Cl)ccc21] |
TABLE 1-continued
| Exemplary compounds of Formulae I, IA, IB, IC, ID, and IE | |
|---|---|
| No | Structure |
| 1366 | 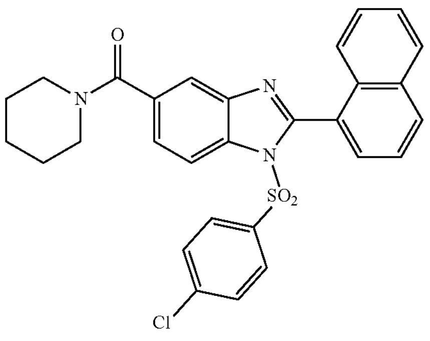 [SMILES: O=C(c1ccc2c(c1)nc(-c1cccc3ccccc13)n2S(=O)(=O)c1ccc(Cl)cc1)N1CCCCC1] |
| 639 | 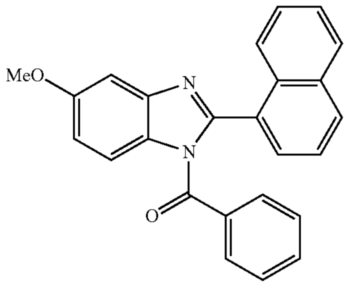 [SMILES: COc1ccc2c(c1)nc(-c1cccc3ccccc13)n2C(=O)c1ccccc1] |
| 1367 | 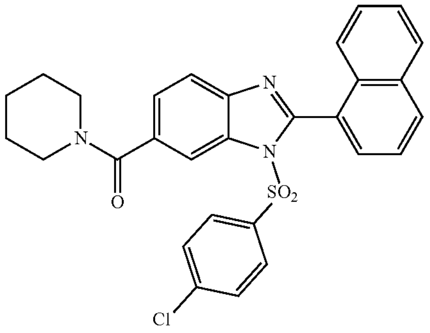 [SMILES: O=C(c1ccc2nc(-c3cccc4ccccc34)n(S(=O)(=O)c3ccc(Cl)cc3)c2c1)N1CCCCC1] |
| 640 | 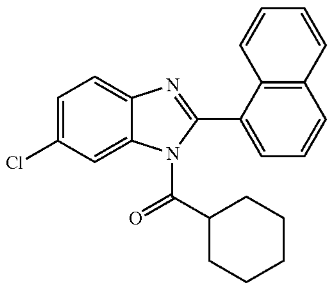 [SMILES: O=C(C1CCCCC1)n1c(-c2cccc3ccccc23)nc2ccc(Cl)cc21] |

TABLE 1-continued
| Exemplary compounds of Formulae I, IA, IB, IC, ID, and IE | |
|---|---|
| No | Structure |
| 1368 | 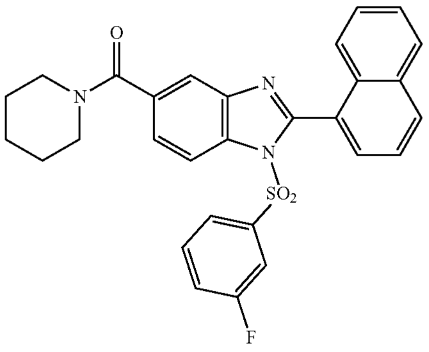 [SMILES: O=C(c1ccc2c(c1)nc(-c1cccc3ccccc13)n2S(=O)(=O)c1cccc(F)c1)N1CCCCC1] |
| 641 | 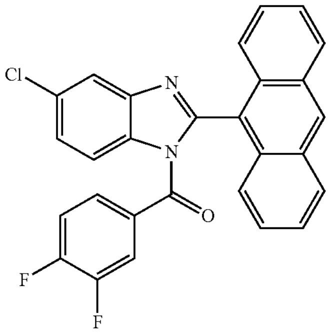 [SMILES: O=C(c1ccc(F)c(F)c1)n1c(-c2c3ccccc3cc3ccccc23)nc2cc(Cl)ccc21] |
| 1369 | 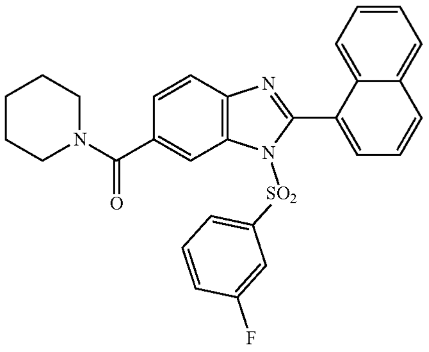 [SMILES: O=C(c1ccc2nc(-c3cccc4ccccc34)n(S(=O)(=O)c3cccc(F)c3)c2c1)N1CCCCC1] |
| 642 | 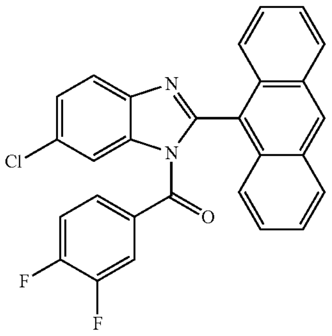 [SMILES: O=C(c1ccc(F)c(F)c1)n1c(-c2c3ccccc3cc3ccccc23)nc2ccc(Cl)cc21] |
TABLE 1-continued
| Exemplary compounds of Formulae I, IA, IB, IC, ID, and IE | |
|---|---|
| No | Structure |
| 1370 | 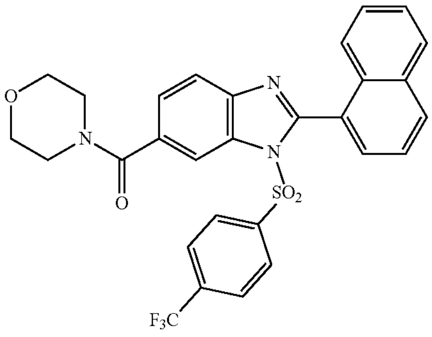 [SMILES: O=C(c1ccc2nc(-c3cccc4ccccc34)n(S(=O)(=O)c3ccc(C(F)(F)F)cc3)c2c1)N1CCOCC1] |
| 643 | 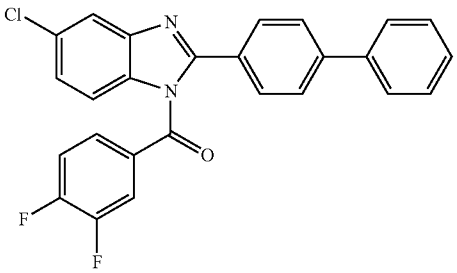 [SMILES: O=C(c1ccc(F)c(F)c1)n1c(-c2ccc(-c3ccccc3)cc2)nc2cc(Cl)ccc21] |
| 1384 | 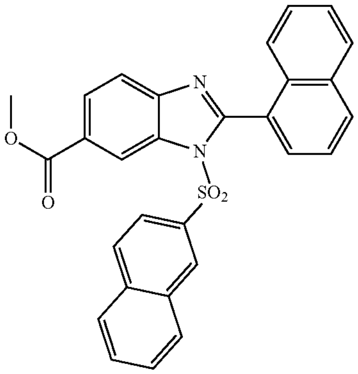 [SMILES: COC(=O)c1ccc2nc(-c3cccc4ccccc34)n(S(=O)(=O)c3ccc4ccccc4c3)c2c1] |
| 644 | 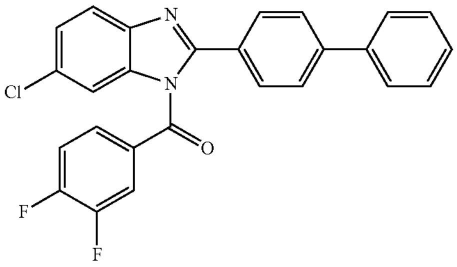 [SMILES: O=C(c1ccc(F)c(F)c1)n1c(-c2ccc(-c3ccccc3)cc2)nc2ccc(Cl)cc21] |

TABLE 1-continued
| Exemplary compounds of Formulae I, IA, IB, IC, ID, and IE | |
|---|---|
| No | Structure |
| 1385 | 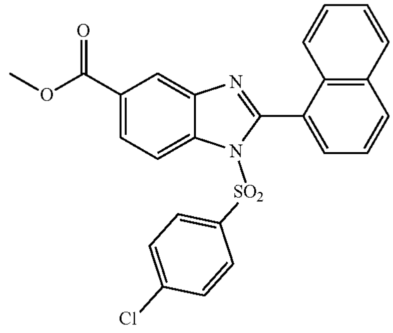 [SMILES: COC(=O)c1ccc2c(c1)nc(-c1cccc3ccccc13)n2S(=O)(=O)c1ccc(Cl)cc1] |
| 645 | 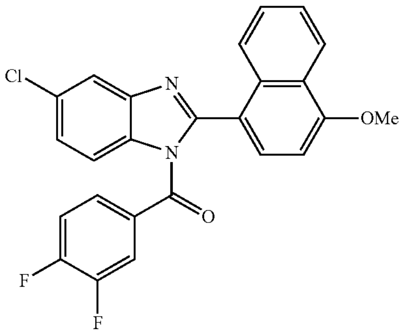 [SMILES: COc1ccc(-c2nc3cc(Cl)ccc3n2C(=O)c2ccc(F)c(F)c2)c2ccccc12] |
| 1386 | 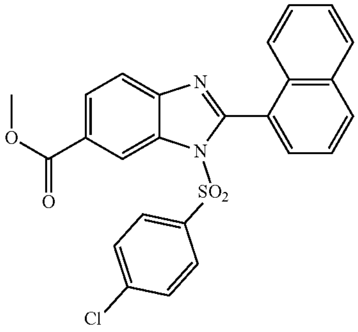 [SMILES: COC(=O)c1ccc2nc(-c3cccc4ccccc34)n(S(=O)(=O)c3ccc(Cl)cc3)c2c1] |
| 681 | 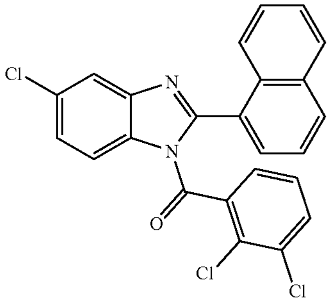 [SMILES: O=C(c1cccc(Cl)c1Cl)n1c(-c2cccc3ccccc23)nc2cc(Cl)ccc21] |
TABLE 1-continued
| Exemplary compounds of Formulae I, IA, IB, IC, ID, and IE | |
|---|---|
| No | Structure |
| 1387 | 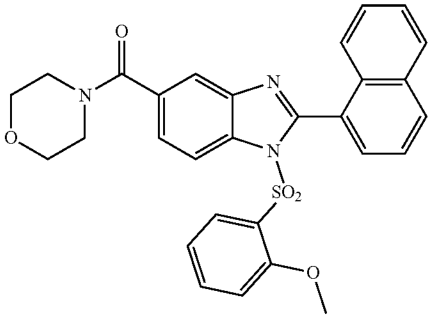 [SMILES: COc1ccccc1S(=O)(=O)n1c(-c2cccc3ccccc23)nc2cc(C(=O)N3CCOCC3)ccc21] |
| 682 | 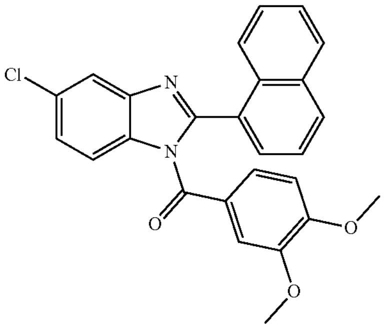 [SMILES: COc1ccc(C(=O)n2c(-c3cccc4ccccc34)nc3cc(Cl)ccc32)cc1OC] |
| 1388 | 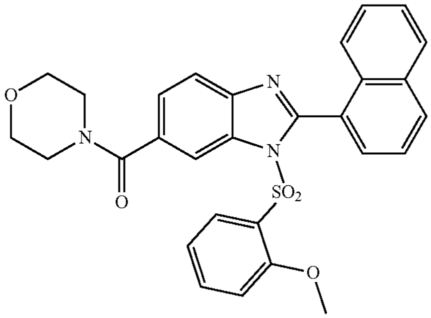 [SMILES: COc1ccccc1S(=O)(=O)n1c(-c2cccc3ccccc23)nc2ccc(C(=O)N3CCOCC3)cc21] |
| 683 | 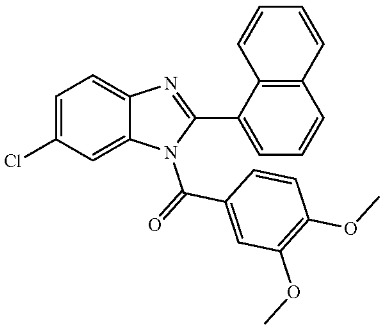 [SMILES: COc1ccc(C(=O)n2c(-c3cccc4ccccc34)nc3ccc(Cl)cc32)cc1OC] |

TABLE 1-continued
Exemplary compounds of Formulae I, IA, IB, IC, ID, and IE
| No | Structure |
|---|---|
| 1389 | 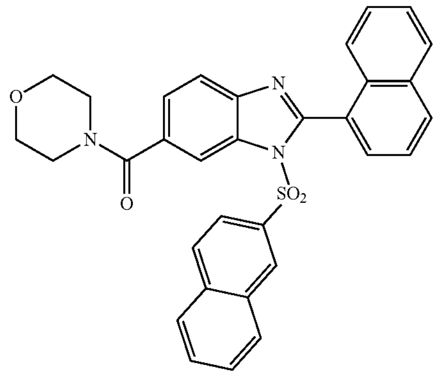 [SMILES: O=C(c1ccc2nc(-c3cccc4ccccc34)n(S(=O)(=O)c3ccc4ccccc4c3)c2c1)N1CCOCC1] |
| 684 | 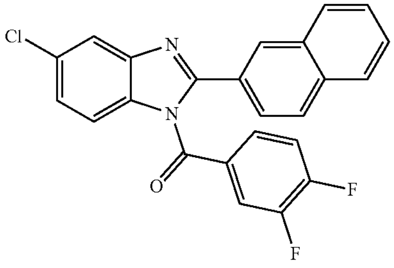 [SMILES: O=C(c1ccc(F)c(F)c1)n1c(-c2ccc3ccccc3c2)nc2cc(Cl)ccc21] |
| 1390 | 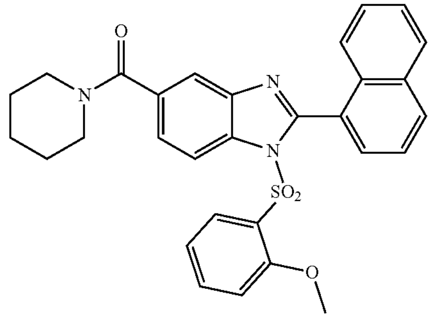 [SMILES: COc1ccccc1S(=O)(=O)n1c(-c2cccc3ccccc23)nc2cc(C(=O)N3CCCCC3)ccc21] |
| 685 | 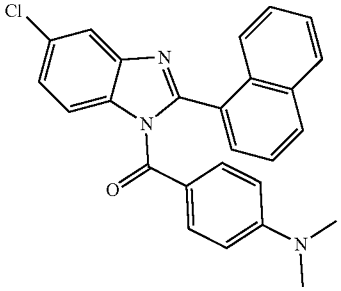 [SMILES: CN(C)c1ccc(C(=O)n2c(-c3cccc4ccccc34)nc3cc(Cl)ccc32)cc1] |
| 1391 | 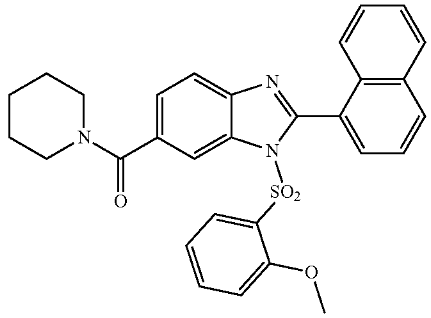 [SMILES: COc1ccccc1S(=O)(=O)n1c(-c2cccc3ccccc23)nc2ccc(C(=O)N3CCCCC3)cc21] |
| 686 | 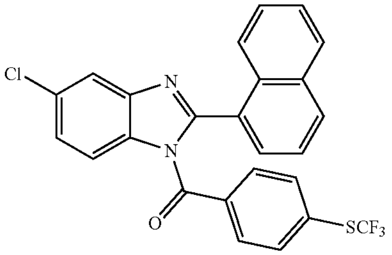 |
| 1392 | 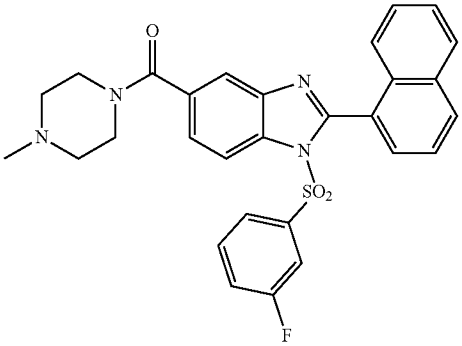 [SMILES: CN1CCN(C(=O)c2ccc3c(c2)nc(-c2cccc4ccccc24)n3S(=O)(=O)c2cccc(F)c2)CC1] |
| 687 | 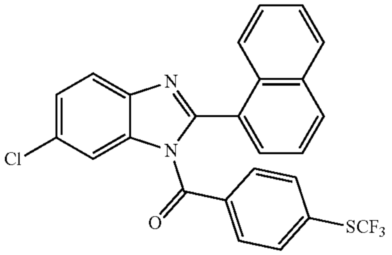 |
| 1393 | 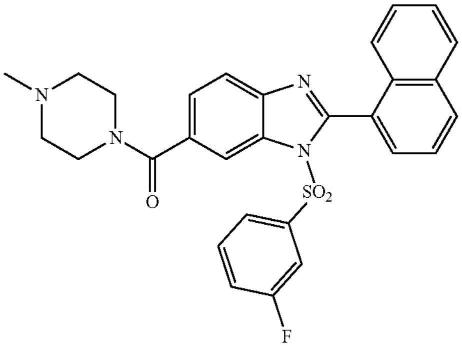 [SMILES: CN1CCN(C(=O)c2ccc3nc(-c4cccc5ccccc45)n(S(=O)(=O)c4cccc(F)c4)c3c2)CC1] |

TABLE 1-continued
Exemplary compounds of Formulae I, IA, IB, IC, ID, and IE
| No | Structure |
| --- | --- |
| 688 | 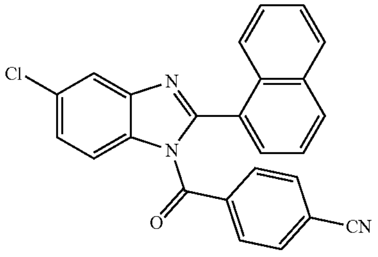 [SMILES: N#Cc1ccc(C(=O)n2c(-c3cccc4ccccc34)nc3cc(Cl)ccc32)cc1] |
| 1401 | 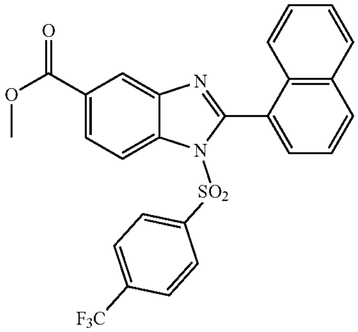 [SMILES: COC(=O)c1ccc2c(c1)nc(-c1cccc3ccccc13)n2S(=O)(=O)c1ccc(C(F)(F)F)cc1] |
| 689 | 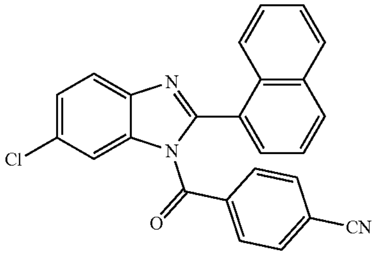 [SMILES: N#Cc1ccc(C(=O)n2c(-c3cccc4ccccc34)nc3ccc(Cl)cc32)cc1] |
| 1402 | 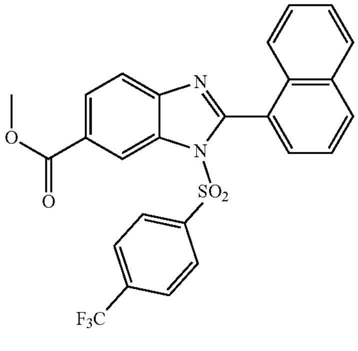 [SMILES: COC(=O)c1ccc2nc(-c3cccc4ccccc34)n(S(=O)(=O)c3ccc(C(F)(F)F)cc3)c2c1] |
| 690 | 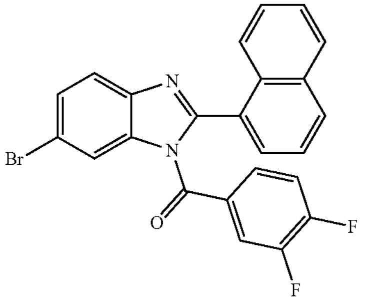 [SMILES: O=C(c1ccc(F)c(F)c1)n1c(-c2cccc3ccccc23)nc2ccc(Br)cc21] |
TABLE 1-continued
Exemplary compounds of Formulae I, IA, IB, IC, ID, and IE
| No | Structure |
| --- | --- |
| 1403 | 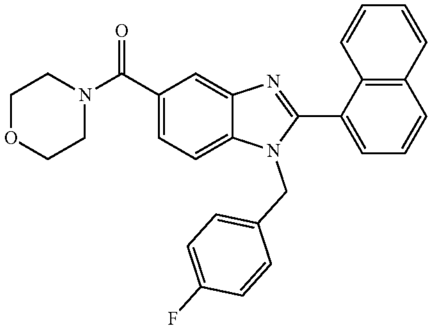 [SMILES: O=C(c1ccc2c(c1)nc(-c1cccc3ccccc13)n2Cc1ccc(F)cc1)N1CCOCC1] |
| 691 | 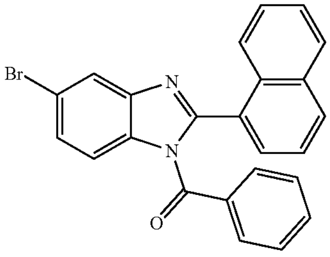 [SMILES: O=C(c1ccccc1)n1c(-c2cccc3ccccc23)nc2cc(Br)ccc21] |
| 1404 | 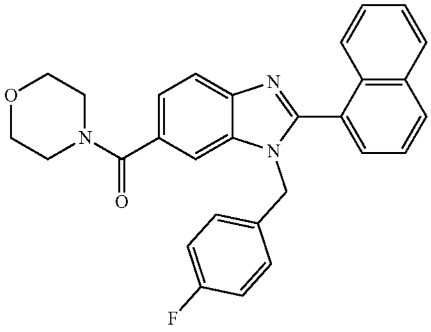 [SMILES: O=C(c1ccc2nc(-c3cccc4ccccc34)n(Cc3ccc(F)cc3)c2c1)N1CCOCC1] |
| 692 | 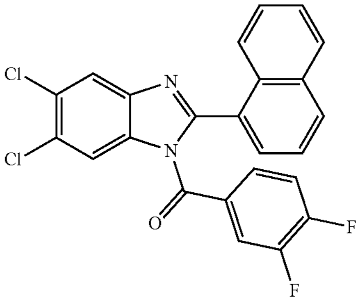 [SMILES: O=C(c1ccc(F)c(F)c1)n1c(-c2cccc3ccccc23)nc2cc(Cl)c(Cl)cc21] |

TABLE 1-continued
| Exemplary compounds of Formulae I, IA, IB, IC, ID, and IE | |
|---|---|
| No | Structure |
| 1405 | 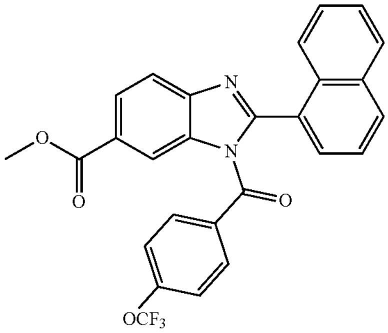 [SMILES: COC(=O)c1ccc2nc(-c3cccc4ccccc34)n(C(=O)c3ccc(OC(F)(F)F)cc3)c2c1] |
| 693 | 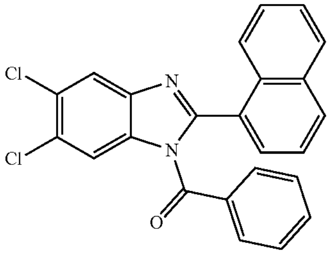 [SMILES: O=C(c1ccccc1)n1c(-c2cccc3ccccc23)nc2cc(Cl)c(Cl)cc21] |
| 1406 | 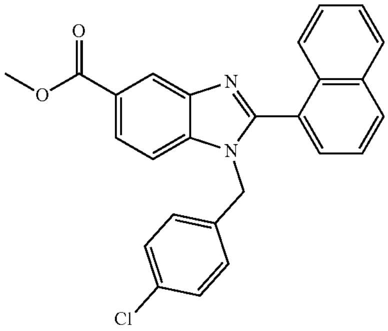 [SMILES: COC(=O)c1ccc2c(c1)nc(-c1cccc3ccccc13)n2Cc1ccc(Cl)cc1] |
| 694 | 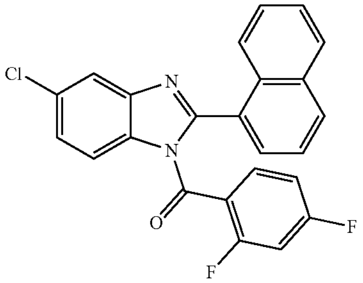 [SMILES: O=C(c1ccc(F)cc1F)n1c(-c2cccc3ccccc23)nc2cc(Cl)ccc21] |
| 1407 | 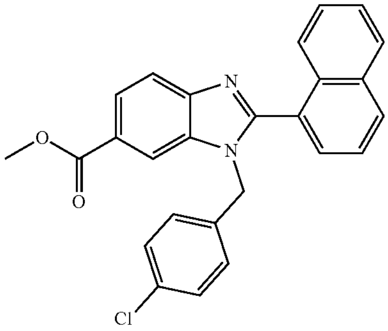 [SMILES: COC(=O)c1ccc2nc(-c3cccc4ccccc34)n(Cc3ccc(Cl)cc3)c2c1] |
TABLE 1-continued
| Exemplary compounds of Formulae I, IA, IB, IC, ID, and IE | |
|---|---|
| No | Structure |
| 695 | 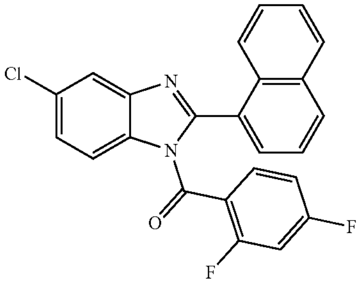 [SMILES: O=C(c1ccc(F)cc1F)n1c(-c2cccc3ccccc23)nc2cc(Cl)ccc21] |
| 1408 | 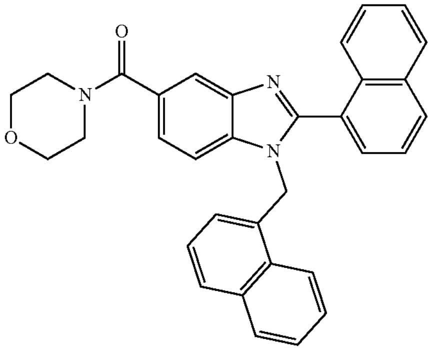 [SMILES: O=C(c1ccc2c(c1)nc(-c1cccc3ccccc13)n2Cc1cccc2ccccc12)N1CCOCC1] |
| 696 | 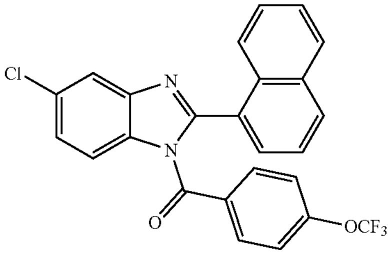 [SMILES: O=C(c1ccc(OC(F)(F)F)cc1)n1c(-c2cccc3ccccc23)nc2cc(Cl)ccc21] |
| 1409 | 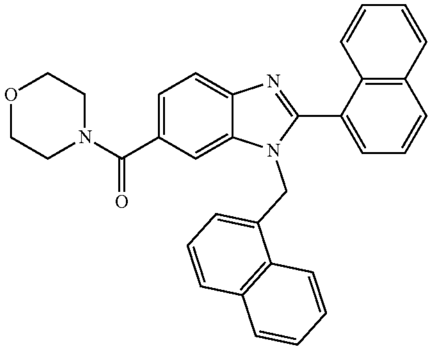 [SMILES: O=C(c1ccc2nc(-c3cccc4ccccc34)n(Cc3cccc4ccccc34)c2c1)N1CCOCC1] |
| 697 | 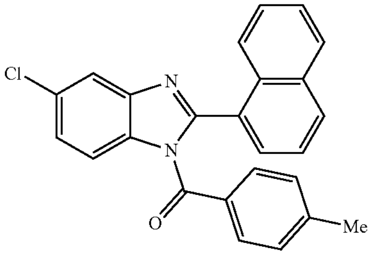 [SMILES: Cc1ccc(C(=O)n2c(-c3cccc4ccccc34)nc3cc(Cl)ccc32)cc1] |

TABLE 1-continued
| No | Structure |
|---|---|
| | Exemplary compounds of Formulae I, IA, IB, IC, ID, and IE |
| 1411 | 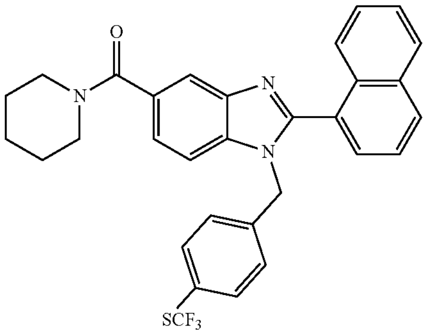 |
| 698 | 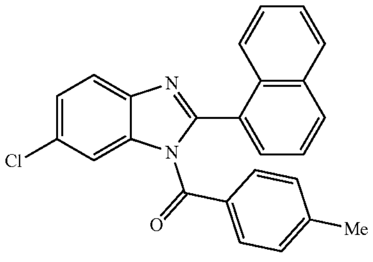 [SMILES: Cc1ccc(C(=O)n2c(-c3cccc4ccccc34)nc3ccc(Cl)cc32)cc1] |
| 1412 | 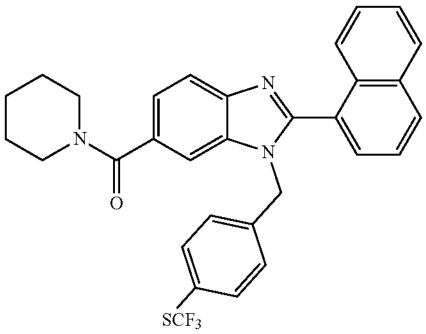 |
| 699 | 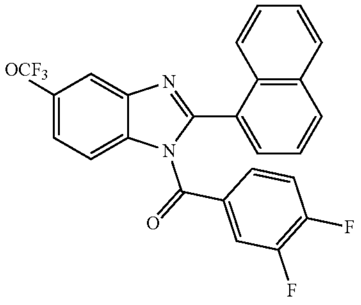 [SMILES: O=C(c1ccc(F)c(F)c1)n1c(-c2cccc3ccccc23)nc2cc(OC(F)(F)F)ccc21] |
TABLE 1-continued
| No | Structure |
|---|---|
| | Exemplary compounds of Formulae I, IA, IB, IC, ID, and IE |
| 1460 | 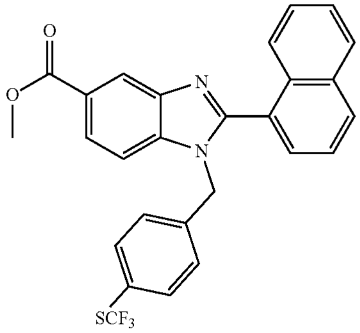 |
| 700 | 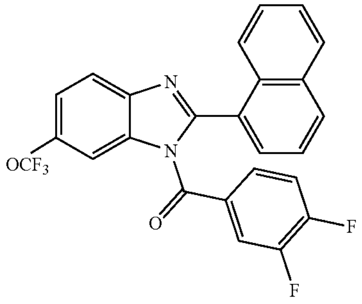 [SMILES: O=C(c1ccc(F)c(F)c1)n1c(-c2cccc3ccccc23)nc2ccc(OC(F)(F)F)cc21] |
| 1461 | 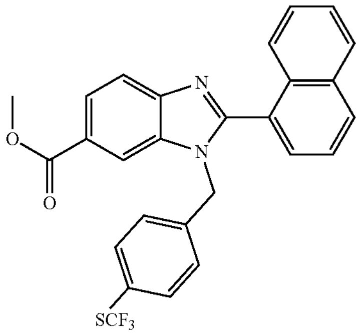 |
| 701 | 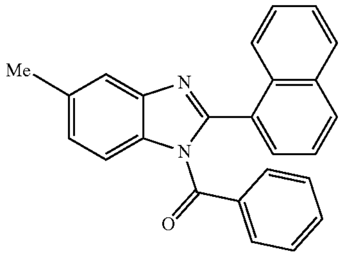 [SMILES: Cc1ccc2c(c1)nc(-c1cccc3ccccc13)n2C(=O)c1ccccc1] |
| 1462 | 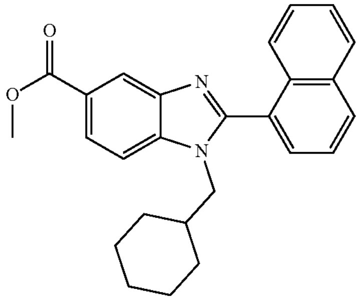 [SMILES: COC(=O)c1ccc2c(c1)nc(-c1cccc3ccccc13)n2CC1CCCCC1] |

TABLE 1-continued
Exemplary compounds of Formulae I, IA, IB, IC, ID, and IE
| No | Structure |
|---|---|
| 702 | 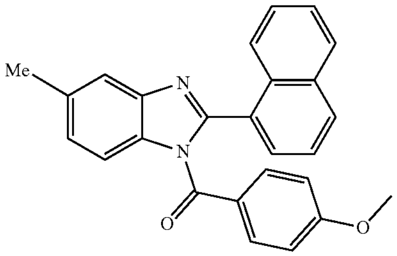 [SMILES: COc1ccc(C(=O)n2c(-c3cccc4ccccc34)nc3cc(C)ccc32)cc1] |
| 1463 | 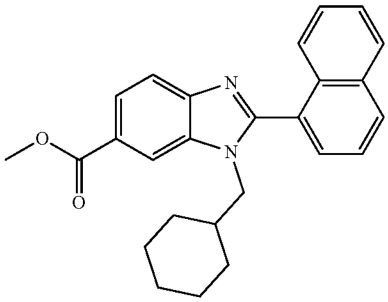 [SMILES: COC(=O)c1ccc2nc(-c3cccc4ccccc34)n(CC3CCCCC3)c2c1] |
| 703 | 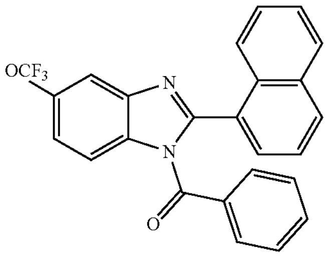 [SMILES: O=C(c1ccccc1)n1c(-c2cccc3ccccc23)nc2cc(OC(F)(F)F)ccc21] |
| 1464 | 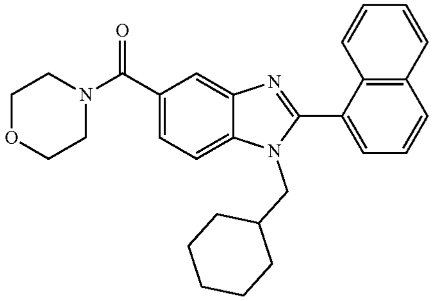 [SMILES: O=C(c1ccc2c(c1)nc(-c1cccc3ccccc13)n2CC1CCCCC1)N1CCOCC1] |
| 704 | 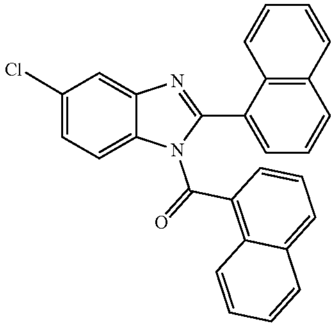 [SMILES: O=C(c1cccc2ccccc12)n1c(-c2cccc3ccccc23)nc2cc(Cl)ccc21] |
TABLE 1-continued
Exemplary compounds of Formulae I, IA, IB, IC, ID, and IE
| No | Structure |
|---|---|
| 1465 | 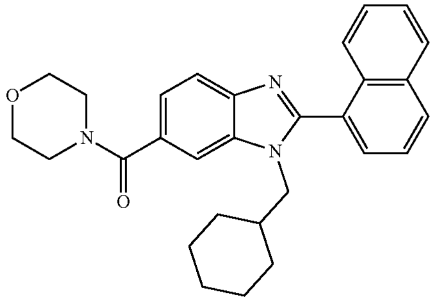 [SMILES: O=C(c1ccc2nc(-c3cccc4ccccc34)n(CC3CCCCC3)c2c1)N1CCOCC1] |
| 763 | 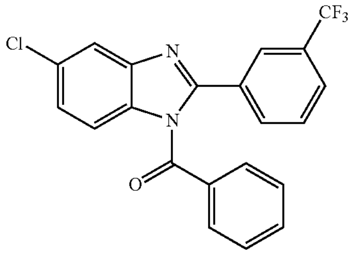 [SMILES: O=C(c1ccccc1)n1c(-c2cccc(C(F)(F)F)c2)nc2cc(Cl)ccc21] |
| 1466 | 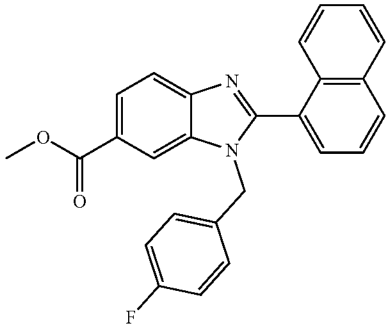 [SMILES: COC(=O)c1ccc2nc(-c3cccc4ccccc34)n(Cc3ccc(F)cc3)c2c1] |
| 764 | 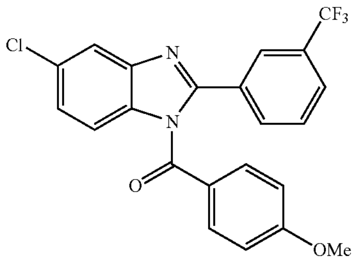 [SMILES: COc1ccc(C(=O)n2c(-c3cccc(C(F)(F)F)c3)nc3cc(Cl)ccc32)cc1] |
| 1467 | 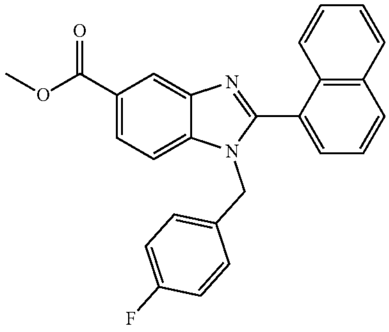 [SMILES: COC(=O)c1ccc2c(c1)nc(-c1cccc3ccccc13)n2Cc1ccc(F)cc1] |

TABLE 1-continued
| Exemplary compounds of Formulae I, IA, IB, IC, ID, and IE | |
|---|---|
| No | Structure |
| 765 | 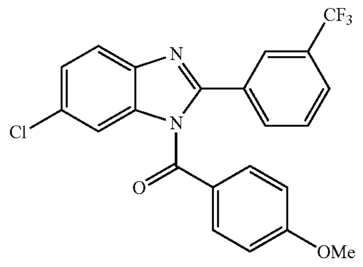 [SMILES: COc1ccc(C(=O)n2c(-c3cccc(C(F)(F)F)c3)nc3ccc(Cl)cc32)cc1] |
| 1468 | 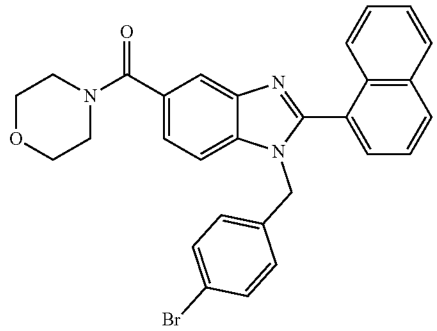 [SMILES: O=C(c1ccc2c(c1)nc(-c1cccc3ccccc13)n2Cc1ccc(Br)cc1)N1CCOCC1] |
| 766 | 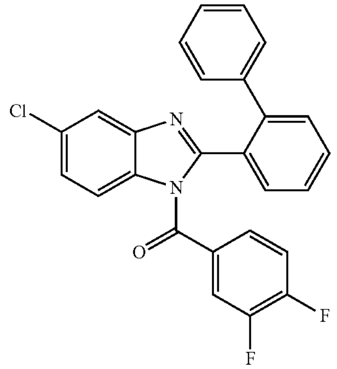 [SMILES: O=C(c1ccc(F)c(F)c1)n1c(-c2ccccc2-c2ccccc2)nc2cc(Cl)ccc21] |
| 1469 | 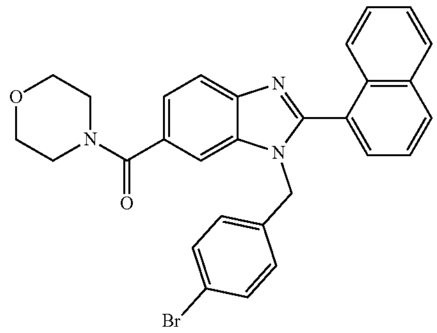 [SMILES: O=C(c1ccc2nc(-c3cccc4ccccc34)n(Cc3ccc(Br)cc3)c2c1)N1CCOCC1] |
TABLE 1-continued
| Exemplary compounds of Formulae I, IA, IB, IC, ID, and IE | |
|---|---|
| No | Structure |
| 767 | 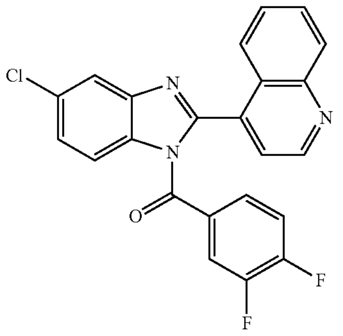 [SMILES: O=C(c1ccc(F)c(F)c1)n1c(-c2ccnc3ccccc23)nc2cc(Cl)ccc21] |
| 1470 | 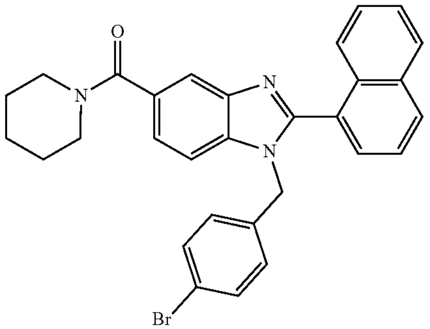 [SMILES: O=C(c1ccc2c(c1)nc(-c1cccc3ccccc13)n2Cc1ccc(Br)cc1)N1CCCCC1] |
| 770 | 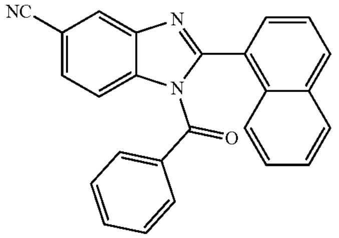 [SMILES: N#Cc1ccc2c(c1)nc(-c1cccc3ccccc13)n2C(=O)c1ccccc1] |
| 1471 | 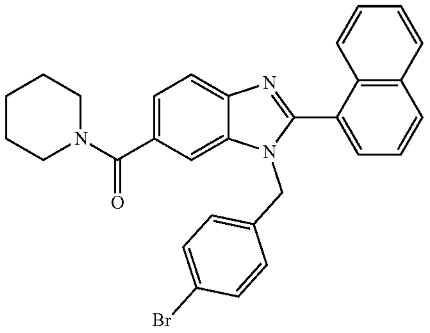 [SMILES: O=C(c1ccc2nc(-c3cccc4ccccc34)n(Cc3ccc(Br)cc3)c2c1)N1CCCCC1] |

TABLE 1-continued
| Exemplary compounds of Formulae I, IA, IB, IC, ID, and IE | |
|---|---|
| No | Structure |
| 771 | 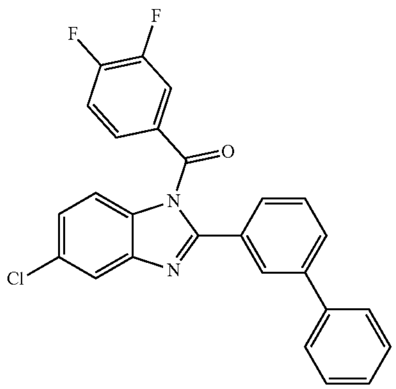 [SMILES: O=C(c1ccc(F)c(F)c1)n1c(-c2cccc(-c3ccccc3)c2)nc2cc(Cl)ccc21] |
| 1472 | 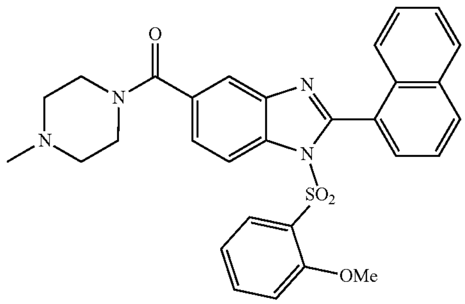 [SMILES: COc1ccccc1S(=O)(=O)n1c(-c2cccc3ccccc23)nc2cc(C(=O)N3CCN(C)CC3)ccc21] |
| 772 | 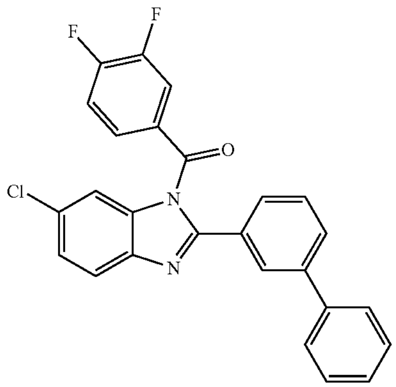 [SMILES: O=C(c1ccc(F)c(F)c1)n1c(-c2cccc(-c3ccccc3)c2)nc2ccc(Cl)cc21] |
| 1473 | 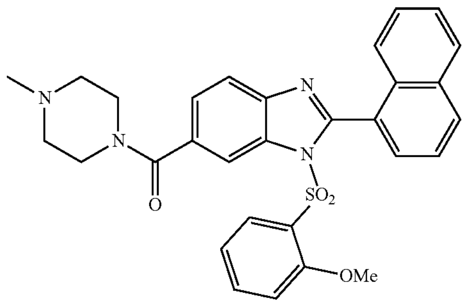 [SMILES: COc1ccccc1S(=O)(=O)n1c(-c2cccc3ccccc23)nc2ccc(C(=O)N3CCN(C)CC3)cc21] |
TABLE 1-continued
| Exemplary compounds of Formulae I, IA, IB, IC, ID, and IE | |
|---|---|
| No | Structure |
| 773 | 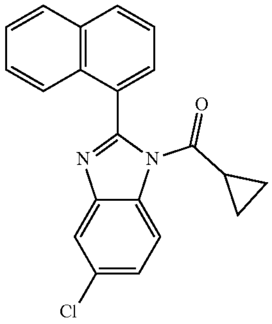 [SMILES: O=C(C1CC1)n1c(-c2cccc3ccccc23)nc2cc(Cl)ccc21] |
| 1474 | 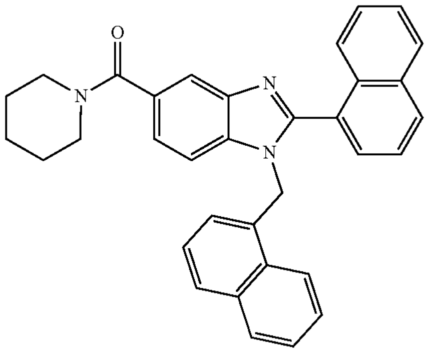 [SMILES: O=C(c1ccc2c(c1)nc(-c1cccc3ccccc13)n2Cc1cccc2ccccc12)N1CCCCC1] |
| 774 | 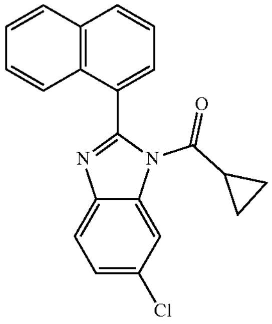 [SMILES: O=C(C1CC1)n1c(-c2cccc3ccccc23)nc2ccc(Cl)cc21] |
| 1475 | 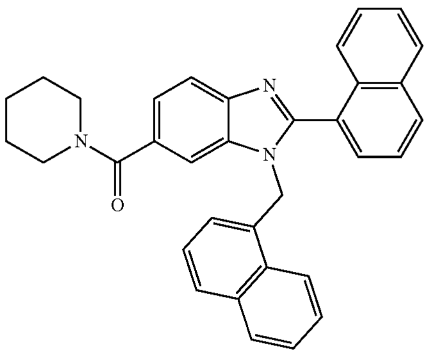 [SMILES: O=C(c1ccc2nc(-c3cccc4ccccc34)n(Cc3cccc4ccccc34)c2c1)N1CCCCC1] |

TABLE 1-continued
| Exemplary compounds of Formulae I, IA, IB, IC, ID, and IE | |
|---|---|
| No | Structure |
| 775 | 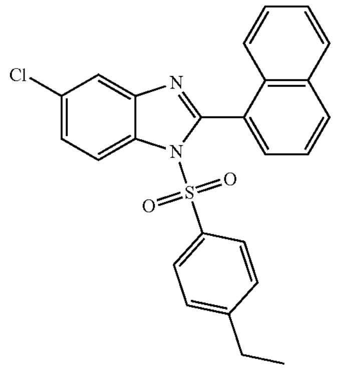 [SMILES: CCc1ccc(S(=O)(=O)n2c(-c3cccc4ccccc34)nc3cc(Cl)ccc32)cc1] |
| 1476 | 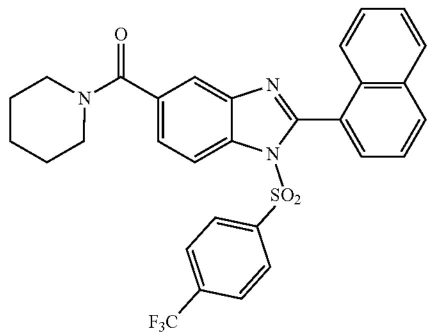 [SMILES: O=C(c1ccc2c(c1)nc(-c1cccc3ccccc13)n2S(=O)(=O)c1ccc(C(F)(F)F)cc1)N1CCCCC1] |
| 776 | 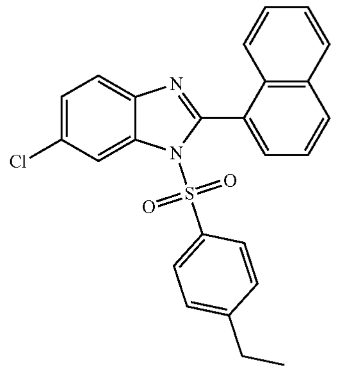 [SMILES: CCc1ccc(S(=O)(=O)n2c(-c3cccc4ccccc34)nc3ccc(Cl)cc32)cc1] |
| 1477 | 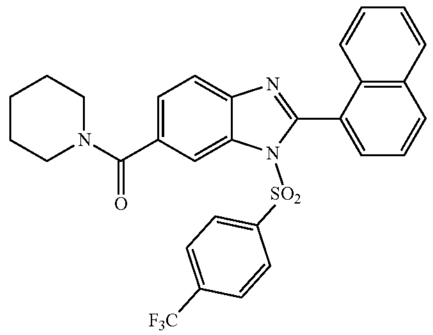 [SMILES: O=C(c1ccc2nc(-c3cccc4ccccc34)n(S(=O)(=O)c3ccc(C(F)(F)F)cc3)c2c1)N1CCCCC1] |
TABLE 1-continued
| Exemplary compounds of Formulae I, IA, IB, IC, ID, and IE | |
|---|---|
| No | Structure |
| 777 | 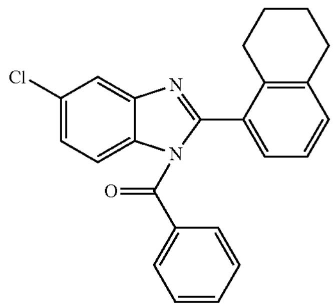 [SMILES: O=C(c1ccccc1)n1c(-c2cccc3c2CCCC3)nc2cc(Cl)ccc21] |
| 1478 | 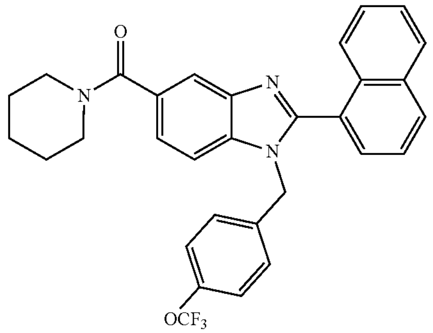 [SMILES: O=C(c1ccc2c(c1)nc(-c1cccc3ccccc13)n2Cc1ccc(OC(F)(F)F)cc1)N1CCCCC1] |
| 778 | 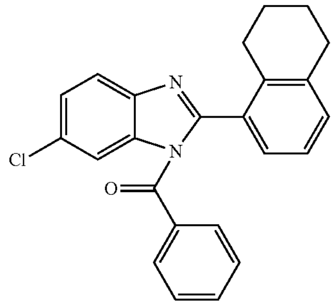 [SMILES: O=C(c1ccccc1)n1c(-c2cccc3c2CCCC3)nc2ccc(Cl)cc21] |
| 1479 | 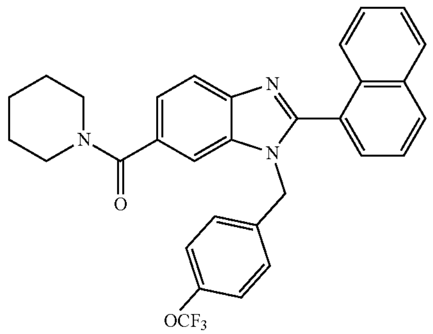 [SMILES: O=C(c1ccc2nc(-c3cccc4ccccc34)n(Cc3ccc(OC(F)(F)F)cc3)c2c1)N1CCCCC1] |

TABLE 1-continued
| Exemplary compounds of Formulae I, IA, IB, IC, ID, and IE | |
|---|---|
| No | Structure |
| 779 | 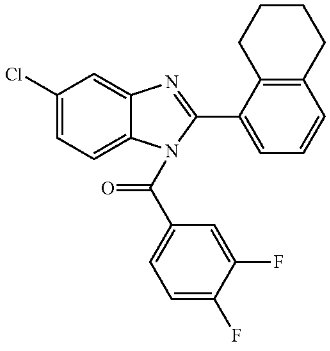 [SMILES: O=C(c1ccc(F)c(F)c1)n1c(-c2cccc3c2CCCC3)nc2cc(Cl)ccc21] |
| 1481 | 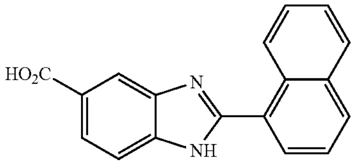 [SMILES: O=C(O)c1ccc2[nH]c(-c3cccc4ccccc34)nc2c1] |
| 780 | 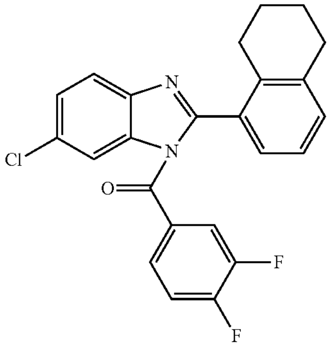 [SMILES: O=C(c1ccc(F)c(F)c1)n1c(-c2cccc3c2CCCC3)nc2ccc(Cl)cc21] |
| 1490 | 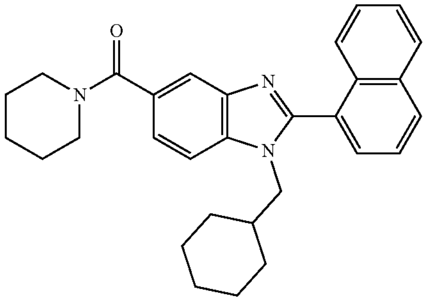 [SMILES: O=C(c1ccc2c(c1)nc(-c1cccc3ccccc13)n2CC1CCCCC1)N1CCCCC1] |
| 781 | 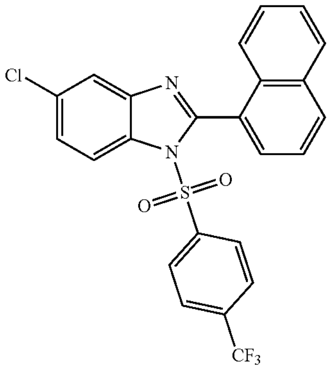 |
TABLE 1-continued
| Exemplary compounds of Formulae I, IA, IB, IC, ID, and IE | |
|---|---|
| No | Structure |
| 1491 | 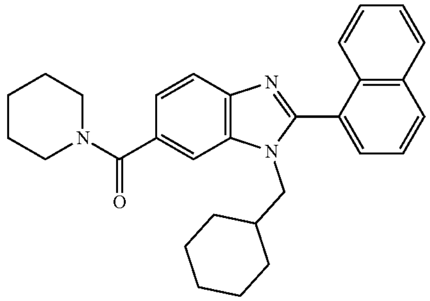 [SMILES: O=C(c1ccc2nc(-c3cccc4ccccc34)n(CC3CCCCC3)c2c1)N1CCCCC1] |
| 782 | 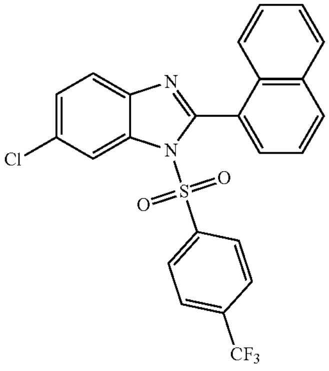 [SMILES: O=S(=O)(c1ccc(C(F)(F)F)cc1)n1c(-c2cccc3ccccc23)nc2ccc(Cl)cc21] |
| 1492 | 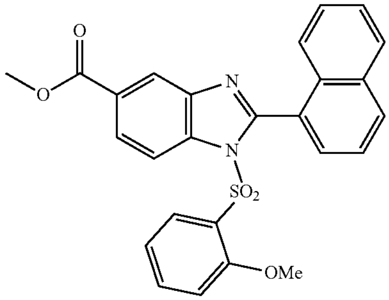 [SMILES: COC(=O)c1ccc2c(c1)nc(-c1cccc3ccccc13)n2S(=O)(=O)c1ccccc1OC] |
| 783 | 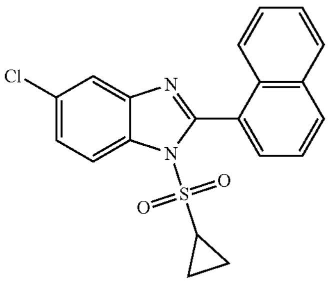 [SMILES: O=S(=O)(C1CC1)n1c(-c2cccc3ccccc23)nc2cc(Cl)ccc21] |

TABLE 1-continued
| Exemplary compounds of Formulae I, IA, IB, IC, ID, and IE | |
|---|---|
| No | Structure |
| 1493 | 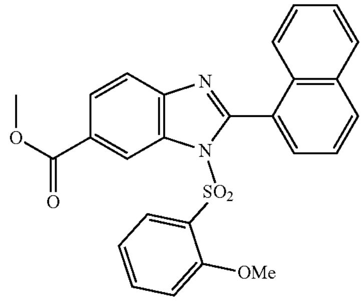 [SMILES: COC(=O)c1ccc2nc(-c3cccc4ccccc34)n(S(=O)(=O)c3ccccc3OC)c2c1] |
| 784 | 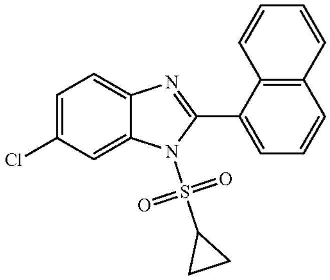 [SMILES: O=S(=O)(C1CC1)n1c(-c2cccc3ccccc23)nc2ccc(Cl)cc21] |
| 1494 | 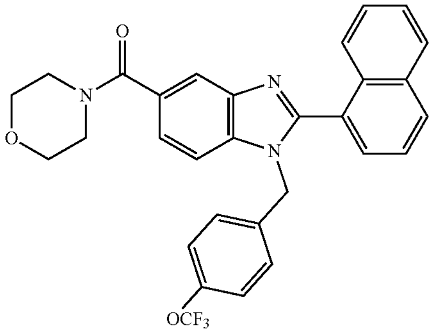 [SMILES: O=C(c1ccc2c(c1)nc(-c1cccc3ccccc13)n2Cc1ccc(OC(F)(F)F)cc1)N1CCOCC1] |
| 785 | 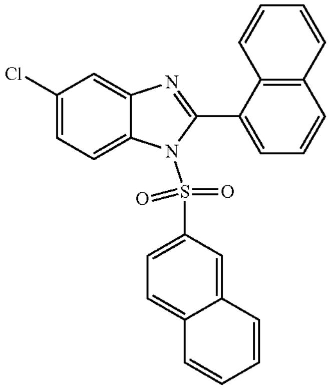 [SMILES: O=S(=O)(c1ccc2ccccc2c1)n1c(-c2cccc3ccccc23)nc2cc(Cl)ccc21] |
TABLE 1-continued
| Exemplary compounds of Formulae I, IA, IB, IC, ID, and IE | |
|---|---|
| No | Structure |
| 1495 | 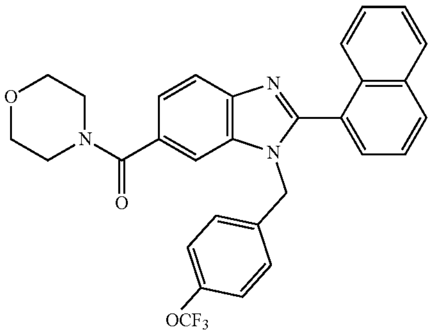 [SMILES: O=C(c1ccc2nc(-c3cccc4ccccc34)n(Cc3ccc(OC(F)(F)F)cc3)c2c1)N1CCOCC1] |
| 786 | 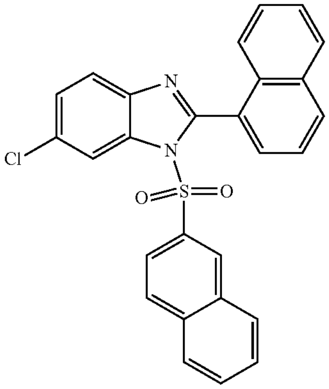 [SMILES: O=S(=O)(c1ccc2ccccc2c1)n1c(-c2cccc3ccccc23)nc2ccc(Cl)cc21] |
| 1496 | 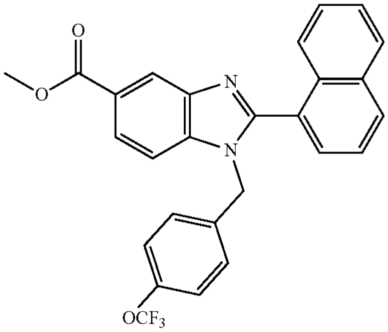 [SMILES: COC(=O)c1ccc2c(c1)nc(-c1cccc3ccccc13)n2Cc1ccc(OC(F)(F)F)cc1] |
| 787 | 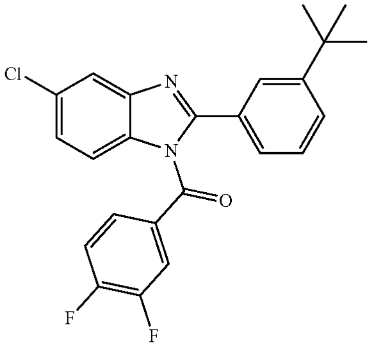 [SMILES: CC(C)(C)c1cccc(-c2nc3cc(Cl)ccc3n2C(=O)c2ccc(F)c(F)c2)c1] |

TABLE 1-continued
| Exemplary compounds of Formulae I, IA, IB, IC, ID, and IE | |
|---|---|
| No | Structure |
| 1497 | 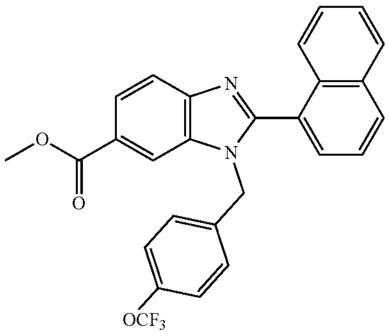 [SMILES: COC(=O)c1ccc2nc(-c3cccc4ccccc34)n(Cc3ccc(OC(F)(F)F)cc3)c2c1] |
| 788 | 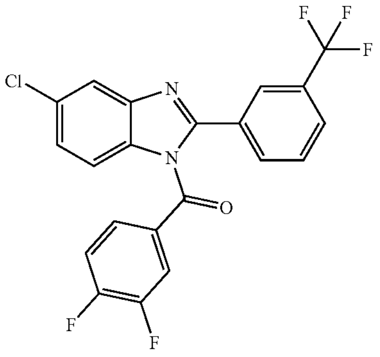 [SMILES: O=C(c1ccc(F)c(F)c1)n1c(-c2cccc(C(F)(F)F)c2)nc2cc(Cl)ccc21] |
| 1498 | 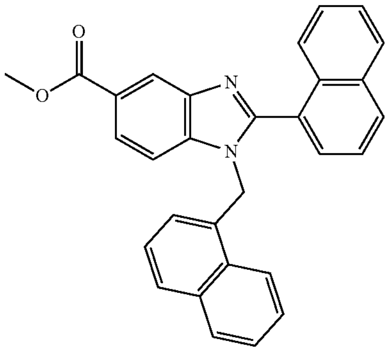 [SMILES: COC(=O)c1ccc2c(c1)nc(-c1cccc3ccccc13)n2Cc1cccc2ccccc12] |
| 789 | 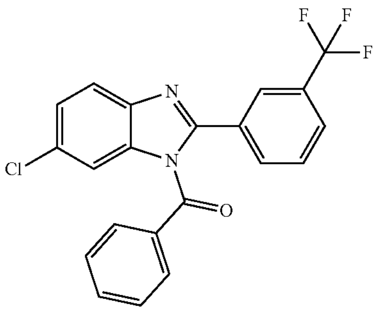 [SMILES: O=C(c1ccccc1)n1c(-c2cccc(C(F)(F)F)c2)nc2ccc(Cl)cc21] |
TABLE 1-continued
| Exemplary compounds of Formulae I, IA, IB, IC, ID, and IE | |
|---|---|
| No | Structure |
| 1499 | 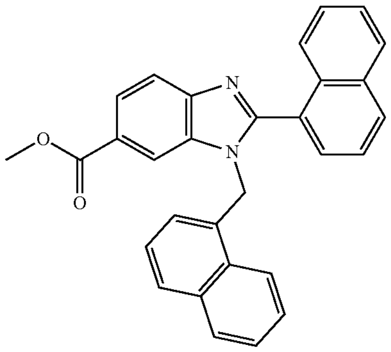 [SMILES: COC(=O)c1ccc2nc(-c3cccc4ccccc34)n(Cc3cccc4ccccc34)c2c1] |
| 790 | 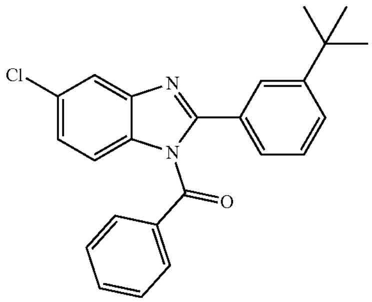 [SMILES: CC(C)(C)c1cccc(-c2nc3cc(Cl)ccc3n2C(=O)c2ccccc2)c1] |
| 1500 | 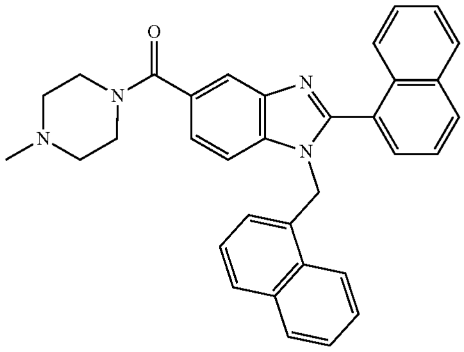 [SMILES: CN1CCN(C(=O)c2ccc3c(c2)nc(-c2cccc4ccccc24)n3Cc2cccc3ccccc23)CC1] |
| 791 | 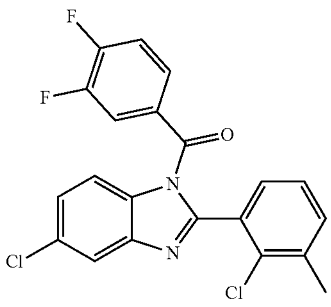 [SMILES: Cc1cccc(-c2nc3cc(Cl)ccc3n2C(=O)c2ccc(F)c(F)c2)c1Cl] |

TABLE 1-continued
| Exemplary compounds of Formulae I, IA, IB, IC, ID, and IE | |
|---|---|
| No | Structure |
| 1501 | 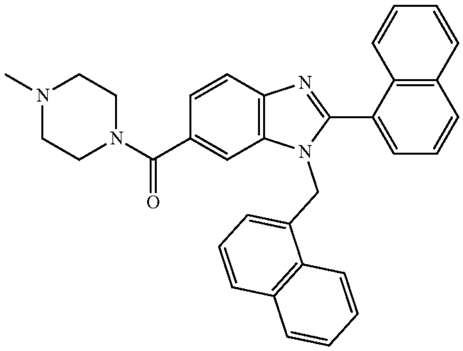 [SMILES: CN1CCN(C(=O)c2ccc3nc(-c4cccc5ccccc45)n(Cc4cccc5ccccc45)c3c2)CC1] |
| 792 | 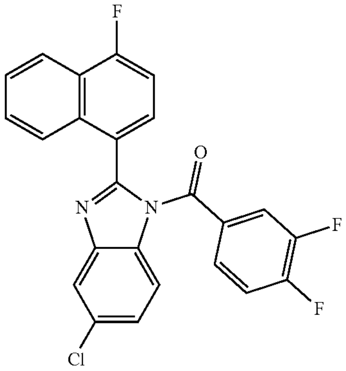 [SMILES: O=C(c1ccc(F)c(F)c1)n1c(-c2ccc(F)c3ccccc23)nc2cc(Cl)ccc21] |
| 1502 | 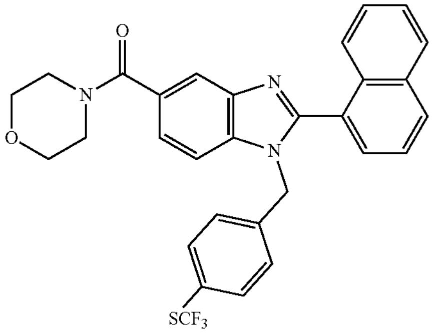 |
| 848 | 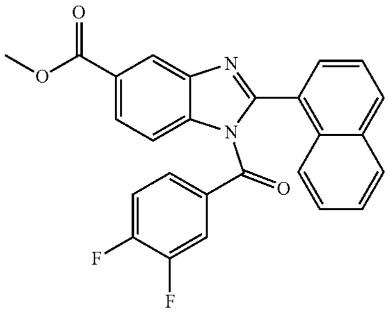 [SMILES: COC(=O)c1ccc2c(c1)nc(-c1cccc3ccccc13)n2C(=O)c1ccc(F)c(F)c1] |
TABLE 1-continued
| Exemplary compounds of Formulae I, IA, IB, IC, ID, and IE | |
|---|---|
| No | Structure |
| 1503 | 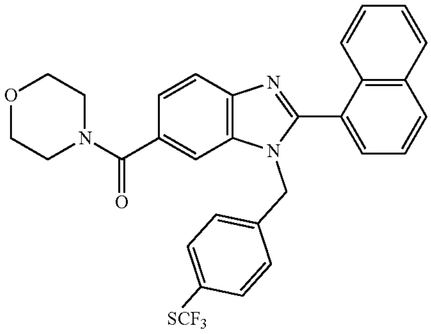 |
| 849 | 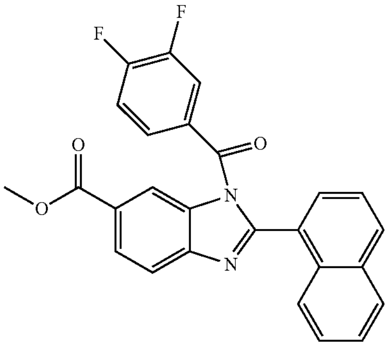 [SMILES: COC(=O)c1ccc2nc(-c3cccc4ccccc34)n(C(=O)c3ccc(F)c(F)c3)c2c1] |
| 1504 | 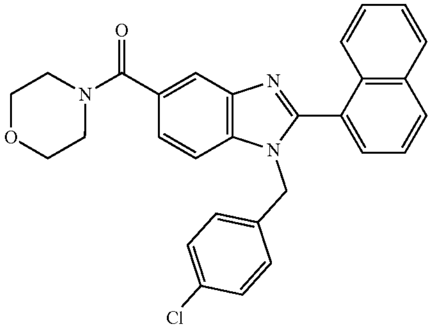 [SMILES: O=C(c1ccc2c(c1)nc(-c1cccc3ccccc13)n2Cc1ccc(Cl)cc1)N1CCOCC1] |
| 850 | 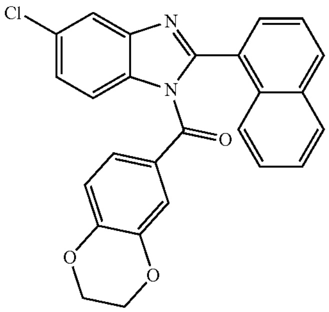 [SMILES: O=C(c1ccc2c(c1)OCCO2)n1c(-c2cccc3ccccc23)nc2cc(Cl)ccc21] |

TABLE 1-continued
| Exemplary compounds of Formulae I, IA, IB, IC, ID, and IE | |
|---|---|
| No | Structure |
| 1505 | 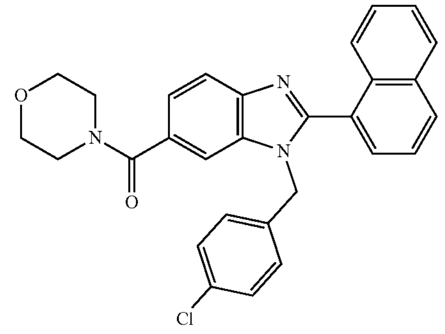 [SMILES: O=C(c1ccc2nc(-c3cccc4ccccc34)n(Cc3ccc(Cl)cc3)c2c1)N1CCOCC1] |
| 851 | 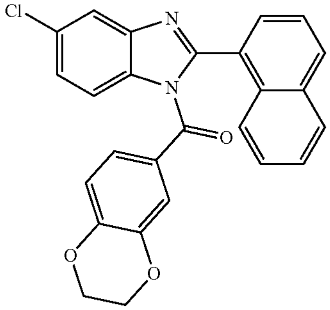 [SMILES: O=C(c1ccc2c(c1)OCCO2)n1c(-c2cccc3ccccc23)nc2cc(Cl)ccc21] |
| 1506 | 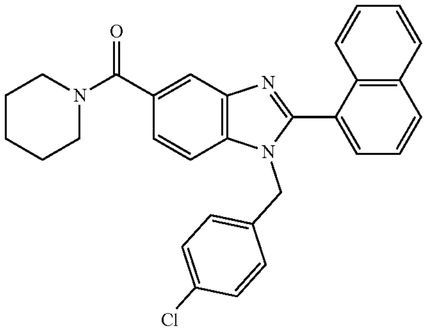 [SMILES: O=C(c1ccc2c(c1)nc(-c1cccc3ccccc13)n2Cc1ccc(Cl)cc1)N1CCCCC1] |
| 852 | 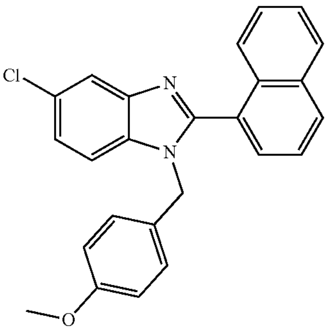 [SMILES: COc1ccc(Cn2c(-c3cccc4ccccc34)nc3cc(Cl)ccc32)cc1] |
TABLE 1-continued
| Exemplary compounds of Formulae I, IA, IB, IC, ID, and IE | |
|---|---|
| No | Structure |
| 1507 | 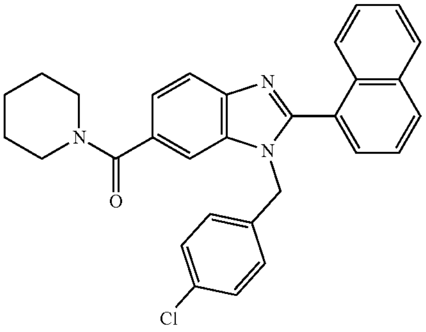 [SMILES: O=C(c1ccc2nc(-c3cccc4ccccc34)n(Cc3ccc(Cl)cc3)c2c1)N1CCCCC1] |
| 853 | 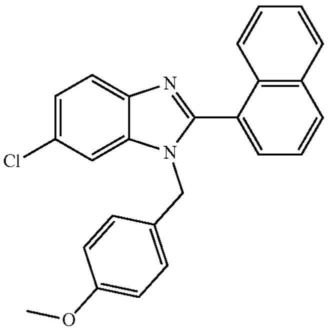 [SMILES: COc1ccc(Cn2c(-c3cccc4ccccc34)nc3ccc(Cl)cc32)cc1] |
| 1508 | 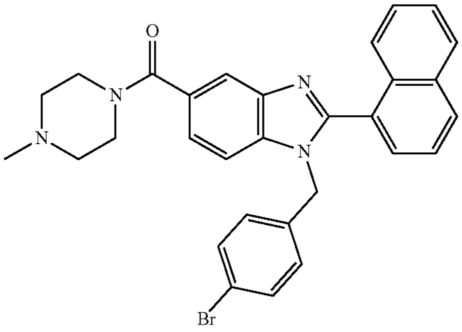 [SMILES: CN1CCN(C(=O)c2ccc3c(c2)nc(-c2cccc4ccccc24)n3Cc2ccc(Br)cc2)CC1] |
| 854 | 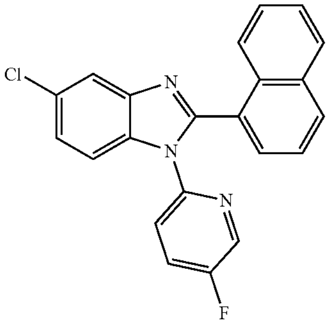 [SMILES: Fc1ccc(-n2c(-c3cccc4ccccc34)nc3cc(Cl)ccc32)nc1] |

TABLE 1-continued
Exemplary compounds of Formulae I, IA, IB, IC, ID, and IE
| No | Structure |
|---|---|
| 1509 | 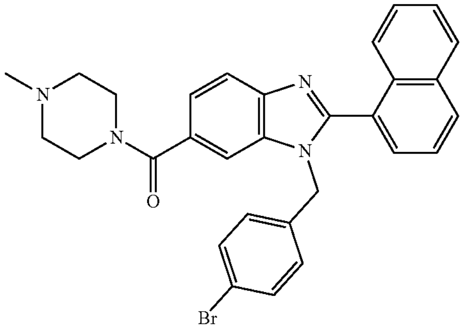 [SMILES: CN1CCN(C(=O)c2ccc3nc(-c4cccc5ccccc45)n(Cc4ccc(Br)cc4)c3c2)CC1] |
| 855 | 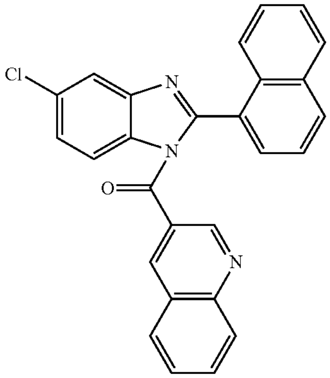 [SMILES: O=C(c1cnc2ccccc2c1)n1c(-c2cccc3ccccc23)nc2cc(Cl)ccc21] |
| 1510 | 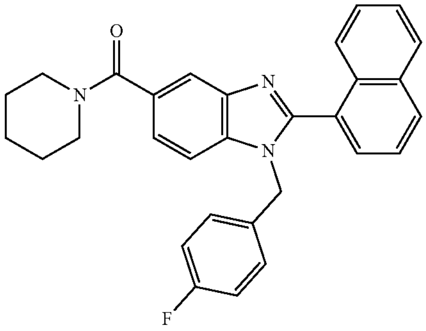 [SMILES: O=C(c1ccc2c(c1)nc(-c1cccc3ccccc13)n2Cc1ccc(F)cc1)N1CCCCC1] |
| 856 | 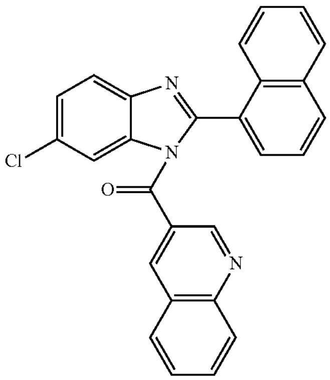 [SMILES: O=C(c1cnc2ccccc2c1)n1c(-c2cccc3ccccc23)nc2ccc(Cl)cc21] |
| 1511 | 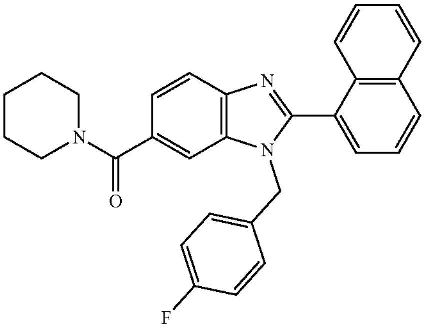 |
TABLE 2
Exemplary compounds of Formula II, IIA, IIB, IIC, IID, and IIE.
| No | Structure |
|---|---|
| 359 | 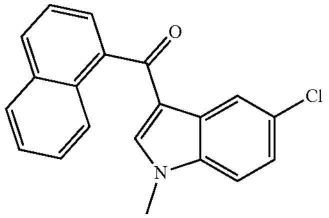 [SMILES: Cn1cc(C(=O)c2cccc3ccccc23)c2cc(Cl)ccc21] |
| 884 | 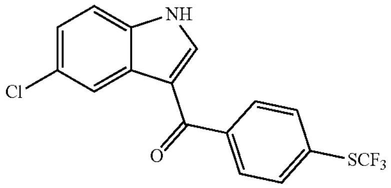 |
| 364 | 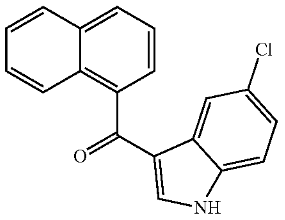 [SMILES: O=C(c1cccc2ccccc12)c1c[nH]c2ccc(Cl)cc12] |
| 885 | 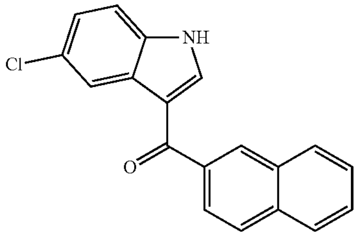 [SMILES: O=C(c1ccc2ccccc2c1)c1c[nH]c2ccc(Cl)cc12] |
| 433 | 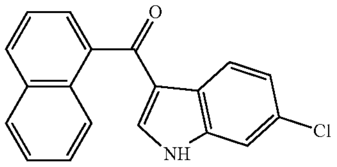 [SMILES: O=C(c1cccc2ccccc12)c1c[nH]c2cc(Cl)ccc12] |

TABLE 2-continued
Exemplary compounds of Formula II, IIA, IIB, IIC, IID, and IIE.
| No | Structure |
| --- | --- |
| 889 | 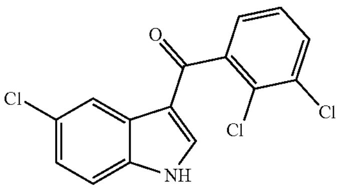 [SMILES: O=C(c1cccc(Cl)c1Cl)c1c[nH]c2ccc(Cl)cc12] |
| 434 | 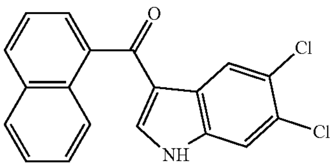 [SMILES: O=C(c1cccc2ccccc12)c1c[nH]c2cc(Cl)c(Cl)cc12] |
| 890 | 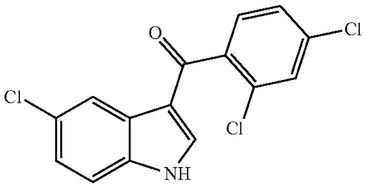 [SMILES: O=C(c1ccc(Cl)cc1Cl)c1c[nH]c2ccc(Cl)cc12] |
| 521 | 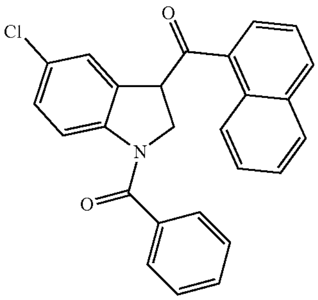 [SMILES: O=C(c1cccc2ccccc12)C1CN(C(=O)c2ccccc2)c2ccc(Cl)cc21] |
| 891 | 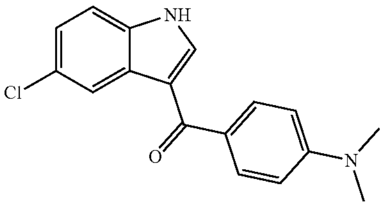 [SMILES: CN(C)c1ccc(C(=O)c2c[nH]c3ccc(Cl)cc23)cc1] |
| 874 | 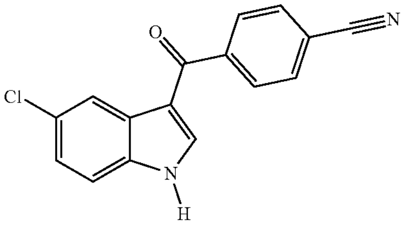 [SMILES: N#Cc1ccc(C(=O)c2c[nH]c3ccc(Cl)cc23)cc1] |
| 892 | 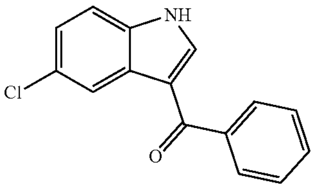 [SMILES: O=C(c1ccccc1)c1c[nH]c2ccc(Cl)cc12] |
TABLE 2-continued
Exemplary compounds of Formula II, IIA, IIB, IIC, IID, and IIE.
| No | Structure |
| --- | --- |
| 881 | 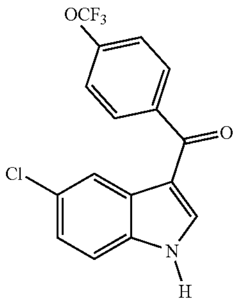 [SMILES: O=C(c1ccc(OC(F)(F)F)cc1)c1c[nH]c2ccc(Cl)cc12] |
| 893 | 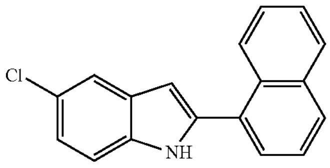 [SMILES: Clc1ccc2[nH]c(-c3cccc4ccccc34)cc2c1] |
| 882 | 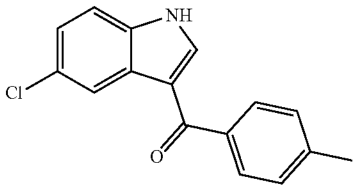 [SMILES: Cc1ccc(C(=O)c2c[nH]c3ccc(Cl)cc23)cc1] |
| 894 | 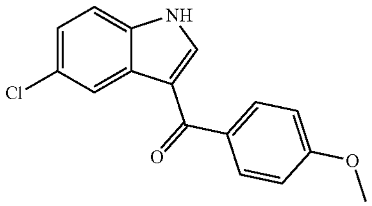 [SMILES: COc1ccc(C(=O)c2c[nH]c3ccc(Cl)cc23)cc1] |
| 883 | 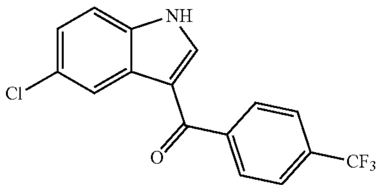 [SMILES: O=C(c1ccc(C(F)(F)F)cc1)c1c[nH]c2ccc(Cl)cc12] |
| 895 | 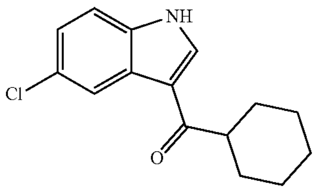 [SMILES: O=C(c1c[nH]c2ccc(Cl)cc12)C1CCCCC1] |

TABLE 3
| Exemplary compounds of Formula III, IIIA, and IIIB | |
|---|---|
| No | Structure |
| 405 | 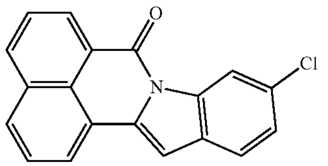 [SMILES: O=c1c2cccc3cccc(c32)c2cc3ccc(Cl)cc3n12] |
| 525 | 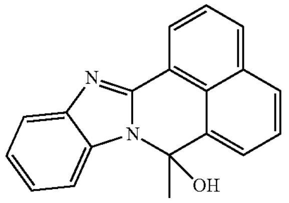 [SMILES: CC1(O)c2cccc3cccc(c23)-c2nc3ccccc3n21] |
| 435 | 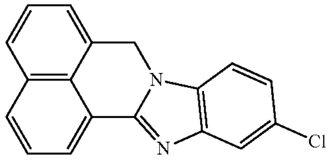 [SMILES: Clc1ccc2c(c1)nc1n2Cc2cccc3cccc-1c23] |
| 523 | 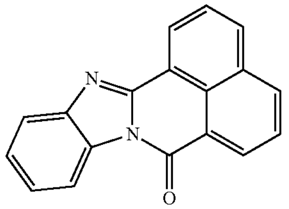 [SMILES: O=c1c2cccc3cccc(c32)c2nc3ccccc3n12] |
| 464 | 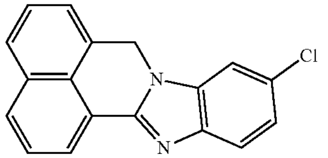 [SMILES: Clc1ccc2nc3n(c2c1)Cc1cccc2cccc-3c12] |
TABLE 4
| Exemplary compounds of Formula IV, IVA, and IVB | |
|---|---|
| No | Structure |
| 524 | 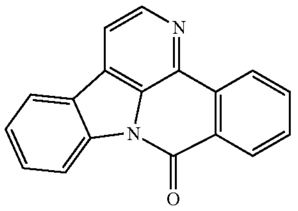 [SMILES: O=c1c2ccccc2c2nccc3c4ccccc4n1c32] |
| 526 | 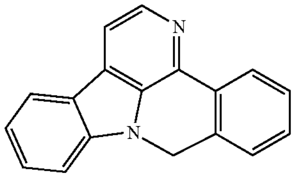 [SMILES: c1ccc2c(c1)Cn1c3ccccc3c3ccnc-2c31] |
TABLE 5
| Additional exemplary Ahr ligands | |
|---|---|
| Compound | Structure |
| 365 | 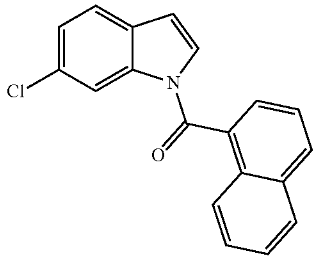 [SMILES: O=C(c1cccc2ccccc12)n1ccc2ccc(Cl)cc21] |
| 406 | 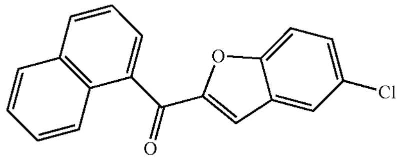 [SMILES: O=C(c1cc2cc(Cl)ccc2o1)c1cccc2ccccc12] |
| 366 | 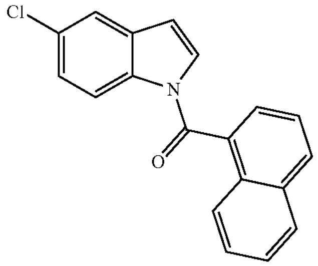 [SMILES: O=C(c1cccc2ccccc12)n1ccc2cc(Cl)ccc21] |
| 488 | 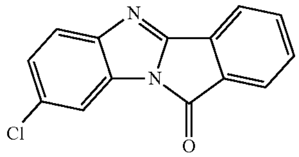 [SMILES: O=C1c2ccccc2-c2nc3ccc(Cl)cc3n21] |
| 972 | 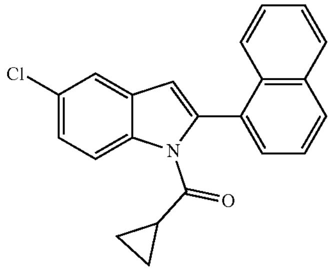 [SMILES: O=C(C1CC1)n1c(-c2cccc3ccccc23)cc2cc(Cl)ccc21] |
| 489 | 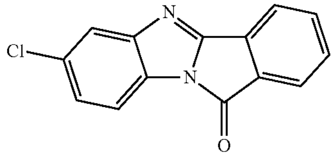 [SMILES: O=C1c2ccccc2-c2nc3cc(Cl)ccc3n21] |

TABLE 5-continued

| Additional exemplary Ahr ligands | |
|---|---|
| Compound | Structure |
| 973 | 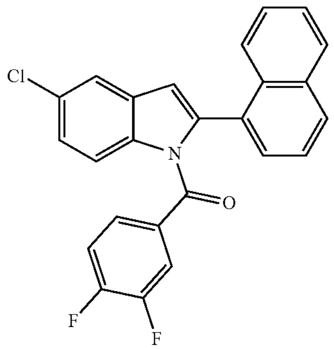 [SMILES: O=C(c1ccc(F)c(F)c1)n1c(-c2cccc3ccccc23)cc2cc(Cl)ccc21] |
| 522 | 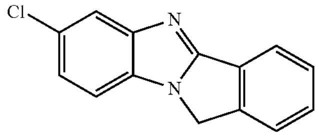 [SMILES: Clc1ccc2c(c1)nc1n2Cc2ccccc2-1] |

AHR Ligand Screening

The AhR is a ligand-activated transcription factor that dimerizes with ARNT to regulate gene expression, and genes that are regulated by AhR ligands have AhR response elements (AhRE) in their promotor regions. Activation of the AhR by novel compounds of interest was measured as previously described by O'Donnell et al. (O'Donnell, E. F.; Saili, K. S.; Koch, D. C.; Kopparapu, P. R.; Farrer, D.; Bisson, W. H.; Mathew, L. K.; Sengupta, S.; Kerkvliet, N. I.; Tanguay, R. L.; Kolluri, S. K. The Anti-Inflammatory Drug Leflunomide Is an Agonist of the Aryl Hydrocarbon Receptor. PLoS ONE 2010, 5; O'Donnell E. F., Jang H. Sang, Pearce M., Kerkvliet N. I., Kolluri S. K. The aryl hydrocarbon receptor is required for induction of $p21^{cip1/waf1}$ expression and growth inhibition by SU5416 in hepatoma cells. *Oncotarget.* 2017; 8: 25211-25225) and Punj et al. (Punj S, Kopparapu P, Jang H S, Phillips J L, Pennington J, Rohlman D, O'Donnell E, Iversen P L, Kolluri S K, Kerkvliet N I. Benzimidazoisoquinolines: A New Class of Rapidly Metabolized Aryl Hydrocarbon Receptor (AhR) Ligands that Induce AhR-Dependent Tregs and Prevent Murine Graft-Versus-Host Disease. PLoS ONE 2014; 9(2): e887264).

Briefly, Hepa1 cells were transfected with a reporter construct consisting of AhRE linked to luciferase. The addition of AhR ligands to the transfected cells induces luciferase production that is directly proportional to the amount of AhR activation. We used this reporter system to identify novel compounds with AhR-activating properties. Transfected Hepa1 cells were plated at a density of $1\times10^4$ cells/well in 100 μL of cell culture media in 96 well plates and grown overnight. The following day, cells were treated for the indicated time or 15 hours with vehicle (DMSO) or the analogs of 11-cl-BBQ. Following incubation with the compounds, the media was removed, and cells were harvested with lysis buffer. The lysates were transferred to opaque 96 well plates, where they were assayed well-by-well for luciferase activity by injection of luciferase assay substrate with a 2 sec mixing time and 15 sec integration period on a Tropix TR717 microplate luminometer. Data were expressed as fold induction of luciferase relative to vehicle (0.1% DMSO) treated cells. The reference compound (11-cl-BBQ), as well as TCDD (2,3,7,8-tetrachlorodibenzo-p-dioxin) were used as positive controls for AhR activation. Compounds that did not induce AhR activation by at least two-fold at 10 micromolar concentration were considered to lack AhR-activating properties.

Table 6 shows AhR activation activity of exemplary compounds.

TABLE 6

AhR activation by exemplary compounds of the disclosure. Fold @ 1 nM, Fold @ 100 nM and Fold @ 10 uM refer to the fold change of luciferase expression after treatment of cells with 1 nM, 100 nM or 10 uM respectively of test compound relative to vehicle (0.1% DMSO) treated cells in the AhR ligand screening assay. Fold relative to benchmark @ 100 nM refers to the fold change of luciferase expression after treatment of cells with 100 nM of test compound relative to the treatment with 100 nM of a benchmark compound (11-c1-BBQ) in the AhR ligand screening assay described above.

| Compound | Fold @ 1 nM | Fold @ 100 nM | Fold @ 10 uM | Fold relative to benchmark @ 100 nM |
|---|---|---|---|---|
| 359 | 1 | 1 | 6 | 0.03 |
| 360 | 1 | 1 | 2 | 0.03 |
| 361 | 1 | 1 | 3 | 0.03 |
| 362 | 16 | 22 | — | 1 |
| 363 | 4 | 14 | 30 | 0.69 |
| 364 | 1 | 2 | 11 | 0.05 |
| 365 | 1 | 1 | 6 | 0.03 |
| 366 | 1 | 1 | 11 | 0.03 |
| 405 | 8 | 31 | — | 0.78 |
| 406 | 1 | 1 | 7.5 | 0.03 |
| 429 | 1 | 2 | 19 | 0.05 |
| 430 | 1 | 2 | 80 | 0.05 |
| 431 | 1 | 1 | 8 | 0.03 |
| 432 | 1 | 1 | 7 | 0.03 |
| 433 | 1 | 1 | 7 | 0.03 |
| 434 | 1 | 1 | 9 | 0.03 |
| 435 | 4 | 28 | 60 | 0.7 |
| 488 | 1 | 1 | 4 | 0.03 |
| 489 | 1 | 1 | 5 | 0.03 |
| 490 | 1 | 1 | 17 | 0.03 |
| 491 | 1 | 1 | 24 | 0.03 |

TABLE 6-continued

AhR activation by exemplary compounds of the disclosure. Fold @ 1 nM, Fold @ 100 nM and Fold @ 10 uM refer to the fold change of luciferase expression after treatment of cells with 1 nM, 100 nM or 10 uM respectively of test compound relative to vehicle (0.1% DMSO) treated cells in the AhR ligand screening assay. Fold relative to benchmark @ 100 nM refers to the fold change of luciferase expression after treatment of cells with 100 nM of test compound relative to the treatment with 100 nM of a benchmark compound (11-c1-BBQ) in the AhR ligand screening assay described above.

| Compound | Fold @ 1 nM | Fold @ 100 nM | Fold @ 10 uM | Fold relative to benchmark @ 100 nM |
|---|---|---|---|---|
| 492 | 1 | 1 | 14 | 0.03 |
| 493 | 1 | 1 | 16 | 0.03 |
| 494 | 1 | 29 | 43 | 0.94 |
| 495 | 2.3 | 25 | 59 | 0.81 |
| 496 | 1 | 1 | 3.5 | 0.03 |
| 497 | 1 | 1.5 | 3.5 | 0.05 |
| 521 | 1 | 1 | 1 | 0.07 |
| 522 | 1 | 1 | 18 | 0.07 |
| 523 | 1.8 | 11.5 | 12 | 0.82 |
| 524 | 1.2 | 4.8 | 20 | 0.34 |
| 525 | 1 | 5.6 | 20 | 0.4 |
| 526 | 2.7 | 10 | 28 | 0.71 |
| 527 | 1 | 15 | 36 | 0.38 |
| 528 | 1 | 19 | 35 | 0.48 |
| 529 | 2 | 41 | 52 | 1.03 |
| 530 | 2 | 39 | 56 | 0.98 |
| 533 | 1 | 1 | 13 | 0.03 |
| 534 | 1 | 1 | 26 | 0.03 |
| 535 | 1 | 38 | 44 | 0.95 |
| 536 | 1 | 39 | 41 | 0.98 |
| 579 | 1 | 1 | 2 | 0.07 |
| 580 | 1 | 3 | 14 | 0.2 |
| 581 | 1 | 1 | 15 | 0.07 |
| 582 | 1 | 1 | 14 | 0.07 |
| 583 | 1 | 5 | 7 | 0.33 |
| 584 | 1 | 3 | 31 | 0.2 |
| 585 | 1 | 1 | 34 | 0.07 |
| 586 | 7 | 20 | 18 | 1.33 |
| 587 | 2 | 16 | 19 | 1.07 |
| 588 | 1 | 5 | 30 | 0.33 |
| 589 | 2 | 12 | 16 | 0.8 |
| 590 | 1 | 3 | 45 | 0.2 |
| 591 | 2 | 2 | 38 | 0.13 |
| 630 | 1 | 5 | 9 | 0.56 |
| 631 | 1 | 1 | 7 | 0.11 |
| 632 | 1 | 2 | 17 | 0.22 |
| 633 | 1 | 2 | 25 | 0.22 |
| 634 | 1 | 2 | 22 | 0.22 |
| 635 | 1 | 2 | 24 | 0.22 |
| 636 | 1 | 1 | 14 | 0.11 |
| 637 | 1 | 2 | 13 | 0.22 |
| 638 | 1 | 12 | 20 | 1.17 |
| 639 | 1 | 1 | 5 | 0.11 |
| 640 | 1 | 10 | 15 | 1.21 |
| 641 | 1 | 1 | 21 | 0.11 |
| 642 | 1 | 1 | 27 | 0.11 |
| 643 | 1 | 1 | 2 | 0.11 |
| 644 | 1 | 1 | 2 | 0.11 |
| 645 | 1 | 1 | 15 | 0.11 |
| 681 | 1 | 25 | 24 | 0.96 |
| 682 | 1 | 18 | 32 | 0.69 |
| 683 | 1 | 26 | 34 | 1 |
| 684 | 1 | 2 | 56 | 0.08 |
| 685 | 1 | 13 | 28 | 0.5 |
| 686 | 1 | 24 | 31 | 0.92 |
| 687 | 1 | 28 | 32 | 1.08 |
| 688 | 2 | 28 | 44 | 1.08 |
| 689 | 1 | 28 | 47 | 1.08 |
| 690 | 2 | 22 | 30 | 0.85 |
| 691 | 2 | 26 | 34 | 1 |
| 692 | 3 | 24 | 85 | 0.92 |
| 693 | 2 | 32 | 87 | 1.23 |
| 694 | 2 | 32 | 35 | 1.23 |
| 695 | 1 | 23 | 30 | 0.88 |
| 696 | 1 | 22 | 51 | 0.85 |
| 697 | 1 | 23 | 22 | 0.88 |
| 698 | 1 | 26 | 30 | 1 |
| 699 | 1 | 22 | 24 | 0.85 |

TABLE 6-continued

AhR activation by exemplary compounds of the disclosure. Fold @ 1 nM, Fold @ 100 nM and Fold @ 10 uM refer to the fold change of luciferase expression after treatment of cells with 1 nM, 100 nM or 10 uM respectively of test compound relative to vehicle (0.1% DMSO) treated cells in the AhR ligand screening assay. Fold relative to benchmark @ 100 nM refers to the fold change of luciferase expression after treatment of cells with 100 nM of test compound relative to the treatment with 100 nM of a benchmark compound (11-c1-BBQ) in the AhR ligand screening assay described above.

| Compound | Fold @ 1 nM | Fold @ 100 nM | Fold @ 10 uM | Fold relative to benchmark @ 100 nM |
|---|---|---|---|---|
| 700 | 1 | 16 | 22 | 0.62 |
| 701 | 1 | 2 | 35 | 0.08 |
| 702 | 1 | 1 | — | 0.04 |
| 703 | 1 | 22 | 23 | 0.85 |
| 704 | 1 | 34 | 17 | 1.31 |
| 763 | 1 | 2 | 22 | 0.08 |
| 764 | 1 | 2 | 20 | 0.08 |
| 765 | 1 | 2 | 14 | 0.08 |
| 766 | 1 | 2 | 31 | 0.08 |
| 767 | 1 | 2 | 23 | 0.08 |
| 770 | 1 | 2 | 2 | 0.08 |
| 771 | 1 | 1 | 2 | 0.04 |
| 772 | 1 | 1 | 1 | 0.04 |
| 773 | 1 | 25 | 40 | 1 |
| 774 | 1 | 21 | 28 | 0.84 |
| 775 | 1 | 19 | 25 | 0.76 |
| 776 | 1 | 15 | 20 | 0.6 |
| 777 | 1 | 2 | 6 | 0.08 |
| 778 | 1 | 1 | 8 | 0.04 |
| 779 | 1 | 1 | 5 | 0.04 |
| 780 | 1 | 1 | 7 | 0.04 |
| 781 | 1 | 20 | 24 | 0.8 |
| 782 | 1 | 23 | 19 | 0.92 |
| 783 | 1 | 1 | 24 | 0.03 |
| 784 | 1 | 2 | 34 | 0.07 |
| 785 | 1 | 16 | 44 | 0.55 |
| 786 | 1 | 31 | 40 | 1.07 |
| 787 | 1 | 1 | 4 | 0.04 |
| 788 | 1 | 2 | 19 | 0.08 |
| 789 | 1 | 3 | 8 | 0.12 |
| 790 | 1 | 1 | 2 | 0.04 |
| 791 | 1 | 1 | 26 | 0.04 |
| 792 | 1 | 2 | 19 | 0.08 |
| 848 | 1 | 1 | 5 | 0.04 |
| 849 | 1 | 1 | 1 | 0.04 |
| 850 | 1 | 22 | 33 | 0.88 |
| 851 | 1 | 21 | 29 | 0.84 |
| 852 | 1 | 1 | 29 | 0.03 |
| 853 | 1 | 1 | 11 | 0.03 |
| 854 | 1 | 1 | 4 | 0.03 |
| 855 | 1 | 33 | 44 | 1.14 |
| 856 | 1 | 38 | 46 | 1.31 |
| 857 | 1 | 12 | 75 | 0.41 |
| 858 | 1 | 10 | 73 | 0.34 |
| 859 | 1 | 12 | 80 | 0.41 |
| 860 | 1 | 3 | 88 | 0.1 |
| 861 | 1 | 2 | 90 | 0.07 |
| 862 | 1 | 2 | 82 | 0.07 |
| 863 | 1 | 2 | 34 | 0.07 |
| 864 | 1 | 2 | 47 | 0.07 |
| 865 | 1 | 7 | 47 | 0.24 |
| 866 | 1 | 34 | 50 | 1.17 |
| 867 | 1 | 2 | 32 | 0.07 |
| 868 | 1 | 2 | 28 | 0.07 |
| 869 | 1 | 12 | 68 | 0.41 |
| 870 | 1 | 9 | 74 | 0.31 |
| 871 | 1 | 1 | 12 | 0.02 |
| 872 | 1 | 1 | 34 | 0.02 |
| 874 | 1 | 7 | 52 | 0.13 |
| 875 | 1 | 3 | 48 | 0.06 |
| 876 | 1 | 3 | 32 | 0.06 |
| 877 | 1 | 3 | 42 | 0.06 |
| 881 | 1 | 2 | 18 | 0.04 |
| 882 | 1 | 1 | 2 | 0.02 |
| 883 | 1 | 1 | 2 | 0.02 |
| 884 | 1 | 2 | 16 | 0.04 |
| 885 | 1 | 1 | 1 | 0.02 |
| 886 | 1 | 14 | 300 | 0.26 |

TABLE 6-continued

AhR activation by exemplary compounds of the disclosure. Fold @ 1 nM, Fold @ 100 nM and Fold @ 10 uM refer to the fold change of luciferase expression after treatment of cells with 1 nM, 100 nM or 10 uM respectively of test compound relative to vehicle (0.1% DMSO) treated cells in the AhR ligand screening assay. Fold relative to benchmark @ 100 nM refers to the fold change of luciferase expression after treatment of cells with 100 nM of test compound relative to the treatment with 100 nM of a benchmark compound (11-c1-BBQ) in the AhR ligand screening assay described above.

| Compound | Fold @ 1 nM | Fold @ 100 nM | Fold @ 10 uM | Fold relative to benchmark @ 100 nM |
|---|---|---|---|---|
| 887 | 1 | 1 | 14 | 0.02 |
| 888 | 1 | 1 | 9 | 0.02 |
| 889 | 1 | 1 | 5 | 0.02 |
| 890 | 1 | 2 | 17 | 0.04 |
| 891 | 1 | 1 | 21 | 0.02 |
| 892 | 1 | 1 | 15 | 0.02 |
| 893 | 1 | 49 | 49 | 0.91 |
| 894 | 1 | 1 | 7 | 0.02 |
| 895 | 1 | 1 | 10 | 0.02 |
| 972 | 1 | 2 | 45 | 0.04 |
| 973 | 1 | 1 | 1 | 0.02 |
| 1328 | 1 | 2 | 11 | 0.07 |
| 1329 | 1 | 1 | 1 | 0.03 |
| 1330 | 1 | 1 | 1 | 0.03 |
| 1336 | 1 | 1 | 6 | 0.03 |
| 1337 | 1 | 1 | 8 | 0.03 |
| 1338 | 1 | 1 | 2 | 0.03 |
| 1339 | 1 | 1 | 4 | 0.03 |
| 1340 | 1 | 1 | 8 | 0.03 |
| 1341 | 1 | 1 | 5 | 0.03 |
| 1342 | 1 | 2 | 2 | 0.07 |
| 1356 | 1 | 1 | 1 | 0.03 |
| 1357 | 1 | 1 | 1 | 0.03 |
| 1358 | 1 | 1 | 2 | 0.03 |
| 1359 | 1 | 1 | 2 | 0.03 |
| 1360 | 1 | 2 | 18 | 0.07 |
| 1361 | 1 | 2 | 2 | 0.07 |
| 1362 | 5 | 3 | 18 | 0.1 |
| 1363 | 1 | 1 | 4 | 0.03 |
| 1364 | 1 | 1 | 3 | 0.03 |
| 1365 | 1 | 1 | 2 | 0.03 |
| 1366 | 1 | 1 | 10 | 0.03 |
| 1367 | 1 | 1 | 3 | 0.03 |
| 1368 | 1 | 2 | 2 | 0.07 |
| 1369 | 1 | 1 | 2 | 0.03 |
| 1370 | 1 | 1 | 4 | 0.03 |
| 1384 | 1 | 2 | 13 | 0.07 |
| 1385 | 1 | 2 | 5 | 0.07 |
| 1386 | 1 | 2 | 6 | 0.07 |
| 1387 | 1 | 1 | 2 | 0.03 |
| 1388 | 1 | 2 | 2 | 0.07 |
| 1389 | 1 | 1 | 3 | 0.03 |
| 1390 | 1 | 1 | 3 | 0.03 |
| 1391 | 1 | 1 | 1 | 0.03 |
| 1392 | 1 | 1 | 4 | 0.03 |
| 1393 | 1 | 1 | 4 | 0.03 |
| 1401 | 1 | 1 | 2 | 0.03 |
| 1402 | 1 | 2 | 3 | 0.07 |
| 1403 | 1 | 2 | 20 | 0.07 |
| 1404 | 1 | 1 | 6 | 0.03 |
| 1405 | 1 | 2 | 30 | 0.07 |
| 1406 | 1 | 1 | 4 | 0.03 |
| 1407 | 1 | 1 | 9 | 0.03 |
| 1408 | 1 | 1 | 4 | 0.03 |
| 1409 | 1 | 1 | 4 | 0.03 |
| 1411 | 1 | 1 | 4 | 0.03 |
| 1412 | 1 | 1 | 6 | 0.03 |

Drug Metabolism/DMPK

1. Preparation of Compounds.

Compound solutions were prepared from powder as 10 mM or 1 mM stock solutions in Dimethyl Sulfoxide (DMSO; Cat. No. #D2650, Sigma Aldrich) and stored at −20° C.

2. Kinetic Solubility.

Test articles were serially diluted in DMSO from concentration range of 10 mM to 0.78 mM in 96 well V bottom dilution plate (#3363 costar). 1 μL of test article from each well was transferred to 96 well Flat bottom clear plates (#655101 Greiner) containing 99 μL of PBS at pH-7.4 so that the DMSO concentration should not exceed >1%. Samples were incubated for one hour at 37° C. followed by measurement of light scattering at 635 nm with a laser based micro plate nephelometer. Concentration (μM) was then calculated by segmental regression. Amiodarone (#A8423 Aldrich) was used as positive control.

3. Solubility in Simulated Gastric and Intestinal Fluids (SGF and SIF).

The following conditions were used:

Simulated Gastric Fluid in Fed state, pH 5.0 (FeSSGF)

Simulated Gastric Fluid in Fasted state, pH 1.2 (FaSSGF)

Simulated Intestinal Fluid in Fasted state, pH 6.5 (FaSSIF)

Simulated Intestinal Fluid in Fed state, pH 5.0 (FeSSIF)

Test article (1 mg) was dissolved in 1 ml of FeSSGF (pH-5.0), FaSSGF (pH-1.2), FaSSIF (pH-6.5) and FeSSIF (pH-5.0) in a transparent glass vial. Reactions were kept in reciprocating water bath at 37° C. for overnight. After 12-14 hrs, all the samples were centrifuged at 10,000 rpm for 15 mM. Supernatant was taken, diluted, and injected in LC-MS/MS (Shimadzu Nexera UPLC with an AB Sciex 4500 detector). Solubility was measured by plotting area of test in simulated fluids versus area of standard. Ketoconazole (#K1003 Aldrich) was used as positive control.

4. Liver Microsomal Stability.

The assessment of metabolic stability of testing compounds was performed using human, mouse, rat, dog and monkey liver microsomes (20 mg protein/ml). Each reaction mixture contained 42.5 μL of 0.1 M potassium phosphate buffer pH 7.4, containing respective LM protein (final concentration 0.5 mg/ml). 2.5 μL of the compound stock solution was added in it (1 μM final concentration). The reaction was initiated by the addition of 5 μL NADPH solution (final Concentration 1 mM). At different time points (0, 5, 15, and 30 minutes), samples were quenched with 200 μL of cold acetonitrile containing ISTD Propranolol. Samples were centrifuged at 3500 rpm for 20 mM at 4° C. Supernatant was subjected to LC-MS/MS analysis for quantification. Verapamil was used as a positive control.

5. CYP Panel Profile: P450 Inhibition

From 10 mM stock solutions of test compounds, a dilution plate was prepared diluting serially starting from 5 mM up to 2 μM in Acetonitrile/DMSO or Methanol/DMSO Human liver Microsomes were added at required concentration as per specific CYP isoform in a deep well assay plate (1A2, 2C9, 2D6, 2B6, 2C8, 2C19, and 3A4). Compounds were spiked in all wells from dilution plate at final concentrations starting from 50 μM up to 0.02 μM, except for positive and negative control. Specific substrate were added to all wells and reactions were pre-incubated for 10 min. To start reactions, NADPH was added to all wells at 1 mM final concentration. Assay plate was mixed by vortexing and incubated at 37° C. for 10 mM for 3A4.20 min for (1A2, 2C9, 2B6, 2C8, 2D6) and 40 mM for 2C19. A quencher with chilled acetonitrile suitable internal standard was added. Samples were centrifuged and supernatants were collected and subjected to LC-MS/MS analysis for determination.

Data for exemplary compounds is presented in Tables 7-9.

TABLE 7

Solubility of exemplary compounds in simulated gastric and intestinal fluids (Fasted and fed conditions)

| Stock DMSO mM | Kinetic Solubility (μM) | FaSSGF (μg/ml) | FaSSIF (μg/ml) | FeSSGF (μg/ml) | FeSSIF (μg/ml) |
|---|---|---|---|---|---|
| <1 | <1 | 8.0 | 1.1 | 1.9 | 8.0 |
| 100 | 7.0 | 0.8 | 8.6 | 0.7 | 29.0 |
| 100 | 9.4 | 3.6 | 25.6 | 16.5 | 26.5 |
| 100 | 5.9 | — | — | — | — |
| 100 | 9.4 | 0.3 | 4.3 | 0.1 | 27.3 |
| 50 | 7.0 | 0.4 | 64.2 | 3.0 | 15.0 |
| 10 | 28.8 | — | — | — | — |
| 100 | 4.7 | 1.7 | 8.7 | 0.5 | 11.5 |
| 100 | 1.8 | 1.1 | 12.8 | 0.1 | 85.4 |
| 50 | 28.1 | — | — | — | — |
| 50 | 14.1 | — | — | — | — |

TABLE 8

CYP inhibition by exemplary compounds

| Compound | CYP-1A2 $IC_{50}$ (μM) | CYP-2C9 $IC_{50}$ (μM) | CYP-2D6 $IC_{50}$ (μM) | CYP-2B6 $IC_{50}$ (μM) | CYP-2C8 $IC_{50}$ (μM) | CYP-2C19 $IC_{50}$ (μM) | CYP-3A4 $IC_{50}$ (μM) |
|---|---|---|---|---|---|---|---|
| 435 | <0.02 | >50 | >50 | >50 | 19.2 | >50 | 5.3 |
| 494 | 0.7 | 4.2 | >50 | >45 | 2.5 | 5.2 | 1.2 |
| 495 | 0.3 | 5.6 | 32.6 | 19.3 | 1.9 | 1.4 | 5.3 |
| 529 | 0.6 | 3.5 | >50 | 9.6 | 9.6 | 3.6 | 1.2 |
| 530 | 0.5 | 5.0 | >50 | 9.4 | 9.4 | 3.4 | 3.7 |
| 535 | 3.9 | 2.5 | >50 | 21.5 | 21.8 | 2.1 | 0.2 |
| 536 | 0.6 | 4.8 | >50 | 16.0 | 17.1 | 2.6 | 1.7 |
| 586 | 1.7 | 7.9 | >50 | 22.0 | 9.1 | 7.1 | 1.3 |
| 587 | 0.4 | 5.3 | 26.0 | 11.6 | 3.2 | 6.7 | 6.3 |
| 638 | 0.3 | 5.2 | 14.5 | 11.6 | 1.8 | 3.4 | 8.1 |
| 640 | 0.6 | 4.5 | 29.0 | 31.1 | 2.3 | 2.4 | 3.8 |
| 643 | 20.7 | 9.2 | >50 | >50 | 12.3 | >50 | >50 |
| 644 | 4.7 | 2.7 | 8.2 | >50 | 1.7 | >50 | >50 |
| 693 | 8.6 | 11.6 | >50 | >50 | 3.5 | 24.1 | 2.0 |
| 703 | 0.8 | 5.3 | >50 | 12.0 | 4.2 | 0.5 | 10.3 |
| 704 | 1.2 | 8.9 | >50 | 8.2 | 5.6 | 4.6 | 3.9 |
| 782 | 47.9 | >50 | >50 | >50 | >50 | 6.0 | 0.4 |

TABLE 8-continued

CYP inhibition by exemplary compounds

| Compound | CYP-1A2 $IC_{50}$ (μM) | CYP-2C9 $IC_{50}$ (μM) | CYP-2D6 $IC_{50}$ (μM) | CYP-2B6 $IC_{50}$ (μM) | CYP-2C8 $IC_{50}$ (μM) | CYP-2C19 $IC_{50}$ (μM) | CYP-3A4 $IC_{50}$ (μM) |
|---|---|---|---|---|---|---|---|
| 848 | 2.6 | 6.3 | 2.9 | 16.7 | 3.5 | 1.1 | 13.7 |
| 849 | 15.1 | 7.7 | 19.3 | >48.0 | 4.1 | 1.5 | >50 |
| 893 | 0.5 | 7.2 | 31.7 | 8.0 | 7.7 | 2.9 | 23.3 |
| 972 | 7.0 | 7.0 | >50 | 4.3 | >48.8 | 0.2 | >50 |
| 973 | >50 | >50 | >50 | >50 | >50 | 23.1 | >50 |

TABLE 9

| Compound | Rem @ HLM × 30 min (%) | Rem @ MLM × 30 min (%) | Rem @ RLM × 30 min (%) | T ½ @ HLM (min) | T ½ @ MLM (min) | T ½ @ RLM (min) | Clint @ HLM (μl/min/mg) | Clint @ MLM (μl/min/mg) | Clint @ RLM (μl/min/mg) |
|---|---|---|---|---|---|---|---|---|---|
| 362 | — | 12.0 | 14.5 | — | 9.8 | 11.4 | — | 141.0 | 121.0 |
| 434 | 63.4 | 10.6 | 41.6 | 48.7 | 10.7 | 28.0 | 28.5 | 129.2 | 49.6 |
| 521 | 58.0 | 64.6 | 45.5 | 40.3 | 60.9 | 24.8 | 34.0 | 23 | 56 |
| 644 | 69.8 | 71.7 | 36.8 | 77.9 | 70.5 | 28.7 | 18 | 20 | 48 |
| 774 | 52.7 | 28.2 | 45.5 | 36.3 | 19.3 | 31.9 | 38.2 | 71.9 | 43.5 |
| 776 | 28.3 | 23.9 | 27.5 | 16.4 | 14.6 | 16.3 | 84.6 | 94.7 | 84.9 |
| 781 | 44.4 | 18.0 | 43.1 | 24.6 | 12.1 | 24.4 | 56.3 | 114.8 | 56.8 |
| 782 | 66.4 | 14.9 | 31.8 | 50.5 | 10.9 | 17.8 | 27.4 | 126.9 | 78.0 |
| 785 | 54.2 | 49.3 | 57.1 | 33.9 | 29.4 | 36.5 | 40.9 | 47.2 | 37.9 |
| 786 | 27.4 | 22.1 | 25.6 | 16.1 | 13.4 | 14.8 | 86.2 | 103.6 | 93.8 |
| 884 | 81.2 | 22.2 | 23.1 | 98.8 | 13.9 | 14.3 | 14 | 100 | 96.7 |
| 885 | 58.1 | 45.1 | 50.2 | 36.8 | 27.5 | 30.7 | 37.7 | 50.4 | 45.1 |
| 889 | 30.2 | 43.5 | 33.5 | 22.6 | 33.9 | 25.6 | 61.2 | 40.9 | 54.2 |
| 890 | 44.7 | 39.3 | 37.4 | 35.2 | 28.2 | 29.0 | 39.4 | 49.1 | 47.8 |
| 891 | 54.3 | 52.4 | 45.2 | 42.4 | 36.3 | 31.0 | 32.7 | 38.2 | 44.7 |
| 892 | 24.7 | 36.7 | 64.9 | 15.3 | 21.0 | 57.0 | 90.7 | 66.1 | 24.3 |
| 893 | 19.6 | 16.7 | 51.7 | 14.1 | 12.2 | 35.8 | 98.5 | 113.5 | 38.8 |
| 894 | 57.9 | 54.5 | 58.1 | 45.3 | 37.6 | 43.0 | 30.6 | 36.9 | 32.3 |
| 972 | 73.0 | 26.7 | 20.7 | 74.9 | 15.9 | 13.3 | 18.5 | 87.1 | 104.6 |
| 973 | 34.2 | 58.7 | 46.3 | 16.7 | 39.9 | 26.5 | 83.1 | 34.8 | 52.3 |

In Vivo PK Study

Pharmacokinetics of Exemplary Compounds 362 and 893 Following an Intravenous and Oral Administration in Male C57BL/6J Mice.

Male C57BL/6J mice, approximately 8-10 weeks old, were obtained from the vivarium of Fundación Ciencia & Vida Chile (Santiago, Chile). Dosing solution of Compound 362 for PO administration was formulated in a vehicle containing 40% DMSO, 20% Kolliphor EL, 40% Propylene Glycol at 0.8 mg/mL. Dosing solution of Compound 362 for IV administration was formulated in a vehicle containing 30% DMSO, 20% Kolliphor EL, 50% PBS at 0.4 mg/Kg.

Male BalbC mice, approximately 8-11 weeks old, 22-27 grams were obtained from the vivarium Fundación Ciencia & Vida Chile (Santiago, Chile). Animals were acclimated for a minimum period of 4 days upon arrival at the testing facility. Animals were weighed, identified by marking the tail with numbers using a non-toxic permanent marker and designated into the following treatment groups on the day of dosing:

Group 1 animals received an IV administration via caudal vein of 2 mg/kg PRXS0362 dosing solution.

Group 2 animals received a PO administration via feeding tubes (20 gauge) of 8 mg/kg PRXS0362 dosing solution.

| Group | No. animals | Route | Dose [mg/Kg] | Dose conc. [mg/mL] | Dose Vol. [mL/Kg] |
|---|---|---|---|---|---|
| 1 | 30 | I.V. | 2 | 0.4 | 5 |
| 2 | 18 | P.O. | 8 | 0.8 | 10 |

Terminal whole blood was collected via cardiac puncture for group 1 at the following time points: 5, 10, 15, 30, 60, 120, 240, 360, and 480 minutes. Non-dosed mice were used to collect samples of zero time points. For the group 2 at the following time point: 15, 30, 60, 120, 240, 360, and 480 minutes.

Whole blood, approximately 300 μL per time point, was collected into microtainer tubes with EDTA (K2). Blood samples were centrifuged immediately at approximately 9,000 G at 4° C. for 5 minutes and plasma separated. Plasma samples were placed into individually labeled tubes and stored in a −80° C. freezer prior to LC/MS/MS analysis.

The whole brain was collected at each point only for both groups, for this the animals were euthanized with $CO_2$, decapitated, the brain was extracted weighed, frozen in liquid nitrogen and stored at −80° C. prior to LC/MS/MS analysis.

Compound 893 was tested by the same protocol as above.

TABLE 10

In vivo PK parameters of exemplary compounds.

| Drug | Route | Dose (mg/Kg) | N/time point | C0_Cmax (mg/L) | tmax (h) | AUClast (h*mg/L) | AUCinf (h*mg/L) | Vd_Vd/F (L/Kg) | CL_CL/F (L/[Kg*h]) | MRT (h) | thalf (h) | F % |
|---|---|---|---|---|---|---|---|---|---|---|---|---|
| 362 | IV (plasma) | 2 | 3 | 0.215 | — | 0.451 | 0.453 | 5.67 | 4.418 | 0.872 | 0.889 | — |
| | PO (plasma) | 8 | 3 | 0.427 | 1 | 1.017 | 1.018 | 8.314 | 7.86 | 1.634 | 0.733 | 56.2 |
| 893 | IV (plasma) | 2 | 3 | 0.174 | — | 0.451 | 0.474 | 8.777 | 4.218 | 2.007 | 1.442 | — |
| | PO (plasma) | 8 | 3 | 0.398 | 1 | 1.327 | 1.394 | 12.846 | 5.739 | 2.663 | 1.551 | 73.5 |

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound of the formula:

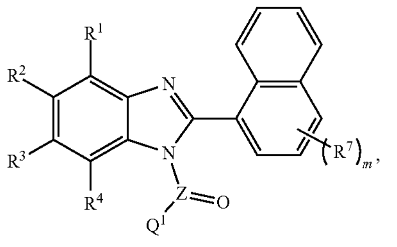

or a tautomer thereof, a stereoisomer thereof, a hydrate thereof, or a pharmaceutically acceptable salt thereof, wherein:

$Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl;

Z is C;

$R^1$ is H or halogen;

$R^2$, $R^3$, and $R^4$ are independently H, halogen, CN, optionally substituted C1-C10 alkyl, optionally substituted C3-C10 cycloalkyl, optionally substituted C1-C6 alkoxy, $SO_2R^5$, $CO_2R^5$, or $CONR^5R^6$, or any one of $R^1$ and $R^2$, $R^2$ and $R^3$, and $R^3$ and $R^4$ pairs, together with the carbon atoms to which they are attached, forms an optionally substituted a five- or six-membered cycloalkenyl, heterocyclenyl, aryl or heteroaryl;

$R^5$ and $R^6$ are independently H, optionally substituted C1-C10 alkyl, or optionally substituted C3-C10 cycloalkyl, or $R^5$ and $R^6$, together with the nitrogen atom to which they are attached, form an optionally substituted 5-membered ring or an optionally substituted 6-membered ring;

$R^7$, at each occurrence, is independently H, halogen, CN, optionally substituted C1-C10 alkyl, optionally substituted C2-C6 alkenyl, optionally substituted C1-C10 heteroalkyl, optionally substituted C1-C10 heterocyclyl, optionally substituted C6-C10 aryl, optionally substituted C5-C10 heteroaryl, optionally substituted C1-C6 alkoxy, optionally substituted C1-C6 cycloalkyloxy, $OCF_3$, $NR^5R^6$, $SCF_3$, or $C(O)NR^5R^6$; and m is an integer from 1 to 7.

2. The compound of claim 1, wherein $Q^1$ is an optionally substituted phenyl, an optionally substituted naphthyl, an optionally substituted optionally substituted C3-C6 cycloalkyl or an optionally substituted quinolinyl.

3. The compound of claim 2, wherein $Q^1$ is a phenyl optionally substituted with one, two, or three substituents independently selected from F, Cl, Br, $OCH_3$, CN, $OCF_3$, $SCF_3$, t-Bu, $NMe_2$, $CONH_2$, piperazyl, piperidyl, $OCH_2CH_2OH$, $OCH_2CH_2NMe_2$, and 1-naphthyl.

4. The compound of claim 1, wherein $R^4$ is H or halogen.

5. The compound of claim 1, wherein all $R^7$ are H.

6. A compound of the formula:

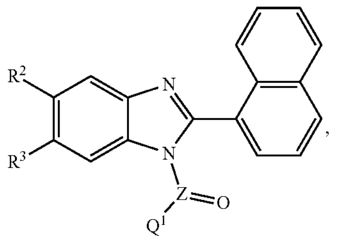

or a tautomer thereof, a stereoisomer thereof, a hydrate thereof, or a pharmaceutically acceptable salt thereof, wherein $R^2$ and $R^3$, independently, F, Cl, Br, O(C1-C5 alkyl), $SCF_3$, $OCF_3$, $CO_2H$, $CO_2$(C1-C5 alkyl), or $CONR^5R^6$, wherein $R^5$ and $R^6$ are independently H, optionally substituted C1-C10 alkyl, optionally substituted C3-C10 cycloalkyl, or $R^5$ and $R^6$, together with the nitrogen atom to which they are attached, form an optionally substituted morpholinyl; and $Q^1$ is an optionally substituted C6-C10 aryl; optionally substituted C5-C10 heteroaryl; optionally substituted C5-C10 heterocyclyl; optionally substituted C1-C10 alkyl, or optionally substituted C3-C10 cycloalkyl; Z is C.

7. The compound of claim 6, wherein $Q^1$ is a phenyl, cyclopropyl, naphthyl, benzodioxanyl, or quinolinyl, each of which is optionally substituted with one, two, or three substituents independently selected from the group consisting of F, Cl, Br, $CF_3$, $SCF_3$, CN, and $OCH_3$.

8. The compound of claim 1, or a tautomer thereof, a stereoisomer thereof, a hydrate thereof, or a pharmaceutically acceptable salt thereof, wherein the compound is selected from the group consisting of:

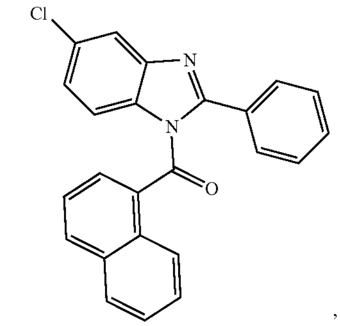
,
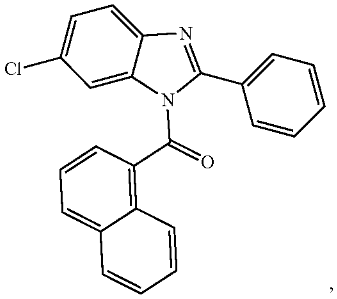
,
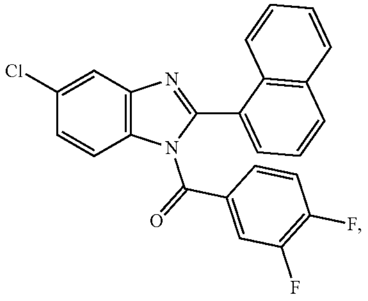
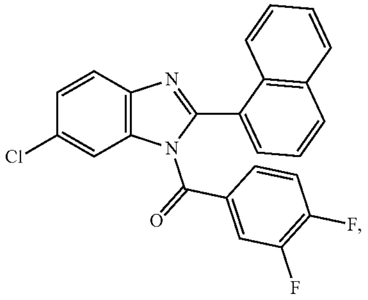
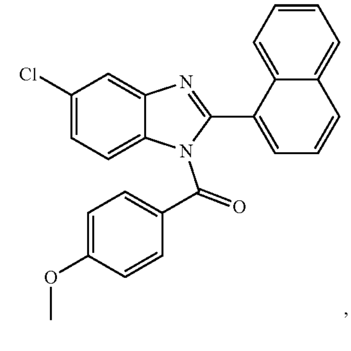
,
-continued
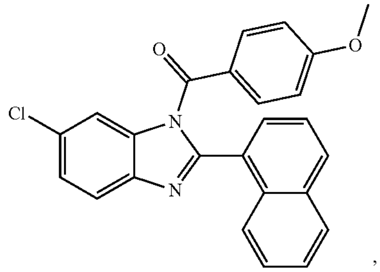
,
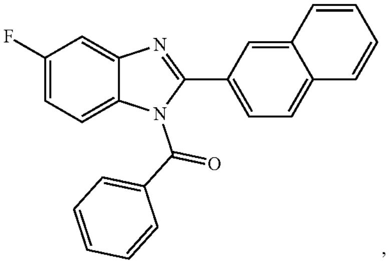
,
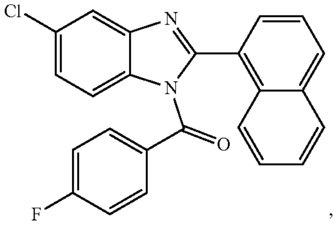
,
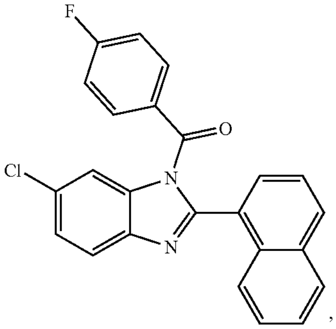
,
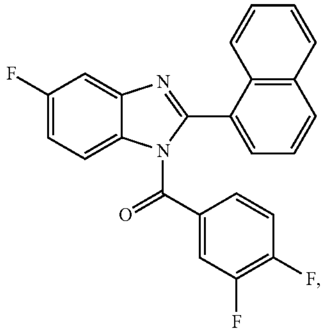
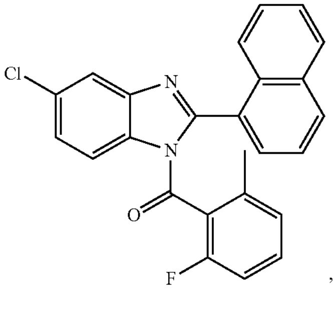
, -continued
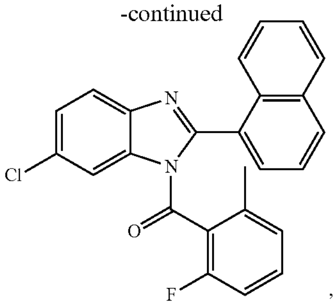
,
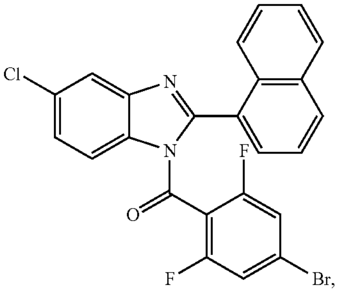
,
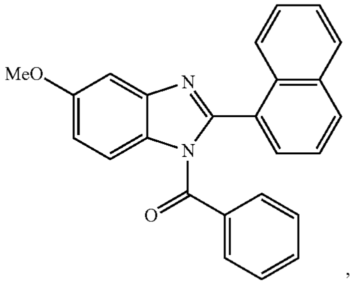
,
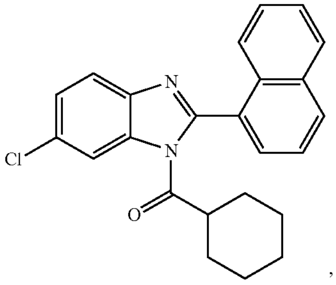
,
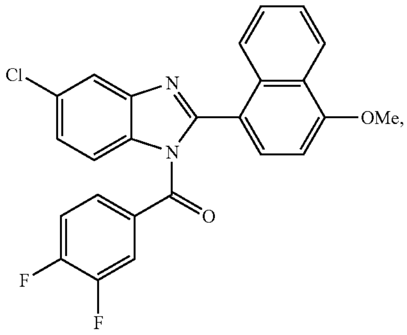
,
-continued
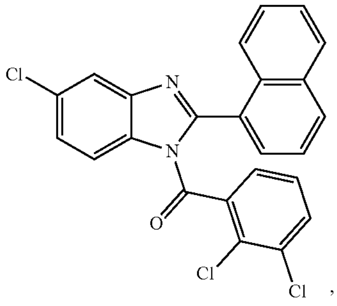
,
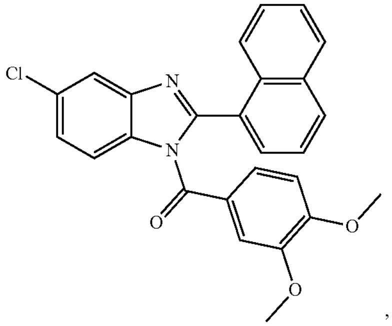
,
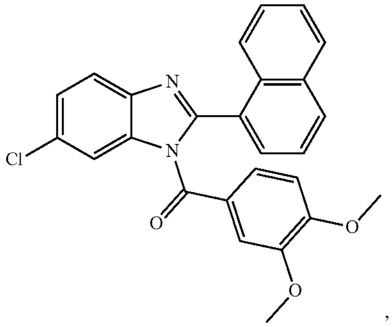
,
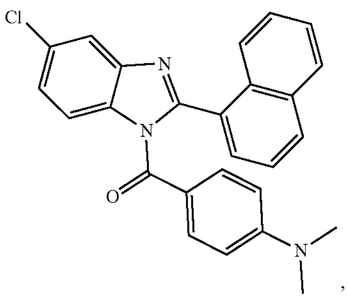
,
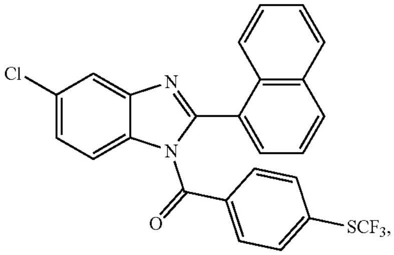
, -continued
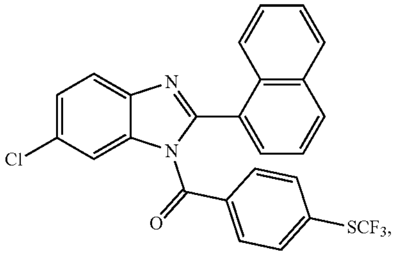
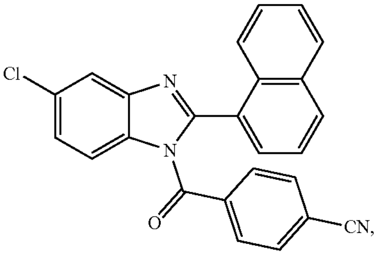
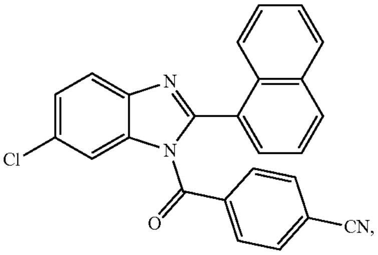
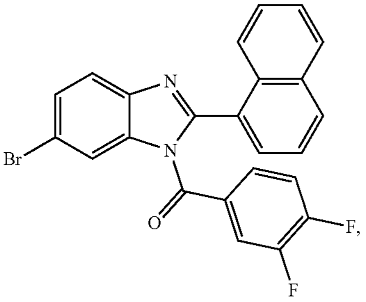
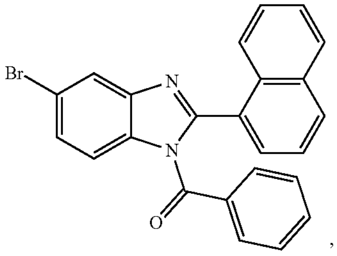
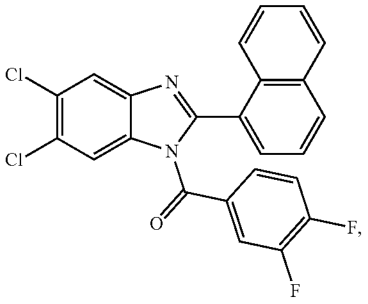
-continued
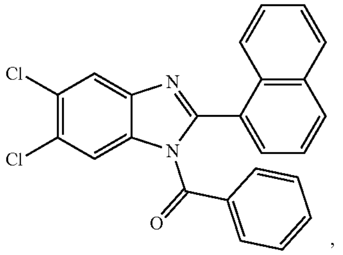
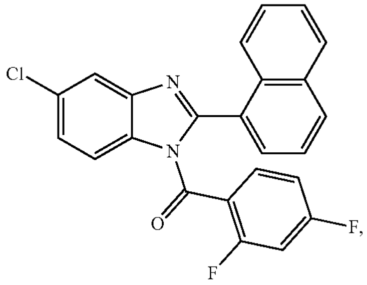
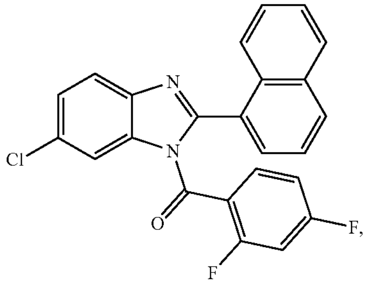
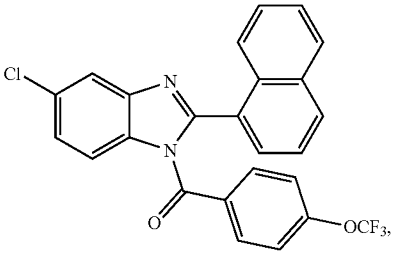
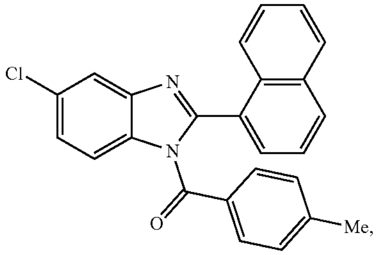
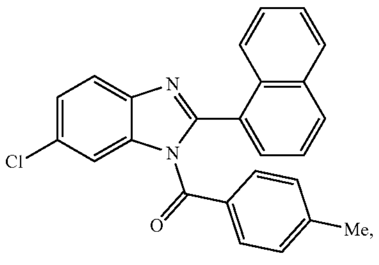

-continued
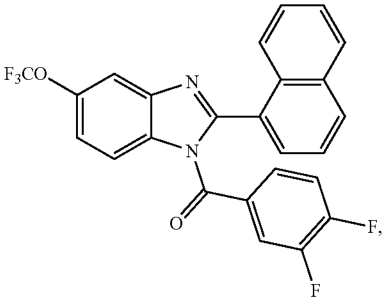
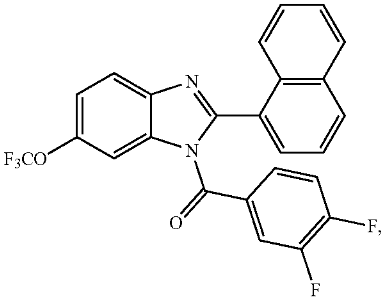
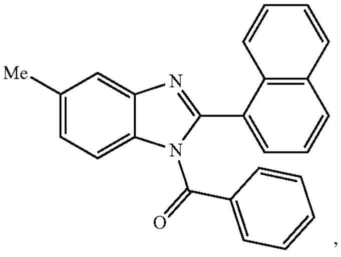
,
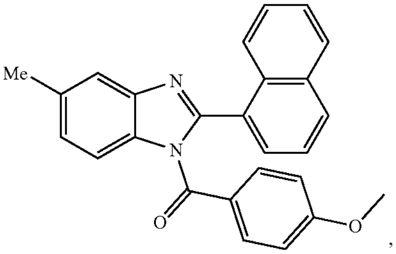
,
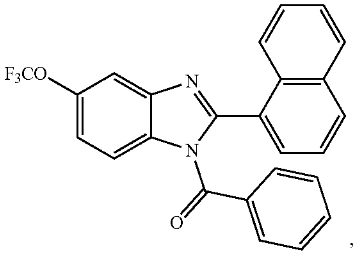
,
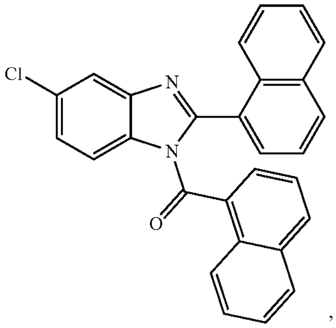
,
-continued
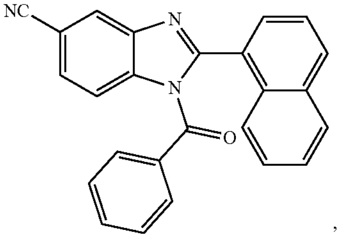
,
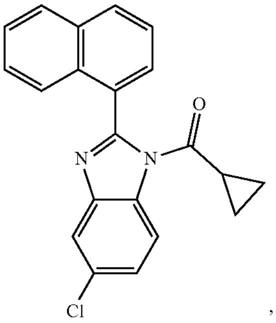
,
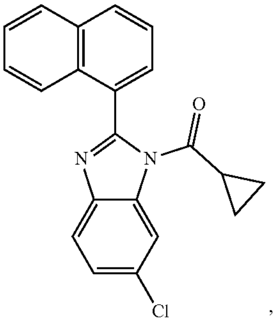
,
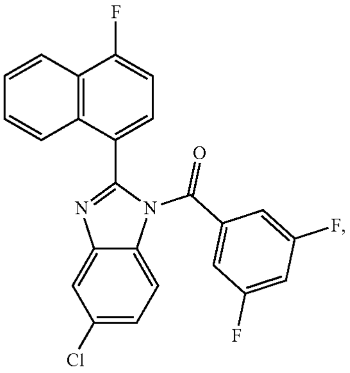
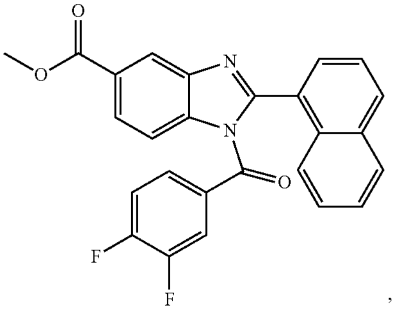
,
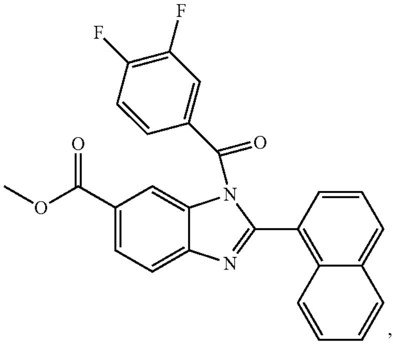
, -continued
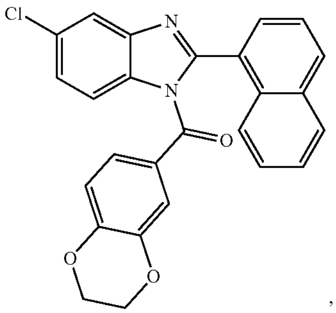
,
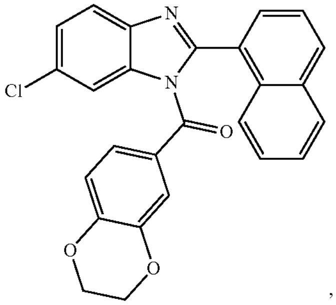
,
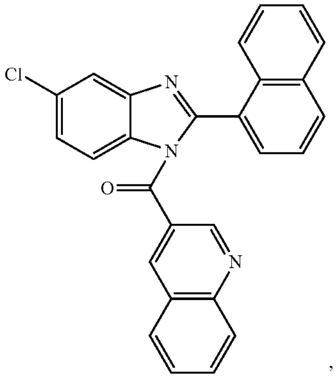
,
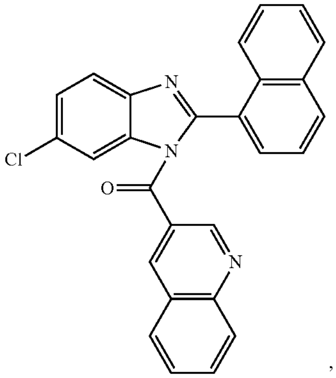
,
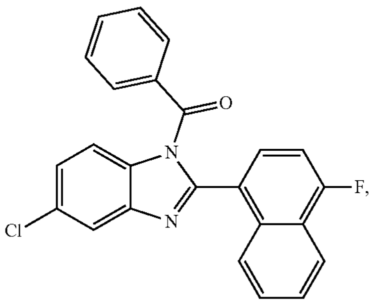
-continued
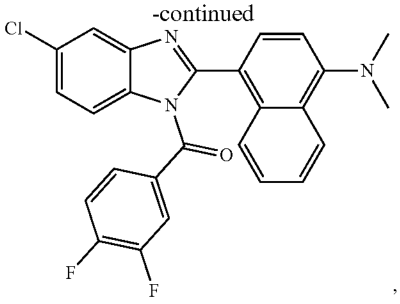
,
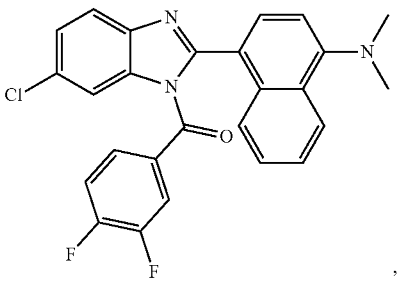
,
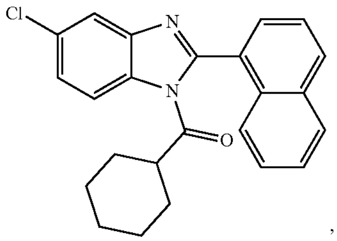
,
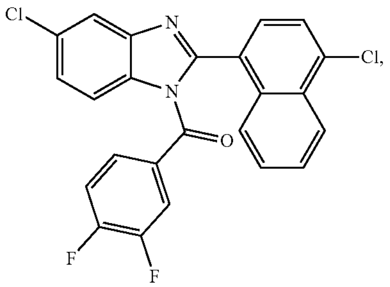
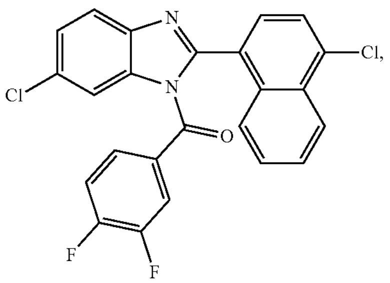

-continued
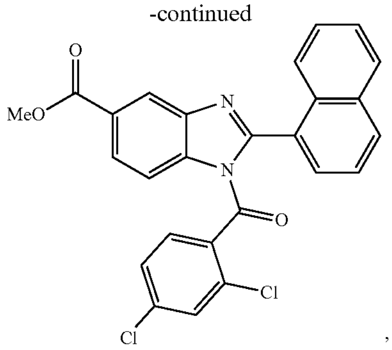
,
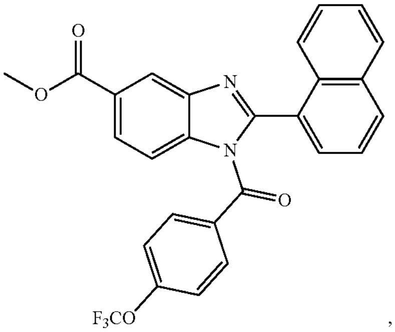
, and
-continued
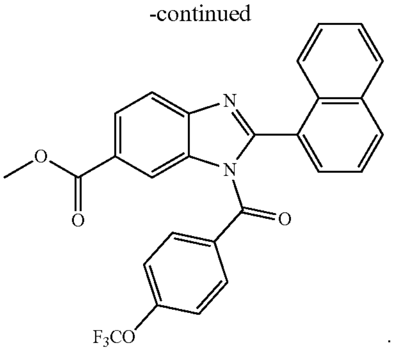
.
9. A pharmaceutical composition comprising a compound of claim 1, or a hydrate thereof, or a pharmaceutically acceptable salt thereof.
10. A pharmaceutical composition comprising a compound of claim 6, or a hydrate thereof, or a pharmaceutically acceptable salt thereof.
* * * * *